(12) United States Patent
Turner et al.

(10) Patent No.: US 6,673,793 B2
(45) Date of Patent: Jan. 6, 2004

(54) OXAZINOQUINOLONES USEFUL FOR THE TREATMENT OF VIRAL INFECTIONS

(75) Inventors: Steven Ronald Turner, Kalamazoo, MI (US); Suvit Thaisrivongs, Kalamazoo, MI (US); Atli Thorarensen, Portage, MI (US)

(73) Assignee: Pharmacia & Upjohn Co., Kalamazoo, MI (US)

( * ) Notice: Subject to any disclaimer, the term of this patent is extended or adjusted under 35 U.S.C. 154(b) by 0 days.

(21) Appl. No.: 09/894,354

(22) Filed: Jun. 28, 2001

(65) Prior Publication Data

US 2002/0103170 A1 Aug. 1, 2002

Related U.S. Application Data

(60) Provisional application No. 60/168,255, filed on Feb. 13, 2001, provisional application No. 60/262,211, filed on Jan. 17, 2001, provisional application No. 60/218,114, filed on Jul. 13, 2000, and provisional application No. 60/217,555, filed on Jul. 12, 2000.

(51) Int. Cl.$^7$ .................. C07D 498/04; A61K 31/5365; A61P 31/22
(52) U.S. Cl. ..................................... 514/230.2; 544/101
(58) Field of Search ........................ 544/101; 514/230.2

(56) References Cited

U.S. PATENT DOCUMENTS

| 4,847,375 A | 7/1989 | Grohe et al. .................. 544/99 |
| 4,959,363 A | 9/1990 | Wentland .................. 514/235.2 |
| 5,583,135 A | 12/1996 | Matsuo et al. ........... 514/230.2 |
| 5,792,774 A | 8/1998 | Haughan et al. ............ 514/294 |

FOREIGN PATENT DOCUMENTS

| JP | 10324631 | 8/1998 |
| WO | WO99/40093 | 8/1999 |
| WO | WO00/40561 | 7/2000 |
| WO | WO01/25239 | 4/2001 |

OTHER PUBLICATIONS

Abstract of Japanese patent JP10324631, Aug. 12, 1998.

*Primary Examiner*—Mukund J. Shah
*Assistant Examiner*—Venkataraman Balasubramanian
(74) *Attorney, Agent, or Firm*—Lucy X. Yang

(57) ABSTRACT

The present invention provides a compound of formula I

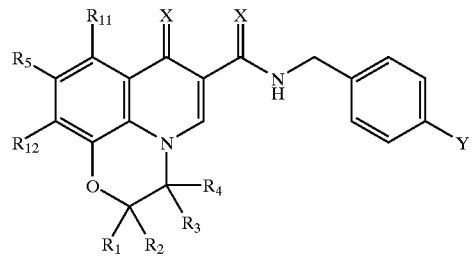

which is useful as antiviral agents, in particular, as agents against viruses of the herpes family.

94 Claims, No Drawings

OXAZINOQUINOLONES USEFUL FOR THE TREATMENT OF VIRAL INFECTIONS

CROSS REFERENCE TO RELATED APPLICATIONS

This application claims the benefit of the following provisional applications: U.S. Serial No. 60/217,555, filed Jul. 12, 2000; U.S. Serial No. 60/218,114, filed Jul. 13, 2000; U.S. Serial No. 60/262,211, filed Jan. 17, 2001; and U.S. Serial No. 60/168,255, filed Feb. 13, 2001 under 35 USC 119(e)(i).

FIELD OF THE INVENTION

The present invention provides oxazinoquinolone and thioxazinoquinolone derivatives having a ring connecting position 4 (N-4) and position 11 (C-11), and more specifically, provides compounds of formula (I) described herein below. These compounds are useful as antiviral agents, in particular, as agents against viruses of the herpes family.

BACKGROUND OF THE INVENTION

The herpesviruses comprise a large family of double stranded DNA viruses. They are also a source of the most common viral illnesses in man. Eight of the herpes viruses, herpes simplex virus types 1 and 2 (HSV-1 and HSV-2), varicella zoster virus (VZV), human cytomegalovirus (HCMV), epstein-Barr virus (EBV), and human herpes viruses 6, 7, and 8 (HHV-6, HHV-7, and (HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causitive agent of chicken pox and shingles. EBV causes infectious mononucleosis. It can also cause lymphomas in immunocompromised patients and has been associated with Burkitt's lymphoma, nasopharyngeal carcinoma, and Hodgkins disease. HHV-6 is the causitive agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

Due to the unique position of the para-substitutent on the N-phenylmethyl of formula I described herein below, compounds of the present invention demonstrate unexpected activity against the above reference herpesviral infections, particularly, human cytomegaloviral infection.

INFORMATION DISCLOSURE

U.S. Pat. No. 5,792,774 discloses oxazino 1,4-dihydro-4-oxoquinolines useful for the treatment of a large number of diseases modulated by tissue necrosis factor (TNF) or phosphodiesterase IV, includng cytomegalovirus (CMV) infections.

U.S. Pat. No. 4,847,375 discloses 1,8-bridged 4-quinoline-3-carboxylic acids useful as antibacterial agents.

U.S. Pat. No. 5,583,135 discloses heterotricyclic derivatives having a strong immunomodulating activity, anti-inflammatory activity and anti-cancer activity.

The abstract of Japanese Patent JP 10324631-A discloses IgE antibody production inhibitor comprise a pyrido(1,2,3-del,4-benzoxazine or a pyrido (1,2,3,-de)-1,4-benzothiazine derivative.

PCT patent application, PCT/US00/21985 discloses oxazinoquinolones useful for the treatment of viral infections.

SUMMARY OF THE INVENTION

The present invention provides a compound of formula I,

I or a pharmaceutically acceptable salt, racemate, solvate, tautomer, optical isomer or prodrug derivative thereof wherein:

each X is independently O or S;

Y is Cl, F, Br, CN or $NO_2$;

$R_1$, $R_2$, $R_3$ and $R_4$ are independently
  a) hydrogen,
  b) $N_3$,
  c) CN,
  d) fluoro,
  e) trifluoromethyl,
  f) aryl,
  g) het,
  h) $C_{1-8}$ alkyl, optionally substituted with $R_6$ or $OR_7$, or
  i) $R_1$ and $R_2$ or $R_3$ and $R_4$ together with the carbon to which they are attached form $C_{3-8}$cycloalkyl or het;

$R_5$ is $C_{1-8}$alkyl, which may be partially unsaturated and optionally substituted with one to three $N_3$, halo, CN, $R_6$ or $R_7$;

$R_6$ is
  a) aryl,
  b) het,
  c) $SO_iR_8$,
  d) $OR_8$,
  e) $C(=O)OR_8$,
  f) $C(=O)R_8$, or
  g) $NR_8R_9$;

$R_7$ is
  a) $P(=O)(OR_{10})_2$,
  b) $CO(CH_2)_jCON(CH_3)(CH_2)_kSO_3^-M^+$,
  c) an amino acid,
  d) $C(=O)C_{1-6}$alkyl, optionally substituted by $NR^{10}R^{10}$, or
  e) $CO(CH_2)_nCO_2H$;

$R_8$ and $R_9$ are independently
  a) hydrogen,
  b) $C_{3-8}$cycloalkyl,
  c) aryl,
  d) het, or
  e) $C_{1-8}$alkyl which is further optionally substituted with one or more aryl, het, halo, CN, $CO_2R_{10}$, $SO_iR_{10}$, $OR_{10}$, $NR_{10}R_{10}$, $CF_3$, or $C_{3-8}$cycloalkyl;

$R_{10}$ is
  a) H or
  b) $C_{1-8}$alkyl, optionally substituted with OH or $OC_{1-4}$alkyl;

$R_{11}$ and $R_{12}$ are independently
  a) hydrogen,
  b) halo,
  c) $NO_2$,
  d) CN,
  e) $R_6$,
  f) $SO_iNR_8R_9$, or
  g) $C_{1-8}$alkyl, which may be partially unsaturated and optionally substituted with one to three $N_3$, halo, CN, $R_6$ or $OR_7$;

aryl is
  a phenyl radical, optionally fused with a saturated or unsaturated carbocyclic or heterocyclic ring; at each occurrence, aryl may be substituted with one or more halo, CN, $CO_2R_{10}$, $SO_iR_{10}$, $OR_{10}$, $NR_{10}R_{10}$, $CF_3$, $C_{3-8}$cycloalkyl, or $C_{1-4}$alkyl wherein $C_{1-4}$alkyl is optionally substituted with $OR_{10}$;

het is
  a four-(4), five- (5), six- (6), or seven- (7) membered saturated or unsaturated heterocyclic ring having 1, 2, or 3 heteroatoms selected from the group consisting of O, S, and NW, wherein W is hydrogen, $C_{1-4}$alkyl, $C(=O)OC_{1-4}$alkyl or absent, wherein het is optionally fused with a benzene ring, a carbcyclic or a heterocyclic ring; at each occurrence, het may be substituted with one or more halo, CN, $CO_2R_{10}$, $SO_iR_{10}$, $OR_{10}$, $NR_{10}R_{10}$, $C_{1-4}$alkyl, $CF_3$, $C_{3-8}$cycloalkyl, oxo or oxine;

at each occurrence, a cycloalkyl group may be substituted with $C_{1-4}$alkyl, $OR^{10}$, oxo, oxine, or a spiro fused het;

i is 0, 1 or 2;
  j is 1, 2, 3, 4, 5, or 6;
  k is 1, 2, 3, 4, 5, or 6;
  n is 1, 2, 3, 4, 5, or 6;
  M is sodium, potassium, or lithium; and with the following provisos:
  a) at least one of $R_1$, $R_2$, $R_3$ and $R_4$ is other than hydrogen;
  b) where $R_1$, $R_2$, $R_3$ and $R_4$ are independently $C_{1-8}$ alkyl, at least one of the alkyl groups is substituted with $R_6$ or $OR_7$.

The present invention further provides a pharmaceutical composition comprising a compound of formula I, or a pharmaceutically acceptable salt thereof, and a pharmaceutically acceptable carrier (the composition preferably comprises an effective antiviral amount of the compound or salt).

The present invention further provides a method of treating or preventing a herpesviral infection, comprising administering to a mammal in need of such treatment, a compound of formula (I) or a pharmaceutically acceptable salt thereof.

The present invention further provides a method of treating or preventing a herpesviral infection comprising administering orally, parenterally, topically, rectally, nasally, sublingually or transdermally an effective amount of a compound of claim 1.

The present invention further provides a compound of formula (I) or a pharmaceutically acceptable salt thereof for use in medical treatment.

The present invention further provides the use of a compound of formula (I) or a pharmaceutically acceptable salt thereof to prepare a medicament for treating or preventing a herpesviral infection in a mammal.

The present invention further provides a method for inhibiting a viral DNA polymerase, comprising contacting (in vitro or in vivo) the polymerase with an effective inhibitory amount of a compound of formula I, or a pharmaceutically acceptable salt thereof.

The invention also provides novel intermediates and processes disclosed herein that are useful for preparing compounds of formula I.

DETAILED DESCRIPTION OF THE INVENTION

The following definitions are used, unless otherwise described. Halo denotes fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $(C_{1-3})$alkyl refers to alkyl of one to three carbon atoms, inclusive, or methyl, ethyl, propyl and isopropyl, straight and branched forms thereof.

Aryl is a phenyl radical, optionally fused with a saturated or unsaturated carbocyclic or heterocyclic ring. At each occurrence, aryl may be substituted with one or more halo, CN, $CO_2R_{10}$, $SO_iR_{10}$, $OR_{10}$, $NR_{10}R_{10}$, $CF_3$, $C_{3-8}$cycloalkyl, or $C_{1-4}$alkyl wherein $C_{1-4}$alkyl is optionally substituted with $OR_{10}$.

Het is a four-(4), five-(5), six-(6), or seven-(7) membered saturated or unsaturated heterocyclic ring having 1, 2, or 3 heteroatoms selected from the group consisting of O, S, and NW, wherein W is hydrogen, $C_{1-4}$alkyl, $C(=O)OC_{1-4}$alkyl or absent, wherein het is optionally fused with a benzene ring, a carbcyclic or a heterocyclic ring. At each occurrence, het may be substituted with one or more halo, CN, $CO_2R_{10}$, $SO_iR_{10}$, $OR_{10}$, $NR_{10}R_{10}$, $C_{1-4}$alkyl, $CF_3$, $C_{3-8}$cycloalkyl, oxo or oxine;

The term "het" also includes piperidinyl, morpholinyl, thiomorpholinyl, piperazinyl, N—$C_{1-4}$alky substituted piperazinyl such as 4-methyl piperazinyl, pyrrolidinyl, pyridyl, imidazolyl, N—$C_{1-4}$alky substituted imidazol such as 1-methyl-1H-imidazol, azetidyl, tetrahydrofuranyl, dioxolanyl, imidazolidinyl, oxathiolanyl, oxazolidinyl, pyran, thiopyran, tetrahydropyran or tetrahydrothiopyran, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 4,5,-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4- thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 7-oxo-2-isoindolyl,1-purinyl, 3-isothiazolyl, 4-isothiazolyl and 5-isothiazolyl, 1,3,4,-oxadiazole, 4-oxo-2-thiazolinyl, or 5-methyl-1,3,4-thiadiazole-2-yl, thiazoledione, 1,2,3,4-thiatriazole, 1,2,4-dithiazolone. Each of these moieties may be substituted as appropriate.

"Amino acid," includes a residue of natural amino acid (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, -methyl-alanine, para-benzoylphenylalanine, phenylglycine, propargylglycine, sarcosine, and tert-butylglycine). An amino acid can conveniently be linked to the remainder of a compound of formula I through the carboxy terminus, the amino terminus, or through any other convenient point of attachment, such as, for example, through the sulfur of cysteine. In particular, an amino acid can conveniently be linked to the remainder of a compound of formula I through the carboxy terminus.

Mammal denotes human and animals, specifically including food animals and companion animals.

It will be appreciated by those skilled in the art that compounds of the invention have one or more achiral center and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art.

The compounds of the present invention are generally named according to the IUPAC or CAS nomenclature system. Other nomenclature systems may also be used. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents.

Specifically, the term "$C_{1-8}$alkyl," or "$C_{1-4}$alkyl" refers to an alkyl group having one to eight or one to four carbon atoms such as, for example, methyl, ethyl, propyl, butyl, pentyl, hexyl, heptyl, octyl, and their isomeric forms thereof.

Specifically, a 5- or 6-membered heterocyclic ring includes piperidinyl, morpholinyl, thiomorpholinyl, piperazinyl, N—$C_{1-4}$alky substituted piperazinyl such as 4-methyl piperazinyl, or pyrrolidinyl.

Specifically, a 5- or 6-membered heterocyclic ring includes pyridyl, imidazolyl, N—$C_{1-4}$alky substituted imidazol such as 1-methyl-1H-imidazol.

Specifically, $R_5$ is $C_{1-8}$alkyl substituted with $OR_7$ or het.

Specifically, $R_5$ is $C_{1-4}$alkyl substituted with OH.

Specifically, $R_5$ is $C_{1-4}$alkyl substituted with het.

Specifically, het is morpholinyl or thiomorpholinyl.

Specifically, $R_5$ is 4-morpholinylmethyl.

Specifically, $R_5$ is $C_{1-8}$alkyl, optionally substituted with $OR_9$.

Specifically, $R_5$ is $C_{1-8}$alkyl which is partially unsaturated and optionally substituted with $OR_9$.

Specifically, $R_5$ is propynyl substituted with OH.

Specifically, $R_5$ is 3-hydroxypropyl.

Specifically, $R_3$ and $R_4$ are independently hydrogen.

Specifically, $R_1$ and $R_2$ are independently hydrogen, fluoro, or $C_{1-8}$ alkyl substituted with $R_6$ or $OR_7$.

Specifically, $R_1$ and $R_2$ are independently hydrogen, fluoro, $C_{1-8}$ alkyl substituted with $R_6$ or $OR_7$; aryl, het, or $R_1$ and $R_2$ together with the carbon to which they are attached form a six-(6) membered cycloalkyl or a het; wherein $R_6$ is het, $SO_tR_8$, $OR_8$ or $NR_8R_9$; wherein $R_7$ is $P(=O)(OR_{10})_2$, $CO(CH_2)_n CON(CH_3)(CH_2)_n SO_3^- M^+$, or $C(=O)C_{1-6}$alkyl, wherein $R_8$ and $R_9$ are independently hydrogen, aryl, het, or $C_{1-8}$alkyl which is further optionally substituted with one or more aryl, het, halo, $CO_2R_{10}$, $SO_tR_{10}$, or $OR_{10}$; wherein $R_{10}$ is H or $C_{1-4}$alkyl, optionally substituted with OH.

Specifically, $R_1$ and $R_2$ are independently H, $C_{1-4}$alkyl substituted with $OR_8$ wherein $R_8$ is H, or $C_{1-4}$alkylsubstituted with $OR_{10}$.

Specifically, $R_1$ is H; $R_2$ is aryl wherein aryl is optionally substituted with one or two halo, CN, $OR_{10}$, or $C_{1-4}$alkylsubstituted with $OR_{10}$.

Specifically, $R_1$ is H; $R_2$ is aryl wherein aryl is fused with a heterocyclic ring.

Specifically, $R_2$ is 1,3-benzodioxolyl or 1,4-benxodioxinyl.

Specifically, $R_1$ is H; $R_2$ is het.

Specifically, het is a five-(5) or six-(6) membered saturated or unsaturated heterocyclic ring having 1, 2, or 3 heteroatoms selected from the group consisting of O, S, and NW, wherein W is hydrogen, $C_{1-4}$alkyl, $C(=O)OC_{1-4}$alkyl or absent, wherein het may be substituted with one or more halo, $C_{1-4}$alkyl, $CF_3$, oxo or oxine.

Specifically, het is pyridinyl.

Specifically, het is a five-(5) membered heterocyclic ring.

Specifically, $R_1$ and $R_2$ together with the carbon to which they are attached form a het, wherein het is a five-(5) or six-(6) membered heterocyclic ring having 1, 2, or 3 heteroatoms selected from the group consisting of O, S, and NW, wherein W is hydrogen, $C_{1-4}$alkyl, or $C(=O)OC_{1-4}$alkyl, wherein het may be substituted with one or more halo, $OR_{10}$, $C_{1-4}$alkyl, $CF_3$, oxo or oxine; more specifically, het is a (6) membered heterocyclic ring; even more specifically, het is pyran, piperdine, or thiopyran.

Specifically, $R_1$ and $R_2$ together with the carbon to which they are attached form a six-(6) membered cycloalkyl; more specifically, cycloalkyl is optionally substituted with oxo, or $OR_{10}$.

Specifically, $R_6$ is het, $SO_tR_8$, $OR_8$ or $NR_8R_9$.

Specifically, $R_7$ is $P=O)(OH)_2$, $(P=O)(C_{1-4}alkoxy)_2$, $C(=O)C_{1-6}$alkyl, or $CO(CH_2)_n CON(CH_3)(CH_2)_n SO_3^- M^+$.

Specifically, $R_8$ and $R_9$ are independently hydrogen, aryl, het, or $C_{1-8}$alkyl which is further optionally substituted with one or more aryl, het, halo, $CO_2R_{10}$, $SO_tR_{10}$, or $OR_{10}$;

Specifically, $R_{10}$ is H or $C_{1-4}$alkyl, optionally substituted with OH.

Specifically, $R_2$ is hydrogen, and $R_1$ is $C_{1-8}$ alkyl substituted with $R_6$ or $OR_7$; where $R_6$ is het, $SR_8$, $OR_8$ or $NR_8R_9$; wherein $R_7$ is $(P=O)(OCH_3)_2$, $CO(CH_2)_nCON(CH_3)(CH_2)_nSO_3^-M^+$, or $C(=O)CH_3$, $R_8$ and $R_9$ are independently hydrogen, het, or $C_{1-8}$alkyl, which is optionally substituted with one or two het, $CO_2R_{10}$, $SOR_{10}$, or $OR_{10}$; $R_{10}$ is H or $C_{1-4}$alkyl, optionally substituted with OH.

Specifically, $R_{11}$ is H, halo, or $C_{1-4}$alkyl optionally substituted with one to three halo.

Specifically, $R_{12}$ is H, $SO_tR_8$, $OR_8$, $C(=O)OR_8$, $C(=O)R_8$, $NR_8R_9$; or $C_{1-8}$alkyl, which may be partially unsaturated and optionally substituted with one to three $N_3$, halo, CN, or $R_6$.

Specifically, $R_{11}$ and $R_{12}$ are hydrogen.

Specifically, het is piperidinyl, morpholinyl, thiomorpholinyl, piperazinyl, N—$C_{1-4}$alky substituted piperazinyl, pyrrolidinyl, pyridyl, imidazolyl, or N—$C_{1-4}$alky substituted imidazol.

Specifically, $R_1$, $R_2$, $R_3$ and $R_4$ are independently hydrogen, hydroxymethyl, morpholinylmethyl, (pyridinylmethyl)aminomethyl, (dimethylamino)methyl, (hydroxyethyl)sulfanylmethyl, (1-methyl-1H-imidazol-2-yl)sulfanylmethyl, —$CH_2OCO(CH_2)_6CON(CH_3)(CH_2)_2SO_3^-M^+$, —$CH_2OC(=O)CH_3$, (4-methyl-1-piperazinyl) methyl 1-pyrrolidinylmethyl, (2,3-dihydroxypropyl) aminomethyl, (2-hydroxyethyl)aminomethyl, 1-piperidinylmethyl, bis(2-hydroxyethyl)aminomethyl, 1H-imidazol-1-ylmethyl, (methylsulfanyl)methyl, (tert-butylsulfanyl)methyl, methylsulfanyl acetate, (2,3-dihydroxypropyl)sulfanylmethyl, phenyl, or fluoro. or $CH_2OP(=O)(OCH_3)_2$.

Specifically, $R_1$, $R_2$, $R_3$ and $R_4$ are independently hydrogen, hydroxymethyl, morpholinylmethyl, (2-pyridinylmethyl)aminomethyl, (3-pyridinylmethyl) aminomethyl, (dimethylamino)methyl, (2-hydroxyethyl) sulfanylmethyl, (1-methyl-1H-imidazol-2-yl) sulfanylmethyl, —$CH_2OCO(CH_2)_6CON(CH_3)(CH_2)_2SO_3^-M^+$, —$CH_2OC(=O)CH_3$, or $CH_2OP(=O)(OCH_3)_2$.

Specifically, $R_1$ and $R_2$ are independently hydrogen, $R_3$ and $R_4$ are independently fluoro, phenyl, or $C_{1-8}$ alkyl substituted with het or OH.

Specifically, $R_1$ is hydrogen and $R_2$ is het.

Specifically, $R_1$ is hydrogen and $R_2$ is 2-pyridinyl, 3-pyridinyl, or 4-pyridinyl.

Specifically, $R_3$ and $R_4$ are independently fluoro or hydroxymethyl.

Specifically, $R_3$ is hydrogen and $R_4$ is phenyl, morpholinylmethyl, or hydroxymethyl.

Specifically, $R_3$ is morpholinylmethyl.

Specifically, a compound of formula I is the following structure I-A;

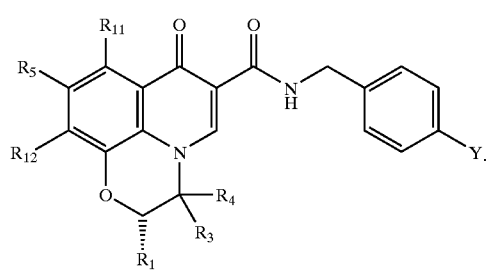

I-A

Specifically, a compound of formula I is the following structure I-B;

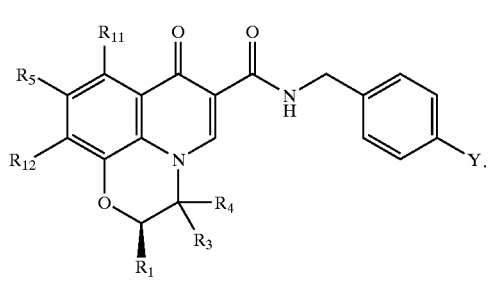

I-B

Specifically, a compound of formula I is the following structure I-C;

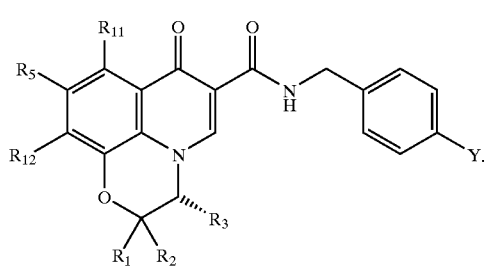

I-C

Specifically, a compound of formula I is the following structure I-D;

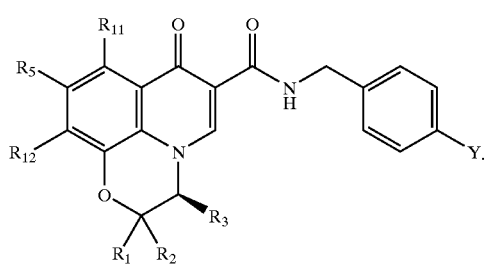

I-D

Specifically, a compound of formula I is the following structure I-E;

I-E
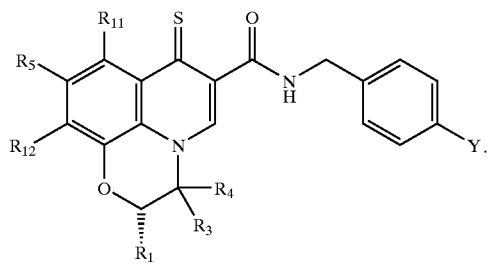

Specifically, a compound of formula I is the following structure I-F;

I-F
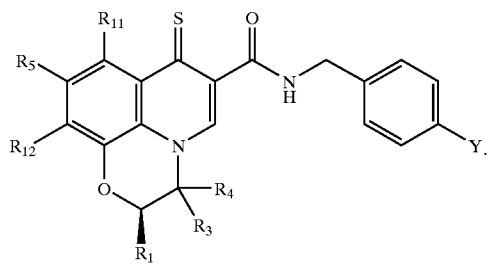

Specifically, a compound of formula I is the following structure I-G;

I-G
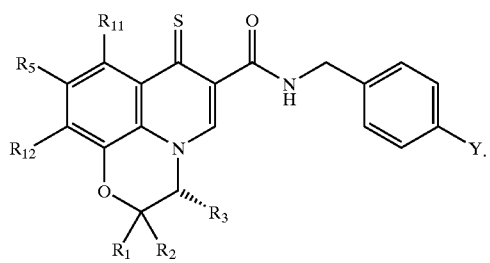

Specifically, a compound of formula I is the following structure I-H;

I-H
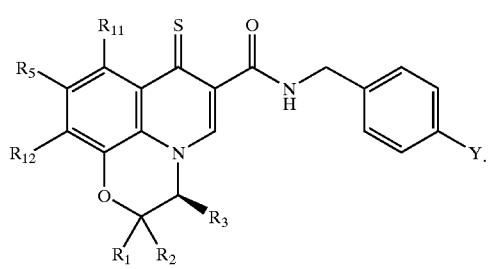

Specifically, a compound of formula I is the following structure I-I;

I-I
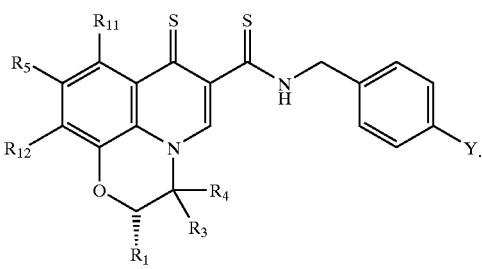

Specifically, a compound of formula I is the following structure I-J;

I-J
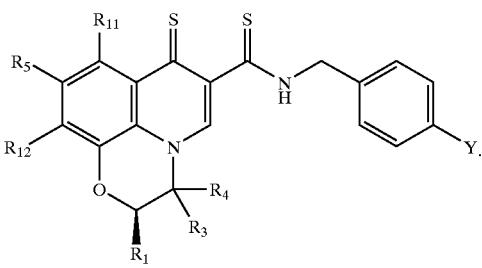

Specifically, a compound of formula I is the following structure I-K;

I-K
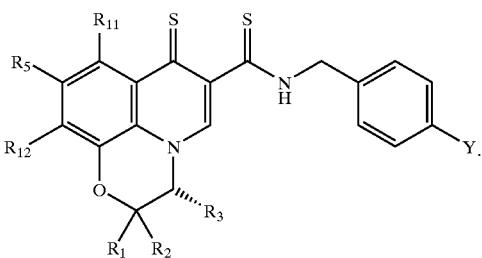

Specifically, a compound of formula I is the following structure I-L;

I-L
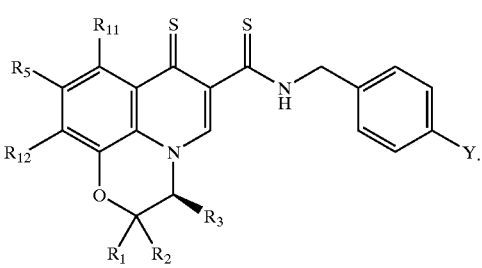

Specifically, a compound of formula I is the following structure I-M;

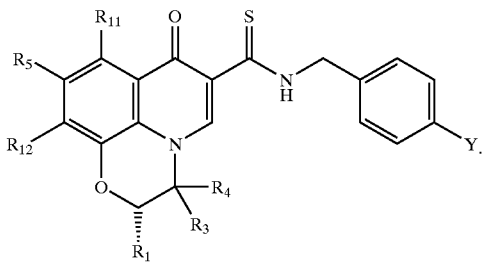

I-M

Specifically, a compound of formula I is the following structure I-N;

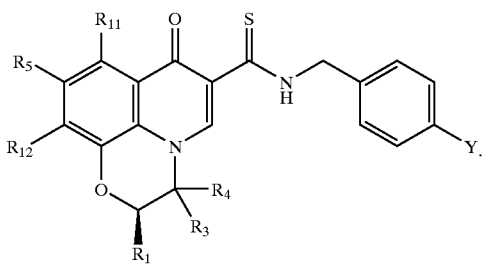

I-N

Specifically, a compound of formula I is the following structure I-O;

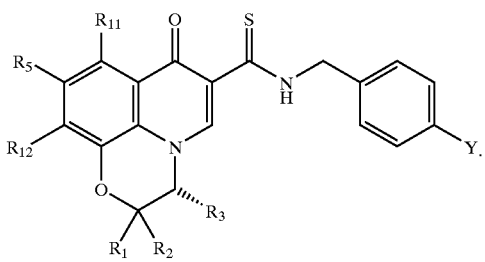

I-O

Specifically, a compound of formula I is the following structure I-P;

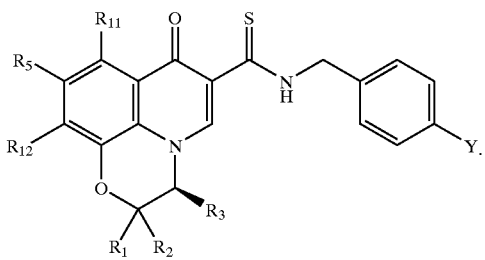

I-P

More specifically, Y is Cl in the formulas I-A to I-P. Examples of the compounds of the present invention are:

a) N-(4-Chlorobenzyl)-2-(hydroxymethyl)-9-(morpholin-4-ylmethyl)-7-oxo-2,3-dihydro-7H-[1,4]oxazino[2,3,4-ij]quinoline-6-carboxamide,
b) N-(4-Chlorobenzyl)-2-(R or S)-(hydroxymethyl)-9-(morpholin-4-ylmethyl)-7-oxo-2,3-dihydro-7H-[1,4]oxazino[2,3,4-ij]quinoline-6-carboxamide,
c) N-(4-Chlorobenzyl)-9-(morpholin-4-ylmethyl)-7-oxo-2-pyridin-3-yl-2,3-dihydro-7H-[1,4]oxazino[2,3,4-ij]quinoline-6-carboxamide,
d) N-(4-Chlorobenzyl)-9-(morpholin-4-ylmethyl)-7-oxo-2-pyridin-4-yl-2,3-dihydro-7H-[1,4]oxazino[2,3,4-ij]quinoline-6-carboxamide,
e) N-(4-Chlorobenzyl)-9-(morpholin-4-ylmethyl)-7-oxo-2-pyridin-2-yl-2,3-dihydro-7H-[1,4]oxazino[2,3,4-ij]quinoline-6-carboxamide,
f) N-(4-Chlorobenzyl)-9-(morpholin-4-ylmethyl)-7-oxo-2-(R or S)-pyridin-3-yl-2,3-dihydro-7H-[1,4]oxazino[2,3,4-ij]quinoline-6-carboxamide,
g) N-(4-Chlorobenzyl)-2,9-bis(morpholin-4-ylmethyl)-7-oxo-2,3-dihydro-7H-[1,4]oxazino[2,3,4-ij]quinoline-6-carboxamide,
h) 2-[(tert-Butylsulfanyl)methyl]-N-(4-chlorobenzyl)-9-(morpholin-4-ylmethyl)-7-oxo-2,3-dihydro-7H-[1,4]oxazino[2,3,4-ij]quinoline-6-carboxamide,
i) N-(4-Chlorobenzyl)-2-{[(2-hydroxyethyl)sulfanyl]methyl}-9-(morpholin-4-ylmethyl)-7-oxo-2,3-dihydro-7H-[1,4]oxazino[2,3,4-ij]quinoline-6-carboxamide,
j) N-(4-Chlorobenzyl)-2-{[(1-methyl-1H-imidazol-2-yl)sulfanyl]methyl}-9-(morpholin-4-ylmethyl)-7-oxo-2,3-dihydro-7H-[1,4]oxazino[2,3,4-ij]quinoline-6-carboxamide,
k) N-(4-Chlorobenzyl)-9-(morpholin-4-ylmethyl)-7-oxo-2-{[(3-pyridinylmethyl)amino]methyl}-2,3-dihydro-7H-[1,4]oxazino[2,3,4-ij]quinoline-6-carboxamide,
l) [6-{[(4-Chlorobenzyl)amino]carbonyl}-9-(morpholin-4-ylmethyl)-7-oxo-2,3-dihydro-7H-[1,4]oxazino[2,3,4-ij]quinolin-2-yl]methyl acetate,
m) N-(4-Chlorobenzyl)-9-(morpholin-4-ylmethyl)-7-oxo-2-(R or S)-{[(3-pyridinylmethyl)amino]methyl}-2,3-dihydro-7H-[1,4]oxazino[2,3,4-ij]quinoline-6-carboxamide,
n) N-(4-Chlorobenzyl)-2-(3-hydroxyphenyl)-9-(morpholin-4-ylmethyl)-7-oxo-2,3-dihydro-7H-[1,4]oxazino[2,3,4-ij]quinoline-6-carboxamide,
o) N-(4-Chlorobenzyl)-9-(morpholin-4-ylmethyl)-7-oxo-2-(R or S)-pyridin-2-yl-2,3-dihydro-7H-[1,4]oxazino[2,3,4-ij]quinoline-6-carboxamide,
p) N-(4-Chlorobenzyl)-2-[3-(hydroxymethyl)phenyl]-9-(morpholin-4-ylmethyl)-7-oxo-2,3-dihydro-7H-[1,4]oxazino[2,3,4-ij]quinoline-6-carboxamide,
q) N-(4-Chlorobenzyl)-2-[2-(hydroxymethyl)phenyl]-9-(morpholin-4-ylmethyl)-7-oxo-2,3-dihydro-7H-[1,4]oxazino[2,3,4-ij]quinoline-6-carboxamide,
r) N-(4-Chlorobenzyl)-2-(1-methyl-1H-imidazol-2-yl)-9-(morpholin-4-ylmethyl)-7-oxo-2,3-dihydro-7H-[1,4]oxazino[2,3,4-ij]quinoline-6-carboxamide,
s) N-(4-Chlorobenzyl)-2-(2-furyl)-9-(morpholin-4-ylmethyl)-7-oxo-2,3-dihydro-7H-[1,4]oxazino[2,3,4-ij]quinoline-6-carboxamide,
t) N-(4-Chlorobenzyl)-2-(3-cyanophenyl)-9-(morpholin-4-ylmethyl)-7-oxo-2,3-dihydro-7H-[1,4]oxazino[2,3,4-ij]quinoline-6-carboxamide,
u) N-(4-Chlorobenzyl)-2-(3-furyl)-9-(morpholin-4-ylmethyl)-7-oxo-2,3-dihydro-7H-[1,4]oxazino[2,3,4-ij]quinoline-6-carboxamide,
v) N-(4-Chlorobenzyl)-9-(morpholin-4-ylmethyl)-7-oxo-2-thien-2-yl-2,3-dihydro-7H-[1,4]oxazino[2,3,4-ij]quinoline-6-carboxamide,
w) N-(4-Chlorobenzyl)-2-(3,5-difluorophenyl)-9-(morpholin-4-ylmethyl)-7-oxo-2,3-dihydro-7H-[1,4]oxazino[2,3,4-ij]quinoline-6-carboxamide,
x) 2-(1,3-Benzodioxol-5-yl)-N-(4-chlorobenzyl)-9-(morpholin-4-ylmethyl)-7-oxo-2,3-dihydro-7H-[1,4]oxazino[2,3,4-ij]quinoline-6-carboxamide, y) N-(4-Chlorobenzyl)-2-(2,3-dihydro-1,4-benzodioxin-6-yl)-9-(morpholin-4-ylmethyl)-7-oxo-2,3-dihydro-7H-[1,4]oxazino[2,3,4-ij]quinoline-6-carboxamide,
z) 2-(1,3-Benzodioxol-4-yl)-N-(4-chlorobenzyl)-9-(morpholin-4-ylmethyl)-7-oxo-2,3-dihydro-7H-[1,4]oxazino[2,3,4-ij]quinoline-6-carboxamide,
aa) 2-[3,5-bis(Methoxymethoxy)phenyl]-N-(4-chlorobenzyl)-9-(morpholin-4-ylmethyl)-7-oxo-2,3-dihydro-7H-[1,4]oxazino[2,3,4-ij]quinoline-6-carboxamide,
bb) N-[(4-Chlorobenzyl)-9-(morpholin-4-ylmethyl)-7-oxo-2-thien-3-yl-2,3-dihydro-7H-[1,4]oxazino[2,3,4-ij]quinoline-6-carboxamide,
cc) N-(4-Chlorobenzyl)-2,2-bis[(methoxymethoxy)methyl]-9-(morpholin-4-ylmethyl)-7-oxo-2,3-dihydro-7H-[1,4]oxazino[2,3,4-ij]quinoline-6-carboxamide,
dd) N-[(4-Chlorophenyl)methyl]-9'-(4-morpholinylmethyl)-4,7'-dioxospiro[cyclohexane-1,2'(3'H)-[7H]pyrido[1,2,3-dr][1,4]benzoxazine]-6'-carboxamide,
ee) N-[(4-Chlorophenyl)methyl]-4-hydroxy-9'-(4-morpholinylmethyl)-7'-oxospiro[cyclohexane-1,2'(3'H)-[7H]pyrido[1,2,3-de][1,4]benzoxazine]-6'-carboxamide,
ff) N-(4-Chlorobenzyl)-3,9-bis(morpholin-4-ylmethyl)-7-oxo-2,3-dihydro-7H-[1,4]oxazino[2,3,4-ij]quinoline-6-carboxamide,
gg) N-(4-Chlorobenzyl)-9-(morpholin-4-ylmethyl)-7-oxo-2-phenyl-2,3-dihydro-7H-[1,4]oxazino[2,3,4-ij]quinoline-6-carboxamide,
hh) N-(4-Chlorobenzyl)-2,2-difluoro-9-(morpholin-4-ylmethyl)-7-oxo-2,3-dihydro-7H-[1,4]oxazino[2,3,4-ij]quinoline-6-carboxamide,
ii) N-(4-Chlorobenzyl)-2-[(methylsulfanyl)methyl]-9-(morpholin-4-ylmethyl)-7-oxo-2,3-dihydro-7H-[1,4]oxazino[2,3,4-ij]quinoline-6-carboxamide,
jj) N-(4-Chlorobenzyl)-2-[(dimethylamino)methyl]-9-(morpholin-4-ylmethyl)-7-oxo-2,3-dihydro-7H-[1,4]oxazino[2,3,4-ij]quinoline-6-carboxamide,
kk) N-(4-Chlorobenzyl)-2-[(4-methyl-1-piperazinyl)methyl]-9-(morpholin-4-ylmethyl)-7-oxo-2,3-dihydro-7H-[1,4]oxazino[2,3,4-ij]quinoline-6-carboxamide,
ll) Methyl ({[6-{[(4-chlorobenzyl)amino]carbonyl}-9-(morpholin-4-ylmethyl)-7-oxo-2,3-dihydro-7H-[1,4]oxazino[2,3,4-ij]quinolin-2-yl]methyl}thio)acetate,
mm) N-(4-Chlorobenzyl)-9-(morpholin-4-ylmethyl)-7-oxo-2-(1-pyrrolidinylmethyl)-2,3-dihydro-7H-[1,4]oxazino[2,3,4-ij]quinoline-6-carboxamide,
nn) N-(4-Chlorobenzyl)-2-{[(2,3-dihydroxypropyl)sulfanyl]methyl}-9-(morpholin-4-ylmethyl)-7-oxo-2,3-dihydro-7H-[1,4]oxazino[2,3,4-ij]quinoline-6-carboxamide,
oo) N-(4-Chlorobenzyl)-2-{[(2,3-dihydroxypropyl)amino]methyl}-9-(morpholin-4-ylmethyl)-7-oxo-2,3-dihydro-7H-[1,4]oxazino[2,3,4-ij]quinoline-6-carboxamide,
pp) N-(4-Chlorobenzyl)-2-{[(2-hydroxyethyl)amino]methyl}-9-(morpholin-4-ylmethyl)-7-oxo-2,3-dihydro-7H-[1,4]oxazino[2,3,4-ij]quinoline-6-carboxamide,
qq) N-(4-Chlorobenzyl)-9-(morpholin-4-ylmethyl)-7-oxo-2-(1-piperidinylmethyl)-2,3-dihydro-7H-[1,4]oxazino[2,3,4-ij]quinoline-6-carboxamide,
rr) 2-{[bis(2-Hydroxyethyl)amino]methyl}-N-(4-chlorobenzyl)-9-(morpholin-4-ylmethyl)-7-oxo-2,3-dihydro-7H-[1,4]oxazino[2,3,4-ij]quinoline-6-carboxamide,
ss) N-(4-Chlorobenzyl)-9-(morpholin-4-ylmethyl)-7-oxo-2-{[(2-pyridinylmethyl)amino]methyl}-2,3-dihydro-7H-[1,4]oxazino[2,3,4-ij]quinoline-6-carboxamide,
tt) 2-[(8-{[6-{[(4-Chlorobenzyl)amino]carbonyl}-9-(morpholin-4-ylmethyl)-7-oxo-2,3-dihydro-7H-[1,4]oxazino[2,3,4-ij]quinolin-2-yl]methoxy}-8-oxooctanoyl)(methyl)amino]ethanesulfonic acid sodium salt,
uu) [6-{[(4-Chlorobenzyl)amino]carbonyl}-9-(morpholin-4-ylmethyl)-7-oxo-2,3-dihydro-7H-[1,4]oxazino[2,3,4-ij]quinolin-2-yl]methyl dimethyl phosphate,
vv) N-(4-Chlorobenzyl)-9-(morpholin-4-ylmethyl)-7-oxo-2-{[(4-pyridinylmethyl)amino]methyl}-2,3-dihydro-7H-[1,4]oxazino[2,3,4-ij]quinoline-6-carboxamide,
ww) N-(4-Chlorobenzyl)-2-(1H-imidazol-1-ylmethyl)-9-(morpholin-4-ylmethyl)-7-oxo-2,3-dihydro-7H-[1,4]oxazino[2,3,4-ij]quinoline-6-carboxamide,
xx) N-(4-Chlorobenzyl)-2-{[(4-chlorobenzyl)amino]methyl}-9-(morpholin-4-ylmethyl)-7-oxo-2,3-dihydro-7H-[1,4]oxazino[2,3,4-ij]quinoline-6-carboxamide,
yy) N-(4-Chlorobenzyl)-3-(hydroxymethyl)-9-(morpholin-4-ylmethyl)-7-oxo-2,3-dihydro-7H-[1,4]oxazino[2,3,4-ij]quinoline-6-carboxamide,
zz) N-(4-Chlorobenzyl)-2-(4-hydroxyphenyl)-9-(morpholin-4-ylmethyl)-7-oxo-2,3-dihydro-7H-[1,4]oxazino[2,3,4-ij]quinoline-6-carboxamide,
aaa) N-(4-Chlorobenzyl)-2-{3-[(methoxymethoxy)methyl]phenyl}-9-(morpholin-4-ylmethyl)-7-oxo-2,3-dihydro-7H-[1,4]oxazino[2,3,4-ij]quinoline-6-carboxamide,
bbb) N-(4-Chlorobenzyl)-2-{2-[(methoxymethoxy)methyl]phenyl}-9-(morpholin-4-ylmethyl)-7-oxo-2,3-dihydro-7H-[1,4]oxazino[2,3,4-ij]quinoline-6-carboxamide,
ccc) N-(4-Chlorobenzyl)-2-(2-hydroxyphenyl)-9-(morpholin-4-ylmethyl)-7-oxo-2,3-dihydro-7H-[1,4]oxazino[2,3,4-ij]quinoline-6-carboxamide,
ddd) N-[(4-Chlorophenyl)methyl]-2,3,5,6-tetrahydro-9'-(4-morpholinylmethyl)-7'-oxospiro[4H-pyran-4,2'(3'H)-[7H]pyrido[1,2,3-de][1,4]benzoxazine]-6'-carboxamide,
eee) 1,1-Dimethylethyl6-[[[(4-chlorophenyl)methyl]amino]carbonyl]-9'-(4-morpholinylmethyl)-7'-oxospiro[piperidine-4,2'(3'H)-[7H]pyrido[1,2,3-de][1,4]benzoxazine]-1-carboxylate,
fff) N-[(4-Chlorophenyl)methyl]-9'-(4-morpholinylmethyl)-7'-oxospiro[piperidine-4,2'(3'H)-[7H]pyrido[1,2,3-de][1,4]benzoxazine]-6'-carboxamide,
ggg) N-(4-Chlorobenzyl)-2,2-bis(hydroxymethyl)-9-(morpholin-4-ylmethyl)-7-oxo-2,3-dihydro-7H-[1,4]oxazino[2,3,4-ij]quinoline-6-carboxamide,
hhh) N-[(4-Chlorophenyl)methyl]-2',3',5',6'-tetrahydro-9-(4-morpholinylmethyl)-7-oxospiro[7H-pyrido[1,2,3-de]-1,4-benzoxazine-2(3H),4'-[4H]thiopyran]-6-carboxamide,
iii) N-(4-Chlorobenzyl)-9-(morpholin-4-ylmethyl)-7-oxo-3-phenyl-2,3-dihydro-7H-[1,4]oxazino[2,3,4-ij]quinoline-6-carboxamide,
jjj) N-(4-Chlorobenzyl)-3,3-bis(hydroxymethyl)-9-(3-hydroxy-1-propynyl)-7-oxo-2,3-dihydro-7H-[1,4]oxazino[2,3,4-ij]quinoline-6-carboxamide,
kkk) N-(4-Chlorobenzyl)-3,3-bis(hydroxymethyl)-9-(3-hydroxypropyl)-7-oxo-2,3-dihydro-7H-[1,4]oxazino[2,3,4-ij]quinoline-6-carboxamide,
lll) N-(4-Chlorobenzyl)-2-[2-(methoxymethoxy)phenyl]-9-(morpholin-4-ylmethyl)-7-oxo-2,3-dihydro-7H-[1,4]oxazino[2,3,4-ij]quinoline-6-carboxamide,
mmm) N-(4-Chlorobenzyl)-2-{4-[(methoxymethoxy)methyl]phenyl}-9-(morpholin-4-ylmethyl)-7-oxo-2,3-dihydro-7H-[1,4]oxazino[2,3,4-ij]quinoline-6-carboxamide,
nnn) 2-[2,3-bis(Methoxymethoxy)phenyl]-N-(4-chlorobenzyl)-9-(morpholin-4-ylmethyl)-7-oxo-2,3-dihydro-7H-[1,4]oxazino[2,3,4-ij]quinoline-6-carboxamide,
ooo) N-[(4-Chlorophenyl)methyl]-1-methyl-9'-(4-morpholinylmethyl)-7'-oxospiro[-piperidine4,2'(3'H)-[7H]pyrido[1,2,3-de][1,4]benzoxazine]-6'-carboxamide, or ppp) N-[(4-Chlorophenyl)methyl]-9"-(4-morpholinylmethyl)dispiro[1,3-dioxolane-2,1'-cyclohexane-4',2"(3"H)-[7H]pyrido[1,2,3-de][1,4]benzoxazine]-6"-carboxamide.

Additional examples of the compounds of the present invention are:

a) N-(4-Chlorobenzyl)-2-(hydroxymethyl)-9-(morpholin-4-ylmethyl)-7-thioxo-2,3-dihydro-7H-[1,4]oxazino[2,3,4-ij]quinoline-6-carboxamide, b) N-(4-Chlorobenzyl)-2-(R or S)-(hydroxymethyl)-9-(morpholin-4-ylmethyl)-7-thioxo-2,3-dihydro-7H-[1,4]oxazino[2,3,4-ij]quinoline-6-carboxamide, c) N-(4-Chlorobenzyl)-9-(morpholin-4-ylmethyl)-7-thioxo-2-pyridin-3-yl-2,3-dihydro-7H-[1,4]oxazino[2,3,4-ij]quinoline-6-carboxamide, d) N-(4-Chlorobenzyl)-9-(morpholin-4-ylmethyl)-7-thioxo-2-pyridin-4-yl-2,3-dihydro-7H-[1,4]oxazino[2,3,4-ij]quinoline-6-carboxamide, e) N-(4-Chlorobenzyl)-9-(morpholin-4-ylmethyl)-7-thioxo-2-pyridin-2-yl-2,3-dihydro-7H-[1,4]oxazino[2,3,4-ij]quinoline-6-carboxamide, f) N-(4-Chlorobenzyl)-9-(morpholin-4-ylmethyl)-7-thioxo-2-(R or S)-pyridin-3-yl-2,3-dihydro-7H-[1,4]oxazino[2,3,4-ij]quinoline-6-carboxamide, g) N-(4-Chlorobenzyl)-2,9-bis(morpholin-4-ylmethyl)-7-thioxo-2,3-dihydro-7H-[1,4]oxazino[2,3,4-ij]quinoline-6-carboxamide, h) 2-[(tert-Butylsulfanyl)methyl]-N-(4-chlorobenzyl)-9-(morpholin-4-ylmethyl)-7-thioxo-2,3-dihydro-7H-[1,4]oxazino[2,3,4-ij]quinoline-6-carboxamide, i) N-(4-Chlorobenzyl)-2-{[(2-hydroxyethyl)sulfanyl]methyl}-9-(morpholin-4-ylmethyl)-7-thioxo-2,3-dihydro-7H-[1,4]oxazino[2,3,4-ij]quinoline-6-carboxamide, j) N-(4-Chlorobenzyl)-2-{[(1-methyl-1H-imidazol-2-yl)sulfanyl]methyl}-9-(morpholin-4-ylmethyl)-7-thioxo-2,3-dihydro-7H-[1,4]oxazino[2,3,4-ij]quinoline-6-carboxamide, k) N-(4-Chlorobenzyl)-9-(morpholin-4-ylmethyl)-7-thioxo-2-{[(3-pyridinylmethyl)amino]methyl}-2,3-dihydro-7H-[1,4]oxazino[2,3,4-ij]quinoline-6-carboxamide, l) [6-{[(4-Chlorobenzyl)amino]carbonyl}-9-(morpholin-4-ylmethyl)-7-thioxo-2,3-dihydro-7H-[1,4]oxazino[2,3,4-ij]quinolin-2-yl]methyl acetate, m) N-(4-Chlorobenzyl)-9-(morpholin-4-ylmethyl)-7-thioxo-2-(R or S)-{[(3-pyridinylmethyl)amino]methyl}-2,3-dihydro-7H-[1,4]oxazino[2,3,4-ij]quinoline-6-carboxamide, n) N-(4-Chlorobenzyl)-2-(3-hydroxyphenyl)-9-(morpholin-4-ylmethyl)-7-thioxo-2,3-dihydro-7H-[1,4]oxazino[2,3,4-ij]quinoline-6-carboxamide, o) N-(4-Chlorobenzyl)-9-(morpholin-4-ylmethyl)-7-thioxo-2-(R or S)-pyridin-2-yl-2,3-dihydro-7H-[1,4]oxazino[2,3,4-ij]quinoline-6-carboxamide, p) N-(4-Chlorobenzyl)-2-[3-(hydroxymethyl)phenyl]-9-(morpholin-4-ylmethyl)-7-thioxo-2,3-dihydro-7H-[1,4]oxazino[2,3,4-ij]quinoline-6-carboxamide, q) N-(4-Chlorobenzyl)-2-[2-(hydroxymethyl)phenyl]-9-(morpholin-4-ylmethyl)-7-thioxo-2,3-dihydro-7H-[1,4]oxazino[2,3,4-ij]quinoline-6-carboxamide, r) N-(4-Chlorobenzyl)-2-(1-methyl-1H-imidazol-2-yl)-9-(morpholin-4-ylmethyl)-7-thioxo-2,3-dihydro-7H-[1,4]oxazino[2,3,4-ij]quinoline-6-carboxamide, s) N-(4-Chlorobenzyl)-2-(2-furyl)-9-(morpholin-4-ylmethyl)-7-thioxo-2,3-dihydro-7H-[1,4]oxazino[2,3,4-ij]quinoline-6-carboxamide, t) N-(4-Chlorobenzyl)-2-(3-cyanophenyl)-9-(morpholin-4-ylmethyl)-7-thioxo-2,3-dihydro-7H-[1,4]oxazino[2,3,4-ij]quinoline-6-carboxamide, u) N-(4-Chlorobenzyl)-2-(3-furyl)-9-(morpholin-4-ylmethyl)-7-thioxo-2,3-dihydro-7H-[1,4]oxazino[2,3,4-ij]quinoline-6-carboxamide, v) N-(4-Chlorobenzyl)-9-(morpholin-4-ylmethyl)-7-thioxo-2-thien-2-yl-2,3-dihydro-7H-[1,4]oxazino[2,3,4-ij]quinoline-6-carboxamide, w) N-(4-Chlorobenzyl)-2-(3,5-difluorophenyl)-9-(morpholin-4-ylmethyl)-7-thioxo-2,3-dihydro-7H-[1,4]oxazino[2,3,4-ij]quinoline-6-carboxamide, x) 2-(1,3-Benzodioxol-5-yl)-N-(4-chlorobenzyl)-9-(morpholin-4-ylmethyl)-7-thioxo-2,3-dihydro-7H-[1,4]oxazino[2,3,4-ij]quinoline-6-carboxamide, y) N-(4-Chlorobenzyl)-2-(2,3-dihydro-1,4-benzodioxin-6-yl)-9-(morpholin-4-ylmethyl)-7-thioxo-2,3-dihydro-7H-[1,4]oxazino[2,3,4-ij]quinoline-6-carboxamide, z) 2-(1,3-Benzodioxol-4-yl)-N-(4-chlorobenzyl)-9-(morpholin-4-ylmethyl)-7-thioxo-2,3-dihydro-7H-[1,4]oxazino[2,3,4-ij]quinoline-6-carboxamide, aa) 2-[3,5-bis(Methoxymethoxy)phenyl]-N-(4-chlorobenzyl)-9-(morpholin-4-ylmethyl)-7-thioxo-2,3-dihydro-7H-[1,4]oxazino[2,3,4-ij]quinoline-6-carboxamide, bb) N-(4-Chlorobenzyl)-9-(morpholin-4-ylmethyl)-7-thioxo-2-thien-3-yl-2,3-dihydro-7H-[1,4]oxazino[2,3,4-ij]quinoline-6-carboxamide, cc) N-(4-Chlorobenzyl)-2,2-bis[(methoxymethoxy)methyl]-9-(morpholin-4-ylmethyl)-7-thioxo-2,3-dihydro-7H-[1,4]oxazino[2,3,4-ij]quinoline-6-carboxamide, dd) N-[(4-Chlorophenyl)methyl]-9'-(4-morpholinylmethyl)-4-oxo-7'-thioxospiro[cyclohexane-1,2'(3'H)-[7H]pyrido[1,2,3-de][1,4]benzoxazine]-6'-carboxamide, ee) N-[(4-Chlorophenyl)methyl]-4-hydroxy-9'-(4-morpholinylmethyl)-7'-thioxospiro[cyclohexane-1,2'(3'H)-[7H]pyrido[1,2,3-de][1,4]benzoxazine]-6'-carboxamide, ff) N-(4-Chlorobenzyl)-3,9-bis(morpholin-4-ylmethyl)-7-thioxo-2,3-dihydro-7H-[1,4]oxazino[2,3,4-ij]quinoline-6-carboxamide, gg) N-(4-Chlorobenzyl)-9-(morpholin-4-ylmethyl)-7-thioxo-2-phenyl-2,3-dihydro-7H-[1,4]oxazino[2,3,4-ij]quinoline-6-carboxamide, hh) N-(4-Chlorobenzyl)-2,2-difluoro-9-(morpholin-4-ylmethyl)-7-thioxo-2,3-dihydro-7H-[1,4]oxazino[2,3,4-ij]quinoline-6-carboxamide, ii) N-(4-Chlorobenzyl)-2-[(methylsulfanyl)methyl]-9-(morpholin-4-ylmethyl)-7-thioxo-2,3-dihydro-7H-[1,4]oxazino[2,3,4-ij]quinoline-6-carboxamide, jj) N-(4-Chlorobenzyl)-2-[(dimethylamino)methyl]-9-(morpholin-4-ylmethyl)-7-thioxo-2,3-dihydro-7H-[1,4]oxazino[2,3,4-ij]quinoline-6-carboxamide, kk) N-(4-Chlorobenzyl)-2-[(4-methyl-1-piperazinyl)methyl]-9-(morpholin-4-ylmethyl)-7-thioxo-2,3-dihydro-7H-[1,4]oxazino[2,3,4-ij]quinoline-6-carboxamide, ll) Methyl ({[6-{[(4-chlorobenzyl)amino]carbonyl}-9-(morpholin-4-ylmethyl)-7-thioxo-2,3-dihydro-7H-[1,4]oxazino[2,3,4-ij]quinolin-2-yl]methyl}thio)acetate, mm) N-(4-Chlorobenzyl)-9-(morpholin-4-ylmethyl)-7-thioxo-2-(1-pyrrolidinylmethyl)-2,3-dihydro-7H-[1,4]oxazino[2,3,4-ij]quinoline-6-carboxamide, nn) N-(4-Chlorobenzyl)-2-{[(2,3-dihydroxypropyl)sulfanyl]methyl}-9-(morpholin-4-ylmethyl)-7-thioxo-2,3-dihydro-7H-[1,4]oxazino[2,3,4-ij]quinoline-6-carboxamide, oo) N-(4-Chlorobenzyl)-2-{[(2,3-dihydroxypropyl)amino]methyl}-9-(morpholin-4-ylmethyl)-7-thioxo-2,3-dihydro-7H-[1,4]oxazino[2,3,4-ij]quinoline-6-carboxamide, pp) N-(4-Chlorobenzyl)-2-{[(2-hydroxyethyl)amino]methyl}-9-(morpholin-4-ylmethyl)-7-thioxo-2,3-dihydro-7H-[1,4]oxazino[2,3,4-ij]quinoline-6-carboxamide, qq) N-(4-Chlorobenzyl)-9-(morpholin-4-ylmethyl)-7-thioxo-2-(1-piperidinylmethyl)-2,3-dihydro-7H-[1,4]oxazino[2,3,4-ij]quinoline-6-carboxamide, rr) 2-{[bis(2-Hydroxyethyl)amino]methyl}-N-(4-chlorobenzyl)-9-(morpholin-4-ylmethyl)-7-thioxo-2,3-dihydro-7H-[1,4]oxazino[2,3,4-ij]quinoline-6-carboxamide, ss) N-(4-Chlorobenzyl)-9-(morpholin-4-ylmethyl)-7-thioxo-2-{[(2-pyridinylmethyl)amino]methyl}-2,3-dihydro-7H-[1,4]oxazino[2,3,4-ij]quinoline-6-carboxamide, tt) 2-[(8-{[6-{[(4-Chlorobenzyl)amino]carbonyl}-9-(morpholin-4-ylmethyl)-2,3-dihydro-7H-[1,4]oxazino[2,3,4-ij]quinolin-2-yl]methoxy}-8-oxooctanoyl)(methyl)amino]ethanesulfonic acid sodium salt, uu) [6-{[(4-Chlorobenzyl)amino]carbonyl}-9-(morpholin-4-ylmethyl)-7-thioxo-2,3-dihydro-7H-[1,4]oxazino[2,3,4-ij]quinolin-2-yl]methyl dimethyl phosphate, vv) N-(4-Chlorobenzyl)-9-(morpholin-4-ylmethyl)-7-thioxo-2-{[(4-pyridinylmethyl)amino]methyl}-2,3-dihydro-7H-[1,4]oxazino[2,3,4-ij]quinoline-6-carboxamide, ww) N-(4-Chlorobenzyl)-2-(1H-imidazol-1-ylmethyl)-9-(morpholin-4-ylmethyl)-7-thioxo-2,3-dihydro-7H-[1,4]oxazino[2,3,4-ij]quinoline-6-carboxamide, xx) N-(4-Chlorobenzyl)-2-{[(4-chlorobenzyl)amino]methyl}-9-(morpholin-4-ylmethyl)-7-thioxo-2,3-dihydro-7H-[1,4]oxazino[2,3,4-ij]quinoline-6-carboxamide, yy) N-(4-Chlorobenzyl)-3-(hydroxymethyl)-9-(morpholin-4-ylmethyl)-7-thioxo-2,3-dihydro-7H-[1,4]oxazino[2,3,4-ij]quinoline-6-carboxamide, zz) N-(4-Chlorobenzyl)-2-(4-hydroxyphenyl)-9-(morpholin-4-ylmethyl)-7-thioxo-2,3-dihydro-7H-[1,4]oxazino[2,3,4-ij]quinoline-6-carboxamide, aaa) N-(4-Chlorobenzyl)-2-{3-[(methoxymethoxy)methyl]phenyl}-9-(morpholin-4-ylmethyl)-7-thioxo-2,3-dihydro-7H-[1,4]oxazino[2,3,4-ij]quinoline-6-carboxamide, bbb) N-(4-Chlorobenzyl)-2-{2-[(methoxymethoxy)methyl]phenyl}-9-(morpholin-4-ylmethyl)-7-thioxo-2,3-dihydro-7H-[1,4]oxazino[2,3,4-ij]quinoline-6-carboxamide, ccc) N-(4-Chlorobenzyl)-2-(2-hydroxyphenyl)-9-(morpholin-4-ylmethyl)-7-thioxo-2,3-dihydro-7H-[1,4]oxazino[2,3,4-ij]quinoline-6-carboxamide, ddd) N-[(4-Chlorophenyl)methyl]-2,3,5,6-tetrahydro-9'-(4-morpholinylmethyl)-7'-thioxospiro[4H-pyran-4,2'(3'H)-[7H]pyrido[1,2,3-de][1,4]benzoxazine]-6'-carboxamide, eee) 1,1-Dimethylethyl 6-[[[(4-chlorophenyl)methyl]amino]carbonyl]-9'-(4-morpholinylmethyl)-7'-thioxospiro[piperidine-4,2'(3'H)-[7H]pyrido[1,2,3-de][1,4]benzoxazine]-1-carboxylate, fff) N-[(4-Chlorophenyl)methyl]-9'-(4-morpholinylmethyl)-7'-thioxospiro[piperidine-4,2'(3'H)-[7H]pyrido[1,2,3-de][1,4]benzoxazine]-6'-carboxamide, ggg) N-(4-Chlorobenzyl)-2,2-bis(hydroxymethyl)-9-(morpholin-4-ylmethyl)-7-thioxo-2,3-dihydro-7H-[1,4]oxazino[2,3,4-ij]quinoline-6-carboxamide, hhh) N-[(4-Chlorophenyl)methyl]-2',3',5',6'-tetrahydro-9-(4-morpholinylmethyl)-7-thioxospiro[7H-pyrido[1,2,3-de]-1,4-benzoxazine-2(3H),4'-[4H]thiopyran]-6-carboxamide, iii) N-(4-Chlorobenzyl)-9-(morpholin-4-ylmethyl)-7-thioxo-3-phenyl-2,3-dihydro-7H-[1,4]oxazino[2,3,4-ij]quinoline-6-carboxamide, jjj) N-(4-Chlorobenzyl)-3,3-bis(hydroxymethyl)-9-(3-hydroxy-1-propynyl)-7-thioxo-2,3-dihydro-7H-[1,4]oxazino[2,3,4-ij]quinoline-6-carboxamide, kkk) N-(4-Chlorobenzyl)-3,3-bis(hydroxymethyl)-9-(3-hydroxypropyl)-7-thioxo-2,3-dihydro-7H-[1,4]oxazino[2,3,4-ij]quinoline-6-carboxamide, lll) N-(4-Chlorobenzyl)-2-[2-(methoxymethoxy)phenyl]-9-(morpholin-4-ylmethyl)-7-thioxo-2,3-dihydro-7H-[1,4]oxazino[2,3,4-ij]quinoline-6-carboxamide, mmm) N-(4-Chlorobenzyl)-2-{4-[(methoxymethoxy)methyl]phenyl}-9-(morpholin-4-ylmethyl)-7-thioxo-2,3-dihydro-7H-[1,4]oxazino[2,3,4-ij]quinoline-6-carboxamide, nnn) 2-[2,3-bis(Methoxymethoxy)phenyl]-N-(4-chlorobenzyl)-9-(morpholin-4-ylmethyl)-7-thioxo-2,3-dihydro-7H-[1,4]oxazino[2,3,4-ij]quinoline-6-carboxamide, ooo) N-[(4-Chlorophenyl)methyl]-1-methyl-9'-(4-morpholinylmethyl)-7'-thioxospiro[piperidine-4,2'(3'H)-[7H]pyrido[1,2,3-de][1,4]benzoxazine]-6'-carboxamide, or a pharmaceutically acceptable salt.

Additional examples of the compounds of the present invention are:

a) N-(4-Chlorobenzyl)-2-(hydroxymethyl)-9-(morpholin-4-ylmethyl)-7-thioxo-2,3-dihydro-7H-[1,4]oxazino[2,3,4-ij]quinoline-6-carboxthioamide, b) N-(4-Chlorobenzyl)-2-(R or S)-(hydroxymethyl)-9-(morpholin-4-ylmethyl)-7-thioxo-2,3-dihydro-7H-[1,4]oxazino[2,3,4-ij]quinoline-6-carboxthioamide, c) N-(4-Chlorobenzyl)-9-(morpholin-4-ylmethyl)-7-thioxo-2-pyridin-3-yl-2,3-dihydro-7H-[1,4]oxazino[2,3,4-ij]quinoline-6-carboxthioamide, d) N-(4-Chlorobenzyl)-9-(morpholin-4-ylmethyl)-7-thioxo-2-pyridin-4-yl-2,3-dihydro-7H-[1,4]oxazino[2,3,4-ij]quinoline-6-carboxthioamide, e) N-(4-Chlorobenzyl)-9-(morpholin-4-ylmethyl)-7-thioxo-2-pyridin-2-yl-2,3-dihydro-7H-[1,4]oxazino[2,3,4-ij]quinoline-6-carboxthioamide, f) N-(4-Chlorobenzyl)-9-(morpholin-4-ylmethyl)-7-thioxo-2-(R or S)-pyridin-3-yl-2,3-dihydro-7H-[1,4]oxazino[2,3,4-ij]quinoline-6-carboxthioamide, g) N-(4-Chlorobenzyl)-9-(morpholin-4-ylmethyl)-7-thioxo-2-(R or S)-pyridin-2-yl-2,3-dihydro-7H-[1,4]oxazino[2,3,4-ij]quinoline-6-carboxthioamide, or a pharmaceutically acceptable salt.

Additional examples of the compounds of the present invention are:

a) N-(4-Chlorobenzyl)-2-(hydroxymethyl)-9-(morpholin-4-ylmethyl)-7-oxo-2,3-dihydro-7H-[1,4]oxazino[2,3,4-ij]quinoline-6-carboxthioamide, b) N-(4-Chlorobenzyl)-2-(R or S)-(hydroxymethyl)-9-(morpholin-4-ylmethyl)-7-oxo-2,3-dihydro-7H-[1,4]oxazino[2,3,4-ij]quinoline-6-carboxthioamide, c) N-(4-Chlorobenzyl)-9-(morpholin-4-ylmethyl)-7-oxo-2-pyridin-3-yl-2,3-dihydro-7H-[1,4]oxazino[2,3,4-ij]quinoline-6-carboxthioamide, d) N-(4-Chlorobenzyl)-9-(morpholin-4-ylmethyl)-7-oxo-2-pyridin-4-yl-2,3-dihydro-7H-[1,4]oxazino[2,3,4-ij]quinoline-6-carboxthioamide, e) N-(4-Chlorobenzyl)-9-(morpholin-4-ylmethyl)-7-oxo-2-pyridin-2-yl-2,3-dihydro-7H-[1,4]oxazino[2,3,4-ij]quinoline-6-carboxthioamide, f) N-(4-Chlorobenzyl)-9-(morpholin-4-ylmethyl)-7-oxo-2-(R or S)-pyridin-3-yl-2,3-dihydro-7H-[1,4]oxazino[2,3,4-ij]quinoline-6-carboxthioamide, g) N-(4-Chlorobenzyl)-9-(morpholin-4-ylmethyl)-7-oxo-2-(R or S)-pyridin-2-yl-2,3-dihydro-7H-[1,4]oxazino[2,3, 4-ij]quinoline-6-carboxthioamide, or a pharmaceutically acceptable salt.

The following Charts A–N describe the preparation of the compounds of formula I of the present invention. All of the starting materials are prepared by procedures described in these charts, by procedures well known to one of ordinary skill in organic chemistry or can be obtained commercially. All of the final compounds of the present invention are prepared by procedures described in these charts or by procedures analogous thereto, which would be well known to one of ordinary skill in organic chemistry. All of the variables used in the charts are as defined below or as in the formula I above.

As shown in CHART A, acid A-1, which is 3-hydroxy-4-nitrobenzoic acid, is reacted with thionyl chloride to give the corresponding acid chloride, which is treated with morpholine to provide amide A-2. Reduction of the nitro group using hydrogen gas and palladium catalyst gives aminophenol A-3, which is alkylated using sodium hydride and diethyl chloromalonate in dimethylformamide to give lactam A-4.

Simultaneous reduction of the three carbonyl groups using borane-methyl sulfide in tetrahydrofuran affords amine A-5. Treatment of the amine with diethyl ethoxymethylenemalonate provides A-6, which is derivatized to acetate A-7 using acetic anhydride and pyridine. Cyclization to A-8 is effected by phosphorus pentoxide in methanesulfonic acid. Treatment of A-8 with p-chlorobenzylamine at 150° C. cleaves the acetate and aminolyzes the ester, giving amide A-9. The alcohol is reacted with methanesulfonyl chloride and 2,4,6-collidine to give the intermediate mesylate A-10, which is subsequently reacted with a nucleophile of formula—$R_8R_9NH$, $R_8SH$ or $R_8OH$ (wherein $R_8$ and $R_9$ are defined previously), or anions thereof, to provide compounds of formula A-11 wherein $R_6$ is $SO_tR_8$, $OR_8$, $NR_8R_9$, aryl, or het.

CHART A

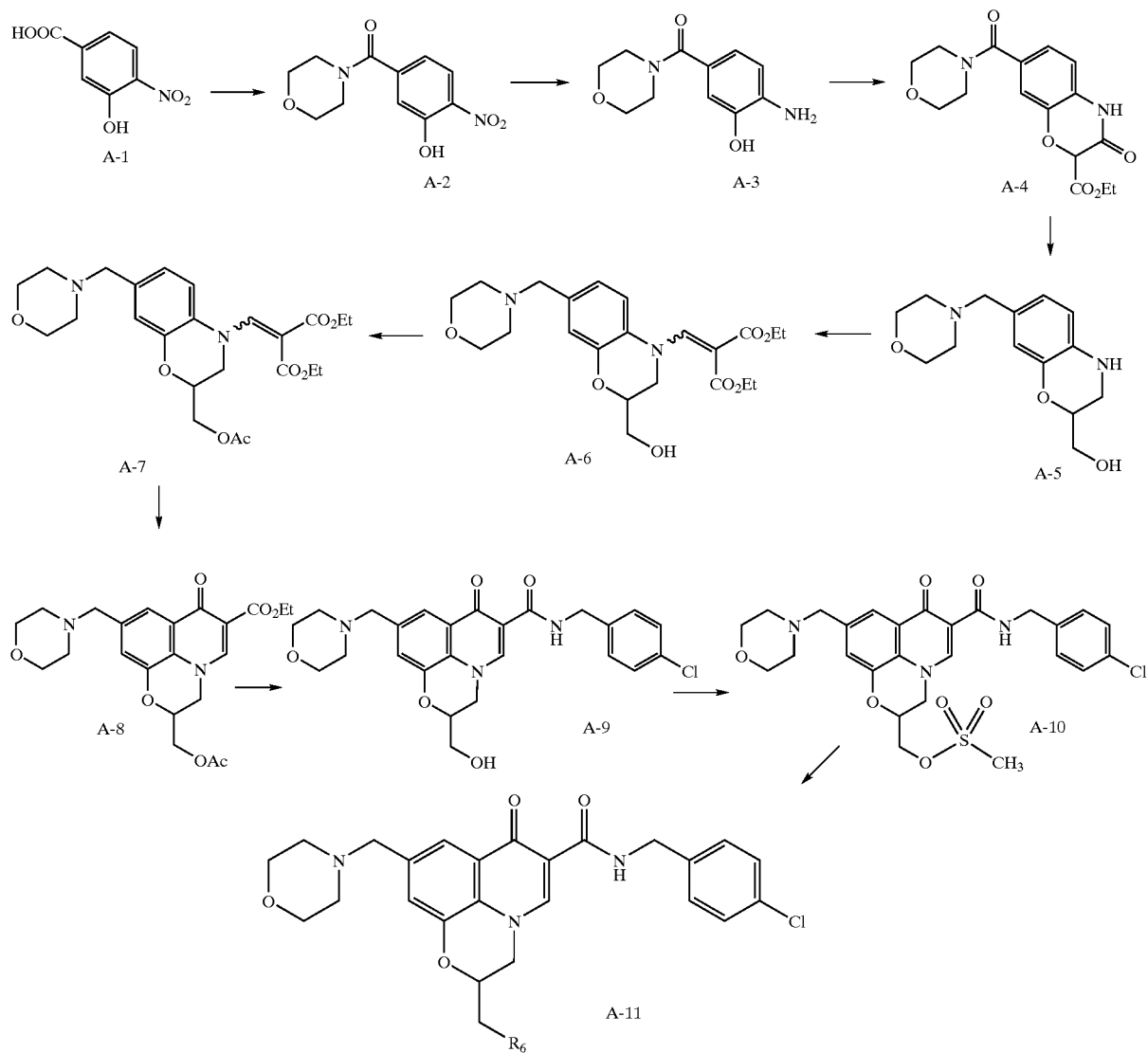

As shown in CHART B, compound A-8, which is a racemic mixture, is resolved into its component enantiomers B-1a and B-1b by preparative chiral HPLC. The individual isomers are carried forth separately through Formulae B-2 and B-3, according to the protocol described for Chart A.

CHART B

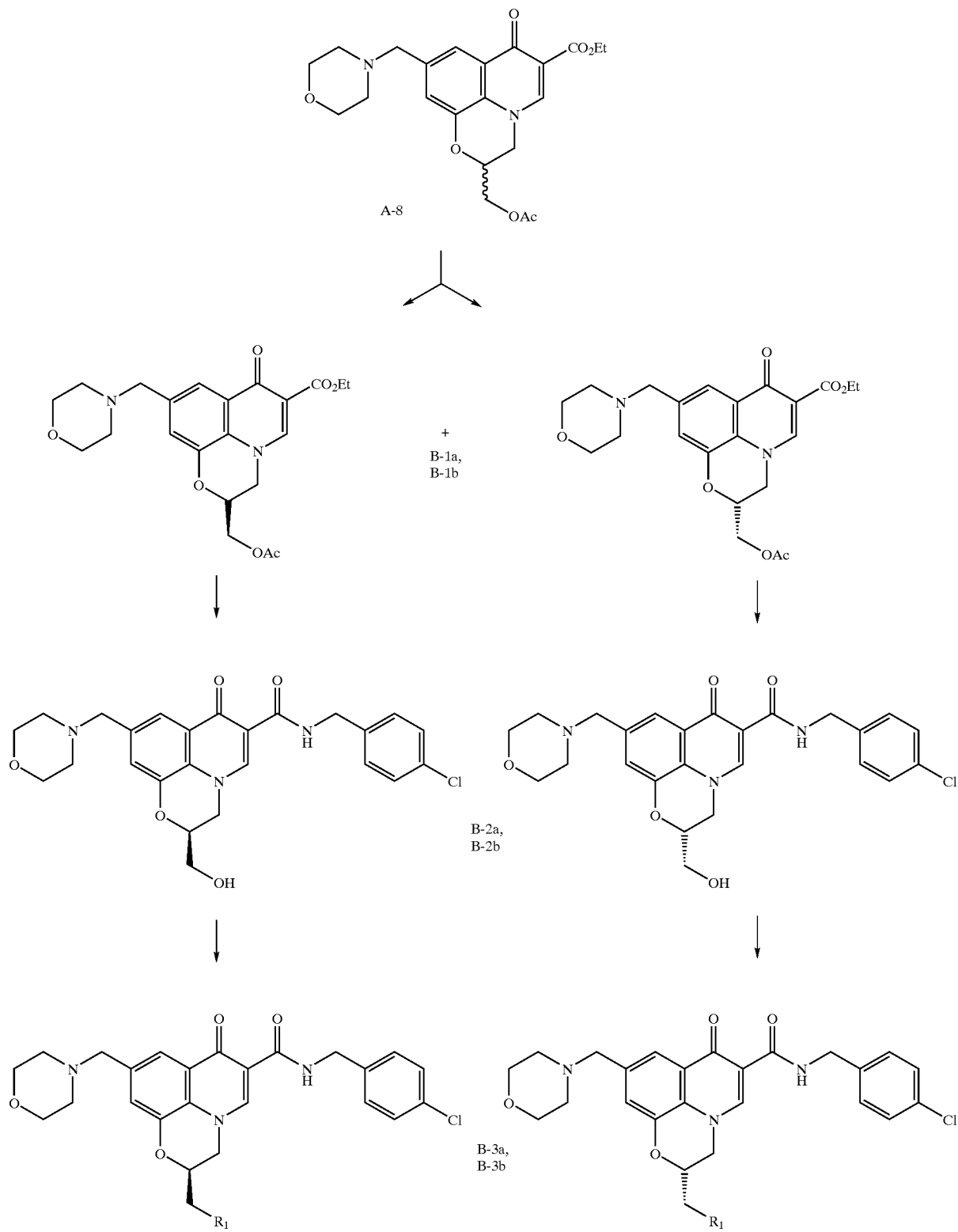

As shown in CHART C, alcohol of Formula A-9 is reacted with acetic anhydride to provide acetate C-1. Alternately, the alcohol can be coupled with a salt of suleptanic acid, which is 8-[Methyl(2-sulfoethyl)amino]-8-oxooctanoic acid, using diisopropylcarbodiimide to afford C-2. Alternately, C-9 can be reacted sequentially with phosphorus oxychoride and then methanol to provide phosphate C-3.

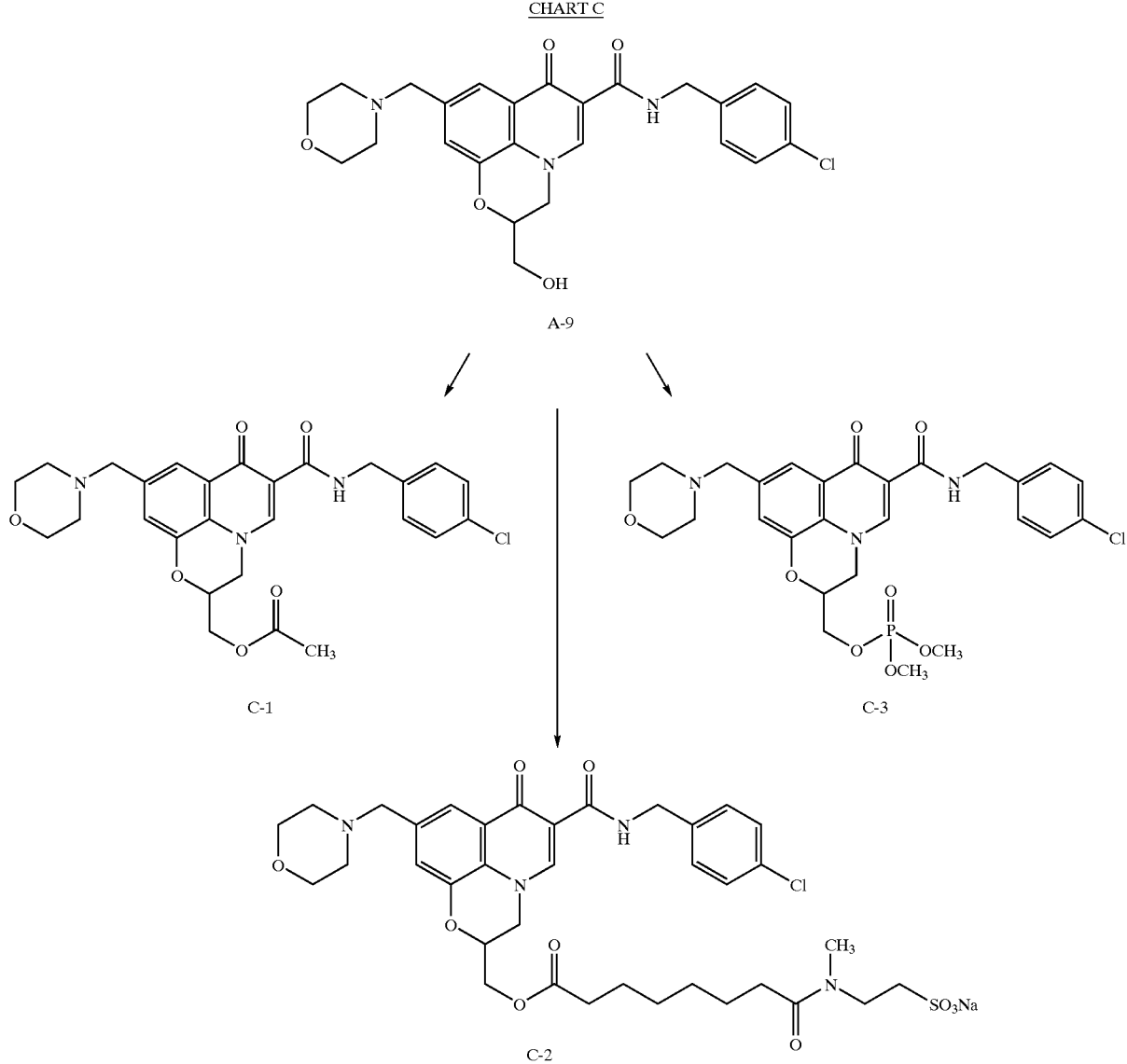

CHART C

As shown in CHART D, aminophenol of Formula A-3 is treated with methyl α-bromophenylacetate and potassium carbonate in refluxing acetone to afford D-1. Reduction of the carbonyl groups using lithium aluminum hydride provides amine D-2, which is reacted with diethyl ethoxymethylenemalonate to furnish D-3. Cyclization to D-4 is effected with polyphosphoric acid, and aminolysis of the ester using p-chlorobenzylamine at 150° C. affords compound D-5.

CHART D

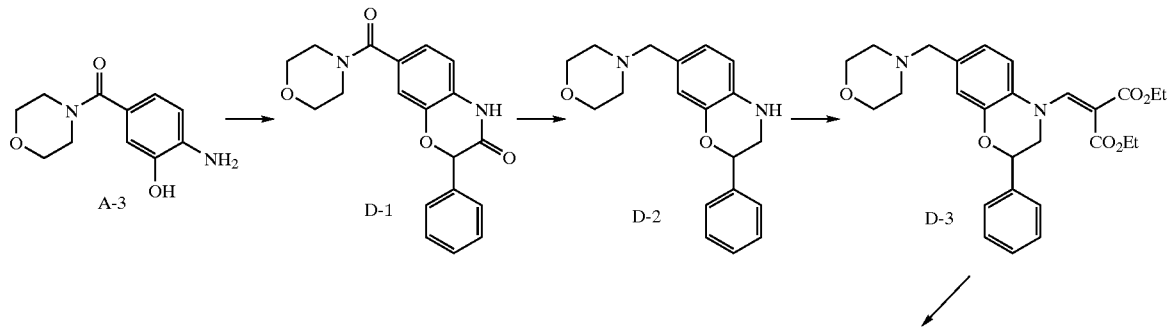

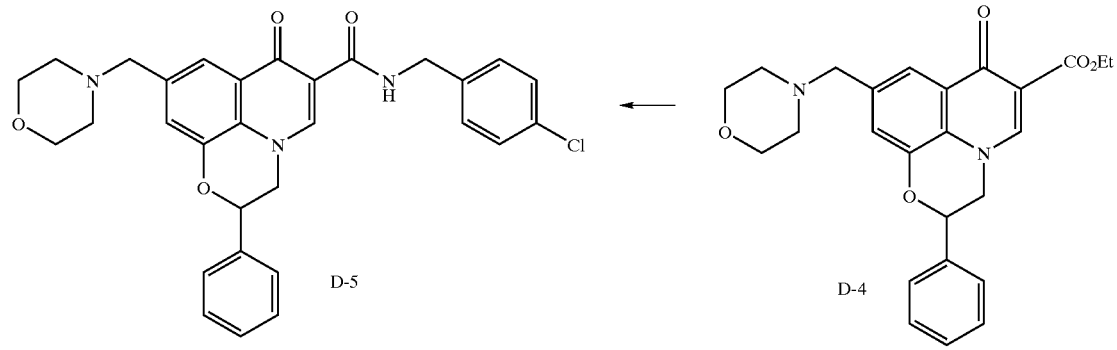

As shown in CHART E, aminophenol of Formula A-3 is treated with ethyl bromodifluoroacetate and sodium hydride in dimethylformamide to afford E-1. Reduction of the carbonyl groups using lithium aluminum hydride provides amine E-2, which is reacted with diethyl ethoxymethylenemalonate to furnish E-3. Cyclization to E-4 is effected with polyphosphoric acid, and aminolysis of the ester using p-chlorobenzylamine at 150° C. affords compound E-5.

bisulfate as a phase transfer catalyst, giving compound F-1. Reduction of the nitro group with tin(II) chloride is followed by spontaneous cyclization to enamine F-2. Reduction of the enamine with sodium borohydride furnishes F-3, which is further reduced using lithium aluminum hydride to afford amine F-4. Reaction with diethyl ethoxymethylenemalonate provides F-5, which is cyclized using polyphosphoric acid to

CHART E

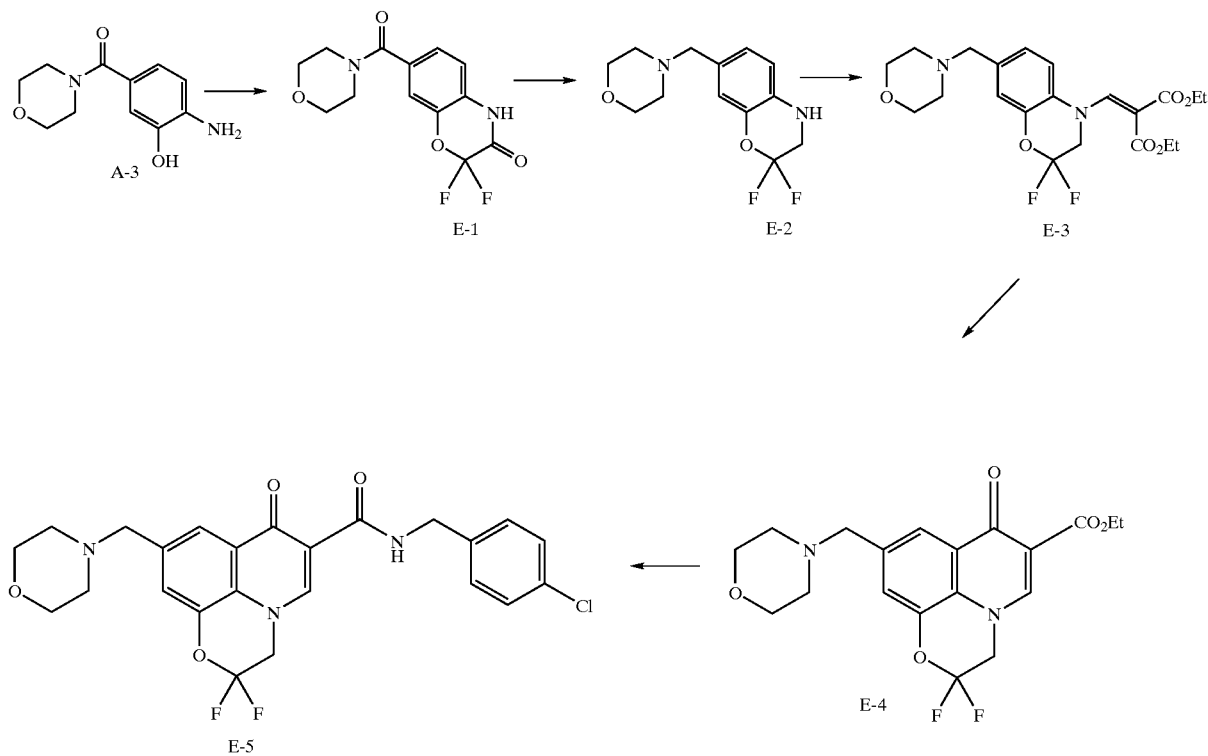

As shown in CHART F, nitrophenol of Formula A-2 is alkylated using phenacyl bromide and tetrabutylammonium give F-6. Aminolysis of the ester using p-chlorobenzylamine at 150° C. affords compound F-7.

CHART F

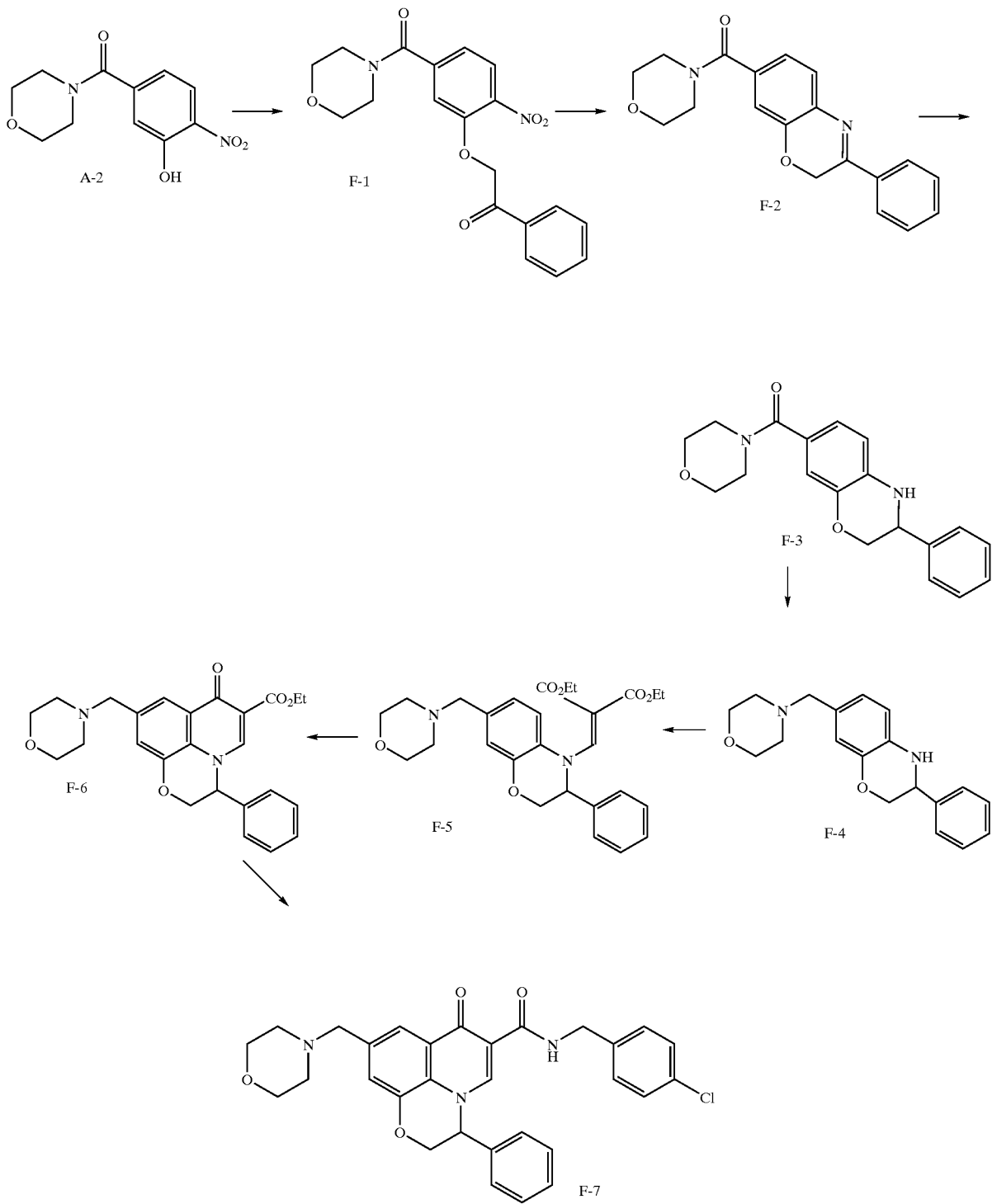

As shown in CHART G, nitro ketone of Formula A-2 is reacted with epichlorohydrin in the presence of sodium hydroxide to give epoxide G1. Reaction of the epoxide with morpholine in refluxing methanol provides amino alcohol G-2. The alcohol is oxidized with dimethyl sulfoxide and trifluoroacetic anhydride, and the resulting ketone is immediately hydrogenated using hydrogen gas and Raney nickel catalyst to give G-3. Reduction of the remaining keto group is accomplished with lithium aluminum hydride, affording amine G4. Treatment of the amine with diethyl ethoxymethylenemalonate, followed by polyphosphoric acid mediated cyclization of the intermediate enamine, provides compound G-5. Aminolysis of the ester using p-chlorobenzylamine at 150° C. provides compound G-6.

CHART G

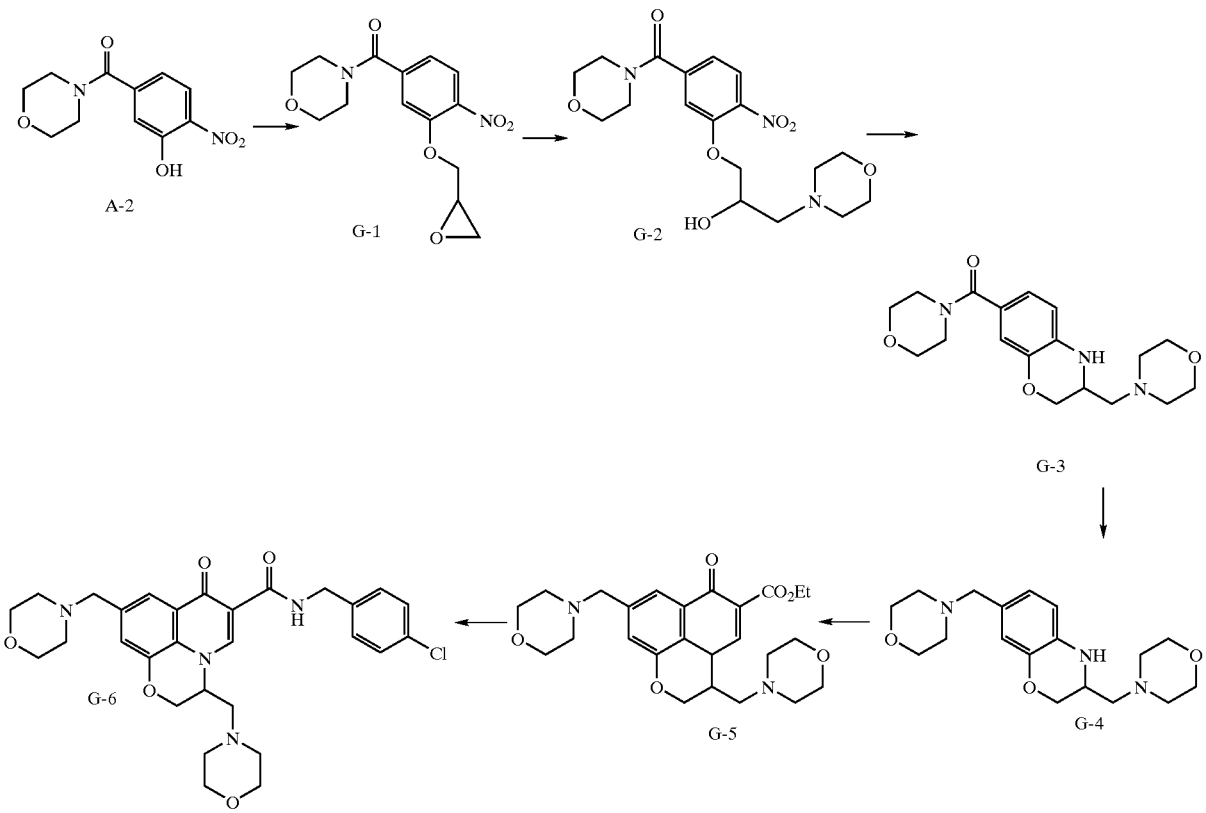

As shown in CHART H, iodination of commercially available 2,3-difluorobenzoic acid H-1 using N-iodosuccinimide in trifluoromethanesulfonic acid provides trihalo-acid H-2. The acid is reacted with carbonyldiimidazole to form the intermediate acyl imidazolide, which is treated with ethyl trimethylsilyl malonate and 1,8-diazabicyclo[5.4.0]undec-7-ene to provide β-ketoester H-3. Compound H-3 is reacted with triethyl orthoformate and acetic acid, followed by tris(hydroxymethyl) methylamine to afford triol H-4. Cyclization is effected using potassium carbonate in DMF, giving tricycle H-5, and aminolysis using p-chlorobenzylamine at 150° C. affords H-6. The hydroxyl groups are masked as tert-butyldimethylsilyl ethers by reaction of the diol with tert-butyldimethylsilyl chloride and imidazole in dimethylformamide, giving H-7. Coupling of the iodide with propargyl alcohol using catalytic bis (triphenylphosphine)palladium (II) dichloride and copper (I) iodide provides H-8. Removal of the silyl ethers using hydrochloric acid in ethanol affords compound H-9. Alternately, the triple bond in H-8 is reduced with hydrogen gas and catalytic platinum on carbon to afford H-10, which is desilylated using hydrochloric acid in ethanol to provide compound H-11.

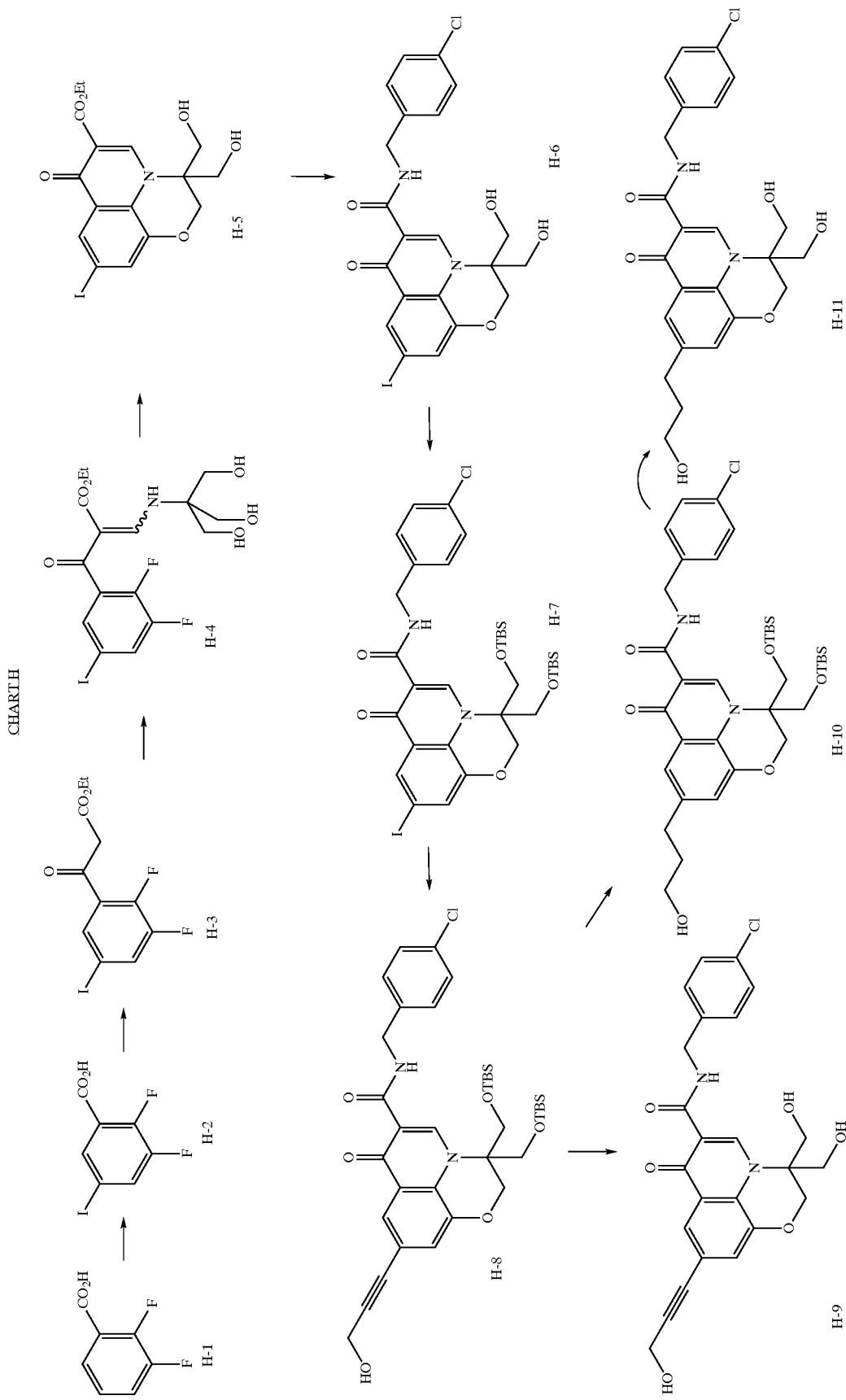
CHART H

As shown in CHART I, treatment of β-ketoester H-3 (Chart H) with triethyl orthoformate in refluxing acetic anhydride forms intermediate enol I-1, which then reacts with amino alcohols I-7 to provide enamines I-2. In Chart I, substitutent T refers to either a het or an aryl group. In some cases, groups T in Chart I may contain functional groups which are protected by suitable protective groups, such as methoxymethyl or tert-butyldimethylsilyl during the course of the synthesis. The protective groups are installed and then removed at the end of the synthesis using methods known to those skilled the art. Cyclization of the enamines to tricycles I-3 is accomplished using cesium carbonate in DMF. Aminolysis of the ethyl ester using neat p-chlorobenzylamine affords amides I-4. The iodide is converted to the aldehyde I-5 using carbon monoxide and tri-n-butylstannane under palladium catalysis. Finally, reductive amination of the aldehyde provides I-6.

Amino alcohols I-7 required for the sequence are prepared in two steps from the corresponding aldehydes I-8, by treatment of the aldehyde with trimethylsilyl cyanide and subsequent reduction of the TMS cyanohydrin with lithium aluminum hydride.

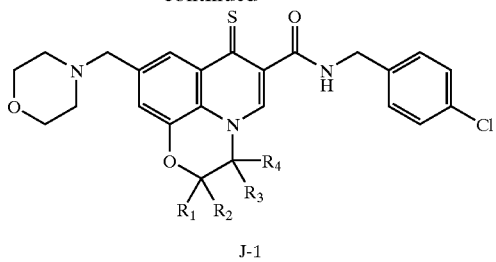

J-1

A morpholino substituted 7-thioxo-2,3-dihydro-7H-[1,4]oxazino[2,3,4-ij]quinoline-6-carboxamide, A-11, in a suitable solvent such as toluene and dichloroethane can be reacted with Lawesson's reagent in the presence of KHMDS. The mixture is then reacted at a suitable temperature range providing the desired thioketone J-1.

CHART I

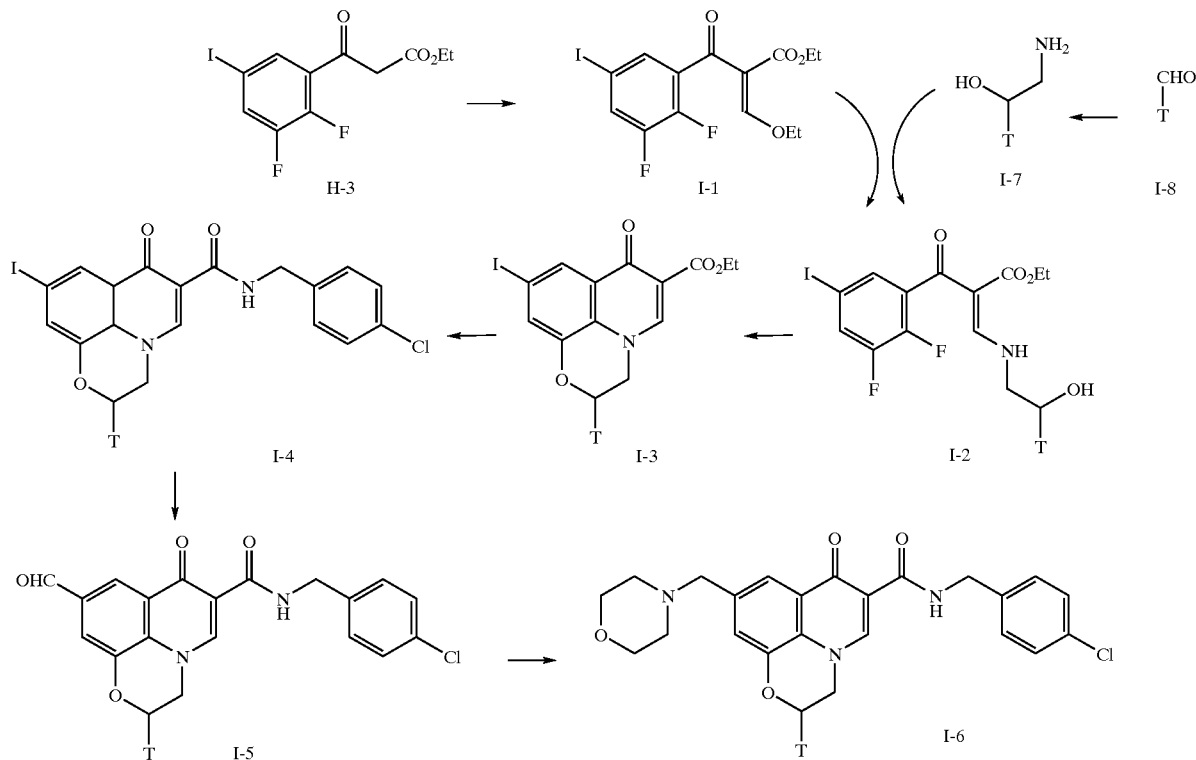

CHART J illustrates a method for converting oxazinoquinolones to thioxazinoquinolones.

CHART J

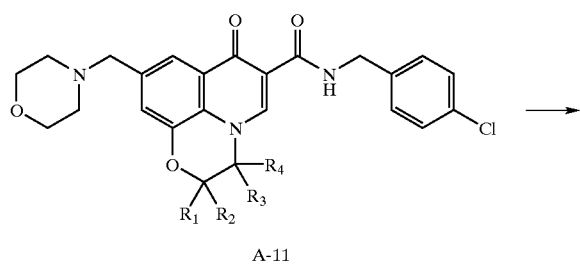

A-11

CHART K provides an alternative method to convert oxazinoquinolones to thioxazinoquinolones when they are substituted with one or more alkyl hydroxy groups. For example, reacting compound H-11 in DMF with TIPSCl in the presence of imidiazole provides K-1 (See Wuts, P. G. *Protecting Groups in Organic Chemistry* 1999, 123). Next, ketone K-1 is reacted with Lawesson's reagent in the presence of KHMDS in refluxing toluene and dichloroethane provides the thioketone K-2. The protected alcohol K-2 is then treated with $Bu_4N^+F^-$ in THF affording the hydroxyl compound K-3 (In Wuts, P. G. *Protecting Groups in Organic Chemistry* 1999, 124).

CHART K

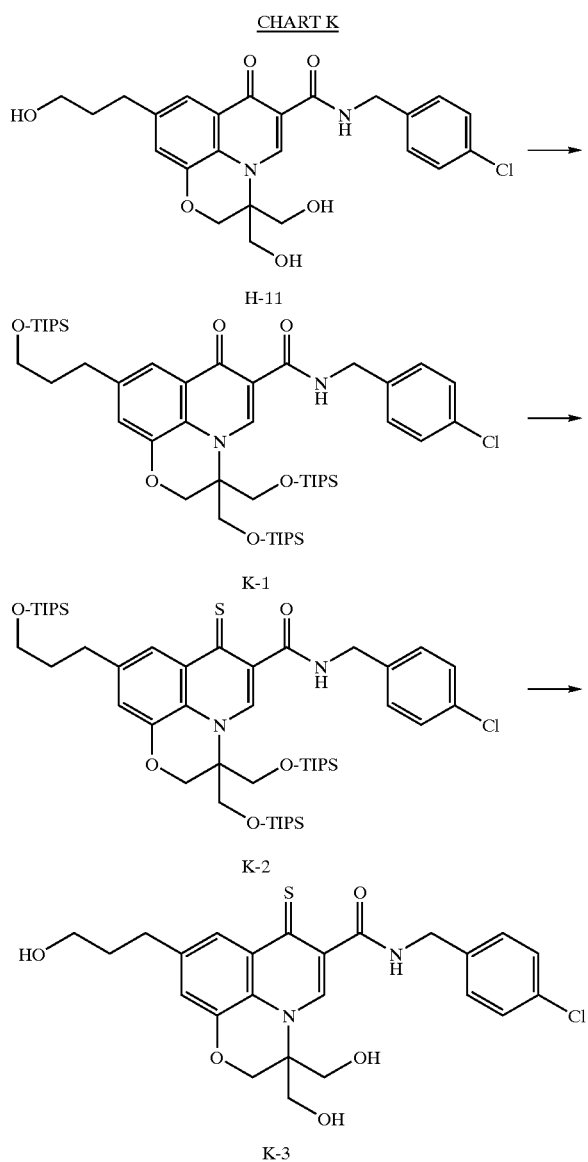

CHART L illustrates a method for converting oxazinoquinolones to thioxazinoquinolone thioamides. A morpholino substituted 7-thioxo-2,3-dihydro-7H-[1,4]oxazino[2,3,4-ij]quinoline-6-carboxamide, A-11, in a suitable solvent such as toluene and dichloroethane can be reacted with excess Lawesson's reagent. The mixture is then reacted at a suitable temperature range providing the desired thioketone L-1.

CHART L

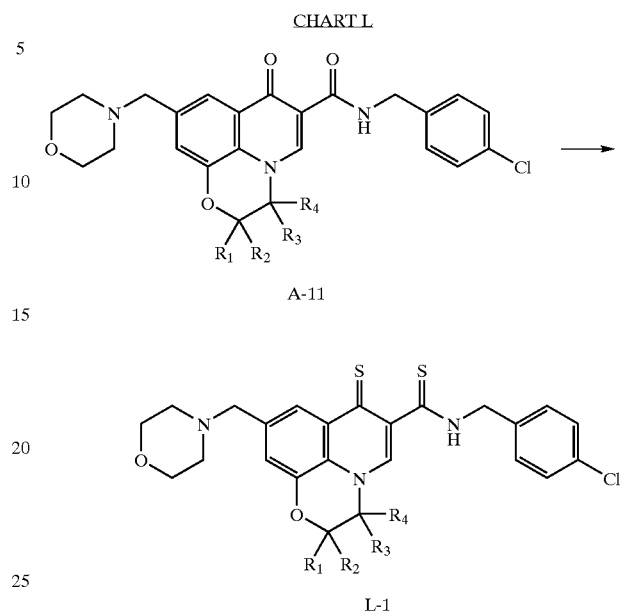

As shown in CHART M, commercially available 2-fluoro-4-iodoaniline of Formula M-1 is reacted with diethyl ethoxymethylenemalnoate under thermal conditions to give the substituted 4-hydroxyquinoline of Formula M-2. Aminolysis of the ethyl ester using p-chlorobenzylamine under thermal conditions provides amide M-3. Palladium catalyzed formylation of the iodide affords aldehyde M-4, which is treated with morpholine and sodium triacetoxyborohydride to furnish amine M-5. Compound M-5 is reacted with various epoxides M-7, using cesium carbonate or calcium ethoxide as base, to provide compounds M-8 or M-9. Where not commercially available, epoxides M-7 may be prepared by treatment of the corresponding carbonyl compounds M-6 with trimethylsulfonium methylsulfate and sodium hydroxide. Epoxides M-7 may also be prepared by other routes familiar to those skilled in the art; for example, by epoxidation of the corresponding olefins. If epoxides M-7 are prepared in optically enriched form, either by synthesis or resolution, the resulting products M-8 and M-9 will also be obtained in optically enriched form. This method for the preparation of the compounds of the present invention is further illustrated in the Preparation 46 and Examples 36–54.

CHART M

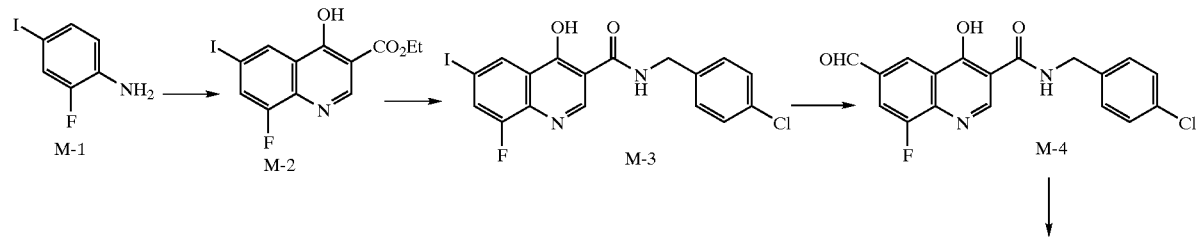

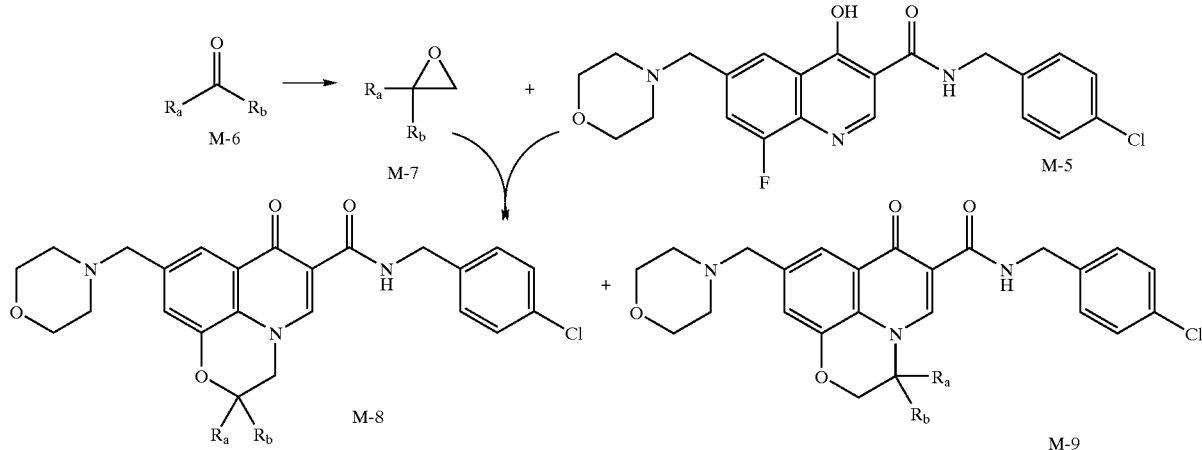

In CHART N, hydroxyalkylbenzyl alcohols N-1 are protected with an appropriate blocking group, such as methoxymethyl or tert-butyldimethylsilyl, giving monoprotected alcohols N-2. Oxidation of the remaining hydroxyl group provides aldehydes N-3. Where hydroxyalkylbenzaldehydes N-4 are commercially available, they may be converted to compounds N-3 using similar protection chemistry. Addition of trimethylsilyl cyanide provides amino alcohols N-5, which are carried forth through the sequence N-6, N-7, N-8, N-9, and N-10 as described for Chart I. Finally, the protecting group is removed from compounds N-10 using standard conditions familiar to those proficient in the art, for example, by treatment with acid in ethanol, to give compounds N-11.

CHART N

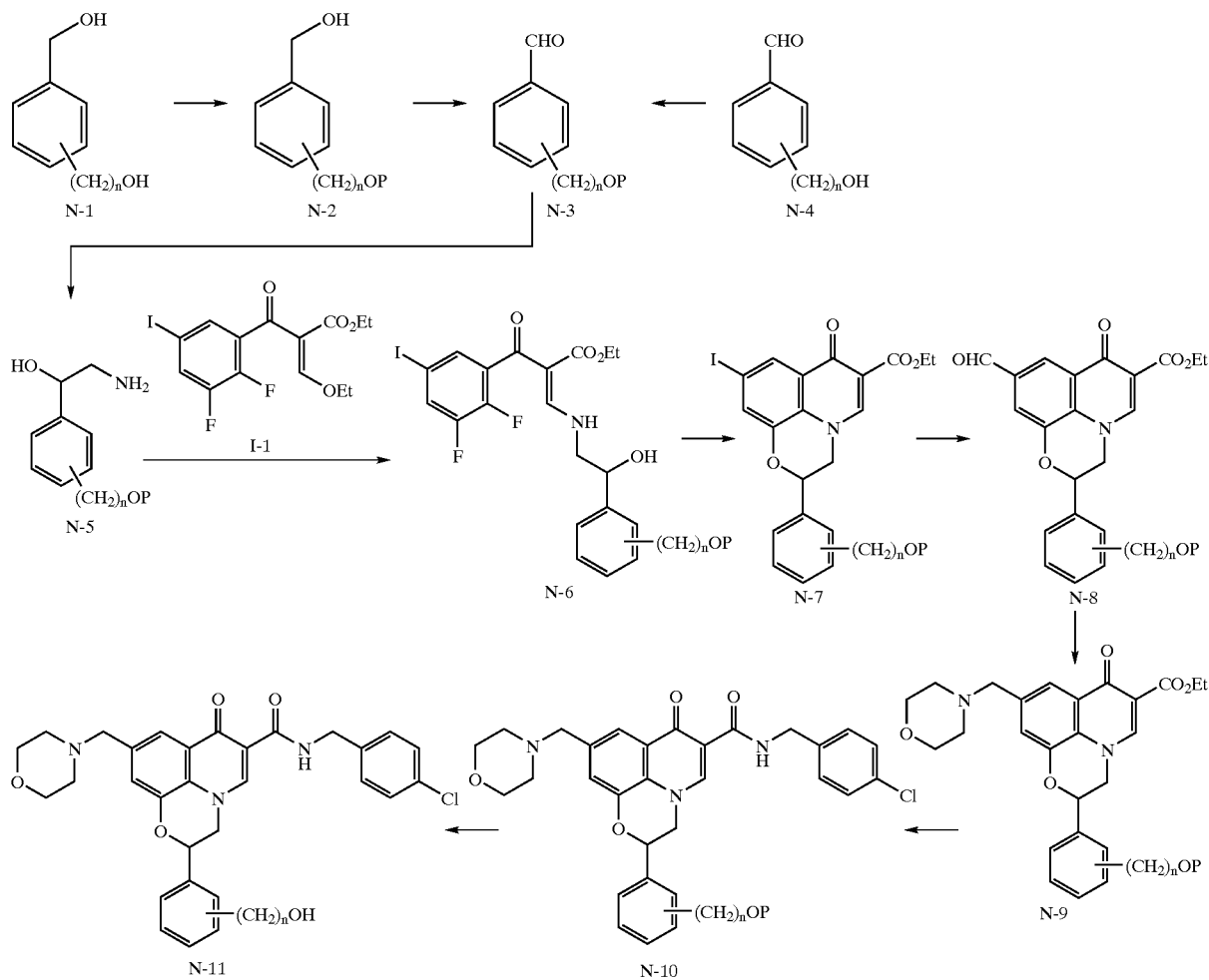

It will be apparent to those skilled in the art that the described synthetic procedures are merely representative in nature and alternative synthetic processes are known to one of ordinary skill in organic chemistry.

The inventive compounds may be used in their native form or as salts. In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, etoglutarate, and glycerophosphate. Suitable inorganic salts may also be formed, including hydrochloride, hydrobromide, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

"Pharmaceutically acceptable salts" refers to those salts which possess the biological effectiveness and properties of the parent compound and which are not biologically or otherwise undesirable.

Compounds of the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 5th Ed., 1975).

The compounds and compositions of the present invention can be administered parenterally (for example, by intravenous, intraperitoneal or intramuscular injection), topically, orally, or rectally, depending on whether the preparation is used to treat internal or external viral infections.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The exact regimen for administration of the compounds and compositions disclosed herein will necessarily be dependent upon the needs of the individual subject being treated, the type of treatment and, of course, the judgment of the attending practitioner.

The exact regimen for administration of the compounds and compositions disclosed herein will necessarily be dependent upon the needs of the individual subject being treated, the type of treatment and, of course, the judgment of the attending practitioner. The compounds of the present invention can be administered to an animal in need of treatment. In most instances, this will be a human being, but the treatment of livestock and companion animals is also specifically contemplated as falling within the scope of the instant invention.

The antiviral activity of a compound of the invention can be determined using pharmacological models which are well known to the art, or using Test A described below.

The compounds of formula (I) and pharmaceutically acceptable salts thereof are useful as antiviral agents. Thus, they are useful to combat viral infections in animals, including man. The compounds are generally active against herpes viruses, and are particularly useful against the varicella zoster virus, the Epstein-Barr virus, the herpes simplex virus, the human herpes virus type 8 (HHV-8) and the cytomegalovirus (CMV).

While many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 µl volume with 5.4 mM HEPES (pH 7.5), 11.7 mM KCl, 4.5 mM MgCl$_2$, 0.36 mg/ml BSA, and 90 nM $^3$H-dTTP. Assays are run with and without CHAPS, (3-[(3-Cholamidopropyl)-dimethylammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 µg/ml BSA, and 0.01% sodium azide. The HCMV polymerase, which is expressed in recombinant baculovirus-infected SF-9 cells and purified according to literature procedures, is added at 10% (or 10 µl) of the final reaction volume, i.e., 100 µl. Compounds are diluted in 50% DMSO and 10 µl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25 C. or 37 C. H$_2$O bath and terminated via the addition of 40 µl/reaction of 0.5 M EDTA (pH 8) per well. Reactions are terminated within the time-frame during which substrate incorporation is linear and varied depending upon the enzyme and conditions used, i.e., 30 min. for HCMV polymerase. Ten µl of streptavidin-SPA beads (20 mg/ml in PBS/10% glycerol) are added following termination of the reaction. Plates are incubated 10 min. at 37 C., then equilibrated to room temperature, and counted on a Packard Topcount. Linear regressions are performed and IC$_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction. Results of the testing of representative compounds of formula I in this assay are shown in Table 1 below.

TABLE 1

Biological Data

| Example | CMV polymerase IC$_{50}$ ($\mu$M) |
|---|---|
| 1 | 0.61 |
| 2 | 0.76 |
| 3 | 0.76 |
| 4 | 1.30 |
| 5 | 1.10 |
| 6 | 0.66 |
| 7 | 0.67 |
| 8 | 1.50 |
| 9 | 0.59 |
| 10 | 0.62 |
| 11 | 0.54 |
| 12 | 0.59 |
| 13 | 0.59 |
| 14 | 0.55 |
| 15 | 0.42 |
| 16 | 0.42 |
| 17 | 0.27 |
| 18 | 0.58 |
| 19 | 0.57 |
| 20 | 0.35 |
| 21 | 0.67 |
| 22 | 0.30 |
| 23 | 1.10 |
| 24 | 0.74 |
| 25 | 1.30 |
| 26 | 0.53 |
| 27 | 0.92 |
| 28 | 0.60 |
| 29 | 1.00 |
| 30 | 0.97 |
| 31 | 5.00 |
| 32 | 3.00 |
| 33 | 0.52 |
| 34 | 0.48 |
| 35 | 0.61 |
| 36 | 0.42 |
| 37 | 0.38 |
| 38 | 0.46 |
| 39 | 0.33 |
| 40 | 0.33 |
| 41 | 0.44 |
| 42 | 0.20 |
| 43 | 0.40 |
| 44 | 1.04 |
| 45 | 0.41 |
| 46 | 0.53 |
| 47 | 0.83 |
| 48 | 2.15 |
| 49 | 2.33 |
| 50 | 1.17 |
| 51 | 0.75 |
| 52 | 0.81 |
| 53 | 0.53 |
| 54 | 0.60 |
| 55 | 0.41 |
| 56 | 0.66 |
| 57 | 0.68 |
| 57 | 0.32 |
| 58 | 0.57 |
| 58 | 0.27 |
| 59 | 0.48 |
| 60 | 0.46 |
| 61 | 0.54 |
| 62 | 0.38 |
| 63 | 0.29 |
| 64 | 1.05 |
| 65 | 0.45 |
| 66 | 0.59 |
| 67 | 1.69 |
| 68 | 0.82 |
| 69 | 0.33 |

The symbol "--" refers to the data are not determined.

The compounds and their preparation of the present invention will be better understood in connection with the following Examples, which are intended as an illustration of and not a limitation upon the scope of the invention.

EXAMPLES

Preparation 1:(3-Hydroxy-4-nitrophenyl)(4-morpholinyl)methanone (Formula A-2 of Chart A)

To a stirred mixture of 55.0 g of 3-hydroxy-4-nitrobenzoic acid in 600 mL of dichloromethane is added 35 mL of thionyl chloride and 5.0 mL of DMF. The mixture is stirred and refluxed with exclusion of moisture for 1–2 h, when it suddenly becomes a clear solution. Refluxing is continued for another hour, then volatiles are removed under reduced pressure. The residual amber oil is dissolved in dichloromethane (200 mL), toluene (200 mL) is added, and the solution again concentrated under reduced pressure. The resulting amber oil is dissolved in 300 mL of dichloromethane, and to this solution, stirred and cooled to 0° C., is added dropwise 65 mL of morpholine in 200 mL of dichloromethane. The resulting mixture is stirred overnight, then washed with water containing sufficient 6N HCl to render the aqueous phase acidic. The aqueous phase is extracted with one additional portion (100 mL) of dichloromethane, and the combined extracts dried (Na$_2$SO$_4$) and concentrated under reduced pressure, affording an orange solid. Recrystallization from 1:3 ethyl acetate in heptane provides 70.34 g of the amide as a solid, mp 105.5–106.5° C.

$^1$H NMR (CDCl$_3$) $\delta$3.40, 3.64, 3.79, 7.01, 7.18, 8.18, 10.63 ppm HRMS (FAB) calcd for C$_{11}$H$_{12}$N$_2$O$_5$+H$_1$ 253.0824, found 253.0832. Anal. Calcd for C$_{11}$H$_{12}$N$_2$O$_5$: C, 52.38, H, 4.80, N, 11.11, Found: C, 52.46; H, 4.85; N, 11.11.

Preparation 2: 2-Amino-5-(4-morpholinylcarbonyl) phenol (Formula A-3 of Chart A)

A mixture of 15.36 g of the product of Preparation 1 and 1.25 g of 5% palladium on carbon in 450 mL of methanol is shaken under 30 psi of hydrogen gas for 3 h, then filtered through Celite. The solid is washed thoroughly with chloroform and methanol, and the combined filtrates concentrated under reduced pressure. The solid residue is suspended in ether, and the resulting solid filtered, washed with ether, and dried in vacuo to provide 13.34 g of the aminophenol as a solid.

$^1$H NMR (DMSO-d$_6$) $\delta$3.48, 3.57, 6.57, 6.68, 6.76, 9.28 ppm.

Preparation 3: Ethyl 7-(4-morpholinylcarbonyl)-3-oxo-3,4-dihydro-2H-1,4-benzoxazine-2-carboxylate (Formula A-4 of Chart A)

To a stirred, cooled (0° C.) mixture of 13.24 g the product of Preparation 2 in 60 mL of dry DMF, under argon, is added in portions 2.4 g of sodium hydride (60% dispersion in mineral oil). The mixture is stirred at 0° C. for 45 m, then 10.7 mL of diethyl chloromalonate is added, and the mixture allowed to warm to ambient temperature. After 18 h, the mixture is partitioned between dichloromethane and water containing sufficient dil. aq. HCl to bring the pH of the aqueous phase to ca. 4. The aqueous phase is extracted with two additional portions of dichloromethane, and the combined extracts dried (MgSO$_4$) and concentrated under reduced pressure to a DMF solution of an intermediate amino ester. This solution is heated at 80° C. under argon for 5 h, and the DMF is then distilled off under reduced pressure. Flash chromatography of the residue on silica using 3% methanol in dichloromethane affords 15.66 g of the title compound as a solid.

$^1$H NMR (CDCl$_3$) δ1.27, 3.7, 4.26, 5.22, 6.89, 7.08, 7.15, 9.15.

Preparation 4: [7-(4-Morpholinylmethyl)-3,4-dihydro-2H-1,4-benzoxazin-2-yl]methanol (Formula A-5 of Chart A)

To a stirred, cold (0° C.) solution of 15.59 g of the product of Preparation 3 in 90 mL of dry THF, under argon, is added 34 mL of borane-dimethyl sulfide complex. Following the addition, the ice bath is removed, whereupon the reaction warms spontaneously nearly to reflux. After the initial exothermic reaction, heat is supplied from an oil bath, and the temperature of the reaction maintained at 50° C. for 18 h. The solution is then cooled to 0° C. and quenched cautiously with methanol. Additional methanol (200 mL) is added, and the solution distilled through a Vigreux column at atmospheric pressure. Methanol is added at intervals until a total of 650 mL has distilled. Flash chromatography of the residual oil on silica using 5–6% methanol in dichloromethane provides 8.07 g of the title compound as a solid.

$^1$H NMR (CDCl$_3$) δ2.4, 3.3, 3.70, 3.8, 4.34, 6.56, 6.72, 6.80.

Preparation 5: Diethyl 2-{[2-(hydroxymethyl)-7-(4-morpholinylmethyl)-2,3-dihydro-4H-1,4-benzoxazin-4-yl]methylene}malonate (Formula A-6 of Chart A)

A mixture of 8.05 g of the product of Preparation 4 and 7.3 g of diethyl ethoxymethylenemalonate is heated at 130° C. under a slow stream of argon for 2 h, then held under vacuum at 130° C. to remove volatile components. Flash chromatography of the residual amber oil on silica using 3% methanol in dichloromethane affords 11.51 g of the title compound as a solid.

$^1$H NMR (CDCl$_3$) δ1.30, 1.33, 2.43, 3.42, 3.58, 3.71, 3.82, 4.19, 4.24, 4.28, 6.9, 8.01. MS (ES+) m/z 435.3.

Preparation 6: Diethyl 2-{[2-[(acetyloxy)methyl]-7-(4-morpholinylmethyl)-2,3-dihydro-4H-1,4-benzoxazin-4-yl]methylene}malonate (Formula A-7 of Chart A)

A solution of 11.48 g of the product of Preparation 5, 11 mL of pyridine, and 5.0 mL of acetic anhydride in 25 mL of dichloromethane is stirred at room temperature for 18 h, then concentrated under reduced pressure with toluene azeotrope to remove pyridine and acetic acid. Flash chromatography of the residual oil on silica using 2% methanol in dichloromethane provides 13.08 g of the title compound as a solid.

$^1$H NMR (CDCl$_3$) δ1.31, 1.33, 2.11, 2.42, 3.42, 3.48, 3.58, 3.71, 4.28, 6.95, 7.99. TLC R$_f$ 0.35 (3% methanol in dichloromethane). HRMS (FAB) calcd for C$_{24}$H$_{32}$N$_2$O$_8$+H$_1$ 477.2237, found 477.2236.

Preparation 7: Ethyl 2-[(acetyloxy)methyl]-9-(4-morpholinylmethyl)-7-oxo-2,3-dihydro-7H-[1,4]oxazino[2,3,4-ij]quinoline-6-carboxylate (Formula A-8 of Chart A)

To 7.1 g of phosphorus pentoxide is added 50 mL of methanesulfonic acid, and the mixture is stirred under argon at 80–100° C. until a clear solution is obtained. The solution is cooled to 10° C., and into this is cannulated a solution of 13.08 g of the product of Preparation 6 in 10 mL of dichloromethane. The resulting solution is stirred at 50° C. for 18 h, then cooled, diluted with dichloromethane (100 mL), and cautiously added to a stirred slurry of 72 g of sodium bicarbonate in 200 mL of water. Phases are separated and the aqueous extracted with four additional portions of dichloromethane, and the combined organic phases dried (Na$_2$SO$_4$) and concentrated under reduced pressure. Flash chromatography of the residue on silica gel using 3.5–4.5% methanol in dichloromethane affords 5.58 g of the title compound as a solid.

$^1$H NMR (CDCl$_3$) δ1.39, 2.16, 2.44, 3.54, 3.70, 4.17, 4.29, 4.34, 4.45, 4.50, 4.59, 7.31, 7.91, 8.28. TLC R$_f$ 0.30 (5% methanol in dichloromethane). MS (ES+) m/z 431.2.

Example 1

N-(4-Chlorobenzyl)-2-(hydroxymethyl)-9-(4-morpholinylmethyl)-7-oxo-2,3-dihydro-7H-[1,4]oxazino[2,3,4-ij]quinoline-6-carboxamide (Formula A-9 of Chart

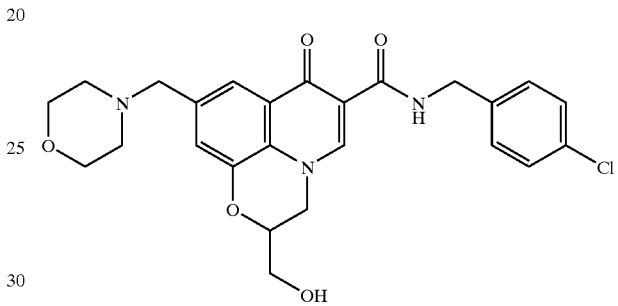

A mixture of 5.17 g of the product of Preparation 7 and 10.2 g of p-chlorobenzylamine is stirred and heated at 145° C. under argon for 18 h, after which the bulk of excess amine is distilled off under reduced pressure. The residual solid is triturated well with ether, filtered and washed with ether, and dried under vacuum to provide 5.91 g of cream colored solid. This is triturated with boiling acetonitrile, filtered and washed with acetonitrile, and dried under vacuum to afford 5.76 g of the title compound as a solid.

$^1$H NMR (DMSO-d$_6$) δ2.38, 3.34, 3.58, 3.75, 4.24, 4.42, 4.56, 4.62, 5.27, 7.27, 7.39, 7.77, 8.75, 10.43. TLC R$_f$ 0.38 (10% methanol in dichloromethane) IR (mull) 1656, 1611, 1572, 1556, 1539, 1504, 1492, 1417, 1347, 1286, 1123, 1112, 1105, 1090, 806 cm$^{-1}$. UV $\lambda_{max}$ 225 (32600, 95% ethanol).

Preparation 8: [6-{[(4-Chlorobenzyl)amino]carbonyl}-9-(4-morpholinylmethyl)-7-oxo-2,3-dihydro-7H-[1,4]oxazino[2,3,4-ij]quinolin-2-yl]methyl methanesulfonate (Formula A-10 of Chart A)

A solution of 726 mg of the product of Example 1 and 0.80 mL of 2,4,6-collidine is prepared with the aid of heat in 12 mL of DMF, and the solution is cooled to 10° C. for the addition of 0.35 mL of methanesulfonyl chloride. The mixture is allowed to warm to ambient temperature and stirred overnight, then partitioned between dichloromethane and water containing 25 mL of saturated aqueous NaHCO$_3$. The aqueous phase is extracted with two additional portions of dichloromethane, and the combined organic phases dried (MgSO$_4$) and concentrated under high vacuum to remove DMF. Flash chromatography of the residue on silica gel using 3% methanol in dichloromethane provides 692 mg of the title compound as a solid.

¹H NMR (CDCl₃+CD₃OD) δ2.45, 3.14, 3.57, 3.70, 4.26, 4.41, 4.57, 7.28, 7.38, 7.94, 8.67, 10.36. TLC R$_f$ 0.29 (5% methanol in dichloromethane). MS (ES+) m/z 561.9.

Example 2

General Procedure for Mesylate Displacement Using Nitrogen Nucleophiles N-(4-Chlorobenzyl)-2,9-bis(4-morpholinylmethyl)-7-oxo-2,3-dihydro-7H-[1,4]oxazino[2,3,4-ij]quinoline-6-carboxamide (Formula A-11 of Chart A)

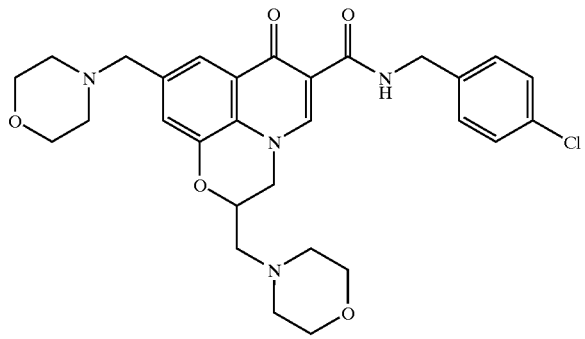

A solution of 91 mg of the product of Preparation 8 and 0.17 mL of morpholine in 1.0 mL of N-methylpyrrolidinone is heated at 80° C. for 6 h, then cooled and partitioned between water and dichloromethane or ethyl acetate. The aqueous phase is extracted with sufficient dichloromethane or ethyl acetate to remove product, and the organic phase is dried (MgSO₄). Volatiles are removed under high vacuum, and the residue purified by flash chromatography on silica using 2–5% methanol in dichloromethane to afford 45.2 mg of the title compound as a white solid. Further purification may be effected by recrystallization from acetonitrile or ethyl acetate-hexane.

Mp 178–180° C. ¹H NMR (CDCl₃) δ2.46, 2.60, 2.72, 2.86, 3.59, 3.77, 4.18, 4.37, 4.47, 4.64, 7.30, 7.93, 8.66, 10.44. TLC R$_f$ 0.22 (5% methanol in dichloromethane). HRMS (FAB) calcd for $C_{29}H_{33}ClN_4O_5+H_1$ 553.2217, found 553.2228. Anal. Calcd for $C_{29}H_{33}ClN_4O_5$: C, 62.98; H, 6.01; N, 10.13; Cl, 6.41; found: C, 62.85; H, 6.10; N, 9.97.

Example 3

N-(4-Chlorobenzyl)-2-[(dimethylamino)methyl]-9-(4-morpholinylmethyl)-7-oxo-2,3-dihydro-7H-[1,4]oxazino[2,3,4-ij]quinoline-6-carboxamide (Formula A-11 of Chart A)

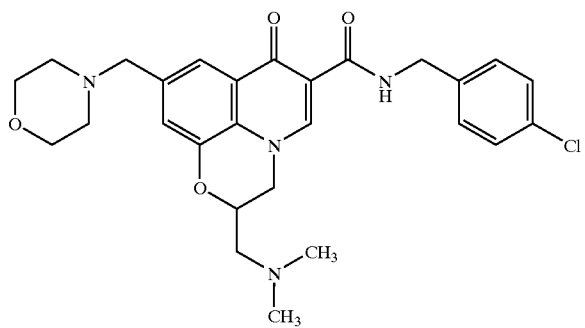

Following the procedure in Example 2, the titled compound is obtained as a solid, mp 168–170° C.

¹H NMR (CDCl₃) δ2.35, 2.45, 2.64, 2.77, 3.57, 3.70, 4.13, 4.35, 4.44, 4.63, 7.30, 7.37, 7.93, 8.65, 10.46. TLC R$_f$ 0.47 (5% methanolic ammonia in dichloromethane). HRMS (FAB) calcd for $C_{27}H_{31}ClN_4O_4+H_1$ 511.2112, found 511.2111. Anal. Calcd for $C_{27}H_{31}ClN_4O_4$: C, 63.46; H, 6.11; N, 10.96; Cl, 6.94; found: C, 63.22; H, 6.24; N, 10.63.

Example 4

N-(4-Chlorobenzyl)-2-[(4-methyl-1-piperazinyl)methyl]-9-(4-morpholinylmethyl)-7-oxo-2,3-dihydro-7H-[1,4]oxazino[2,3,4-ij]quinoline-6-carboxamide (Formula A-11 of Chart A)

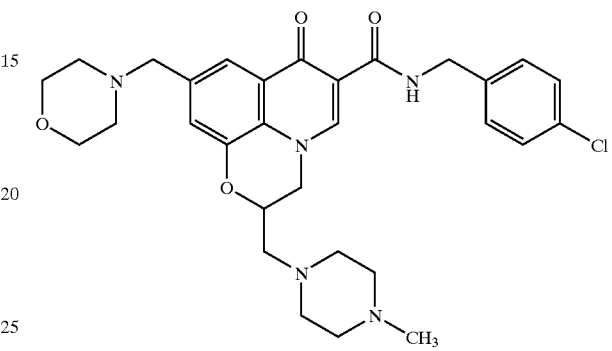

Following the procedure in Example 2, the titled compound is obtained as a solid, mp 201–208 (d).

¹H NMR (CDCl₃) δ2.33, 2.4–2.7, 2.72, 2.86, 3.57, 3.70, 4.15, 4.36, 4.48, 4.64, 7.29, 7.35, 7.92, 8.65, 10.46. TLC R$_f$ 0.37 (7% methanolic ammonia in dichloromethane). HRMS (FAB) calcd for $C_{30}H_{36}ClN_5O_4+H_1$ 566.2534, found 566.2547. Anal. Calcd for $C_{30}H_{36}ClN_5O_4$: C, 63.65; H, 6.41; N, 12.37; Cl, 6.26; found (av): C, 63.00; H, 6.37; N, 11.95.

Example 5

N-(4-Chlorobenzyl)-9-(4-morpholinylmethyl)-7-oxo-2-(1-pyrrolidinylmethyl)-2,3-dihydro-7H-[1,4]oxazino[2,3,4-ij]quinoline-6-carboxamide (Formula A-11 of Chart A)

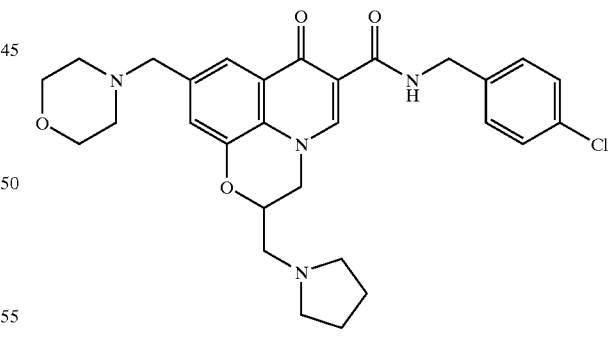

Following the procedure in Example 2, the titled compound is obtained as a solid, mp 209.5–212.0° C.

¹H NMR (CDCl₃) δ1.82, 2.45, 2.63, 2.89, 3.58, 3.70, 4.16, 4.38, 4.45, 4.64, 7.30, 7.37, 7.93, 8.65, 10.47. TLC R$_f$ 0.31 (3% methanolic ammonia in dichloromethane). IR (drift) 2960, 2799, 1655, 1627, 1608, 1553, 1501, 1412, 1348, 1330, 1319, 1281, 1221, 1117, 808 cm$^{-1}$ HRMS (FAB) calcd for $C_{29}H_{33}ClN_4O_4+H_1$ 537.2268, found 537.2259 Anal. Calcd for $C_{29}H_{33}ClN_4O_4$: C, 64.86; H, 6.19; N, 10.43; Cl, 6.60; found: C, 64.89; H, 6.25; N, 10.38.

Example 6

N-(4-Chlorobenzyl)-2-{[(2,3-dihydroxypropyl)amino]methyl}-9-(4-morpholinylmethyl)-7-oxo-2,3-dihydro-7H-[1,4]oxazino[2,3,4-ij]quinoline-6-carboxamide (Formula A-11 of Chart A)

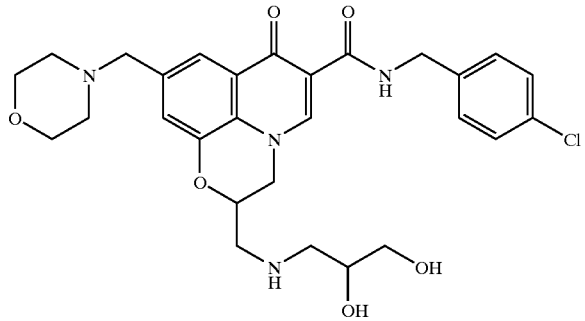

Following the procedure in Example 2, the titled compound is obtained.

$^1$H NMR (CDCl$_3$+CD$_3$OD) δ2.47, 2.79, 3.53, 3.65, 3.74, 4.15, 4.39, 4.63, 7.30, 7.37, 7.92, 8.63, 10.58. TLC R$_f$ 0.22 (12% methanolic ammonia in dichloromethane). IR (drift) 1654, 1626, 1608, 1555, 1503, 1414, 1349, 1330, 1282, 1223, 1114, 1094, 1014, 869, 807 cm$^{-1}$ HRMS (FAB) calcd for C$_{28}$H$_{33}$ClN$_4$O$_6$+H$_1$ 557.2167, found 557.2153 Anal. Calcd for C$_{28}$H$_{33}$ClN$_4$O$_6$: C, 60.37; H, 5.97; N, 10.06; Cl, 6.36; found (av): C, 59.87; H, 5.99; N, 9.94.

Example 7

N-(4-Chlorobenzyl)-2-{[(2-hydroxyethyl)amino]methyl}-9-(4-morpholinylmethyl)-7-oxo-2,3-dihydro-7H-[1,4]oxazino[2,3,4-ij]quinoline-6-carboxamide (Formula A-11 of Chart A)

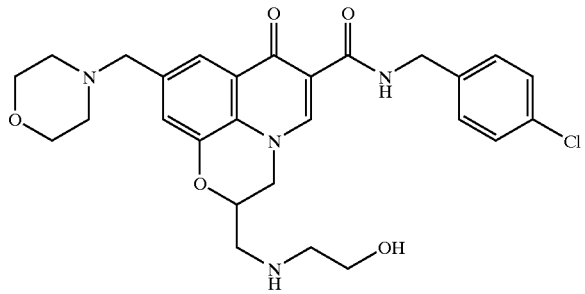

Following the procedure in Example 2, the titled compound is obtained.

$^1$H NMR (CDCl$_3$+CD$_3$OD) δ2.47, 2.85, 3.07, 3.60, 3.71, 4.24, 4.45, 4.63, 7.31, 7.38, 7.92, 8.63, 10.59. TLC R$_f$ 0.15 (6% methanolic ammonia in dichloromethane). IR (drift) 1653, 1626, 1607, 1580, 1557, 1502, 1414, 1348, 1293, 1281, 1273, 1224, 1116, 869, 807 cm$^{-1}$ HRMS (FAB) calcd for C$_{27}$H$_{31}$ClN$_4$O$_5$+H$_1$ 527.2061, found 527.2067 Anal. Calcd for C$_{27}$H$_{31}$ClN$_4$O$_5$: C, 61.53; H, 5.93; N, 10.63; Cl, 6.73; found (av): C, 61.15; H, 5.98; N, 10.64.

Example 8

N-(4-Chlorobenzyl)-9-(4-morpholinylmethyl)-7-oxo-2-(1-piperidinylmethyl)-2,3-dihydro-7H-[1,4]oxazino[2,3,4-ij]quinoline-6-carboxamide (Formula A-11 of Chart

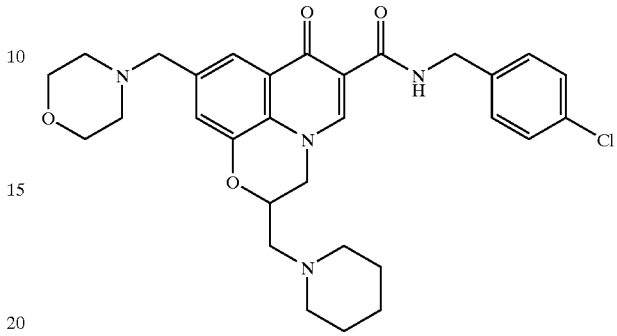

Following the procedure in Example 2, the titled compound is obtained as a solid, mp 213–215° C. $^1$H NMR (CDCl$_3$) δ1.46, 1.60, 2.5, 2.63, 2.81, 3.57, 3.70, 4.13, 4.39, 4.46, 4.64, 7.30, 7.34, 7.92, 8.66, 10.46.

TLC R$_f$ 0.25 (5% methanol in dichloromethane). IR (drift) 2931, 1653, 1607, 1572, 1552, 1500, 1411, 1349, 1330, 1284, 1225, 1113, 1087, 810, 800 cm$^{-1}$ HRMS (FAB) calcd for C$_{30}$H$_{35}$ClN$_4$O$_4$+H$_1$ 551.2425, found 551.2435 Anal. Calcd for C$_{30}$H$_{35}$ClN$_4$O$_4$: C, 65.39; H, 6.40; N, 10.17; Cl, 6.43; found: C, 65.34; H, 6.46; N, 10.12.

Example 9

2-{[bis(2-Hydroxyethyl)amino]methyl}-N-(4-chlorobenzyl)-9-(4-morpholinylmethyl)-7-oxo-2,3-dihydro-7H-[1,4]oxazino[2,3,4-ij]quinoline-6-carboxamide (Formula A-11 of Chart A)

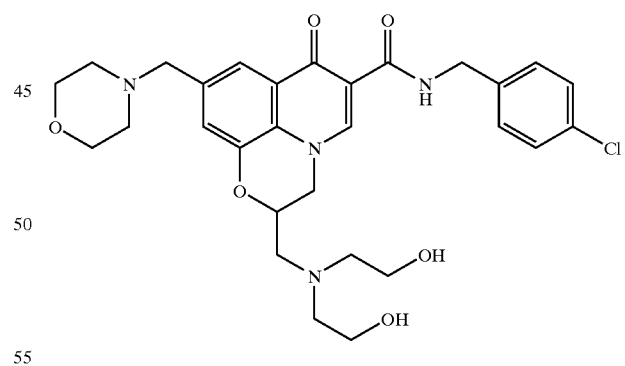

Following the procedure in Example 2, the titled compound is obtained.

$^1$H NMR (CDCl$_3$) δ2.44, 2.7, 2.97, 3.54, 3.58, 3.69, 4.24, 4.3, 4.5, 4.55, 7.27, 7.28, 7.86, 8.59, 10.51. TLC R$_f$ 0.28 (10% methanol in dichloromethane). IR (drift) 2953, 2843, 2810, 1660, 1608, 1552, 1500, 1411, 1355, 1329, 1284, 1113, 1085, 808, 799 cm$^{-1}$ HRMS (FAB) calcd for C$_{29}$H$_{35}$ClN$_4$O$_6$+H$_1$ 571.2323, found 571.2328 Anal. Calcd for C$_{29}$H$_{35}$ClN$_4$O$_6$: C, 60.99; H, 6.18; N, 9.81; Cl, 6.21; found: C, 60.67; H, 6.24; N, 9.68.

Example 10

N-(4-Chlorobenzyl)-9-(4-morpholinylmethyl)-7-oxo-2-{[(2-pyridinylmethyl)amino]methyl}-2,3-dihydro-7H-[1,4]oxazino[2,3,4-ij]quinoline-6-carboxamide (Formula A-11 of Chart A)

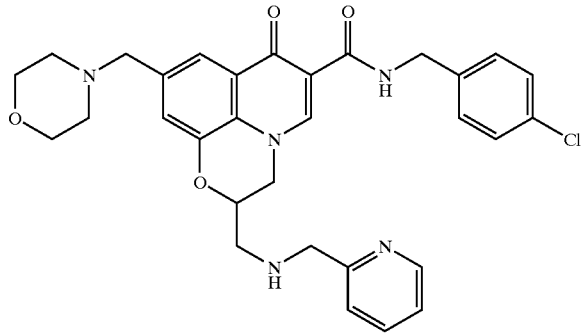

Following the procedure in Example 2, the titled compound is obtained.

$^1$H NMR (CDCl$_3$) δ2.48, 3.13, 3.60, 3.72, 4.02, 4.30, 4.48, 4.63, 7.21, 7.29, 7.33, 7.40, 7.68, 7.93, 8.58, 8.64, 10.44. TLC R$_f$ 0.51 (7% methanolic ammonia in dichloromethane). IR (drift) 1654, 1626, 1607, 1554, 1500, 1453, 1412, 1348, 1330, 1282, 1223, 1113, 810, 801, 760 cm$^{-1}$ HRMS (FAB) calcd for C$_{31}$H$_{32}$CLN$_5$O$_4$+H$_1$ 574.2221, found 574.2233 Anal. Calcd for C$_{31}$H$_{32}$ClN$_5$O$_4$: C, 64.86; H, 5.62; N, 12.20; Cl, 6.18; found: C, 64.66; H, 5.62; N, 12.05.

Example 11

N-(4-Chlorobenzyl)-9-(4-morpholinylmethyl)-7-oxo-2-{[(3-pyridinylmethyl)amino]methyl}-2,3-dihydro-7H-[1,4]oxazino[2,3,4-ij]quinoline-6-carboxamide (Formula A-11 of Chart A)

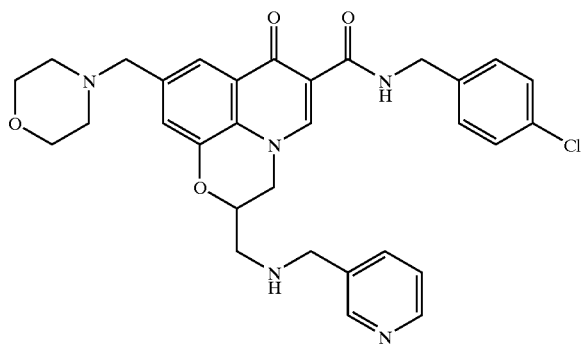

Following the procedure in Example 2, the titled compound is obtained.

$^1$H NMR (CDCl$_3$) δ2.46, 3.06, 3.08, 3.59, 3.71, 3.91, 4.27, 4.43, 4.63, 7.30, 7.36, 7.71, 7.93, 8.54, 8.60, 8.64, 10.44. TLC R$_f$ 0.36 (6% methanolic ammonia in dichloromethane). HRMS (FAB) calcd for C$_{31}$H$_{32}$CLN$_5$O$_4$+H$_1$ 574.2221, found 574.2221 Anal. Calcd for C$_{31}$H$_{32}$ClN$_5$O$_4$: C, 64.86; H, 5.62; N, 12.20; Cl, 6.18; found: C, 64.65; H, 5.68; N, 12.07.

Example 12

N-(4-Chlorobenzyl)-9-(4-morpholinylmethyl)-7-oxo-2-{[(4-pyridinylmethyl)amino]methyl}-2,3-dihydro-7H-[1,4]oxazino[2,3,4-ij]quinoline-6-carboxamide (Formula A-11 of Chart A)

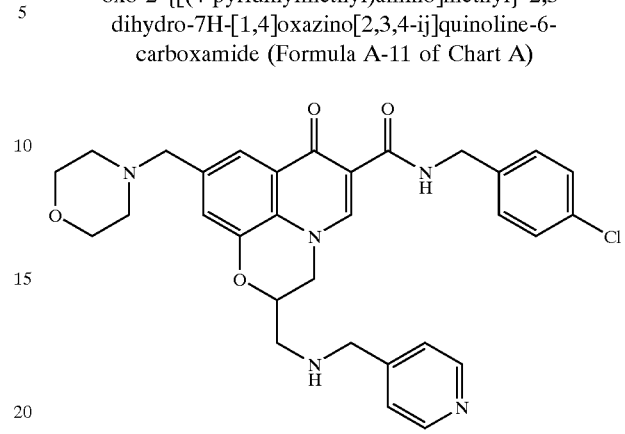

Following the procedure in Example 2, the titled compound is obtained as a solid, mp 164–167° C.

$^1$H NMR (CDCl$_3$) δ2.47, 3.04, 3.10, 3.59, 3.71, 3.92, 4.3, 4.44, 4.63, 7.30, 7.37, 7.94, 8.57, 8.65, 10.44. TLC R$_f$ 0.40 (6% methanolic ammonia in dichloromethane). HRMS (FAB) calcd for C$_{31}$H$_{32}$CLN$_5$O$_4$+H$_1$ 574.2221, found 574.2216 Anal. Calcd for C$_{31}$H$_{32}$ClN$_5$O$_4$: C, 64.86; H, 5.62; N, 12.20; Cl, 6.18; found: C, 64.17; H, 5.70; N, 12.07.

Example 13

N-(4-Chlorobenzyl)-2-(1H-imidazol-1-ylmethyl)-9-(4-morpholinylmethyl)-7-oxo-2,3-dihydro-7H-[1,4]oxazino[2,3,4-ij]quinoline-6-carboxamide (Formula A-11 of Chart A)

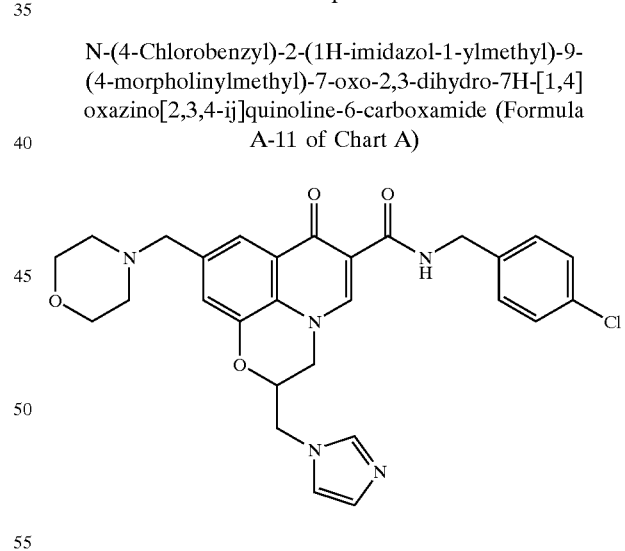

Following the procedure in Example 2, the titled compound is obtained as a solid, mp 217–219° C. (d).

$^1$H NMR (CDCl$_3$+CD$_3$OD) δ2.49, 3.62, 3.73, 3.97, 4.29, 4.40, 4.44, 4.58, 4.61, 7.10, 7.15, 7.30, 7.42, 7.72, 7.94, 8.59, 10.44. TLC R$_f$ 0.30 (5% methanol in dichloromethane). IR (drift) 2916, 2804, 1656, 1608, 1570, 1550, 1500, 1411, 1347, 1295, 1280, 1231, 1223, 1110, 800 cm$^{-1}$ HRMS (FAB) calcd for C$_{28}$H$_{28}$CLN$_5$O$_4$+H$_1$ 534.1908, found 534.1907 Anal. Calcd for C$_{28}$H$_{28}$ClN$_5$O$_4$: C, 62.98; H, 5.28; N, 13.11; Cl, 6.64; found: C, 62.65; H, 5.30; N, 13.21.

Example 14

N-(4-Chlorobenzyl)-2-[(methylsulfanyl)methyl]-9-(4-morpholinylmethyl)-7-oxo-2,3-dihydro-7H-[1,4]oxazino[2,3,4-ij]quinoline-6-carboxamide (Formula A-11 of Chart A)

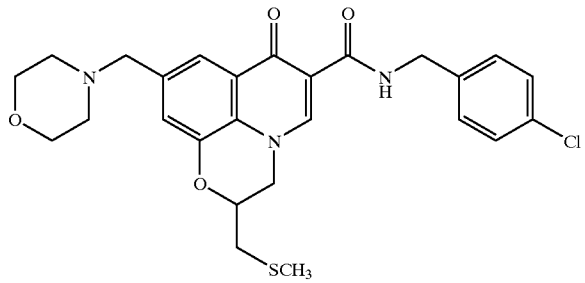

A mixture of 112 mg of the product of Preparation 8 and 112 mg of sodium methanethiolate in 0.5 mL of DMF is stirred at ambient temperature for 18 h, then partitioned between water and chloroform. The aqueous layer is extracted with two additional portions of chloroform, and the combined organic phases dried ($MgSO_4$) and concentrated under reduced pressure. Flash chromatography of the residue on silica using 1–2% methanol in dichloromethane provides 72.5 mg of the title compound as a yellow solid. Recrystallization from acetonitrile gives a white solid, mp 190–191° C.

$^1$H NMR ($CDCl_3$) δ2.26, 2.46, 2.83, 3.01, 3.58, 3.70, 4.21, 4.48, 4.64, 7.29, 7.36, 7.94, 8.66, 10.43. TLC $R_f$ 0.45 (5% methanol in dichloromethane). HRMS (FAB) calcd for $C_{26}H_{28}ClN_3O_4S+H_1$ 514.1567, found 514.1568. Anal. Calcd for $C_{26}H_{28}ClN_3O_4S$: C, 60.75; H, 5.49; N, 8.17; Cl, 6.90; S, 6.24; found: C, 60.60; H, 5.52; N, 8.12; Cl 6.85; S, 6.15.

Example 15

2-[(tert-Butylsulfanyl)methyl]-N-(4-chlorobenzyl)-9-(4-morpholinylmethyl)-7-oxo-2,3-dihydro-7H-[1,4]oxazino[2,3,4-ij]quinoline-6-carboxamide (Formula A-11 of Chart A)

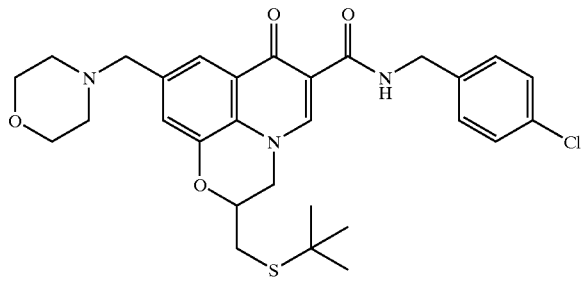

Following the procedure in Example 14, the titled compound is obtained as a solid, mp 198–201° C. $^1$H NMR ($CDCl_3$) δ1.37, 2.45, 2.81, 3.06, 3.57, 3.69, 4.13, 4.43, 4.63, 7.29, 7.35, 7.92, 8.64, 10.42. TLC $R_f$ 0.33 (3% methanol in dichloromethane). HRMS (FAB) calcd for $C_{29}H_{34}ClN_3O_4S+H_1$ 556.2037, found 556.2052 Anal. Calcd for $C_{29}H_{34}ClN_3O_4S$: C, 62.63; H, 6.16; N, 7.56; Cl, 6.38; S, 5.76; found: C, 62.46; H, 6.24; N, 7.50; Cl, 6.34; S, 5.74.

Example 16

N-(4-Chlorobenzyl)-2-{[(2-hydroxyethyl)sulfanyl]methyl}-9-(4-morpholinylmethyl)-7-oxo-2,3-dihydro-7H-[1,4]oxazino[2,3,4-ij]quinoline-6-carboxamide (Formula A-11 of Chart A)

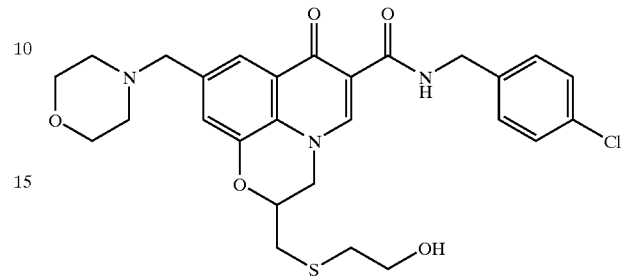

Following the procedure in Example 14, the titled compound is obtained.

$^1$H NMR ($CDCl_3+CD_3OD$) δ2.48, 2.85, 2.93, 3.04, 3.60, 3.72, 3.80, 4.24, 4.55, 4.63, 7.31, 7.38, 7.92, 8.63, 10.51. TLC $R_f$ 0.40 (10% methanol in dichloromethane). IR (drift) 1651, 1607, 1578, 1555, 1500, 1413, 1347, 1329, 1281, 1272, 1232, 1113, 1014, 869, 807 cm$^{-1}$ HRMS (FAB) calcd for $C_{27}H_{30}ClN_3O_5S+H_1$ 544.1673, found 544.1672 Anal. Calcd for $C_{27}H_{30}ClN_3O_5S$: C, 59.60; H, 5.56; N, 7.72; Cl, 6.52; S, 5.89; found (av): C, 59.15; H, 5.55; N, 7.55.

Example 17

N-(4-Chlorobenzyl)-2-{[(1-methyl-1H-imidazol-2-yl)sulfanyl]methyl}-9-(4-morpholinylmethyl-7-oxo-2,3-dihydro-7H-[1,4]oxazino[2,3,4-ij]quinoline-6-carboxamide (Formula A-11 of Chart A)

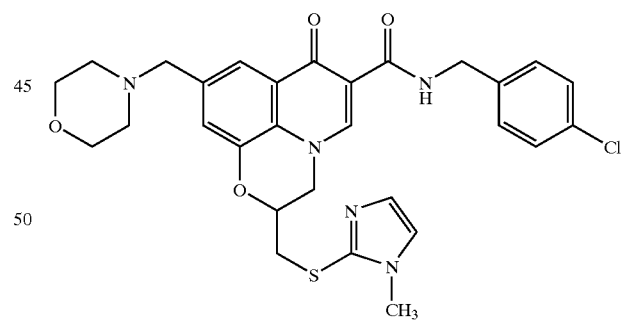

Following the procedure in Example 14, the titled compound is obtained as a solid, $^1$H NMR ($CDCl_3$) δ2.45, 3.39, 3.55, 3.56, 3.63, 3.69, 4.27, 4.50, 4.63, 4.72, 6.92, 6.95, 7.29, 7.35, 7.92, 8.64, 10.42. TLC $R_f$ 0.22 (5% methanol in dichloromethane). IR (drift) 1655, 1626, 1607, 1578, 1560, 1499, 1457, 1414, 1357, 1347, 1280, 1273, 1117, 869, 807 cm$^{-1}$ HRMS (FAB) calcd for $C_{29}H_{30}ClN_5O_4S+H_1$ 580.1785, found 580.1776 Anal. Calcd for $C_{29}H_{30}ClN_5O_4S$: C, 60.04; H, 5.21; N, 12.07; Cl, 6.11; S, 5.53; found: C, 59.93; H, 5.15; N, 12.03.

Example 18

Methyl ({[6-{[(4-chlorobenzyl)amino]carbonyl}-9-(4-morpholinylmethyl)-7-oxo-2,3-dihydro-7H-[1,4]oxazino[2,3,4-ij]quinolin-2-yl]methyl}sulfanyl)acetate (Formula A-11 of Chart A)

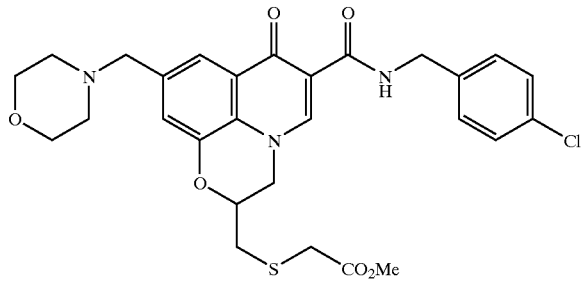

Following the procedure described in Example 14, the titled compound is obtained as a solid, mp 182.5–183.0° C.

$^1$H NMR (CDCl$_3$) δ2.45, 3.03, 3.16, 3.40, 3.58, 3.70, 3.75, 4.25, 4.41, 4.56, 4.63, 7.30, 7.36, 7.94, 8.66, 10.42. TLC R$_f$ 0.42 (5% methanol in dichloromethane). IR (drift) 1735, 1653, 1607, 1553, 1501, 1411, 1352, 1329, 1281, 1226, 1141, 1113, 1008, 810, 802 cm$^{-1}$ HRMS (FAB) calcd for C$_{28}$H$_{30}$ClN$_3$O$_6$S+H$_1$ 572.1622, found 572.1624 Anal. Calcd for C$_{28}$H$_{30}$ClN$_3$O$_6$S: C, 58.79; H, 5.28; N, 7.34; Cl, 6.20; S, 5.60; found: C, 58.67; H, 5.26; N, 7.33.

Example 19

N-(4-Chlorobenzyl)-2-{[(2,3-dihydroxypropyl)sulfanyl]methyl}-9-(4-morpholinylmethyl)-7-oxo-2,3-dihydro-7H-[1,4]oxazino[2,3,4-ij]quinoline-6-carboxamide (Formula A-11 of Chart A)

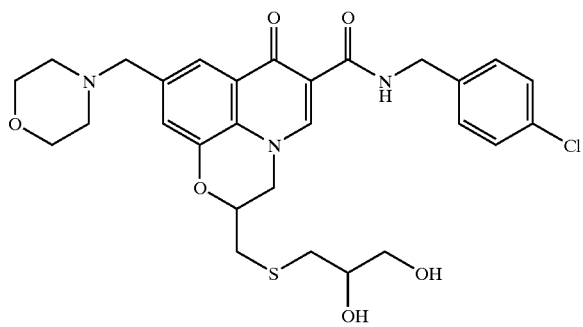

Following the procedure described in Example 14, the titled compound is obtained.

$^1$H NMR (CDCl$_3$) δ2.45, 2.8, 3.06, 3.54, 3.58, 3.68, 3.83, 4.16, 4.46, 4.58, 7.27, 7.32, 7.90, 8.62, 10.52. TLC R$_f$ 0.32 (10% methanol in dichloromethane). MS (ES+) m/z 574.4

Preparation 9: Ethyl 2-(R or S)-[(acetyloxy)methyl]-9-(4-morpholinylmethyl)-7-oxo-2,3-dihydro-7H-[1,4]oxazino[2,3,4-ij]quinoline-6-carboxylate (Formula B-1 of Chart B)

Racemic acetate (3.2 g of the product of Preparation 7) is resolved using a 5×50 cm Chiralcel OD column at 30° C. with absolute ethanol as the mobile phase at a flow rate of 75 mL/min with UV detection at 326 nm. 1 g injections are made in 35 mL of 1:4 CHCl$_3$/EtOH. Following HPLC resolution, the compounds are purified by silica gel chromatography using 4% methanol in dichloromethane. Of the first eluting isomer, there is obtained 1.228 g; of the second peak, there is obtained 1.47 g. Analytical samples are prepared by recrystallization from ethyl acetate-hexane.

For Isomer 1

Mp 142.5–144.0° C.

$^1$H NMR (CDCl$_3$) δ1.39, 2.16, 2.44, 3.54, 3.70, 4.17, 4.27, 4.35, 4.45, 4.49, 4.59, 7.32, 7.91, 8.29. TLC R$_f$ 0.38 (8% methanol in dichloromethane). IR (drift) 1745, 1682, 1637, 1609, 1556, 1505, 1324, 1292, 1273, 1237, 1222, 1181, 1113, 879, 799 cm$^{-1}$ HRMS (FAB) calcd for C$_{22}$H$_{26}$N$_2$O$_7$+H$_1$ 431.1818, found 431.1821 Anal. Calcd for C$_{22}$H$_{26}$N$_2$O$_7$: C, 61.39; H, 6.09; N, 6.51; found: C, 61.24; H, 6.13; N, 6.49.

For Isomer 2

Mp 143.0–144.5° C.

$^1$H NMR (CDCl$_3$) δ1.39, 2.16, 2.44, 3.54, 3.70, 4.17, 4.27, 4.35, 4.45, 4.49, 4.59, 7.31, 7.91, 8.28. TLC R$_f$ 0.38 (8% methanol in dichloromethane). IR (drift) 1745, 1726, 1682, 1637, 1609, 1556, 1505, 1324, 1291, 1273, 1237, 1223, 1181, 1113, 799 cm$^{-1}$ HRMS (FAB) calcd for C$_{22}$H$_{26}$N$_2$O$_7$+H$_1$ 431.1818, found 431.1831 Anal. Calcd for C$_{22}$H$_{26}$N$_2$O$_7$: C, 61.39; H, 6.09; N, 6.51; found: C, 61.29; H, 6.12; N, 6.50.

Example 20

N-(4-Chlorobenzyl)-2-(R or S)-(hydroxymethyl)-9-(4-morpholinylmethyl)-7-oxo-2,3-dihydro-7H-[1,4]oxazino[2,3,4-ij]quinoline-6-carboxamide (Formula B-2 of Chart B, isomer 1)

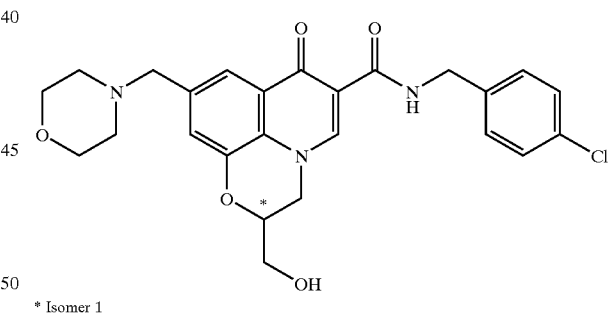

\* Isomer 1

A mixture of 1.20 g of the product of Preparation 9 (isomer 1) and 2.4 g of p-chlorobenzylamine is heated under argon at 150° C. for 18 h, then excess amine is distilled off in vacuo. Flash chromatography of the residue on silica using 5–8% methanol in dichloromethane provides 1.27 g of the title amide as a tan solid. The solid is triturated well with ether, filtered, washed well with ether, and dried under vacuum to afford 1.22 g of the title compound as a solid.

$^1$H NMR (CDCl$_3$+CD$_3$OD) δ2.49, 3.62, 3.73, 3.95, 4.4, 4.64, 7.31, 7.40, 7.91, 8.65, 10.63. TLC R$_f$ 0.30 (10% methanol in dichloromethane).

Example 21

N-(4-Chlorobenzyl)-2-(R or S)-(hydroxymethyl)-9-(4-morpholinylmethyl)-7-oxo-2,3-dihydro-7H-[1,4]oxazino[2,3,4-ij]quinoline-6-carboxamide (Formula B-2 of Chart B, isomer 2)

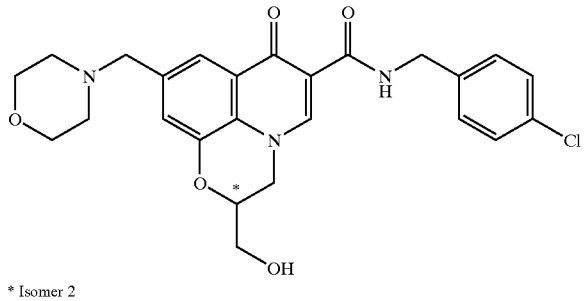

* Isomer 2

According to the procedure described for isomer 1 in Example 20, 1.41 g of the product of Preparation 9 (isomer 2) is converted to 1.43 g of the corresponding amide.

$^1$H NMR (CDCl$_3$+CD$_3$OD) δ2.48, 3.61, 3.72, 3.95, 4.4, 4.64, 7.31, 7.38, 7., 8.64 (s, 1H), 10.62. TLC R$_f$ 0.30 (10% methanol in dichloromethane).

Example 22

N-(4-chlorobenzyl)-9-(4-morpholinylmethyl)-7-oxo-2-(R or S)-{[(3-pyridinylmethyl)amino]methyl}-2,3-dihydro-7H-[1,4]oxazino[2,3,4-ij]quinoline-6-carboxamide Isomer 1 (Formula B-3 of Chart B, where R$_1$=3-pyridinylmethyl, R$_2$=H, and X=N)

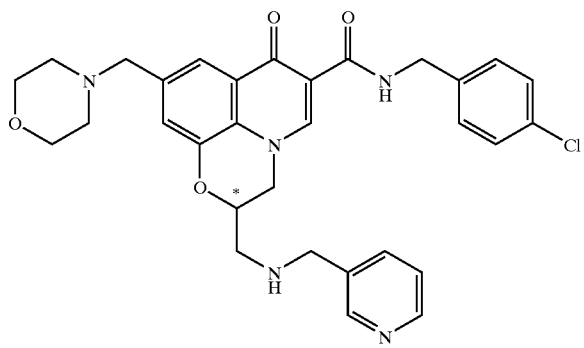

* Isomer 1

The compound is prepared using the procedures described in Preparation 8 and Example 2, using resolved isomer 1 of Example 20 and proceeding through the mesylate.

$^1$H NMR (CDCl$_3$) δ2.45, 3.05, 3.09, 3.57, 3.70, 3.91, 4.27, 4.43, 4.63, 7.29, 7.35, 7.70, 7.93, 8.54, 8.60, 8.64, 10.44. TLC R$_f$ 0.40 (6% methanolic ammonia in dichloromethane). MS (ES+) m/z 574.2.

Example 23

N-(4-Chlorobenzyl)-9-(4-morpholinylmethyl)-7-oxo-2-(R or S)-{[3-pyridinylmethyl)amino]methyl}-2,3-dihydro-7H-[1,4]oxazino[2,3,4-ij]quinoline-6-carboxamide Isomer 2 (Formula B-3 of Chart B, where R$_1$=3-pyridinylmethyl, R$_2$=H, and X=N)

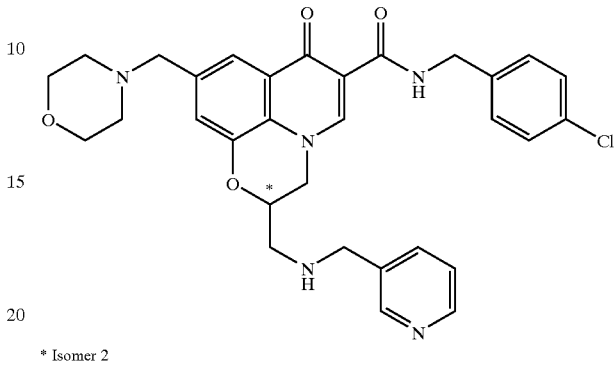

* Isomer 2

The compound is prepared using the procedures described in Preparation 8 and Example 2, using resolved isomer 2 of Example 21 and proceeding through the mesylate.

$^1$H NMR (CDCl$_3$) δ2.45, 3.05, 3.09, 3.57, 3.70, 3.91, 4.27, 4.43, 4.63, 7.29, 7.35, 7.70, 7.93, 8.54, 8.60, 8.64, 10.44. TLC R$_f$ 0.40 (6% methanolic ammonia in dichloromethane). MS (ES+) m/z 574.3.

Example 24

[6-{[(4-Chlorobenzyl)amino]carbonyl}-9-(4-morpholinylmethyl)-7-oxo-2,3-dihydro-7H-[1,4]oxazino[2,3,4-ij]quinolin-2-yl]methyl acetate (Formula C-1 of Chart C)

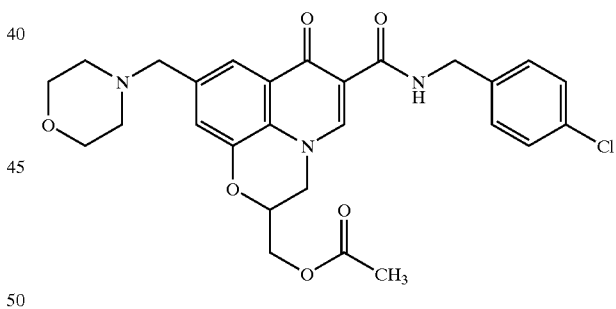

A mixture of 97 mg of the product of Example 1, 0.19 mL of acetic anhydride, and 1 mL of chloroform is stirred for 18 h, then concentrated under reduced pressure with toluene azeotrope to remove acetic acid. Flash chromatography of the residue on silica using 2–3% methanol in dichloromethane provides 106.5 mg of the title compound as a white solid. An analytical sample is recrystallized from acetonitrile, giving white solid, mp 215–218° C.

$^1$H NMR (CDCl3) δ2.16, 2.46, 3.59, 3.71, 4.22, 4.33, 4.4, 4.56, 4.63, 7.30, 7.40, 7.95, 8.65, 10.41. TLC R$_f$ 0.39 (5% methanol in dichloromethane). IR (drift) 1745, 1652, 1626, 1607, 1558, 1502, 1413, 1347, 1280, 1274, 1223, 1119, 1094, 1043, 808 cm$^{-1}$ HRMS (FAB) calcd for C$_{27}$H$_{28}$ClN$_3$O$_6$+H$_1$ 526.1744, found 526.1741 Anal. Calcd for C$_{27}$H$_{28}$ClN$_3$O$_6$: C, 61.65; H, 5.36; N, 7.99; Cl, 6.74; found: C, 61.56; H, 5.44; N, 7.96.

Example 25

2-[(8-{[6-{[(4-Chlorobenzyl)amino]carbonyl}-9-(4-morpholinylmethyl)-7-oxo-2,3-dihydro-7H-[1,4]oxazino[2,3,4-ij]quinolin-2-yl]methoxy}-8-oxooctanoyl)(methyl)amino]ethanesulfonic acid sodium salt (Formula C2 of Chart C)

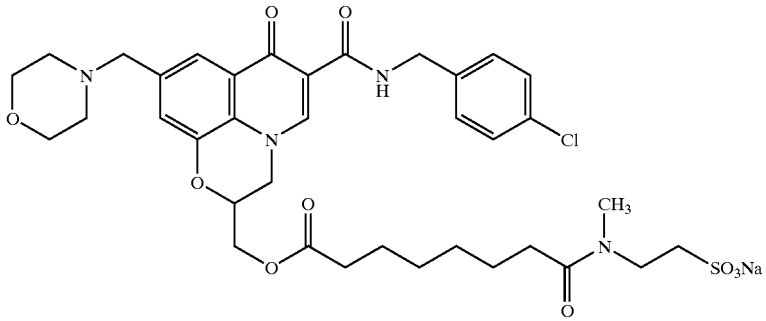

To a mixture of 97 mg of the product of Example 1 and 27 mg of DMAP in 0.5 mL of dry DMF is added 0.46 mL of a 0.65 M solution of suleptanic acid triethylammonium salt, which is 8-[methyl(2-sulfoethyl)amino]-8-oxooctanoic acid triethylammonium salt, in acetonitrile, followed by 38 μL of diisopropylcarbodiimide. After 5 days, volatile components are removed under vacuum, and the residue chromatographed on silica using 3–6% methanolic ammonia in dichloromethane to afford the triethylammonium salt of the product. This is dissolved in n-butanol and chloroform, and the solution stirred with an equal volume of saturated aqueous sodium sulfate solution. The aqueous phase is extracted with two additional portions of chloroform, and the combined organic phases filtered through anhydrous sodium sulfate and concentrated under reduced pressure to provide 92.5 mg of the title compound as a solid.

$^1$H NMR (CDCl3) δ1.3, 1.6, 2.4, 3.1, 3.6, 3.7, 4.2–4.7, 7.3, 7.9, 8.68, 10.45 ppm. TLC R$_f$ 0.21 (10% methanol and 5% methanolic ammonia in dichloromethane). MS (ES+) m/z 761.3. MS (FAB) m/z 761 (MH$^+$), 97, 95, 85, 83, 81, 69, 67, 55, 43, 23 HRMS (FAB) calcd for C$_{36}$H$_{45}$CLN$_4$O$_{10}$S+H$_1$ 761.2623, found 761.2643.

Example 26

[6-{[(4-Chlorobenzyl)amino]carbonyl}-9-(4-morpholinylmethyl)-7-oxo-2,3-dihydro-7H-[1,4]oxazino[2,3,4-ij]quinolin-2-yl]methyl dimethyl phosphate (Formula C-3 of Chart C)

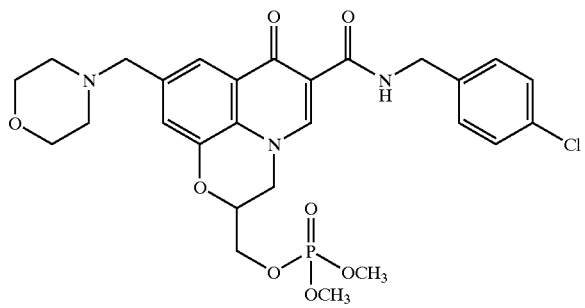

To a stirred mixture of 97 mg of the product of Example 1 in 1 mL of chloroform is added 0.19 mL of phosphorus oxychloride. After the mixture is stirred for 18 h, 15 mL of methanol is added, and the solution is allowed to stand for 3 days. The solution is then concentrated under reduced pressure, and the residue partitioned between chloroform and aqueous NaHCO$_3$. The aqueous phase is extracted with additional chloroform, and the combined organic phases are dried (Na$_2$SO$_4$) and concentrated under reduced pressure. Flash chromatography of the residue on silica using 4% methanol in dichloromethane provides 56.0 mg of the title compound as a solid.

$^1$H NMR (CDCl3) δ2.46, 3.58, 3.71, 3.82, 3.86, 4.4, 4.58, 4.63, 7.29, 7.38, 7.95, 8.67, 10.38. TLC R$_f$ 0.25 (5% methanol in dichloromethane). MS (ES+) m/z 592.2.

Preparation 10: 7-(4-Morpholinylcarbonyl)-2-phenyl-2H-1,4-benzoxazin-3(4H)-one (Formula D-1 of Chart D)

A mixture of 1.11 g of the product of Preparation 2, 760 mg of potassium carbonate, and 0.86 mL of methyl α-bromophenylacetate in 10 mL of acetone is refluxed for 18 h, then cooled and partitioned between water and dichloromethane. The aqueous phase is extracted with additional dichloromethane, and the combined organic phases dried (Na$_2$SO$_4$) and concentrated under reduced pressure. Flash chromatography of the residue on silica using 1.5–3% methanol in dichloromethane provides 1.27 g of the title compound as a solid.

$^1$H NMR (CDCl$_3$) δ3.68, 5.70, 6.85, 7.01, 7.09, 7.33, 7.43, 9.82. TLC R$_f$0.20 (3% methanol in dichloromethane). MS (ES+) m/z 339.2

Preparation 11: 7-(4-Morpholinylmethyl)-2-phenyl-3,4-dihydro-2H-1,4-benzoxazine (Formula D-2 of Chart D)

To a stirred, cooled (0° C.) solution of 1.27 g of the product of Preparation 10 in 15 mL of dry THF under argon is added in portions 290 mg of LAH. The mixture is allowed to warm to room temperature, stirred for 18 h, and then quenched with 0.29 mL of water, 0.29 mL of 3N NaOH, and 0.85 mL of water. The mixture is filtered and the solid washed well with dichloromethane, and the filtrate is concentrated under reduced pressure. Flash chromatography of the residue on silica using 3% methanol in dichloromethane provides 1.00 g of the title compound as a solid.

$^1$H NMR (CDCl$_3$) δ2.43, 3.32, 3.37, 3.46, 3.69, 3.92, 5.05, 6.60, 6.75, 6.89, 7.4. TLC R$_f$ 0.33 (5% methanol in dichloromethane).

Preparation 12: Diethyl 2-{[7-(4-morpholinylmethyl)-2-phenyl-2,3-dihydro-4H-1,4-benzoxazin-4-yl]methylene}malonate (Formula D-3 of Chart D)

A mixture of 1.00 g of the product of Preparation 11 and 0.80 g of diethyl ethoxymethylenemalonate is heated under argon at 140° C. for 1 h, then under vacuum for 20 m. The mixture is cooled and chromatographed on silica gel using 2–3% methanol in dichloromethane to provide 1.32 g of the title compound as a solid.

$^1$H NMR (CDCl$_3$) δ1.19, 1.31, 2.46, 3.46, 3.56, 3.64, 3.72, 4.16, 4.25, 5.05, 6.97, 7.04, 7.07, 7.4, 8.04. TLC R$_f$ 0.38 (5% methanol in dichloromethane). MS (ES+) m/z 481.3.

Preparation 13: Ethyl 9-(4-morpholinylmethyl)-7-oxo-2-phenyl-2,3-dihydro-7H-[1,4]oxazino[2,3,4-ij]quinoline-6-carboxylate (Formula D-4 of Chart D)

An intimate mixture of 1.32 g of the product of Preparation 12, 7.0 g of polyphosphoric acid, and 4 mL of toluene is heated at 90° C. for 18 h, then transferred using a spatula to a stirred slurry of 8 g of NaHCO$_3$ in 100 mL of water. The mixture is extracted with three portions of dichloromethane, and the combined organic phases dried (Na$_2$SO$_4$) and concentrated under reduced pressure. Flash chromatography of the residue on silica using 3% methanol in dichloromethane affords 960 mg of the title compound as an orange solid. An analytical sample is recrystallized from acetonitrile, giving white solid, mp 213–215° C.

$^1$H NMR (CDCl$_3$) δ1.40, 2.47, 3.59, 3.70, 4.24, 4.30, 4.37, 5.31, 7.4–7.5, 7.98, 8.31. TLC R$_f$ 0.27 (5% methanol in dichloromethane). HRMS (FAB) calcd for C$_{25}$H$_{26}$N$_2$O$_5$+H$_1$ 435.1920, found 435.1923 Anal. Calcd for C$_{25}$H$_{26}$N$_2$O$_5$: C, 69.11; H, 6.03; N, 6.45; found: C, 69.06; H, 6.13; N, 6.54.

Example 27

N-(4-Chlorobenzyl)-9-(4-morpholinylmethyl)-7-oxo-2-phenyl-2,3-dihydro-7H-[1,4]oxazino[2,3,4-ij]quinoline-6-carboxamide (Formula D-5 of Chart D)

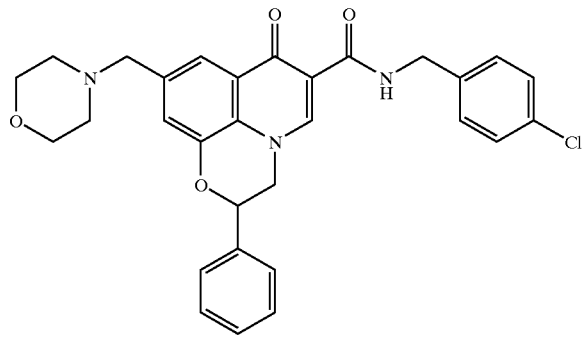

A mixture of 219 mg of the product of Preparation 13 and 0.5 g of p-chlorobenzylamine is heated at 150° C. under nitrogen for 18 h, after which time excess amine is removed in vacuo. Flash chromatography of the residue on silica using 1.5–3% methanol in dichloromethane provides 251 mg of the title compound.

$^1$H NMR (CDCl$_3$) δ2.48, 3.62, 3.71, 4.30, 4.40, 4.61, 5.30, 7.29, 7.49, 7.98, 8.68, 10.45. TLC R$_f$ 0.28 (3% methanol in dichloromethane). MS (ES+) m/z 530.3.

Preparation 14: 2,2-Difluoro-7-(4-morpholinylcarbonyl)-2H-1,4-benzoxazin-3(4H)-one (Formula E-1 of Chart E)

To a cold (0° C.), stirred slurry of 1.11 g of the product of Preparation 2 in 5 mL of dry DMF under argon is added in portions 200 mg of sodium hydride (60% oil dispersion). The mixture is stirred for 20 m at 0° C., then 0.63 mL of ethyl bromodifluoroacetate is added dropwise. After 15 m, the mixture is allowed to warm to room temperature, and after 1 h is heated to 90° C. After 3 h, the mixture is cooled and partitioned between ethyl acetate and water, and the aqueous phase is extracted with two additional portions of ethyl acetate. The combined organic phases are washed with water and brine, dried (MgSO$_4$), and concentrated under reduced pressure. Flash chromatography of the residue on silica using 2.5–3.5% methanol in dichloromethane affords 1.05 g of yellow solid. This is triturated well with 10 mL of 1:1 ethyl acetate-hexane and the solid filtered, washed with 1:1 ethyl acetate-hexane, and dried under vacuum to provide 824 mg of the title compound as an off-white solid. The solid is further purified by recrystallization from ethyl acetate-hexane, mp 214–217° C.

$^1$H NMR (CDCl$_3$+CD$_3$OD) δ3.74, 7.09, 7.22, 7.25. TLC R$_f$ 0.27 (5% methanol in dichloromethane). IR (drift) 1739, 1617, 1586, 1464, 1433, 1288, 1265, 1256, 1228, 1217, 1117, 1111, 1070, 824, 758 cm$^{-1}$ HRMS (FAB) calcd for C$_{13}$H$_{12}$F$_2$N$_2$O$_4$+H$_1$ 299.0843, found 299.0836 Anal. Calcd for C$_{13}$H$_{12}$F$_2$N$_2$O$_4$: C, 52.35; H, 4.05; N, 9.39; found: C, 52.09; H, 4.07; N, 9.47.

Preparation 15: 2,2-Difluoro-7-(4-morpholinylmethyl)-3,4-dihydro-2H-1,4-benzoxazine (Formula E-2 of Chart E)

To a cold (0° C.), stirred solution of 805 mg of the product of Preparation 14 in 15 mL of dry THF, under argon, is added in portions 205 mg of LAH. The mixture is allowed to warm to room temperature and stirred overnight, then quenched cautiously with 0.2 mL of water, 0.2 mL of 3N NaOH, and 0.6 mL of water. Dichloromethane and Na$_2$SO$_4$ are added, and the mixture is filtered and the solid washed with dichloromethane. The filtrate is concentrated under reduced pressure, and the residue chromatographed on silica using 2% methanol in dichloromethane to afford 423 mg of the title compound as a solid.

$^1$H NMR (CDCl$_3$) δ2.41, 3.38, 3.50, 3.69, 4.02, 6.69, 6.88, 6.94. TLC R$_f$ 0.34 (5% methanol in dichloromethane). IR (drift) 3309, 1526, 1354, 1320, 1312, 1266, 1250, 1216, 1188, 1108, 999, 964, 885, 856, 793 cm$^{-1}$ HRMS (FAB) calcd for C$_{13}$H$_{16}$F$_2$N$_2$O$_2$+H$_1$ 271.1258, found 271.1264.

Preparation 16: Diethyl 2-{[2,2-difluoro-7-(4-morpholinylmethyl)-2,3-dihydro-4H-1,4-benzoxazin-4-yl]methylene}malonate (Formula E-3 of Chart E)

A mixture of 414 mg of the product of Preparation 15 and 870 mg of diethyl ethoxymethylenemalonate is heated under argon at 150° C. for 90 m, then cooled and chromatographed on silica using 2% methanol in dichloromethane to provide 739 mg of the title compound as a thick yellow oil.

$^1$H NMR (CDCl$_3$) δ1.31, 1.34, 2.44, 3.47, 3.71, 3.78, 4.26, 4.30, 7.1, 7.91. TLC R$_f$ 0.31 (3% methanol in dichloromethane). HRMS (FAB) calcd for C$_{21}$H$_{26}$F$_2$N$_2$O$_6$+H$_1$ 441.1837, found 441.1844.

Preparation 17: Ethyl 2,2-difluoro-9-(4-morpholinylmethyl)-7-oxo-2,3-dihydro-7H-[1,4]oxazino[2,3,4-ij]quinoline-6-carboxylate (Formula E-4 of Chart E)

An intimate mixture of 675 mg of the product of Preparation 15 and 4.0 g of polyphosphoric acid is heated at 90° C. under argon, with occasional mechanical stirring, for 90 m, then cooled and added to a stirred slurry of 5 g of NaHCO$_3$ in 50 mL of water. The mixture is extracted three times with dichloromethane, and the combined organic phases dried (MgSO$_4$) and concentrated under reduced pressure. Flash chromatography of the residue on silica using 2–3% methanol in dichloromethane provides 477 mg of the title compound. An analytical sample is recrystallized from ethyl acetate-hexane, giving the titled compound as crystals, mp176–177° C.

$^1$H NMR (CDCl$_3$) δ1.37, 2.45, 3.58, 3.71, 4.32, 4.56, 7.46, 8.02, 8.35. TLC R$_f$ 0.34 (5% methanol in dichloromethane). IR (drift) 1678, 1614, 1560, 1510, 1325, 1285, 1261, 1242, 1228, 1201, 1191, 1112, 943, 847, 809 cm$^{-1}$ HRMS (FAB) calcd for C$_{19}$H$_{20}$F$_2$N$_2$O$_5$+H$_1$ 395.1418, found 395.1421. Anal. Calcd for C$_{19}$H$_{20}$F$_2$N$_2$O$_5$: C, 57.87; H, 5.11; N, 7.10; found: C, 57.67; H, 5.16; N, 7.10.

Example 28

N-(4-Chlorobenzyl)-2,2-difluoro-9-(4-morpholinylmethyl)-7-oxo-2,3-dihydro-7H-[1,4]oxazino[2,3,4-ij]quinoline-6-carboxamide (Formula E-5 of Chart 5)

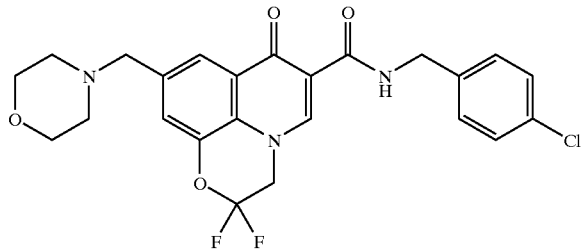

A mixture of 118 mg of the product of Preparation 17 and 0.21 g of p-chlorobenzylamine is heated at 160° C. for 18 h, then placed under vacuum to remove excess amine. Chromatography of the residue on silica using 2–3% methanol in dichloromethane affords 135.8 mg of product as a yellow solid. Recrystallization from acetonitrile provides 111 mg of the title compound as white needles, mp 213.5–216.5° C.

$^1$H NMR (CDCl$_3$) δ2.46, 3.61, 3.72, 4.57, 4.63, 7.29, 7.54, 8.08, 8.76, 10.26. TLC R$_f$ 0.25 (3% methanol in dichloromethane). IR (drift) 1658, 1611, 1582, 1562, 1508, 1493, 1327, 1285, 1258, 1243, 1229, 1192, 1126, 1116, 808 cm$^{-1}$ HRMS (FAB) calcd for C$_{24}$H$_{22}$ClF$_2$N$_3$O$_4$+H$_1$ 490.1345, found 490.1343 Anal. Calcd for C$_{24}$H$_{22}$ClF$_2$N$_3$O$_4$: C, 58.84; H, 4.53; N, 8.58; Cl, 7.24; found: C, 58.78; H, 4.56; N, 8.52.

Preparation 18: 2-[5-(4-Morpholinylcarbonyl)-2-nitrophenoxy]-1-phenylethanone (Formula F-1 of Chart F)

A mixture of 1.01 g of the product of Preparation 1, 800 mg of phenacyl bromide, 1.11 g of potassium carbonate, and 20 mg of tetrabutylammonium bisulfate in 4.0 mL of dichloromethane and 3 mL of water is stirred vigorously at room temperature for 18 h. The phases are then separated, and the aqueous phase extracted with one additional portion of dichloromethane. The combined organic phases are dried (Na$_2$SO$_4$) and concentrated under reduced pressure. Flash chromatography of the residue on silica using 50% ethyl acetate in dichloromethane affords 1.465 g of the title compound as a white solid. An analytical sample is prepared by recrystallization from ethyl acetate-hexane, giving white crystals, mp 171.5–173° C.

$^1$H NMR (CDCl$_3$) δ3.35, 3.6, 5.52, 6.97, 7.08, 7.53, 7.66, 7.90, 7.96. TLC R$_f$ 0.30 (50% ethyl acetate in dichloromethane). HRMS (FAB) calcd for C$_{19}$H$_{18}$N$_2$O$_6$+H$_1$ 371.1243, found 371.1241 Anal. Calcd for C$_{19}$H$_{18}$N$_2$O$_6$: C, 61.62; H, 4.90; N, 7.56; found: C, 61.52; H, 4.90; N, 7.51.

Preparation 19: 7-(4-morpholinylcarbonyl)-3-phenyl-2H-1,4-benzoxazine (Formula F-2 of Chart F)

To a solution of 3.13 g of stannous chloride dihydrate in 12 mL of ethanol is added 1.026 g of the product of Preparation 18, and the mixture is stirred and heated at 60° C. for 30 m. Dilute aqueous NaOH is added in sufficient quantity to dissolve the precipitate which initially forms, and the mixture is extracted thrice with dichloromethane. The combined organic phases are dried (Na$_2$SO$_4$) and concentrated under reduced pressure, and the residue chromatographed on silica using 50–75% ethyl acetate in dichloromethane to provide 622 mg of the title compound as a pale yellow crystalline solid. Recrystallization from ethyl acetate-hexane gives white needles, mp 175–177° C.

$^1$H NMR (CDCl$_3$) δ3.7, 5.09, 6.98, 7.05, 7.5, 7.94. TLC R$_f$ 0.32 (50% ethyl acetate in dichloromethane). IR 2856, 1633, 1568, 1458, 1432, 1280, 1244, 1114, 1025, 732, 691 cm$^{-1}$. HRMS (FAB) calcd for C$_{19}$H$_{18}$N$_2$O$_3$+NA$_1$ 345.1215, found 345.1212 Anal. Calcd for C$_{19}$H$_{18}$N$_2$O$_3$: C, 70.79; H, 5.63; N, 8.69; found: C, 70.63; H, 5.77; N, 8.57.

Preparation 20: 7-(4-Morpholinylcarbonyl)-3-phenyl-3,4-dihydro-2H-1,4-benzoxazine (Formula F-3 of Chart F)

A mixture of 586 mg of the product of Preparation 19 and 138 mg of sodium borohydride in 10 mL of ethanol is stirred at room temperature for 18 h, then added to 100 mL of stirred water. The resulting solid is filtered, washed with water, and dried under vacuum to give 401 mg of white solid. The aqueous phases are extracted thrice with dichloromethane, and the combined organic phases dried (Na$_2$SO$_4$) and concentrated under reduced pressure to provide an additional 203 mg of solid. The combined solids are chromatographed on silica using 50–75% ethyl acetate in dichloromethane to afford 510 mg of the title compound as a solid.

$^1$H NMR (CDCl$_3$) δ3.68, 3.98, 4.30, 4.52, 6.66, 6.93, 6.94, 7.4. TLC R$_f$ 0.32 (50% ethyl acetate in dichloromethane). IR 3306, 2856, 1612, 1456, 1430, 1303, 1284, 1243, 1114, 1022, 730, 701 cm$^{-1}$. MS (ES+) m/z 325.2.

Preparation 21: 7-(4-Morpholinylmethyl)-3-phenyl-3,4-dihydro-2H-1,4-benzoxazine (Formula F-4 of Chart F)

To a cold (0° C.), stirred solution of 576 mg of the product of Preparation 20 in 5.0 mL of dry THF is added in portions 135 mg of LAH. The mixture is allowed to warm to room temperature and stirred for 3 h, then quenched cautiously with 0.16 mL of water, 0.16 mL of 3N NaOH, and 0.48 mL of water. Dichloromethane and Na$_2$SO$_4$ are added, the mixture is filtered, and the solid washed with additional dichloromethane. The filtrates are concentrated under reduced pressure, and the residue flash chromatographed on silica using ethyl acetate and 3% methanol in ethyl acetate to afford 389 mg of white crystalline solid. An analytical sample is recrystallized from ethyl acetate-hexane to give the title compound as white crystals, mp 135.5–136.5° C.

$^1$H NMR (CDCl$_3$) δ2.44, 3.38, 3.70, 3.98, 4.0, 4.27, 4.49, 6.61, 6.75, 6.82, 7.4. TLC R$_f$ 0.28 (ethyl acetate). IR 3348, 2806, 1516, 1454, 1292, 1116, 1006, 701 cm$^{-1}$. HRMS (FAB) calcd for $C_{19}H_{22}N_2O_2+H_1$ 311.1759, found 311.1761 Anal. Calcd for $C_{19}H_{22}N_2O_2$: C, 73.52; H, 7.14; N, 9.02; found: C, 73.38; H, 7.19; N, 8.93.

Preparation 22: Diethyl 2-{[7-(4-morpholinylmethyl)-3-phenyl-2,3-dihydro-4H-1,4-benzoxazin-4-yl]methylene}malonate (Formula F-5 of Chart F)

A mixture of 378 mg of the product of Preparation 21 and 350 mg of diethyl ethoxymethylenemalonate is heated at 140° C. under argon for 2 h. Additional malonate (ca. 150 mg) is added, and the mixture heated at 120° C. for 18 h. Flash chromatography of the residue on silica using ethyl acetate provides 509 mg of the title compound as a solid.

$^1$H NMR (CDCl$_3$) δ0.90, 1.26, 2.42, 3.43, 3.70, 3.9–4.2, 4.32, 4.50, 5.27, 6.83, 6.99, 7.1–7.3, 8.11. IR 2980, 2808, 1708, 1598, 1509, 1249, 1219, 1196, 1117, 1071 cm$^{-1}$. HRMS (FAB) calcd for $C_{27}H_{32}N_2O_6+H_1$ 481.2338, found 481.2344.

Preparation 23: Ethyl 9-(4-morpholinylmethyl)-7-oxo-3-phenyl-2,3-dihydro-7H-[1,4]oxazino[2,3,4-ij]quinoline-6-carboxylate (Formula F-6 of Chart 6)

An intimate mixture of 509 mg of the product of Preparation 22 and 2.4 g of polyphosphoric acid is heated at 90° C., with occasional mechanical stirring, for 18 h. The resulting gum is added to a stirred slurry of 2.5 g of Na$_2$HCO$_3$ in 50 mL of water, and the mixture is extracted with three portions of dichloromethane. The combined organic phases are dried (MgSO$_4$) and concentrated under reduced pressure. Flash chromatography of the residue on silica using 3–5% methanol in dichloromethane affords 375 mg of solid. Recrystallization from acetonitrile-water provides 184 mg of white crystals, mp>190° C.

$^1$H NMR (CDCl$_3$) δ1.35, 2.47, 3.59, 3.71, 4.33, 4.56, 5.30, 7.15, 7.33, 7.4, 8.03, 8.23. TLC R$_f$ 0.25 (5% methanol in dichloromethane). IR 2809, 1723, 1691, 1608, 1556, 1500, 1315, 1226, 1116, 1073, 808, 730 cm$^{-1}$. HRMS (FAB) calcd for $C_{25}H_{26}N_2O_5+H_1$ 435.1920, found 435.1920 Anal. Calcd for $C_{25}H_{26}N_2O_5$: C, 69.11; H, 6.03; N, 6.45; found: C, 68.87; H, 6.19; N, 6.32.

Example 29

N-(4-Chlorobenzyl)-9-(4-morpholinylmethyl)-7-oxo-3-phenyl-2,3-dihydro-7H-[1,4]oxazino[2,3,4-ij]quinoline-6-carboxamide (Formula F-7 of Chart F)

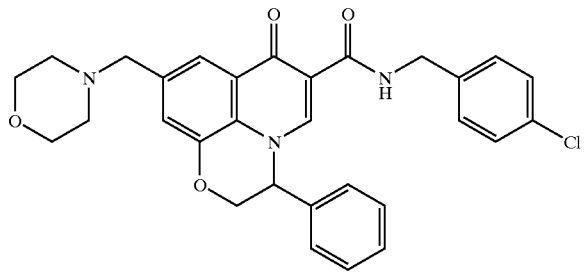

A mixture of 103 mg of the product of Preparation 23 and 200 mg of p-chlorobenzylamine is heated at 150° C. for 18 h, then placed under vacuum to remove excess amine. Flash chromatography of the residue on silica using 2% methanol in dichloromethane affords 125.3 mg of the title compound as a white solid. An analytical sample is recrystallized from toluene to give the title compound as white crystals.

$^1$H NMR (CDCl$_3$) δ2.48, 3.61, 3.72, 4.58, 4.59, 5.37, 7.13, 7.28, 7.40, 8.02, 8.59, 10.44. TLC R$_f$ 0.28 (3% methanol in dichloromethane). HRMS (FAB) calcd for $C_{30}H_{28}ClN_3O_4+H_1$ 530.1846, found 530.1841 Anal. Calcd for $C_{30}H_{28}ClN_3O_4$: C, 67.98; H, 5.32; N, 7.93; Cl, 6.69; found: C, 68.12; H, 5.38; N, 7.71.

Preparation 24: 5-(4-Morpholinylcarbonyl)-2-nitrophenyl 2-oxiranylmethyl ether (Formula G-1 of Chart G)

A mixture of 504 mg of the product of Preparation 1 and 120 mg of powdered NaOH in 2 mL of epichlorohydrin is heated at 120° C. for 18 h, then cooled and partitioned between dil aqueous HCl and ethyl acetate. The organic phase is washed with brine, dried (MgSO$_4$) and concentrated under reduced pressure. Flash chromatography of the residue on silica using 2% methanol in dichloromethane provides 496 mg of the title compound. Recrystallization from ethyl acetate-hexane gives the title compound as solid, mp 156.5–158.0° C.

$^1$H NMR (CDCl$_3$) δ2.85, 2.93, 3.39, 3.7, 4.13, 4.49, 7.06, 7.21, 7.87 TLC R$_f$ 0.47 (5% methanol in dichloromethane). IR 2859, 1637, 1607, 1522, 1437, 1288, 1240, 1114, 1016, 842 cm$^{-1}$. HRMS (FAB) calcd for $C_{14}H_{16}N_2O_6+NA_1$ 331.0906, found 331.0893 Anal. Calcd for $C_{14}H_{16}N_2O_6$: C, 54.54; H, 5.23; N, 9.09; found: C, 54.16; H, 5.25; N, 8.92.

Preparation 25: 1-(4Morpholinyl)-3-[5-(4-morpholinylcarbonyl)-2-nitrophenoxy]-2-propanol (Formula G-2 of Chart G)

A solution of 442 mg of the product of Preparation 24 and 0.25 mL of morpholine in 2 mL of methanol is refluxed for 18 h, then concentrated under reduced pressure. Flash chromatography of the residue on silica using 2–5% methanol in dichloromethane provides 546 mg of the title compound as a solid.

$^1$H NMR (CDCl$_3$) δ2.6, 3.41, 3.7, 4.15, 4.23, 7.05, 7.21, 7.89. TLC R$_f$ 0.19 (5% methanol in dichloromethane). IR 3425, 2856, 1637, 1607, 1523, 1437, 1288, 1242, 1115, 1031, 842 cm$^{-1}$. MS (ES+) m/z 396.3.

Preparation 26: 7-(4-Morpholinylcarbonyl)-3-(4-morpholinylmethyl)-3,4-dihydro-2H-1,4-benzoxazine (Formula G-3 of Chart G)

To a cold (−78° C.), stirred solution of 0.17 mL of DMSO in 2 mL of dichloromethane, under argon, is added dropwise 0.29 mL of trifluoroacetic anhydride. The solution is stirred 15 m, then a solution of 546 mg of the product of Preparation 25 in 1 mL of dichloromethane is added via cannula. The solution is warmed to −30° C. and stirred at that temperature for 30 m, then 0.96 mL of diisopropylethylamine is added. The solution is warmed to room temperature and partitioned between dichloromethane and water containing 2.0 mL of 1N HCl. The aqueous phase is extracted with two additional portions of dichloromethane, and the combined organic phases dried (Na$_2$SO$_4$), diluted with 40 mL of ethanol, and concentrated under reduced pressure to ca. 5 mL volume. To this solution is added Raney 2800 nickel catalyst, which is isolated from 3 mL of commercially available aqueous slurry by filtration and washing with ethanol with minimal exposure to air. The mixture is shaken under 50 psi hydrogen gas for 18 h, then filtered through Celite with dichloromethane and methanol rinses. The filtrate is concentrated under reduced pressure, and the residue chromatographed on silica using 2–4% methanol in dichloromethane to provide 264 mg of the title compound as a white crystalline solid. Recrystallization from ethyl acetate in hexane gives the title compound as white crystals, mp 125–126° C.

$^1$H NMR (CDCl$_3$) δ2.37, 2.60, 3.5–3.9, 3.84, 4.21, 4.72, 6.59, 6.88. TLC R$_f$ 0.36 (5% methanol in dichloromethane). HRMS (FAB) calcd for C$_{18}$H$_{25}$N$_3$O$_4$+H$_1$ 348.1923, found 348.1921 Anal. Calcd for C$_{18}$H$_{25}$N$_3$O$_4$: C, 62.23; H, 7.25; N, 12.10; found: C, 62.21; H, 7.22; N, 11.97.

Preparation 27: 3,7-bis(4-Morpholinylmethyl)-3,4-dihydro-2H-1,4-benzoxazine (Formula G-4 of Chart G)

To a cold (0° C.), stirred solution of 237 mg of the product of Preparation 26 in 2.0 mL of dry THF, under argon, is added 52 mg of LAH. The mixture is allowed to warm to room temperature and stirred for 30 m, then quenched cautiously with 50 μL of water, 50 μL of 3N NaOH, and 0.15 mL of water. Dichloromethane and Na$_2$SO$_4$ are added, and the mixture filtered through Celite. The filtrate is concentrated under reduced pressure, and the residue flash chromatographed on silica using 2–6% methanol in dichloromethane to afford 211 mg of the title compound as a solid.

$^1$H NMR (CDCl$_3$) δ2.40, 2.59, 3.36, 3.55, 3.72, 3.86, 4.21, 4.4, 6.58, 6.76. TLC R$_f$ 0.31 (5% methanol in dichloromethane). IR 3355, 2808, 1517, 1290, 1116, 1005, 865 cm$^{-1}$. MS (ES+) m/z 334.3.

Preparation 28: Ethyl 3,9-bis(4-morpholinylmethyl)-7-oxo-2,3-dihydro-7H-[1,4]oxazino[2,3,4-ij]quinoline-6-carboxylate (Formula G-5 of Chart G)

A mixture of 211 mg of the product of Preparation 27 and 274 mg of diethyl ethoxymethylenemalonate is heated under argon at 140° C. for 2 h, then cooled and chromatographed on silica using 2–4% methanol in dichloromethane to provide 230 mg of the intermediate enamide, which is diethyl 2-{[3,7-bis(4-morpholinylmethyl)-2,3-dihydro-4H-1,4-benzoxazin4-yl]methylene}malonate, as an orange foam. This is mixed thoroughly with 1.5 g of polyphosphoric acid, and the mixture is heated at 90° C. for 18 h, then cooled and added to excess aqueous NaHCO$_3$. The mixture is extracted thrice with dichloromethane, and the organic phases dried (Na$_2$SO$_4$) and concentrated under reduced pressure. Flash chromatography of the residue on silica using 2–5% methanol in dichloromethane affords 117 mg of the title compound.

$^1$H NMR (CDCl$_3$) δ1.41, 2.44, 2.67, 3.55, 3.69, 4.22, 4.40, 4.57, 7.27, 7.95, 8.37. TLC R$_f$ 0.25 (5% methanol in dichloromethane). IR 2811, 1722, 1600, 1555, 1502, 1319, 1292, 1227, 1116, 912, 867, 731 cm$^{-1}$. MS (ES+) m/z 458.3.

Example 30

N-(4-Chlorobenzyl)-3,9-bis(4-morpholinylmethyl)-7-oxo-2,3-dihydro-7H-[1,4]oxazino[2,3,4-ij]quinoline-6-carboxamide (Formula G-6 of Chart G)

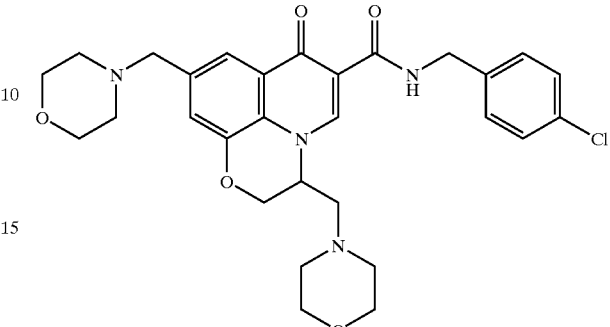

A mixture of 117 mg of the product of Preparation 28 and 0.20 g of p-chlorobenzylamine is heated at 150° C. for 18 h, then excess amine is removed under vacuum. Flash chromatography of the residue on silica using 2–4% methanol in dichloromethane affords 11.6 mg of the title compound.

$^1$H NMR (CDCl$_3$) δ2.41, 2.63, 2.77, 3.57, 3.69, 4.31, 4.66, 7.30, 7.33, 7.96, 8.68 (s, 1H), 10.46. TLC R$_f$ 0.31 (5% methanol in dichloromethane). IR 2812, 1658, 1608, 1551, 1500, 1286, 1116, 867, 809, 730 cm$^{-1}$ HRMS (FAB) calcd for C$_{29}$H$_{33}$ClN$_4$O$_5$+H$_1$ 553.2217, found 553.2213.

Preparation 29: 2,3-Difluoro-5-iodobenzoic acid (Formula H-2 of Chart H)

To a cold (0° C.), stirred solution of 4.74 g of 2,3-difluorobenzoic acid in 15.0 mL of trifluoromethanesulfonic acid is added in portions 8.1 g of powdered N-iodosuccinimide. Following the addition, the mixture is allowed to warm to room temperature, stirred for 5 h, then poured onto 200 mL of cracked ice containing 5 g of sodium bisulfite. The mixture is stirred well for 15 m, then filtered, and the solid washed well with water and dried under vacuum to provide 6.78 g of the title compound as a solid.

$^1$H NMR (CDCl$_3$) δ7.81, 8.09. IR 3082, 1713, 1473, 1280 cm$^{-1}$ MS (ES–) m/z 282.8.

Preparation 30: Ethyl 3-(2,3-difluoro-5-iodophenyl)-3-oxopropanoate (Formula H-3 of Chart H)

To a stirred solution of 2.02 g of the product of Preparation 29 in 10 mL of dry THF, under argon, is added 1.42 g of carbonyldiimidazole and 20 mg of DMAP. In a separate flask, 1.49 g of ethyl potassium malonate is suspended in 10 mL of CH$_3$CN at 0° C. under argon, and to the slurry is added 1.0 mL of chlorotrimethylsilane. The mixture is stirred at ambient temperature for 18 h, then re-cooled to 0° C. To the mixture is added 2.3 mL of DBU, and after 30 min the acyl imidazolide solution prepared above is added via cannula. The mixture is stirred for 4 h at room temperature, then partitioned between ether and excess dilute HCl. The aqueous phase is back extracted with one additional portion of ether, and the combined organic phases washed with 0.1 N HCl and brine, dried (MgSO$_4$), and concentrated under reduced pressure. Flash chromatography of the residue on silica using 5% EtOAc in heptane provides 2.13 g of the title compound as a white solid.

$^1$NMR (CDCl$_3$) δ1.34, 4.26, 5.81, 7.57, 7.95. TLC R$_f$ 0.44 (10% EtOAc in hexane). IR 1622, 1490, 1420, 1213, 1036, 958, 800 cm$^{-1}$ MS (ES−) m/z 352.9.

Preparation 31: Ethyl (2-E and Z)-2-(2,3-difluoro-5-iodobenzoyl)-3-{[2-hydroxy-1,1-bis(hydroxymethyl)ethyl]amino}-2-propenoate (Formula H-4 of Chart H)

A solution of 2.12 g of the product of Preparation 30 and 1.5 mL of triethyl orthoformate in 6 mL of acetic anhydride is refluxed under nitrogen for 2 h, then concentrated under reduced pressure to a viscous oil. This is dissolved in 6 mL of ethanol, and 1.45 g of tris(hydroxymethyl) aminomethane is added. The solution is stirred at room temperature for 18 h, then concentrated under reduced pressure. Flash chromatography of the residue on silica using 5–7% methanol in dichloromethane affords 2.77 g of the title compound as a tan foam.

$^1$NMR (CDCl$_3$) (E/Z mixture of isomers) δ0.87, 0.93, 3.78, 3.98, 4.23, 7.35, 7.49, 8.46, 10.09, 11.33. TLC R$_f$ 0.32 (10% methanol in dichloromethane). IR 3400, 1670, 1622, 1481, 1430, 1323, 1296, 1274, 1256, 1222, 1056, 912, 733 cm$^{-1}$. HRMS (FAB) calcd for C$_{16}$H$_{18}$F$_2$INO$_6$+H$_1$ 486.0227, found 486.0240.

Preparation 32: Ethyl 3,3-bis(hydroxymethyl)-9-iodo-7-oxo-2,3-dihydro-7H-[1,4]oxazino[2,3,4-ij]quinoline-6-carboxylate (Formula H-5 of Chart H)

A mixture of 2.77 g of the product of Preparation 31 and 1.74 g of potassium carbonate in 20 mL of DMF is heated at 130° C. under argon for 2 days, after which DMF is distilled off under reduced pressure. To the brown residue is added water, and the mixture is stirred for 20 m then filtered. The solid is washed with water, ethyl acetate, and ether, and dried under vacuum to provide 1.76 g of the title compound as a solid.

$^1$NMR (CDCl$_3$+TFA) δ1.48, 4.24, 4.42, 4.60, 4.63, 8.03, 8.62, 9.49. HRMS (FAB) calcd for C$_{16}$H$_{16}$INO$_6$+H$_1$ 446.0102, found 446.0100.

Preparation 33: N-(4-Chlorobenzyl)-3,3-bis(hydroxymethyl)-9-iodo-7-oxo-2,3-dihydro-7H-[1,4]oxazino[2,3,4-ij]quinoline-6-carboxamide (Formula H-6 of Chart H)

A mixture of 1.69 g of the product of Preparation 32 and 3.2 g of p-chlorobenzylamine is heated under argon at 160° C. for 18 h, then cooled and triturated with dichloromethane. The resulting solid is filtered, washed with dichloromethane, and dried under vacuum to provide 1.50 g of the title compound as a solid.

$^1$NMR (CDCl$_3$+TFA) δ64.12, 4.35, 4.56, 4.64, 7.3, 7.91, 8.54, 9.25, 9.4. MS (ES+) m/z 541.0.

Preparation 34: 3,3-bis({[tert-Butyl(dimethyl)silyl]oxy}methyl)-N-(4-chlorobenzyl)-9-iodo-7-oxo-2,3-dihydro-7H-[1,4]oxazino[2,3,4-ij]quinoline-6-carboxamide (Formula H-7 of Chart H)

A mixture of 1.49 g of the product of Preparation 33, 661 mg of imidazole, and 1.25 g of tert-butyldimethylsilyl chloride in 6 mL of DMF is stirred at room temperature for 18 h, then partitioned between ethyl acetate and aqueous NaHCO$_3$. The organic phase is washed with water and brine, dried (Na$_2$SO$_4$), and concentrated under reduced pressure. Flash chromatography of the residue on silica using 20% ethyl acetate in heptane affords 1.72 g of the title compound as a white solid. An analytical sample is recrystallized from methanol to give the title compound as a solid, mp 157.5–159.0° C.

$^1$NMR (CDCl$_3$) δ0.00 (used as reference peak), 0.03, 0.82, 3.94, 4.02, 4.37, 4.92, 7.26, 7.53, 8.39, 8.81, 10.27. TLC R$_f$ 0.38 (20% ethyl acetate in hexane). IR (drift) 2953, 2930, 2856, 1670, 1572, 1543, 1483, 1467, 1252, 1122, 1088, 841, 837, 800, 776 cm$^{-1}$ HRMS (FAB) calcd for C$_{33}$H$_{46}$ClIN$_2$O$_5$Si$_2$+H$_1$ 769.1758, found 769.1748 Anal. Calcd for C$_{33}$H$_{46}$ClIN$_2$O$_5$Si$_2$: C, 51.52; H, 6.03; N, 3.64; Cl, 4.61; found (av): C, 51.14; H, 6.06; N, 3.59.

Preparation 35: 3,3-bis({[tert-Butyl(dimethyl)silyl]oxy}methyl)-N-(4-chlorobenzyl)-9-(3-hydroxy-1-propynyl)-7-oxo-2,3-dihydro-7H-[1,4]oxazino[2,3,4-ij]quinoline-6-carboxamide (Formula H-8 of Chart H)

To a mixture of 385 mg of the product of Preparation 34, 70 mg of copper (I) iodide, and 18 mg of bis(triphenylphosphine)palladium (II) dichloride is added 40 μL of propargyl alcohol in 4 mL of diethylamine. The mixture is stirred overnight at room temperature, becoming a clear red solution. Volatile components are removed under reduced pressure and the residue flash chromatographed on silica using 10–15% ethyl acetate in dichloromethane to provide 333 mg of the title compound as a solid.

$^1$NMR (CDCl$_3$) δ0.00 (used as reference peak), 0.03, 0.82, 4.02, 4.38, 4.43, 4.63, 7.02, 7.3, 7.78, 8.73, 10.34. TLC R$_f$ 0.35 (10% ethyl acetate in dichloromethane). MS (ES+) m/z 697.3.

Example 31

N-(4-Chlorobenzyl)-3,3-bis(hydroxymethyl)-9-(3-hydroxy-1-propynyl)-7-oxo-2,3-dihydro-7H-[1,4]oxazino[2,3,4-ij]quinoline-6-carboxamide (Formula H-9 of Chart H)

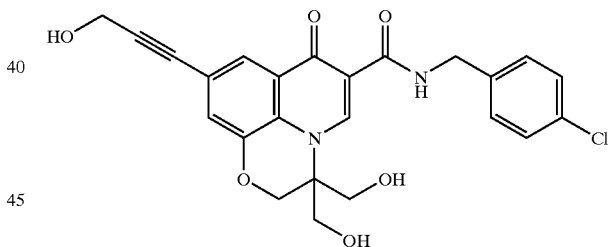

A mixture of 52 mg of the product of Preparation 35, 0.5 mL of concentrated hydrochloric acid, and 1 mL of ethanol is stirred at room temperature for 3 days, then added to 10 mL of rapidly stirred water. The resulting solid is filtered, washed with water, and dried under vacuum to provide 34 mg of buff solid. Chromatography of this material on silica using 5–10% methanol in dichloromethane affords 29.4 mg of the title compound as a solid.

$^1$NMR (CDCl$_3$+CD$_3$OD) δ3.88, 4.09, 4.45, 4.63, 7.28, 7.31, 8.03, 8.92. TLC R$_f$ 0.38 (10% methanol in dichloromethane). MS (ES+) m/z 469.0.

Preparation 36: 3,3-bis({[tert-Butyl(dimethyl)silyl]oxy}methyl)-N-(4-chlorobenzyl)-9-(3-hydroxypropyl)-7-oxo-2,3-dihydro-7H-[1,4]oxazino[2,3,4-ij]quinoline-6-carboxamide (Formula H-10 of Chart H)

A mixture of 175 mg of the product of Preparation 35 and 70 mg of 5% platinum on carbon in 6 mL of ethyl acetate is shaken under 40 psi $H_2$ for 5 h, then filtered through Celite. The filtrate is concentrated under reduced pressure and the residue chromatographed on silica using 30% ethyl acetate in dichloromethane to provide 142 mg of the title compound as a pale yellow solid. An analytical sample is recrystallized from ethanol to give the title compound as white needles.

Physical properties are as follows:

$^1$NMR (CDCl$_3$) δ0.00 (used as reference peak), 0.03, 0.83, 1.94, 2.82, 3.68, 3.97, 4.02, 4.37, 4.63, 7.11, 7.3, 7.90, 8.80, 10.43. TLC R$_f$ 0.32 (30% ethyl acetate in dichloromethane). IR (drift) 2951, 2930, 2858, 1662, 1604, 1572, 1554, 1491, 1253, 1115, 1092, 1064, 840, 802, 780 cm$^{-1}$ HRMS (FAB) calcd for $C_{36}H_{53}ClN_2O_6Si_2+H_1$ 701.3209, found 701.3202 Anal. Calcd for $C_{36}H_{53}ClN_2O_6Si_2$: C, 61.64; H, 7.61; N, 3.99; Cl, 5.05; found: C, 61.35; H, 7.74; N, 3.97.

Example 32

N-(4-Chlorobenzyl)-3,3-bis(hydroxymethyl)-9-(3-hydroxypropyl)-7-oxo-2,3-dihydro-7H-[1,4]oxazino[2,3,4-ij]quinoline-6-carboxamide (Formula H-11 of Chart H)

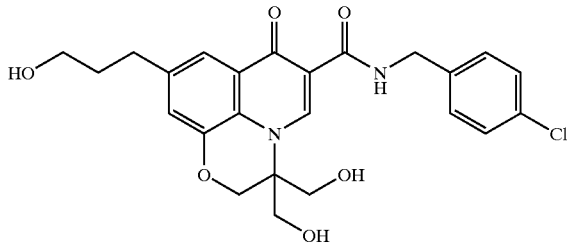

A solution of 132 mg of the product of Preparation 36 in 2.0 mL of ethanol and 1.0 mL of concentrated hydrochloric acid is stirred at room temperature for 18 h, then concentrated under reduced pressure. Flash chromatography of the residue on silica using 5–8% methanol in dichloromethane provides 85.3 mg of the title compound as a white solid. An analytical sample is recrystallized from methanol to give the title compound as white crystals, mp 173.0–174.5° C.

$^1$NMR (CDCl$_3$+CD$_3$OD) δ1.90, 2.81, 3.61, 3.88, 4.10, 4.43, 4.64, 7.16, 7.31, 7.84, 8.90. TLC R$_f$ 0.35 (10% methanol in dichloromethane). IR (drift) 3363, 1654, 1628, 1605, 1552, 1492, 1367, 1348, 1338, 1301, 1291, 1266, 1090, 1061, 801 cm$^{-1}$ HRMS (FAB) calcd for $C_{24}H_{25}ClN_2O_6+H_1$ 473.1479, found 473.1471 Anal. Calcd for $C_{24}H_{25}ClN_2O_6$: C, 60.95; H, 5.33; N, 5.92; Cl, 7.50; found: C, 59.00; H, 5.63; N, 5.70.

Preparation 37: 2-Amino-1-(2-pyridinyl)ethanol (I-7 of Chart I, T=2-pyridyl)

To 2.68 g of 2-pyridylcarboxaldehyde, stirred under argon at 0° C., is added 3.7 mL of trimethylsilyl cyanide. After 10 min the ice bath is removed and the yellow liquid stirred for 30 min at ambient temperature. The resulting TMS cyanohydrin is dissolved in 10 mL of dry ether. In a three-necked flask fitted with argon inlet and overhead mechanical stirrer is placed 1.05 g of LAH and 50 mL of dry ether. The slurry is cooled to 0° C. under argon and stirred vigorously while the cyanohydrin solution is added dropwise via cannula. Following the addition, the reaction is stirred at room temperature for 2 h, then recooled to 0° C. and cautiously quenched with 1.0 mL of water (dissolved in 10 mL of THF), 1.0 mL of 3N NaOH, and 3.0 mL of water, added sequentially. CH$_2$Cl$_2$ (30 mL) and Na$_2$SO$_4$ are added, and the mixture is well stirred for 30 min and then filtered. The filter cake is washed well with 1:1 CH$_2$Cl$_2$:ether, and the combined filtrates concentrated under reduced pressure to provide 5.02 g of crude title compound as a deep red oil. The crude material is used directly in the subsequent reaction.

$^1$H NMR (CDCl$_3$) δ2.87, 3.12, 4.71, 7.20, 7.35, 7.69, 8.55.

Preparation 38: Ethyl 2-(2,3-difluoro-5-iodobenzoyl)-3-{[2-hydroxy-2-(2-pyridinyl)ethyl]amino}-2-propenoate (I-2 of Chart I, T=2-pyridyl)

A solution of 1.79 g of β-ketoester H-3 of Preparation 30 and 1.3 mL of triethyl orthoformate in 5 mL of acetic anhydride is refluxed for 2 h, then concentrated under reduced pressure. The residual oil is stirred at 70° C. under 0.1 mmHg for 20 min to remove volatile components, providing the crude enol ether. This is dissolved in 2 mL of ethanol, and a solution of approximately 25 mmol of amino alcohol I-7 of Preparation 37 in 10 mL of ethanol is added. The resulting deep red solution is stirred at room temperature for 15 h, then concentrated under reduced pressure. The residual oil is partitioned between EtOAc and water, and the organic phase is washed with two additional portions of water, once with brine, dried (MgSO$_4$), and concentrated under reduced pressure. Flash chromatography of the crude material on silica using EtOAc provides 2.14 g of the title compound as an orange gum. The NMR spectrum is complex due to E/Z isomerism. TLC R$_f$ 0.36 (EtOAc).

Preparation of 39: Ethyl 9-iodo-7-oxo-2-(2-pyridinyl)-2,3-dihydro-7H-[1,4]oxazino[2,3,4-ij]quinoline-6-carboxylate (I-3 of Chart I, T=2-pyridyl)

A stirred mixture of 2.13 g of I-2 of Preparation 38 and 3.04 g of cesium carbonate in 8 mL of DMF is heated at 100° C. under argon for 18 h, then cooled and diluted with 100 mL of water. The resulting solid is filtered, washed well with water, and dried under vacuum. Flash chromatography of the solid on silica using 3% MeOH in CH$_2$Cl$_2$ affords 2.06 g of the title compound as a peach-colored solid. A sample recrystallized from acetonitrile provides white crystals, mp 224–225° C.

$^1$NMR (CDCl$_3$) δ1.38, 4.34, 4.53, 4.64, 5.54, 7.33, 7.62, 7.64, 7.81, 8.27, 8.30, 8.61. TLC R$_f$ 0.45 (5% MeOH in CH$_2$Cl$_2$.) IR 1682, 1637, 1611, 1589, 1550, 1491, 1399, 1367, 1316, 1267, 1248, 1235, 1183, 800, 770 cm$^{-1}$. OAMS supporting ions at: ESI+ 463.0 HRMS (FAB) 463.0150 Anal. found: C, 49.36; H, 3.30; N, 6.09.

Preparation 40: N-(4-Chlorobenzyl)-9-iodo-7-oxo-2-(2-pyridinyl)-2,3-dihydro-7H-[1,4]oxazino[2,3,4-ij]quinoline-6-carboxamide (I-4 of Chart I, T=2-pyridyl)

A mixture of 1.86 g of I-3 of Preparation 39 and 3.5 g of p-chlorobenzylamine is stirred and heated at 150° C. After 18 h, excess amine is distilled off under vacuum, and the residue is adsorbed onto silica gel and flash chromatographed on silica using 1–3% MeOH in CH$_2$Cl$_2$ to provide 1.69 g of the amide as a pale yellow solid.

$^1$NMR (CDCl$_3$+CD$_3$OD) δ4.61, 4.62, 4.76, 5.55, 7.30, 7.38, 7.62, 7.73, 7.85, 8.38, 8.66, 8.71. TLC R$_f$ 0.37 (2% MeOH in CH$_2$Cl$_2$) OAMS supporting ions at: ESI+ 558.0.

Preparation 41: N-(4-Chlorobenzyl)-9-formyl-7-oxo-2-(2-pyridinyl)-2,3-dihydro-7H-[1,4]oxazino[2,3,4-ij]quinoline-6-carboxamide (I-5 Chart I, T=2-pyridyl)

In a dry 50 mL recovery flask fitted with a Liebig condenser topped with a rubber septum is placed 520 mg of iodide I-4 of Preparation 40, 80 mg of tetrakis (triphenylphosphine) palladium (0), 5 mL of dry DMF, and 5 mL of dry THF. The mixture is stirred and heated at 55° C. while a slow stream of carbon monoxide is introduced below the surface of the liquid using a long 18 gauge needle. To the mixture is added, via syringe pump over about 5 h, a solution of 0.32 mL of tri-n-butylstannane in 10 mL of dry THF. Following the addition, solvents are removed in vacuo, and the remaining solid is washed with several portions of EtOAc and ether, and then dried under vacuum to provide 393 mg of the aldehyde as a poorly soluble tan solid.

$^1$NMR (DMSO-d$_6$) δ4.58, 4.75, 4.98, 5.76, 7.3, 7.70, 7.78, 7.95, 8.45, 8.64, 8.93, 10.10, 10.24. TLC R$_f$ 0.44 (3% MeOH in dichoromethane).

Example 33

N-(4-Chlorobenzyl)-9-(4-morpholinylmethyl)-7-oxo-2-(2-pyridinyl)-2,3-dihydro-7H1-[1,4]oxazino[2,3,4-ij]quinoline-6-carboxamide (I-6 of Chart I, T=2-pyridyl)

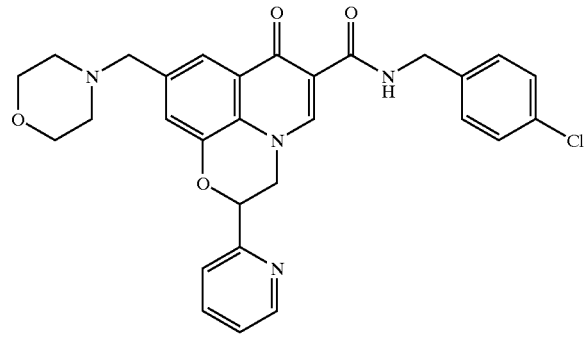

A mixture of 138 mg of aldehyde I-5 of Preparation 41, 79 μL of morpholine, and 34 μL of acetic acid in 3.0 mL, of dry THF is stirred at ambient temperature for 30 minutes, then 50 mg of sodium triacetoxyborohydride is added. After 30 min, a second 50 mg portion of triacetoxyborohydride is added, and the resulting mixture stirred overnight. The following day, additional portions of triacetoxyborohydride sufficient to result in complete reduction are added over the course of 8 h. The reaction is partitioned between CH$_2$Cl$_2$ and aqueous sodium bicarbonate, and the aqueous phase is extracted with additional CH$_2$Cl$_2$. The combined organic phases are dried (Na$_2$SO$_4$) and concentrated under reduced pressure, and the residue flash chromatographed on silica using 3% MeOH in CH$_2$Cl$_2$ to afford 152 mg of the product as a white solid. Recrystallization from 10 mL of acetonitrile provides 129 mg of the title compound as fine needles, mp 208–216° C.

$^1$NMR (CDCl$_3$) δ2.47, 3.61, 3.72, 4.58, 4.64, 4.72, 5.51, 7.3, 7.51, 7.63, 7.79, 7.97, 8.63, 8.72, 10.44. TLC R$_f$ 0.38 (5% MeOH in CH$_2$Cl$_2$). IR 3035, 1655, 1608, 1569, 1551, 1499, 1452, 1410, 1357, 1346, 1329, 1283, 1212, 1113, 810 cm$^{-1}$ OAMS supporting ions at: ESI+ 531.2 HRMS (FAB) 531.1813 Anal. found: C, 65.39; H, 5.13; N, 10.47.

Example 34

N-(4-Chlorobenzyl)-9-(4-morpholinylmethyl)-7-oxo-2-(3-pyridinyl)-2,3-dihydro-7H-[1,4]oxazino[2,3,4-ij]quinoline-6-carboxamide (I-6 of Chart I, T=3-pyridyl)

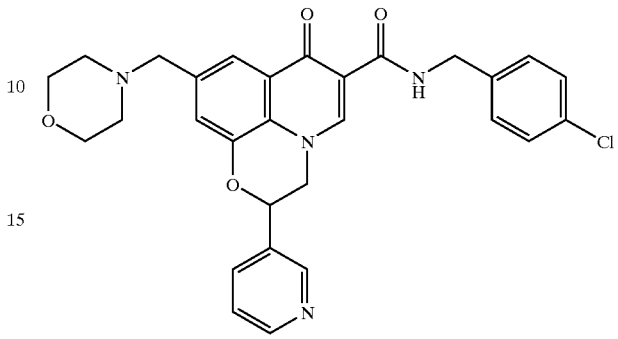

Following the procedures in Preparations 37–41 and Example 33 without making major changes except using 3-pyridylcarboxaldehyde as a starting material, the title compound is obtained as solid.

$^1$H NMR (CDCl$_3$) δ2.47, 3.61, 3.71, 4.33, 4.43, 4.63, 5.38, 7.30, 7.45, 7.85, 8.00, 8.69, 8.74, 8.79, 10.40. TLC R$_f$ 0.28 (5% MeOH in CH$_2$Cl$_2$). IR 3038, 1656, 1607, 1580, 1553, 1498, 1457, 1409, 1345, 1331, 1320, 1282, 1115, 810, 711 cm$^{-1}$ OAMS supporting ions at: ESI+ 531.2 HRMS (FAB) 531.1798 Anal. found: C, 65.62; H, 5.18; N, 10.53.

Example 35

N-(4-Chlorobenzyl)-9-(4-morpholinylmethyl)-7-oxo-2-(4-pyridinyl)-2,3-dihydro-7H-[1,4]oxazino[2,3,4-ij]quinoline-6-carboxamide (I-6 of Chart I, T=4-pyridyl)

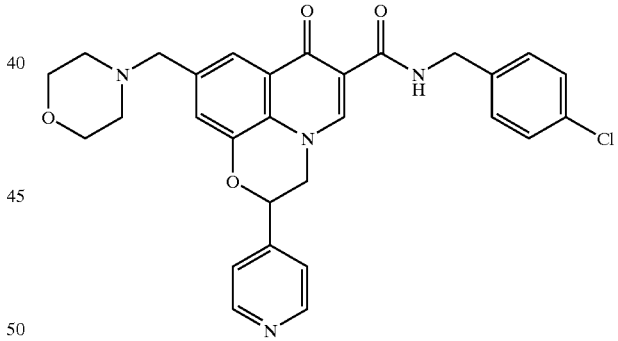

Following the procedure in Preparations 37–41 and Example 33 without making major changes except using 4-pyridylcarboxaldehyde as a starting material, the title compound is obtained as solid.

$^1$H NMR (CDCl$_3$) δ2.47, 3.61, 3.71, 4.25, 4.49, 4.60, 5.34, 7.27, 7.45, 7.49, 7.99, 8.70, 8.74, 10.41. TLC R$_f$ 0.26 (5% MeOH in CH$_2$Cl$_2$). IR 2859, 1666, 1608, 1551, 1500, 1411, 1352, 1331, 1285, 1271, 1220, 1114, 1090, 821, 806 cm$^{-1}$ OAMS supporting ions at: ESI+ 531.2 HRMS (FAB) 531.1791 Anal. found: C, 65.26; H, 5.18; N, 10.50.

Preparation 42: Ethyl 8-fluoro-4-hydroxy-6-iodoquinoline-3-carboxylate (Formula M-2 of Chart M)

A mixture of 2-fluoro-4-iodoaniline (11.85 g) and diethylethoxymethylene malonate (10.81 g) is heated to 130° C.

in a flask equipped with a Dean-Stark trap to collect EtOH formed. The mixture is then cooled to 75° C. and diluted with hexanes. The resulting solid is collected and dried. The solid is then dissolved in 60 mL Ph$_2$O and heated to 250° C. for 3 h in a flask equipped with a Dean-Stark trap to collect the EtOH formed. The solution is allowed to cool to room temperature and the resulting solid is collected and dried to yield 11.73 g of ethyl-8-fluoro-4-hydroxy-6-iodoquinoline-3-carboxylate. M.p. 287–289° C.

$^1$H NMR (DMSO-d$_6$) δ12.60, 8.38, 8.23, 8.04, 4.22, 1.28 IR (drift) 3165, 3080, 3070, 3059, 2969, 1709, 1616, 1603, 1564, 1527, 1296, 1249, 1173, 1141, 865 cm$^{-1}$ HRMS (FAB) calcd for C$_{12}$H$_9$FINO$_3$+H$_1$ 361.9691, found 361.9696 Anal. Calcd for C$_{12}$H$_9$FINO$_3$: C, 39.91; H, 2.51; N, 3.88. found: C, 39.71; H, 2.42; N, 3.88.

Preparation 43: N-(4-Chlorobenzyl)-8-fluoro-4-hydroxy-6-iodoquinoline-3-carboxamide (Formula M-3 of Chart M)

Compound M-2 of Preparation 42 (0.55 g) and 4-chlorobenzylamine (3 mL) are heated at 180° C. for 1 h. The reaction is cooled and poured into 75 mL diethyl ether. The resulting solid is filtered and recrystallized from EtOAc/hexanes to give the product as an off-white solid (0.45 g), m.p. 268–270° C.

$^1$H NMR (DMSO-d$_6$) δ10.17, 8.59, 8.29, 8.05, 7.37, 7.33, 4.51 IR (mull) 3180, 3078, 3059, 3004, 1647, 1607, 1551, 1524, 1489, 1344, 1297, 1285, 1240, 1183, 805 cm$^{-1}$; MS (ESI) for m/z 456.9 (M+H)$^+$, 454.9 (M−H)$^-$ HRMS (FAB) calcd for C$_{17}$H$_{11}$ClFIN$_2$O$_2$+H$_1$ 456.9618, found 456.9628 Anal. Calcd for C$_{17}$H$_{11}$ClFIN$_2$O$_2$: C, 44.72; H, 2.43; N, 6.14. found: C, 45.45; H, 2.82; N, 6.05.

Preparation 44: N-(4-Chlorobenzyl)-8-fluoro-6-formyl-4-hydroxyquinoline-3-carboxamide (Formula M-4 of Chart M)

A mixture of 4.57 g of compound M-3 of Preparation 43 and 810 mg of tetrakis(triphenylphosphine)palladium (0) in 35 mL of dry DMF and 10 mL of dry THF is stirred and purged with CO for 10 minutes, and then heated to 60° C. Passage of CO through the mixture is continued while 3.3 mL of tributyltin hydride in 6.7 mL of dry THF is added very slowly, via syringe pump over about 6 h. The reaction mixture is then cooled and concentrated under reduced pressure to a semisolid. Ether (70 mL) is added and the resulting solid filtered, washed well with ether, and dried in vacuo to provide 3.54 g of the aldehyde.

$^1$H NMR (CDCl$_3$+CD$_3$OD) δ4.65, 7.32, 7.93, 8.68, 8.75, 10.07, 10.43 ppm. TLC R$_f$ 0.29 (3% methanol in dichloromethane). OAMS supporting ions at: ESI− 358.1.

Preparation 45: N-(4-Chlorobenzyl)-8-fluoro-4-hydroxy-6-(morpholin-4-ylmethyl)quinoline-3-carboxamide (Formula M-5 of Chart M)

To a stirred solution of 2.42 g of aldehyde M-4 of Preparation 44 in 50 mL of THF is added 1.8 mL of morpholine and 0.77 mL of acetic acid. The resulting slurry is stirred well for 15 min, then 1.42 g of sodium triacetoxyborohydride is added. Additional portions of triacetoxyborohydride are periodically added until TLC analysis indicates completion of reaction. The reaction is then partitioned between dichloromethane and aqueous NaHCO$_3$, and the aqueous phase extracted with additional dichloromethane. The combined organic extract is dried (Na$_2$SO$_4$) and concentrated under reduced pressure. Flash chromatography of the residue on silica gel using 4–5% methanol in dichloromethane affords 2.29 g of the title compound as a tan solid. Recrystallization from acetonitrile provides tan plates, mp 227.5–230.0° C.

$^1$H NMR (CDCl$_3$+CD$_3$OD) δ2.47, 3.62, 3.72, 4.64, 7.31, 7.56, 8.06, 8.70, 10.63 ppm. TLC R$_f$ 0.33 (5% methanol in dichloromethane). IR (diffuse reflectance) 3080, 3025, 2971, 2929, 2861, 1660, 1613, 1575, 1542, 1508, 1349, 1268, 1118, 806, 799 cm$^{-1}$ OAMS supporting ions at: ESI+ 430.3 HRMS (FAB) calcd for C$_{22}$H$_{21}$ClFN$_3$O$_3$+H$_1$ 430.1334, found 430.1339 Anal. Calcd for C$_{22}$H$_{21}$ClFN$_3$O$_3$: C, 61.47; H, 4.92; N, 9.77; Cl, 8.25; F, 4.42; found: C, 61.09; H, 4.92; N, 9.66.

Preparation 46: General procedure for preparation of epoxides (M-7)

Step 1: Trimethylsulfonium methylsulfate:

Dimethyl sulfide (25.0 mL) is cooled to 0° C., and dimethyl sulfate (25.0 mL) is added. The liquid is stirred at 0° C. and allowed to warm slowly as the ice in the cooling bath melts. The following day, ether is added and the solid mass crushed with a stirring rod. The solid is filtered, washed well with ether, and dried in vacuo to provide 48.0 g of the salt as a white crystalline solid.

Step 2: Epoxidation: 3-Oxiran-2-ylbenzonitrile (Formula M-7 of Chart M, where R$_a$=3-cyanophenyl and R$_b$=H)

To a solution of 1.31 g of 3-cyanobenzaldehyde (Formula M-6 of Chart M where R$_a$ is 3-cyanophenyl and R$_b$ is H) and 25 mg of tetra-n-butylammonium bromide in 30 mL of dichloromethane is added a solution of 3.92 g of trimethylsulfonium methylsulfate in 10 mL of water, followed by 20 mL of 50% aqueous NaOH. The biphasic mixture is stirred and refluxed for 5 h, then cooled, diluted with brine (~20 mL) and ether (~50 mL), and filtered to remove solids. The phases are separated and the aqueous phase extracted with additional ether as necessary to remove product. The combined organic phase is dried (Na$_2$SO$_4$) and concentrated under reduced pressure, or at atmospheric pressure through a Vigreux column. Kugelrohr distillation of the residue at ca. 0.5 mmHg and 160° C. oven temperature affords 1.20 g of the epoxide as a colorless liquid.

$^1$H NMR (CDCl$_3$) δ2.76, 3.19, 3.90, 7.47, 7.52, 7.58, 7.70 ppm. OAMS supporting ions at: ESI− 144.0

Using the general procedure of Preparation 46, the following epoxides (M-7) are obtained.

3-Oxiran-2-ylfuran (Formula M-7 of Chart M, where R$_a$=furan-3-yl and R$_b$=H)

As a colorless liquid following kugelrohr distillation at ca. 0.5 mmHg and 40° C. oven temperature.

$^1$H NMR (CDCl$_3$) δ2.88, 3.11, 3.80, 6.28, 7.39, 7.52 ppm. OAMS supporting ions at: ESI+ 111.2.

2-Thien-2-yloxirane (Formula M-7 of Chart M, where Ra=thien-2-yl and R$_b$=H)

As a colorless liquid following kugelrohr distillation at ca. 0.5 mmHg and 75° C. oven temperature.

$^1$H NMR (CDCl$_3$) δ3.00, 3.19, 4.10, 6.98, 7.13, 7.25 ppm. OAMS supporting ions at: ESI+ 127.1.

2-(3,5-Difluorophenyl)oxirane (Formula M-7 of Chart M, where R$_a$=3,5-difluorophenyl and R$_b$=H)

As a colorless liquid following kugelrohr distillation at ca. 0.5 mmHg and 75° C. oven temperature.

$^1$H NMR (CDCl$_3$) δ2.72, 3.15, 3.84, 6.73, 6.81 ppm.

5-Oxiran-2-yl-1,3-benzodioxole (Formula M-7 of Chart M, where R$_a$=1,3-benzodioxol-5-yl and R$_b$=H)

As a colorless liquid following kugelrohr distillation at ca. 0.5 mmHg and 150° C. oven temperature.

$^1$H NMR (CDCl$_3$) δ2.75, 3.10, 3.79, 5.95, 6.7, 6.8 ppm. OAMS supporting ions at: ESI+ 165.2.

6-Oxiran-2-yl-2,3-dihydro-1,4-benzodioxine (Formula M-7 of Chart M, where $R_a$=2,3-dihydro-1,4-benzodioxin-6-yl and $R_b$=H)

As a colorless oil following kugelrohr distillation at ca. 0.5 mmHg and 175° C. oven temperature.

$^1$H NMR (CDCl$_3$) δ2.75, 3.08, 3.75, 4.23, 6.76, 6.83 ppm. OAMS supporting ions at: ESI+ 179.2.

4-Oxiran-2-yl-1,3-benzodioxole (Formula M-7 of Chart M, where $R_a$=1,3-benzodioxol-4-yl and $R_b$=H)

As a colorless liquid following kugelrohr distillation at ca. 0.5 mmHg and 125° C. oven temperature.

$^1$H NMR (CDCl$_3$) δ3.02, 3.14, 3.96, 5.97, 6.00, 6.70, 6.8 ppm.

2-[3,5-bis(Methoxymethoxy)phenyl]oxirane (Formula M-7 of Chart M, where $R_a$=3,5-bis(methoxymethoxy)phenyl and $R_b$=H)

As a colorless liquid following kugelrohr distillation at ca. 0.5 mmHg and 200° C. oven temperature.

$^1$H NMR (CDCl$_3$) δ2.76, 3.11, 3.47, 3.81, 5.14, 5.16, 6.63, 6.67 ppm. OAMS supporting ions at: ESI+ 241.2.

2-[2,3-bis(Methoxymethoxy)phenyl]oxirane (Formula M-7 of Chart M, where $R_a$=2,3-bis(methoxymethoxy)phenyl and $R_b$=H)

As a colorless liquid following kugelrohr distillation at ca. 0.5 mmHg and 200° C. oven temperature.

$^1$H NMR (CDCl$_3$) δ2.74, 3.16, 3.50, 3.60, 4.28, 5.17, 5.19, 5.21, 6.81, 7.03, 7.09 ppm. OAMS supporting ions at: ESI– 239.1.

2-Thien-3-yloxirane (Formula M-7 of Chart M, where $R_a$=thien-3-yl and $R_b$=H)

As a colorless liquid following kugelrohr distillation at ca. 0.5 mmHg and 75° C. oven temperature.

$^1$H NMR (CDCl$_3$) δ2.90, 3.13, 3.93, 6.96, 7.29 ppm. OAMS supporting ions at: ESI+ 127.1.

1,6-Dioxaspiro[2.5]octane (Formula M-7 of Chart M, where $R_a$, $R_b$=4-tetrahydropyran)

As a colorless liquid following kugelrohr distillation at ca. 0.5 mmHg and 100–200° C. oven temperature. The poor yield is thought to be due to troublesome distillation behavior, with sequestering of product in the viscous pot residue.

$^1$H NMR (CDCl$_3$) δ1.54, 1.87, 2.70, 3.84 ppm.

6-Methyl-1-oxa-6-azaspiro[2.5]octane (Formula M-7 of Chart M, where $R_a$, $R_b$=N-methyl-4-piperidine)

As a colorless liquid following kugelrohr distillation at ca. 0.5 mmHg and 50° C. oven temperature.

$^1$H NMR (CDCl$_3$) δ1.56, 1.87, 2.34, 2.5, 2.66 ppm. OAMS supporting ions at: ESI+ 128.2.

1,7,10-Trioxadispiro[2.2.4.2]dodecane (Formula M-7 of Chart M, where $R_a$, $R_b$=cyclohexane-4-ethylene ketal)

As a white crystalline solid, melting at slightly above room temperature, following kugelrohr distillation at ca. 0.5 mmHg and 130° C. oven temperature.

$^1$H NMR (CDCl$_3$) δ1.58, 1.77, 1.9, 2.68, 3.98 ppm. OAMS supporting ions at: ESI+ 171.1.

1-Oxa-6-thiaspiro[2.5]octane (Formula M-7 of Chart M, where $R_a$, $R_b$=tetrahydrothiopyran)

As a white crystalline solid following kugelrohr distillation at ca. 0.5 mmHg and 120° C. oven temperature.

$^1$H NMR (CDCl$_3$) δ1.74, 2.00, 2.60, 2.65, 2.91 ppm.

Preparation 47: tert-Butyl 1-oxa-6-azaspiro[2.5]octane-6-carboxylate (Formula M-7 of Chart M, where $R_a$, $R_b$=N-Boc-4-piperidine)

Step 1

To a stirred mixture of 3.07 g of 4-piperidone hydrochloride hydrate and 4.80 g of di-tert-butyl dicarbonate in 20 mL of THF is added 7.0 mL of 3N aqueous NaOH. The biphasic mixture is stirred well for 18 h, then diluted with chloroform. The phases are separated and the aqueous phase extracted with one portion of chloroform, and the combined extract dried (Na$_2$SO$_4$) and concentrated under reduced pressure. Flash chromatography of the residue on silica using 10–20% ethyl acetate in dichloromethane provides 4.08 g of tert-butyl 4-oxopiperidine-1-carboxylate (Boc-piperidone) as a white crystalline solid.

$^1$H NMR (CDCl$_3$) δ1.50, 2.44, 3.72 ppm. TLC R$_f$ 0.38 (10% ethyl acetate in dichloromethane). OAMS supporting ions at: ESI+ 200.1

Step 2

Using the general procedure of Preparation 46, the ketone product of step 1 is converted to the epoxide as a white crystalline solid.

$^1$H NMR (CDCl$_3$) δ1.45, 1.48, 1.80, 2.70, 3.43, 3.7 ppm. OAMS supporting ions at: ESI+ 214.2.

Preparation 48: 2,2-bis[(Methoxymethoxy)methyl]oxirane (Formula M-7 of Chart M, where $R_a$, $R_b$=methoxymethoxymethyl)

Step 1

To a cold (0° C.), stirred mixture of 3.60 g of dihydroxyacetone dimer and 16 mL of diisopropylethylamine in 40 mL of dichloromethane is added 6.1 mL of chloromethyl methyl ether. The mixture is stirred and allowed to warm slowly to room temperature. After 18 h, the clear solution is partitioned between ether and dilute HCl. The aqueous phase is placed in a continuous extractor and extracted overnight with ether. The combined organic phase is then dried (MgSO$_4$) and concentrated under reduced pressure. Kugelrohr distillation of the residue at ~0.5 mmHg and 150° C. oven temperature affords 2.79 g of 2,4,8,10-tetraoxaundecan-6-one as a pale yellow oil.

$^1$H NMR (CDCl$_3$) δ3.40, 4.34, 4.69 ppm.

Step 2

Using the general procedure of Preparation of 46, the ketone product of Step 1 is converted to the epoxide as a white crystalline solid after kugelrohr distillation at ca. 0.5 mmHg and 150° C. oven temperature.

$^1$H NMR (CDCl$_3$) δ2.83, 3.37, 3.72, 4.65 ppm.

Example 36

General procedure for epoxide alkylation: N-(4-Chlorobenzyl)-2-(3-cyanophenyl)-9-(morpholin-4-ylmethyl)-7-oxo-2,3-dihydro-7H-[1,4]oxazino[2,3,4-ij]quinoline-6-carboxamide (Formula M-8 of Chart M, where $R_a$=3-cyanophenyl and $R$=H)

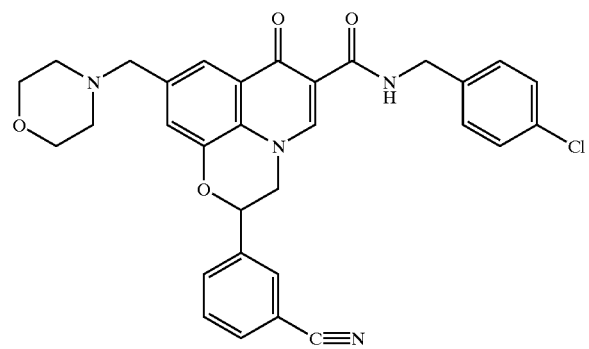

To a mixture of 172 mg of fluorodihydroquinoline M-5 of Preparation 45 and 261 mg of cesium carbonate in 1 mL of DMF is added 116 mg of 3-oxiran-2-ylbenzonitrile (Formula M-7 of Chart M where $R_a$ is 3-cyanophenyl and $R_b$ is H). The mixture is stirred and heated at 90° C. for 4–5 h, and then a second 116 mg portion of epoxide is added and heating continued overnight. The reaction is then cooled and partitioned between chloroform and water, and the aqueous phase extracted with additional chloroform as needed to remove product. The combined organic phase is dried ($Na_2SO_4$) and concentrated under reduced pressure, and the residue chromatographed on silica gel using 2.5–3.5% methanol in dichloromethane to afford 125 mg of the title compound. Recrystallization from acetonitrile provides orange needles.

$^1$H NMR ($CDCl_3+CD_3OD$) δ2.49, 3.63, 3.73, 4.26, 4.59, 4.63, 5.40, 7.30, 7.50, 7.64, 7.78, 7.90, 7.99, 8.65, 10.54 ppm. TLC $R_f$ 0.40 (5% methanol in dichloromethane). OAMS supporting ions at: ESI+ 555.3.

Example 37

N-(4-Chlorobenzyl)-2-(3-furyl)-9-(morpholin-4-ylmethyl)-7-oxo-2,3-dihydro-7H-[1,4]oxazino[2,3,4-ij]quinoline-6-carboxamide (Formula M-8 of Chart M, where $R_a$=furan-3-yl and $R_b$=H)

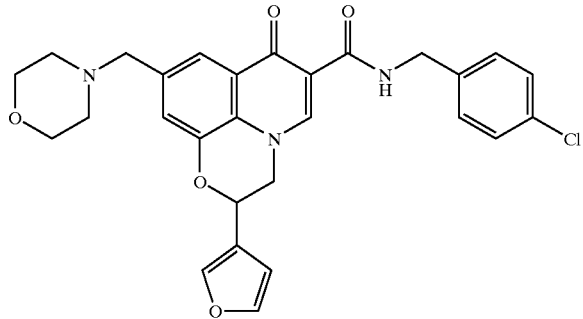

The title compound is prepared according to the general procedure of Example 36, and is purified by flash chromatography on silica gel using 2% methanol in dichloromethane. Recrystallization from acetonitrile provides tan crystals, mp 193–196° C.

$^1$H NMR ($CDCl_3$) δ2.46, 3.59, 3.70, 4.34, 4.41, 4.63, 5.37, 6.49, 7.30, 7.41, 7.51, 7.60, 7.96, 8.67, 10.44 ppm. TLC $R_f$ 0.22 (3% methanol in dichloromethane). IR (diffuse reflectance) 1655, 1627, 1608, 1569, 1551, 1500, 1411, 1347, 1329, 1282, 1218, 1114, 885, 875, 809 cm$^{-1}$ OAMS supporting ions at: ESI+ 520.4 HRMS (FAB) calcd for $C_{28}H_{26}ClN_3O_5+H_1$ 520.1639, found 520.1634 Anal. Calcd for $C_{28}H_{26}ClN_3O_5$: C, 64.68; H, 5.04; N, 8.08; Cl, 6.82; found: C, 64.50; H, 5.09; N, 8.05.

Example 38

N-(4-Chlorobenzyl)-9-(morpholin-4-ylmethyl)-7-oxo-2-thien-2-yl-2,3-dihydro-7H-[1,4]oxazino[2,3,4-ij]quinoline-6-carboxamide (Formula M-8 of Chart M, where $R_a$=thien-2-yl and $R_b$=H)

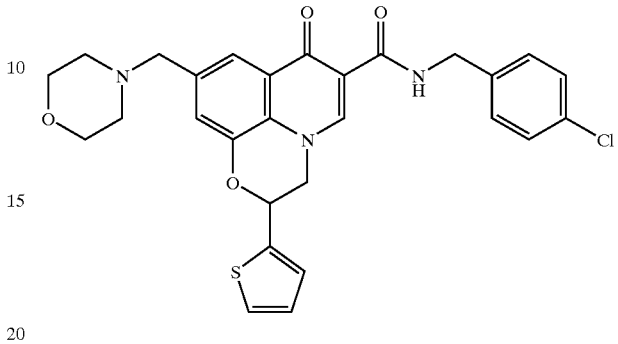

The title compound is prepared according to the general procedure of Example 36, and is purified by flash chromatography on silica gel using 2% methanol in dichloromethane. Recrystallization from acetonitrile provides pale yellow crystals.

$^1$H NMR ($CDCl_3$) δ2.46, 3.59, 3.70, 4.44, 4.50, 4.63, 5.64, 7.09, 7.20, 7.30, 7.44, 7.98, 8.68, 10.43 ppm. TLC $R_f$ 0.28 (3% methanol in dichloromethane). IR (diffuse reflectance) 2954, 2926, 2799, 1666, 1610, 1568, 1551, 1500, 1343, 1287, 1275, 1110, 887, 860, 798 cm$^{-1}$ OAMS supporting ions at: ESI+ 536.3 HRMS (FAB) calcd for $C_{28}H_{26}ClN_3O_4S+H_1$ 536.1411, found 536.1411 Anal. Calcd for $C_{28}H_{26}ClN_3O_4S$: C, 62.74; H, 4.89; N, 7.84; Cl, 6.61; S, 5.98; found: C, 62.72; H, 4.92; N, 7.86.

Example 39

N-(4-Chlorobenzyl)-2-(3,5-difluorophenyl)-9-(morpholin-4-ylmethyl)-7-oxo-2,3-dihydro-7H-[1,4]oxazino[2,3,4-ij]quinoline-6-carboxamide (Formula M-8 of Chart M, where $R_a$=3,5-difluorophenyl and $R_b$=H)

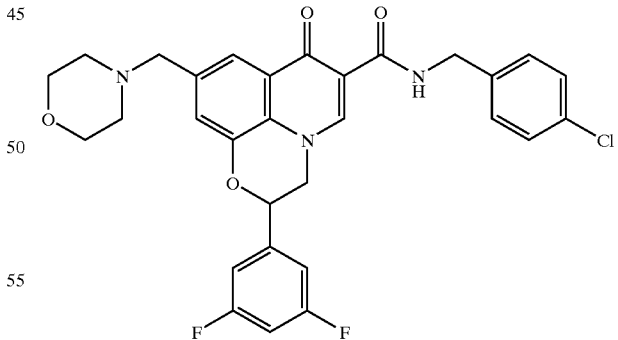

The title compound is prepared according to the general procedure of Example 36, and is purified by flash chromatography on silica gel using 2% methanol in dichloromethane. Recrystallization from acetonitrile containing about 10% methanol affords white crystals, mp 234–236° C.

$^1$H NMR ($CDCl_3$) δ2.47, 3.61, 3.71, 4.23, 4.41, 4.63, 5.30, 6.91, 7.06, 7.29, 7.48, 8.00, 8.67, 10.40 ppm. TLC $R_f$ 0.32 (3% methanol in dichloromethane). IR (diffuse reflectance) 1650, 1628, 1603, 1575, 1552, 1532, 1500, 1466, 1452, 1411, 1347, 1281, 1121, 864, 811 cm$^{-1}$ OAMS supporting ions at: ESI+ 566.4 HRMS (FAB) calcd for $C_{30}H_{26}ClF_2N_3O_4+H_1$ 566.1658, found 566.1654 Anal. Calcd for $C_{30}H_{26}ClF_2N_3O_4$: C, 63.66; H, 4.63; N, 7.42; Cl, 6.26; F, 6.71; Found: C, 63.22; H, 4.73; N, 7.82.

Example 40
2-(1,3-Benzodioxol-5-yl)-N-(4-chlorobenzyl)-9-(morpholin-4-ylmethyl)-7-oxo-2,3-dihydro-7H-[1,4]oxazino[2,3,4-ij]quinoline-6-carboxamide (Formula M-8 of Chart M, where $R_a$=1,3-benzodioxol-5-yl and $R_b$=H)

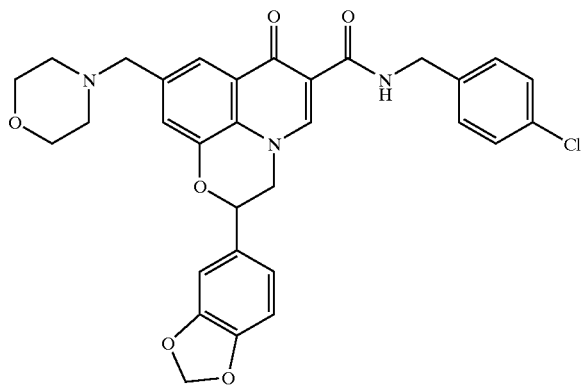

The title compound is prepared according to the general procedure of Example 36, and is purified by flash chromatography on silica gel using 2–3% methanol in dichloromethane. Recrystallization from acetonitrile containing about 10% methanol affords pale yellow crystals, mp 227–231° C.

$^1$H NMR (CDCl$_3$+CD$_3$OD) δ2.49, 3.62, 3.72, 4.29, 4.47, 4.63, 5.24, 6.04, 6.90, 6.98, 7.31, 7.45, 7.95, 8.64, 10.59 ppm. TLC R$_f$ 0.30 (3% methanol in dichloromethane). IR (diffuse reflectance) 1650, 1627, 1608, 1552, 1500, 1449, 1411, 1353, 1330, 1282, 1246, 1225, 1116, 1038, 810 cm$^{-1}$ OAMS supporting ions at: ESI+ 574.4 HRMS (FAB) calcd for $C_{31}H_{28}ClN_3O_6+H_1$ 574.1744, found 574.1760 Anal. Calcd for $C_{31}H_{28}ClN_3O_6$: C, 64.86; H, 4.92; N, 7.32; Cl, 6.18; found: C, 64.75; H, 4.96; N, 7.24.

Example 41
N-(4-Chlorobenzyl)-2-(2,3-dihydro-1,4-benzodioxin-6-yl)-9-(morpholin-4-ylmethyl)-7-oxo-2,3-dihydro-7H-[1,4]oxazino[2,3,4-ij]quinoline-6-carboxamide (Formula M-8 of Chart M, where $R_a$= 2,3-dihydro-1,4-benzodioxin-6-yl and $R_b$=H)

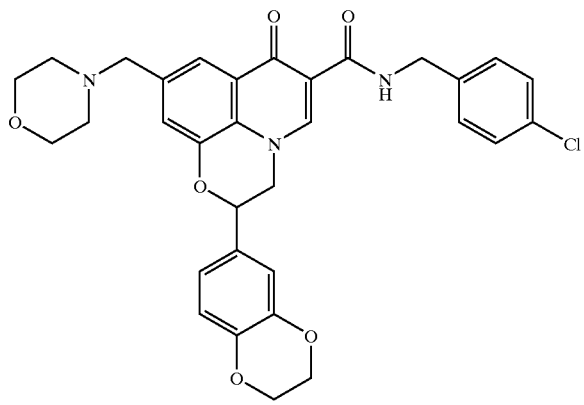

The title compound is prepared according to the general procedure of Example 36, and is purified by flash chromatography on silica gel using 2% methanol in dichloromethane. Recrystallization from acetonitrile containing about 10% methanol affords white crystals, mp 240–243° C.

$^1$H NMR (CDCl$_3$+CD$_3$OD) δ2.48, 3.62, 3.72, 4.29, 4.31, 4.43, 4.63, 5.21, 6.96, 7.02, 7.31, 7.44, 7.95, 8.64, 10.57 ppm. TLC R$_f$ 0.30 (3% methanol in dichloromethane). IR (diffuse reflectance) 1648, 1607, 1552, 1502, 1411, 1330, 1308, 1293, 1281, 1261, 1120, 1116, 1068, 891, 811 cm$^{-1}$ OAMS supporting ions at: ESI+ 588.4 HRMS (FAB) calcd for $C_{32}H_{30}ClN_3O_6+H_1$ 588.1901, found 588.1905 Anal. Calcd for $C_{32}H_{30}ClN_3O_6$: C, 65.36; H, 5.14; N, 7.14; Cl, 6.03; found: C, 65.15; H, 5.19; N, 7.04.

Example 42
2-(1,3-Benzodioxol-4-yl)-N-(4-chlorobenzyl)-9-(morpholin-4-ylmethyl)-7-oxo-2,3-dihydro-7H-[1,4]oxazino[2,3,4-ij]quinoline-6-carboxamide (Formula M-8 of Chart M, where $R_a$=1,3-benzodioxol-4-yl and $R_b$=H)

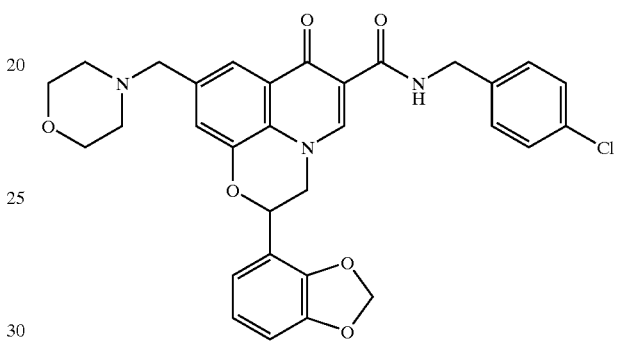

The title compound is prepared according to the general procedure of Example 36, and is purified by flash chromatography on silica gel using 2% methanol in dichloromethane. Recrystallization from acetonitrile containing about 10% methanol affords white crystals, mp 221–225° C. (d).

$^1$H NMR (CDCl$_3$) δ2.46, 3.60, 3.70, 4.43, 4.48, 4.63, 5.45, 6.02, 6.07, 6.91, 6.95, 7.02, 7.3, 7.46, 7.97, 8.68, 10.45 ppm. TLC R$_f$ 0.30 (3% methanol in dichloromethane). IR (diffuse reflectance) 1654, 1606, 1553, 1498, 1463, 1411, 1349, 1283, 1272, 1249, 1223, 1119, 871, 808, 797 cm$^{-1}$ OAMS supporting ions at: ESI+ 574.4 HRMS (FAB) calcd for $C_{31}H_{28}ClN_3O_6+H_1$ 574.1744, found 574.1763 Anal. Calcd for $C_{31}H_{28}ClN_3O_6$: C, 64.86; H, 4.92; N, 7.32; Cl, 6.18; found: C, 64.77; H, 4.98; N, 7.37.

Example 43
2-[3,5-bis(Methoxymethoxy)phenyl]-N-(4-chlorobenzyl)-9-(morpholin-4-ylmethyl)-7-oxo-2,3-dihydro-7H-[1,4]oxazino[2,3,4-ij]quinoline-6-carboxamide (Formula M-8 of Chart M, where $R_a$= 3,5-bis(methoxymethoxy)phenyl and $R_b$=H)

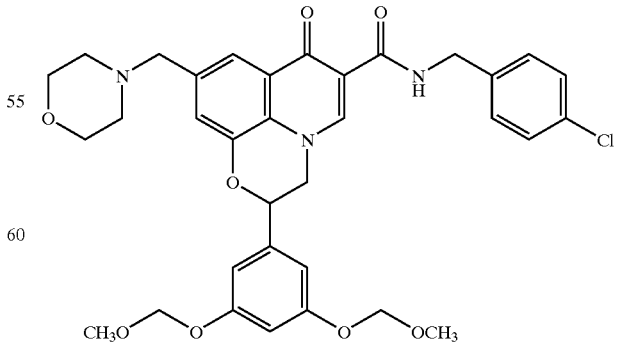

The title compound is prepared according to the general procedure of Example 36, and is purified by flash chromatography on silica gel using 2% methanol in dichloromethane. Recrystallization from acetonitrile affords pale pink crystals, mp 187–189° C.

$^1$H NMR (CDCl$_3$) δ2.47, 3.50, 3.60, 3.71, 4.29, 4.37, 4.63, 5.18, 5.21, 5.23, 6.82, 7.3, 7.46, 7.97, 8.66, 10.45 ppm. TLC R$_f$ 0.33 (3% methanol in dichloromethane). IR (diffuse reflectance) 3031, 2937, 2922, 2861, 1655, 1607, 1578, 1569, 1551, 1499, 1288, 1147, 1086, 1025, 1011, 925 cm$^{-1}$ OAMS supporting ions at: ESI+ 650.5 HRMS (FAB) calcd for C$_{34}$H$_{36}$ClN$_3$O$_8$+H$_1$ 650.2269, found 650.2283 Anal. Calcd for C$_{34}$H$_{36}$ClN$_3$O$_8$: C, 62.81; H, 5.58; N, 6.46; Cl, 5.45; found: C, 62.63; H, 5.59; N, 6.45.

Example 44
2-[2,3-bis(Methoxymethoxy)phenyl]-N-(4-chlorobenzyl)-9-(morpholin-4-ylmethyl)-7-oxo-2,3-dihydro-7H-[1,4]oxazino[2,3,4-ij]quinoline-6-carboxamide (Formula M-8 of Chart M, where R$_a$= 2,3-bis(methoxymethoxy)phenyl and R$_b$=H)

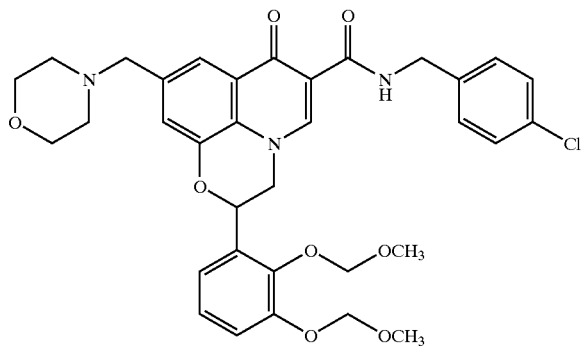

The title compound is prepared according to the general procedure of Example 36, and is purified by flash chromatography on silica gel using 2% methanol in dichloromethane. Recrystallization from acetonitrile affords white crystals, mp 177–180° C.

$^1$H NMR (CDCl$_3$) δ2.47, 3.45, 3.53, 3.61, 3.71, 4.16, 4.60, 4.64, 5.18, 5.21, 5.25, 5.70, 7.2, 7.3, 7.46, 7.99, 8.67, 10.49 ppm. TLC R$_f$ 0.40 (3% methanol in dichloromethane). IR (diffuse reflectance) 1648, 1605, 1571, 1551, 1526, 1500, 1482, 1280, 1260, 1159, 1115, 1077, 1004, 957, 924 cm$^{-1}$ OAMS supporting ions at: ESI+ 650.5 HRMS (FAB) calcd for C$_{34}$H$_{36}$ClN$_3$O$_8$+H$_1$ 650.2269, found 650.2279 Anal. Calcd for C$_{34}$H$_{36}$ClN$_3$O$_8$: C, 62.81; H, 5.58; N, 6.46; Cl, 5.45; found: C, 62.63; H, 5.57; N, 6.39.

Example 45
N-(4-Chlorobenzyl)-9-(morpholin-4-ylmethyl)-7-oxo-2-thien-3-yl-2,3-dihydro-7H-[1,4]oxazino[2,3,4-ij]quinoline-6-carboxamide (Formula M-8 of Chart M, where R$_a$=thien-3-yl and R$_b$=H)

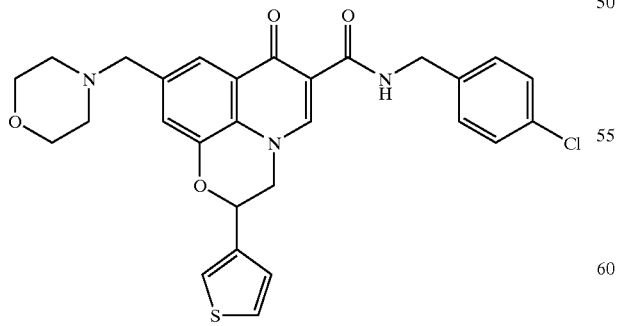

The title compound is prepared according to the general procedure of Example 36, and is purified by flash chromatography on silica gel using 2% methanol in dichloromethane. Recrystallization from acetonitrile affords yellow crystals, mp 241–245° C. (d).

$^1$H NMR (CDCl$_3$) δ2.46, 3.60, 3.70, 4.37, 4.44, 4.63, 5.45, 7.19, 7.3, 7.44, 7.47, 7.97, 8.68, 10.44 ppm. TLC R$_f$ 0.35 (3% methanol in dichloromethane). IR (diffuse reflectance) 1656, 1627, 1608, 1569, 1551, 1500, 1411, 1348, 1330, 1319, 1282, 1227, 1113, 810, 797 cm$^{-1}$ OAMS supporting ions at: ESI+ 536.4 HRMS (FAB) calcd for C$_{28}$H$_{26}$ClN$_3$O$_4$S+H$_1$ 536.1411, found 536.1417 Anal. Calcd for C$_{28}$H$_{26}$ClN$_3$O$_4$S: C, 62.74; H, 4.89; N, 7.84; Cl, 6.61; S, 5.98; found: C, 62.68; H, 4.94; N, 7.77.

Example 46
N-[(4-Chlorophenyl)methyl]-2,3,5,6-tetrahydro-9'-(4-morpholinylmethyl)-7'-oxospiro[4H-pyran-4,2'(3'H)-[7H]pyrido[1,2,3-de][1,4]benzoxazine]-6'-carboxamide (Formula M-8 of Chart M, where R$_a$, R$_b$=4-tetrahydropyran)

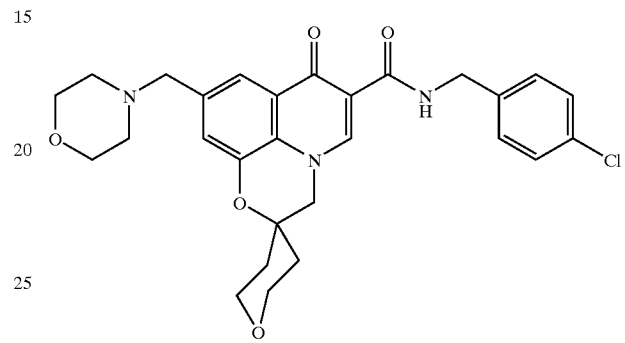

The title compound is prepared according to the general procedure of Example 36, and is purified by flash chromatography on silica gel using 3% methanol in dichloromethane. Recrystallization from acetonitrile affords white crystals, mp 251–254° C.

$^1$H NMR (CDCl$_3$) δ1.80, 2.47, 3.59, 3.72, 3.86, 4.04, 4.64, 7.30, 7.40, 7.94, 8.65, 10.44 ppm. TLC R$_f$ 0.30 (5% methanol in dichloromethane). IR (diffuse reflectance) 2861, 1655, 1607, 1568, 1552, 1504, 1411, 1323, 1277, 1245, 1217, 1113, 1015, 882, 811 cm$^{-1}$ OAMS supporting ions at: ESI+ 524.4 HRMS (FAB) calcd for C$_{28}$H$_{30}$ClN$_3$O$_5$+H$_1$ 524.1952, found 524.1957 Anal. Calcd for C$_{28}$H$_{30}$ClN$_3$O$_5$: C, 64.18; H, 5.77; N, 8.02; Cl, 6.77; found: C, 64.12; H, 5.78; N, 8.03.

Example 47
1,1-Dimethylethyl 6-[[[(4-chlorophenyl)methyl]amino]carbonyl]-9'-(4-morpholinylmethyl)-7'-oxospiro[piperidine-4,2'(3'H)-[7H]pyrido[1,2,3-de][1,4]benzoxazine]-1-carboxylate (Formula M-8 of Chart M, where R$_a$, R$_b$=N-Boc-4-piperidine)

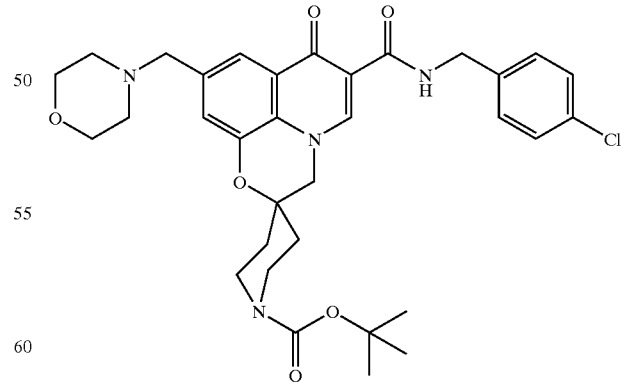

The title compound is prepared according to the general procedure of Example 36, and is purified by flash chromatography on silica gel using 2% methanol in dichloromethane. Recrystallization from acetonitrile affords white crystals, mp 213° C. (d).

¹H NMR (CDCl₃) δ1.47, 1.67, 1.81, 2.46, 3.23, 3.59, 3.71, 3.97, 4.03, 4.64, 7.30, 7.38, 7.94, 8.63, 10.43 ppm. TLC R_f 0.45 (5% methanol in dichloromethane). IR (diffuse reflectance) 1694, 1662, 1647, 1605, 1570, 1551, 1537, 1500, 1413, 1366, 1281, 1249, 1151, 1113, 811 cm⁻¹ OAMS supporting ions at: ESI+ 623.5 HRMS (FAB) calcd for C₃₃H₃₉ClN₄O₆+H₁ 623.2636, found 623.2628 Anal. Calcd for C₃₃H₃₉ClN₄O₆: C, 63.61; H, 6.31; N, 8.99; Cl, 5.69; found: C, 63.38; H, 6.30; N, 9.02.

Example 48
N-[(4-Chlorophenyl)methyl]-9'-(4-morpholinylmethyl)-7'-oxospiro[piperidine-4,2' (3'H)-[7H]pyrido[1,2,3-de][1,4]benzoxazine]-6'-carboxamide (Formula M-8 of Chart M, where R_a, R_b=4-piperidine)

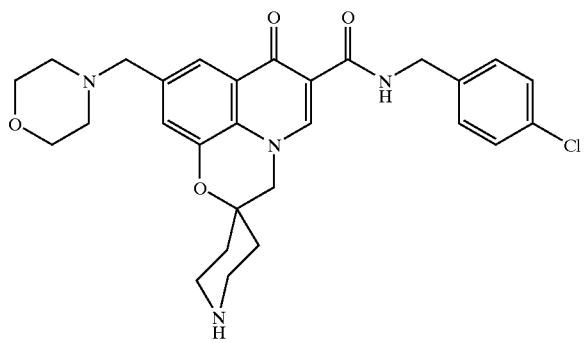

A solution of 102 mg of the product of Example 47 in 1 mL of 1:1 TFA-dichloromethane is allowed to stand for 1 h, then partitioned between excess aqueous NaHCO₃ and dichloromethane. The organic phase is dried (Na₂SO₄) and concentrated under reduced pressure. Flash chromatography of the residue on silica using 5–8% methanolic ammonia in dichloromethane provides 73 mg of the title compound as a white solid. Recrystallization from acetonitrile containing ca. 10% methanol affords white crystals, mp 246–250° C. (d).
¹H NMR (CDCl₃) δ1.68, 1.80, 2.46, 2.92, 3.08, 3.59, 3.71, 4.03, 4.64, 7.30, 7.38, 7.92, 8.64, 10.47 ppm. TLC R_f 0.25 (8% methanolic ammonia in dichloromethane). IR (diffuse reflectance) 2963, 2936, 2916, 1655, 1607, 1569, 1551, 1503, 1411, 1322, 1281, 1218, 1113, 882, 811 cm⁻¹ OAMS supporting ions at: ESI+ 523.5 HRMS (FAB) calcd for C₂₈H₃₁ClN₄O₄+H₁ 523.2112, found 523.2122 Anal. Calcd for C₂₈H₃₁ClN₄O₄: C, 64.30; H, 5.97; N, 10.71; Cl, 6.78; found: C, 64.08; H, 6.04; N, 10.76.

Example 49
N-[(4-Chlorophenyl)methyl]-1-methyl-9'-(4-morpholinylmethyl)-7'-oxospiro[piperidine-4,2' (3'H)-[7H]pyrido[1,2,3-de][1,4]benzoxazine]-6'-carboxamide (Formula M-8 of Chart M, where R_a, R_b=N-methyl4-piperidine)

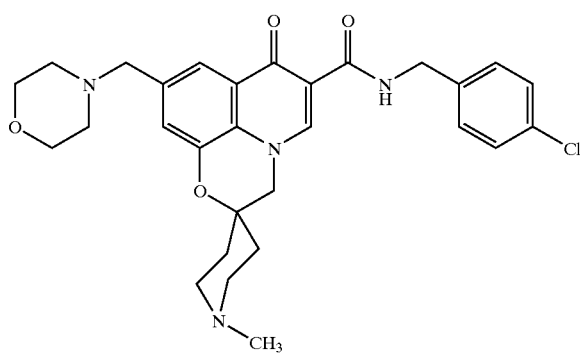

The title compound is prepared according to the general procedure of Example 36, and is purified by flash chromatography on silica gel using 3% methanolic ammonia in dichloromethane. Recrystallization from acetonitrile affords fine white needles, mp 234–237° C. (d).
¹H NMR (CDCl₃) δ1.83, 2.36, 2.46, 2.64, 3.59, 3.72, 4.02, 4.64, 7.30, 3.38, 7.93, 8.64, 10.45 ppm. TLC R_f 0.41 (5% methanolic ammonia in dichloromethane). IR (diffuse reflectance) 2951, 2938, 2797, 1653, 1607, 1552, 1501, 1413, 1306, 1289, 1276, 1216, 1144, 1116, 811 cm⁻¹ OAMS supporting ions at: ESI+ 537.2 HRMS (FAB) calcd for C₂₉H₃₃ClN₄O₄+H₁ 537.2268, found 537.2271 Anal. Calcd for C₂₉H₃₃ClN₄O₄: C, 64.86; H, 6.19; N, 10.43; Cl, 6.60; found: C, 64.73; H, 6.16; N, 10.36.

Example 50
N-[(4-Chlorophenyl)methyl]-9"-(4-morpholinylmethyl)dispiro[1,3-dioxolane-2,1'-cyclohexane-4',2"(3"H)-[7H]pyrido[1,2,3-de][1,4]benzoxazine]-6"-carboxamide (Formula M-8 of Chart M, where R_a, R_b=cyclohexane-4-ethylene ketal)

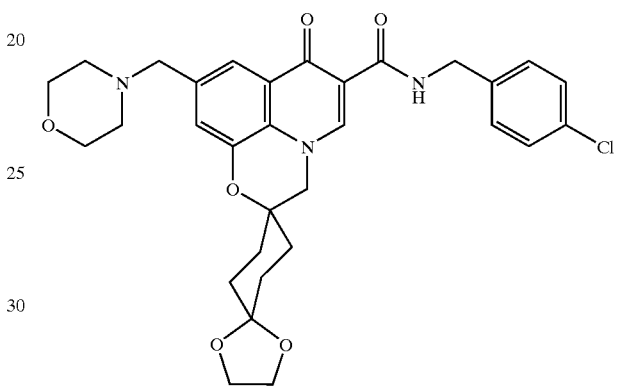

The title compound is prepared according to the general procedure of Example 36, and is purified by flash chromatography on silica gel using 2% methanol in dichloromethane. Recrystallization from acetonitrile affords white crystals, mp>260° C.
¹H NMR (CDCl₃) δ1.66, 1.84, 2.01, 2.46, 3.58, 3.71, 3.99, 4.02, 4.64, 7.30, 7.36, 7.92, 8.63, 10.47 ppm. TLC R_f 0.43 (5% methanol in dichloromethane). IR (diffuse reflectance) 2958, 2933, 1649, 1606, 1568, 1551, 1503, 1412, 1286, 1272, 1256, 1116, 1102, 917, 810 cm⁻¹ OAMS supporting ions at: ESI+ 580.3 HRMS (FAB) calcd for C₃₁H₃₄ClN₃O₆+H₁ 580.2214, found 580.2227 Anal. Calcd for C₃₁H₃₄ClN₃O₆: C, 64.19; H, 5.91; N, 7.24; Cl, 6.11; found: C, 64.15; H, 5.92; N, 7.13.

Example 51
N-(4-Chlorobenzyl)-2,2-bis[(methoxymethoxy)methyl]-9-(morpholin-4-ylmethyl)-7-oxo-2,3-dihydro-7H-[1,4]oxazino[2,3,4-ij]quinoline-6-carboxamide (Formula M-8 of Chart M, where R_a, R_b=methoxymethoxymethyl)

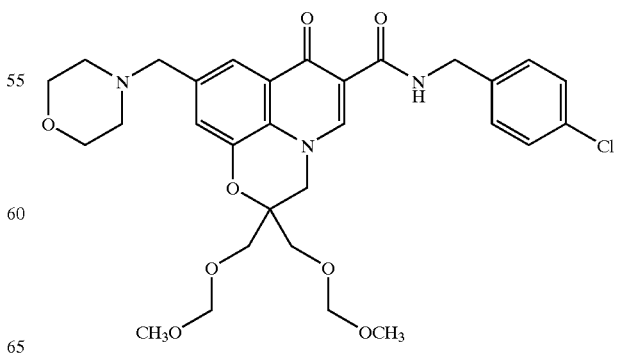

The title compound is prepared according to the general procedure of Example 36, and is purified by flash chromatography on silica gel using 2% methanol in dichloromethane. Recrystallization from ethyl acetate affords white crystals, mp 147–149° C.

$^1$H NMR (CDCl$_3$) δ2.45, 3.33, 3.57, 3.66, 3.70, 3.77, 4.33, 4.63, 4.64, 7.31, 7.38, 7.94, 8.67, 10.45 ppm. TLC R$_f$ 0.40 (5% methanol in dichloromethane). IR (diffuse reflectance) 2954, 2931, 2888, 1653, 1608, 1569, 1552, 1501, 1411, 1280, 1150, 1113, 1045, 919, 809 cm$^{-1}$ OAMS supporting ions at: ESI+ 602.2 HRMS (FAB) calcd for C$_{30}$H$_{36}$ClN$_3$O$_8$+H$_1$ 602.2269, found 602.2269 Anal. Calcd for C$_{30}$H$_{36}$ClN$_3$O$_8$: C, 59.85; H, 6.03; N, 6.98; Cl, 5.89; found: C, 59.77; H, 5.96; N, 6.95.

Example 52

N-(4-Chlorobenzyl)-2,2-bis(hydroxymethyl)-9-(morpholin-4-ylmethyl)-7-oxo-2,3-dihydro-7H-[1,4]oxazino[2,3,4-ij]quinoline-6-carboxamide (Formula M-8 of Chart M, where R$_a$, R$_b$=hydroxymethyl)

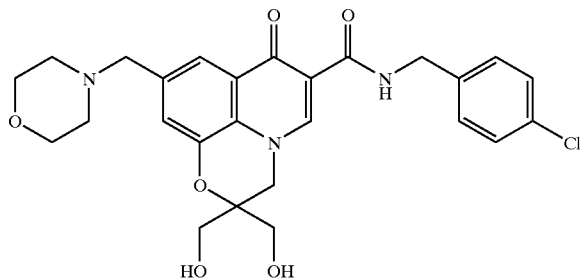

A mixture of 151 mg of the product of Example 51 in 2 mL of THF and 1 mL of conc. HCl is stirred for 18 h, then partitioned between chloroform and excess aqueous NaHCO$_3$. The organic phase is dried (Na$_2$SO$_4$) and concentrated under reduced pressure. Flash chromatography of the residue on silica gel using 7–10% methanol in dichloromethane affords 104 mg of the title compound as a white solid. Trituration and recrystallization from acetonitrile provides white solid with mp 230–233° C.

$^1$H NMR (CDCl$_3$+CD$_3$OD+TFA-d$_6$) δ3.05, 3.40, 3.70, 3.78, 3.9, 4.33, 4.39, 4.64, 7.31, 7.49, 7.90, 8.73 ppm. TLC R$_f$ 0.24 (10% methanol in dichloromethane). IR (diffuse reflectance) 1653, 1606, 1561, 1500, 1411, 1353, 1327, 1288, 1242, 1232, 1111, 1058, 886, 811, 795 cm$^{-1}$ OAMS supporting ions at: ESI+ 514.3 HRMS (FAB) calcd for C$_{26}$H$_{28}$ClN$_3$O$_6$+H$_1$ 514.1744, found 514.1745 Anal. Calcd for C$_{26}$H$_{28}$ClN$_3$O$_6$: C, 60.76; H, 5.49; N, 8.18; Cl, 6.90; found: C, 60.52; H, 5.60; N, 8.22.

Example 53

N-[(4-Chlorophenyl)methyl]-2',3',5',6'-tetrahydro-9-(4-morpholinylmethyl)-7-oxospiro[7H-pyrido[1,2,3-de]-1,4-benzoxazine-2(3H),4'-[4H]thiopyran]-6-carboxamide (Formula M-8 of Chart M, where R$_a$, R$_b$=4-tetrahydrothiopyran)

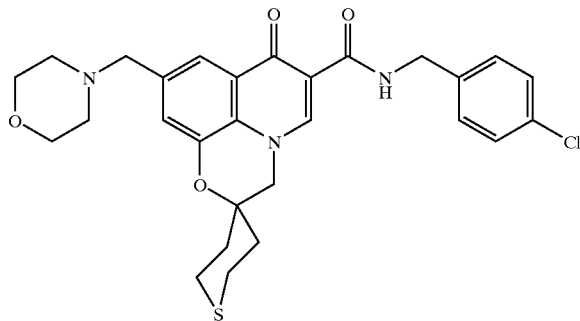

The product is prepared according to the general procedure of Example 36, and is purified by flash chromatography on silica gel using 2% methanol in dichloromethane. Recrystallization from ethyl acetate affords white crystals, mp 147–149° C.

$^1$H NMR (CDCl$_3$) δ1.88, 2.14, 2.47, 3.11, 3.59, 3.72, 3.99, 4.64, 7.30, 7.40, 7.94, 8.63, 10.43 ppm. TLC R$_f$ 0.35 (3% methanol in dichloromethane). IR (diffuse reflectance) 1652, 1607, 1556, 1503, 1412, 1330, 1317, 1285, 1270, 1245, 1229, 1193, 1112, 810, 798 cm$^{-1}$ OAMS supporting ions at: ESI+ 540.1 HRMS (FAB) calcd for C$_{28}$H$_{30}$ClN$_3$O$_4$S+H$_1$ 540.1724, found 540.1722 Anal. Calcd for C$_{28}$H$_{30}$ClN$_3$O$_4$S: C, 62.27; H, 5.60; N, 7.78; Cl, 6.56; S, 5.94; found: C, 61.98; H, 5.71; N, 7.67.

Example 54

N-[(4-Chlorophenyl)methyl]-9'-(4-morpholinylmethyl)-4,7'-dioxospiro[cyclohexane-1,2'(3'H)-[7H]pyrido[1,2,3-de][1,4]benzoxazine]-6'-carboxamide (Formula M-8 of Chart M, where R$_a$, R$_b$=4-cyclohexanone)

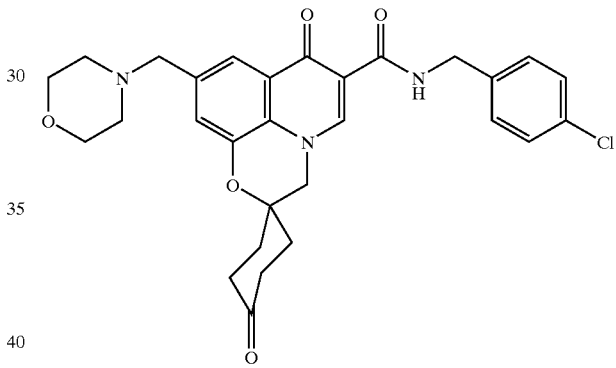

A mixture of 104 mg of compound M-8 of Example 50 (where R$_a$, R$_b$=cyclohexane-4-ethylene ketal), 3 mL of acetone, 3 mL of THF, and 1 mL of 6N HCl is stirred for 18 h, the partitioned between chloroform and aqueous NaHCO$_3$. The organic phase is dried (Na$_2$SO$_4$) and concentrated under reduced pressure. Flash chromatography of the residue on silica gel using 2–3% methanol in dichloromethane affords 101 mg of the title compound as a white solid. Recrystallization from acetonitrile provides white needles, mp 249.5–252.0° C.

$^1$H NMR (CDCl$_3$) δ1.98, 2.24, 2.40, 2.47, 2.78, 3.61, 3.72, 4.13, 4.64, 7.31, 7.44, 7.98, 8.66, 10.42 ppm. TLC R$_f$ 0.33 (5% methanol in dichloromethane). IR (diffuse reflectance) 1717, 1658, 1608, 1576, 1550, 1502, 1412, 1312, 1296, 1275, 1192, 1145, 1109, 875, 809 cm$^{-1}$ OAMS supporting ions at: ESI+ 536.2 HRMS (FAB) calcd for C$_{29}$H$_{30}$ClN$_3$O$_5$+H$_1$ 536.1952, found 536.1951 Anal. Calcd for C$_{29}$H$_{30}$ClN$_3$O$_5$: C, 64.98; H, 5.64; N, 7.84; Cl, 6.61; found: C, 64.85; H, 5.83; N, 7.85.

Example 55

N-[(4-Chlorophenyl)methyl]-4-hydroxy-9'-(4-morpholinylmethyl)-7'-oxospiro[cyclohexane-1,2'(3'H)-[7H]pyrido[1,2,3-de][1,4]benzoxazine]-6'-carboxamide (Formula M-8 of Chart M, where $R_a$, $R_b$=4-cyclohexanol)

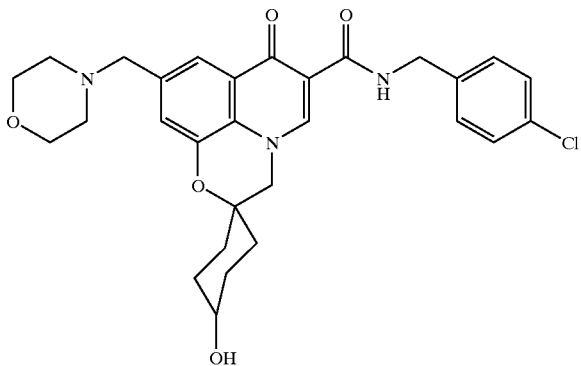

To a stirred solution of 118 mg of the produce of Example 54 in 2 mL of dichloromethane and 1 mL of methanol, cooled at 0° C., is added 10 mg of sodium borohydride. After ten minutes, the reaction mixture is partitioned between water and dichloromethane, and the organic phase is dried ($Na_2SO_4$) and concentrated under reduced pressure. Flash chromatography of the residue on silica gel using 4–6% methanol in dichloromethane affords 69 mg of the title compound as a yellow solid. Recrystallization from acetonitrile provides pale yellow needles, mp 229–234° C.

$^1$H NMR (CDCl$_3$) δ1.54, 1.6–2.0, 2.46, 3.59, 3.72, 3.78, 4.00, 4.64, 7.3, 7.38, 7.93, 8.62, 10.47 ppm. TLC $R_f$ 0.29 (7% methanol in dichloromethane). IR (diffuse reflectance) 1653, 1607, 1574, 1552, 1504, 1411, 1324, 1281, 1250, 1240, 1114, 1107, 881, 810, 801 cm$^{-1}$ OAMS supporting ions at: ESI+ 538.3 Anal. Calcd for $C_{29}H_{32}ClN_3O_5$: C, 64.74; H, 5.99; N, 7.81; Cl, 6.59; found: C, 64.63; H, 5.98; N, 7.79.

Example 56

N-(4-Chlorobenzyl)-2-{[(4-chlorobenzyl)amino]methyl}-9-(morpholin-4-ylmethyl)-7-oxo-2,3-dihydro-7H-[1,4]oxazino[2,3,4-ij]quinoline-6-carboxamide (A-11 of Chart A, where $R_6$ is 4-chlorobenzylamino)

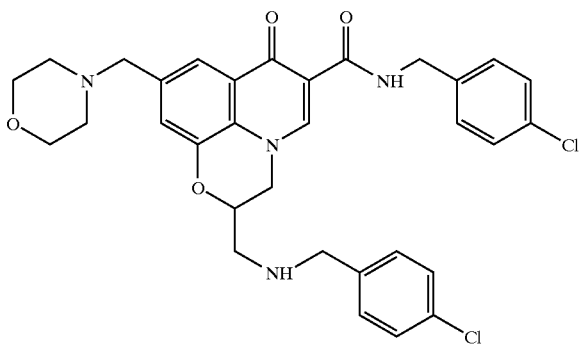

Following the procedure in Example 2, the title compound is obtained.

$^1$H NMR (CDCl$_3$) δ1.88, 2.45, 3.03, 3.57, 3.70, 3.85, 4.3, 4.4, 4.63, 7.30, 7.34, 7.92, 8.63, 10.45 ppm. IR (diffuse reflectance) 2858, 1648, 1627, 1607, 1570, 1551, 1536, 1499, 1451, 1411, 1330, 1283, 1112, 811, 800 cm$^{-1}$. OAMS supporting ions at: ESI+ 609.2 HRMS (FAB) calcd for $C_{32}H_{32}CL_2N_4O_4+H_1$ 607.1879, found 607.1872. Anal. Calcd for $C_{32}H_{32}Cl_2N_4O_4$: C, 63.26; H, 5.31; N, 9.22; Cl, 11.67; found: C, 63.12; H, 5.29; N, 9.19.

Example 57

N-(4-Chlorobenzyl)-9-(morpholin-4-ylmethyl)-7-oxo-2-(R or S)-pyridin-2-yl-2,3-dihydro-7H-[1,4]oxazino[2,3,4-ij]quinoline-6-carboxamide (I-6 of Chart I, T=2-pyridyl)

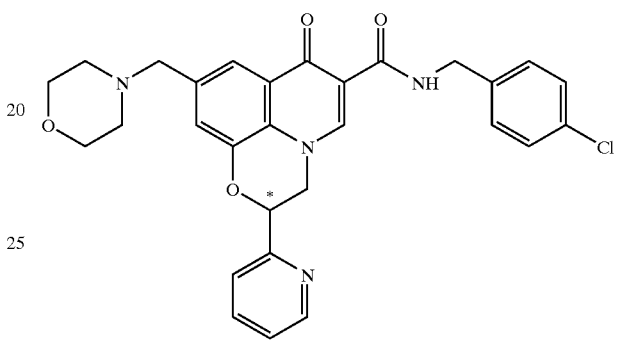

The enantiomers are prepared by resolution of racemic compound of Example 33 on chiral HPLC using a chiralcel OD column eluted with 0.025% diethylamine in ethanol, giving Isomer 1 (first eluting) and Isomer 2 (second eluting).

$^1$H NMR (CDCl$_3$) δ2.47, 3.61, 3.72, 4.58, 4.63, 4.72, 5.51, 7.3, 7.50, 7.63, 7.79, 7.97, 8.63, 8.72, 10.44 ppm. OAMS supporting ions at: ESI+ 531.3.

Example 58

N-(4-Chlorobenzyl)-9-(morpholin-4-ylmethyl)-7-oxo-2-(R or S)-pyridin-3-yl-2,3-dihydro-7H-[1,4]oxazino[2,3,4-ij]quinoline-6-carboxamide (I-6 of Chart I, T=3-pyridyl)

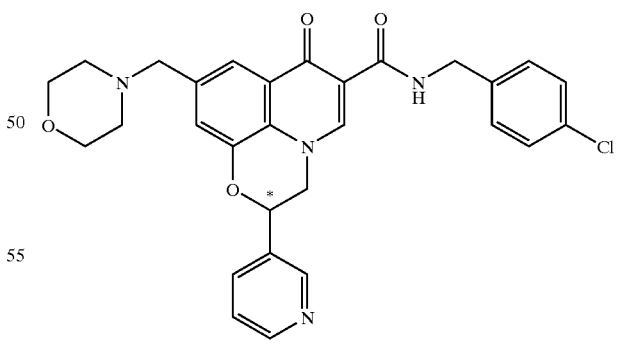

The enantiomers are prepared by resolution of racemic compound of Example 34 on chiral HPLC using a chiralcel OD column eluted with 0.1% diethylamine in ethanol, giving Isomer 1 (first eluting) and Isomer 2 (second eluting).

$^1$H NMR (CDCl$_3$) δ2.46, 3.60, 3.71, 4.32, 4.47, 4.60, 5.37, 7.27, 7.44, 7.84, 7.99, 8.70, 8.72, 8.79, 10.41 ppm. OAMS supporting ions at: ESI+ 531.2.

Example 59

N-(4-Chlorobenzyl)-2-(1-methyl-1H-imidazol-2-yl)-9-(morpholin-4-ylmethyl)-7-oxo-2,3-dihydro-7H-[1,4]oxazino[2,3,4-ij]quinoline-6-carboxamide (I-6 of Chart I, T=1-methylimidazol-2-yl)

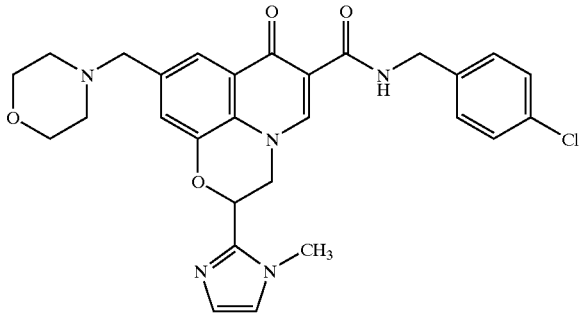

Following the procedure in Preparations 37–41 and Example 33 without making major changes except using 1-methylimidazole-2-carboxaldehyde as the starting aldehyde, the title compound is obtained as a light brown solid. Recrystallization from acetonitrile gives tan granular crystals, mp>260° C.

$^1$H NMR (CDCl$_3$) δ2.46, 3.56, 3.60, 3.70, 3.85, 4.63, 4.69, 4.95, 5.46, 7.00, 7.03, 7.30, 7.38, 7.97, 8.75, 10.43 ppm. TLC Rf 0.23 (5% methanol in dichloromethane). IR (diffuse reflectance) 3047, 2988, 2851, 1652, 1627, 1607, 1569, 1550, 1500, 1458, 1411, 1347, 1279, 1119, 810 cm$^{-1}$ OAMS supporting ions at: ESI+ 534.4 HRMS (FAB) calcd for C$_{28}$H$_{28}$ClN$_5$O$_4$+H$_1$ 534.1908, found 534.1913 Anal. Calcd for C$_{28}$H$_{28}$ClN$_5$O$_4$: C, 62.98; H, 5.28; N, 13.11; Cl, 6.64; found: C, 63.06; H, 5.32; N, 13.11.

Example 60

N-(4-Chlorobenzyl)-2-(2-furyl)-9-(morpholin-4-ylmethyl)-7-oxo-2,3-dihydro-7H-[1,4]oxazino[2,3,4-ij]quinoline-6-carboxamide (I-6 of Chart I, T-2-furyl)

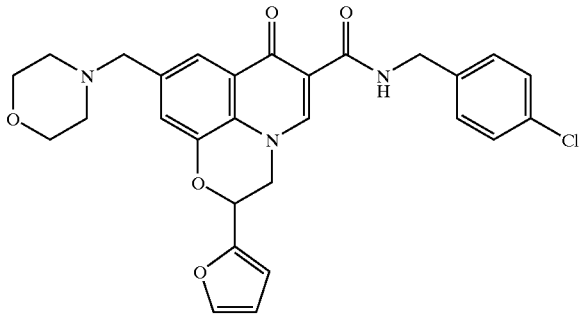

Following the procedure in Preparations 37–41 and Example 33 without making major changes except using furfural as the starting aldehyde, the title compound is obtained as a light yellow solid. Recrystallization from acetonitrile gives tan needles, mp 220.0–222.5° C.

$^1$H NMR (CDCl$_3$) δ2.45, 3.58, 3.69, 4.48, 4.61, 4.63, 5.44, 6.44, 6.50, 7.30, 7.41, 7.50, 7.97, 8.70, 10.44 ppm. TLC Rf 0.31 (3% methanol in dichloromethane). IR(diffuse reflectance) 1655, 1627, 1608, 1551, 1500, 1411, 1347, 1330, 1282, 1225, 1114, 1011, 882, 809, 760 cm$^{-1}$ OAMS supporting ions at: ESI+ 520.3 HRMS (FAB) calcd for C$_{28}$H$_{26}$ClN$_3$O$_5$+H$_1$ 520.1639, found 520.1638. Anal. Calcd for C$_{28}$H$_{26}$ClN$_3$O$_5$: C, 64.68; H, 5.04; N, 8.08; Cl, 6.82; found: C, 64.47; H, 5.04; N, 8.08.

Preparation 49: {3-[(Methoxymethoxy)methyl]phenyl}methanol (N-2 of Chart N, where substitution is meta, n=1, and P=methoxymethyl)

To a stirred, cooled (0° C.) solution of 6.91 g of 1,3-benzenedimethanol and 9.6 mL of diisopropylethylamine in 50 mL of dichloromethane is added 3.8 mL of chloromethyl methyl ether. After 90 min, 25 mL of 1N HCl is added, the phases separated, and the aqueous extracted with two additional portions of dichloromethane. The combined organic phase is dried (Na$_2$SO$_4$) and concentrated under reduced pressure. Flash chromatography on silica using 40% ethyl acetate in dichloromethane affords 4.76 g of the monoprotected compound as a pale yellow liquid.

$^1$H NMR (CDCl$_3$) δ2.03, 3.41, 4.59, 4.68, 4.70, 7.3 ppm. TLC Rf 0.36 (1:1 ethyl acetate in dichloromethane, vanillin staining).

Preparation 50: 3-[(Methoxymethoxy)methyl]benzaldehyde (N-3 of Chart N, where substitution is meta, n=1, and P=methoxymethyl)

To a well-stirred mixture of 10.8 g of PCC and 820 mg of sodium acetate in 20 mL of dichloromethane is added a solution of 1.82 g of alcohol of Preparation 49 in 10 mL of dichloromethane. After 18 h, silica gel is added and the mixture filtered through a short plug of silica gel, which is rinsed with 1:1 ethyl acetate-dichloromethane. The filtrate is concentrated under reduced pressure, and the residue flash chromatographed on silica gel using 1:1 ether-hexane to afford 1.61 g of the title aldehyde as a colorless liquid.

$^1$H NMR (CDCl$_3$) δ3.43, 4.68, 4.74, 7.53, 7.64, 7.82, 7.89, 10.03 ppm. TLC Rf 0.32 (1:1 ether-hexane).

Preparation 51: 2-Amino-1-{3-[(methoxymethoxy)methyl]phenyl}ethanol (N-5 of Chart N, where substitution is meta, n=1, and P=methoxymethyl)

To a mixture of 1.58 g of aldehyde of Preparation 50 and 1.3 mL of TMSCN, stirred neat under argon, is added a catalytic amount (ca. 10 mg) of ZnI$_2$. After 16 h, the resulting yellow liquid is dissolved in 15 mL of dry ether and added dropwise via cannula to a cooled (0° C.), mechanically stirred slurry of 370 mg of LAH in 20 mL of dry ether. Efficient stirring is required at this stage to assure complete reaction and reasonable product yield. Following the cyanohydrin addition, the reaction mixture is allowed to warm to ambient temperature and stirred vigorously for 2 h. The mixture is then recooled to 0° C. and quenched cautiously with 0.37 mL of water in 10 mL of THF, 0.37 mL of 3N NaOH, and 1.0 mL of water. Sodium sulfate and dichloromethane were added, and the mixture stirred well for 30–90 minutes, then filtered. The filter cake is washed well with ether-dichloromethane and then concentrated under reduced pressure to afford 2.08 g of the amino alcohol as a yellow oil.

$^1$H NMR (CDCl$_3$) δ2.2, 2.81, 2.99, 3.42, 4.60, 4.6, 4.71, 7.3 ppm. OAMS supporting ions at: ESI+ 212.1

Preparation 52: Ethyl 2-(2,3-difluoro-5-iodobenzoyl)-3-[(2-hydroxy-2-{3-[(methoxymethoxy)methyl]phenyl}ethyl)amino]prop-2-enoate (N-6 of Chart N, where substitution is meta, n=1, and P=methoxymethyl)

To a stirred solution of 5.0 mmol of compound I-1 (prepared as described in Preparation 38) in 15 mL of ethanol is added 2.0 g of crude amino alcohol of Preparation 51. The solution is stirred for 18 h, then concentrated under reduced pressure. Flash chromatography of the residue on silica using 10–20% ethyl acetate in dichloromethane provides 2.31 g of the title compound as an yellow foam.

$^1$H NMR (CDCl$_3$) is complex due to E/Z isomers: δ0.90, 1.02, 3.3, 3.6, 4.0, 4.58, 4.69, 4.85, 7.3, 8.1 ppm. TLC R$_f$ 0.20 (10% ethyl acetate in dichloromethane). OAMS supporting ions at: ESI+ 576.2.

Preparation 53: Ethyl 9-iodo-2-{3-[(methoxymethoxy)methyl]phenyl}-7-oxo-2,3-dihydro-7H-[1,4]oxazino[2,3,4-ij]quinoline-6-carboxylate (N-7 of Chart N, where substitution is meta, n=1, and P=methoxymethyl)

A mixture of 2.3 g of compound N-6 of Preparation 52 and 2.9 g of cesium carbonate in 8 mL of DMF is stirred at 100° C. under argon for 18 h, then cooled and partitioned between dichloromethane and dilute HCl. The organic phase is dried (Na$_2$SO$_4$) and concentrated under reduced pressure. Flash chromatography on silica gel using 2% methanol in dichloromethane provides 1.60 g of the title compound as a brown solid. Recrystallization from acetonitrile affords tan crystals, mp 153.3–156.0° C.

$^1$H NMR (CDCl$_3$) δ1.37, 3.44, 4.27, 4.32, 4.66, 4.75, 5.38, 7.5, 7.57, 8.22, 8.26 ppm. TLC R$_f$ 0.47 (5% methanol in dichloromethane). IR (diffuse reflectance) 1680, 1632, 1610, 1586, 1550, 1496, 1316, 1257, 1224, 1182, 1148, 1113, 1048, 921, 799 cm$^{-1}$; OAMS supporting ions at: ESI+ 536.1; HRMS (FAB) calcd for C$_{23}$H$_{22}$INO$_6$+H$_1$ 536.0572, found 536.0587; Anal. Calcd for C$_{23}$H$_{22}$INO$_6$: C, 51.60; H, 4.14; N, 2.62; found: C, 51.40; H, 4.25; N, 2.50.

Preparation 54: Ethyl 9-formyl-2-{3-[(methoxymethoxy)methyl]phenyl}-7-oxo-2,3-dihydro-7H-[1,4]oxazino[2,3,4-ij]quinoline-6-carboxylate (N-8 of Chart N, where substitution is meta, n=1, and P=methoxymethyl)

A mixture of 1.46 g of iodide N-7 of Preparation 53 and 220 mg of tetrakis (triphenylphosphine) palladium (0) in 15 mL of dry DMF is purged with CO, via a needle reaching to the bottom of the flask, and heated to 55° C. To the stirred mixture is added, via syringe pump, 1.0 mL of tributyltin hydride in 9 mL of dry THF. Bubbling of CO through the mixture is continued throughout the addition, which took about 5 h. The mixture is then cooled and concentrated under reduced pressure. Flash chromatography of the residue on silica gel using 2% methanol in dichloromethane affords 970 mg of the title compound as a tan solid.

$^1$H NMR (CDCl$_3$) δ1.41, 3.44, 4.33, 4.40, 4.67, 4.75, 5.36, 7.5, 7.80, 8.36, 8.54, 10.06 ppm. TLC R$_f$ 0.31 (3% methanol in dichloromethane). OAMS supporting ions at: ESI+ 438.2.

Preparation 55: Ethyl 2-{3-[(methoxymethoxy)methyl]phenyl}-9-(morpholin-4-ylmethyl)-7-oxo-2,3-dihydro-7H-[1,4]oxazino[2,3,4-ij]quinoline-6-carboxylate (N-9 of Chart N, where substitution is meta, n=1, and P=methoxymethyl)

To a mixture of 0.97 g of aldehyde of Preparation 54, 0.58 mL of morpholine, and 0.25 mL of acetic acid in 20 mL of THF is added 940 mg of sodium triacetoxyborohydride. After 4 h, additional borohydride (300 mg) is added, and the mixture is stirred for 2 h and then partitioned between dichloromethane and aqueous NaHCO$_3$. The organic phase is dried (Na$_2$SO$_4$) and concentrated under reduced pressure. Flash chromatography of the residue on silica using 3–4% methanol in dichloromethane provides 940 mg of the title compound as a grey solid. Recrystallization from ethyl acetate gave white needles, mp 148–153° C.

$^1$H NMR (CDCl$_3$) δ1.37, 2.45, 3.44, 3.55, 3.69, 4.24, 4.3, 4.33, 4.67, 4.75, 5.36, 7.36, 7.47, 7.55, 7.93, 8.26 ppm. TLC R$_f$ 0.30 (5% methanol in dichloromethane). IR (diffuse reflectance) 2953, 1686, 1638, 1608, 1555, 1506, 1322, 1291, 1271, 1221, 1183, 1148, 1115, 1041, 796 cm$^{-1}$; OAMS supporting ions at: ESI+ 509.4; HRMS (FAB) calcd for C$_{28}$H$_{32}$N$_2$O$_7$+H$_1$ 509.2288, found 509.2285; Anal. Calcd for C$_{28}$H$_{32}$N$_2$O$_7$: C, 66.13; H, 6.34; N, 5.51; found: C, 66.15; H, 6.41; N, 5.43.

Example 61
N-(4-Chlorobenzyl)-2-{3-[(methoxymethoxy)methyl]phenyl}-9-(morpholin-4-ylmethyl)-7-oxo-2,3-dihydro-7H-[1,4]oxazino[2,3,4-ij]quinoline-6-carboxamide (N-10 of Chart N, where substitution is meta, n=1, and P=methoxymethyl)

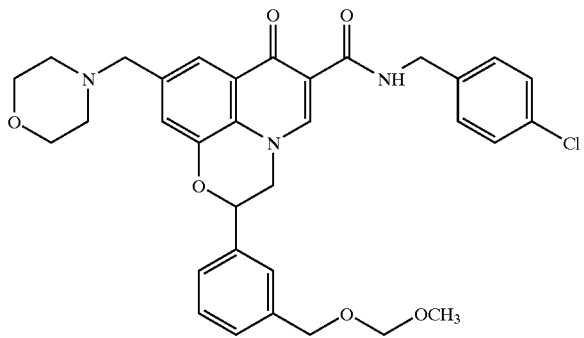

A mixture of 780 mg of ester of Preparation 55 and 1.3 g of p-chlorobenzylamine is stirred neat at 150° C. for 18 h, then concentrated in vacuo. Flash chromatography of the residue on silica using 2% methanol in dichloromethane provides 790 mg of the title compound as a white solid. Recrystallization from acetonitrile-methanol affords fine white needles, mp 186.5–189.0° C.

$^1$H NMR (CDCl$_3$) δ2.46, 3.43, 3.59, 3.70, 4.30, 4.41, 4.60, 4.65, 4.74, 5.30, 7.27, 7.44, 7.52, 7.97, 8.68, 10.44 ppm. TLC R$_f$ 0.29 (3% methanol in dichloromethane). IR (diffuse reflectance) 1649, 1607, 1552, 1501, 1411, 1350, 1284, 1270, 1223, 1147, 1115, 1092, 1047, 810, 799 cm$^{-1}$; OAMS supporting ions at: ESI+ 604.3; HRMS (FAB) calcd for C$_{33}$H$_{34}$ClN$_3$O$_6$+H$_1$ 604.2214, found 604.2225; Anal. Calcd for C$_{33}$H$_{34}$ClN$_3$O$_6$: C, 65.61; H, 5.67; N, 6.96; Cl, 5.87; found: C, 65.57; H, 5.72; N, 6.90.

Example 62
N-(4-Chlorobenzyl)-2-[3-(hydroxymethyl)phenyl]-9-(morpholin-4-ylmethyl)-7-oxo-2,3-dihydro-7H-[1,4]oxazino[2,3,4-ij]quinoline-6-carboxamide (N-11 of Chart N, where substitution is meta, n=1, and P=methoxymethyl)

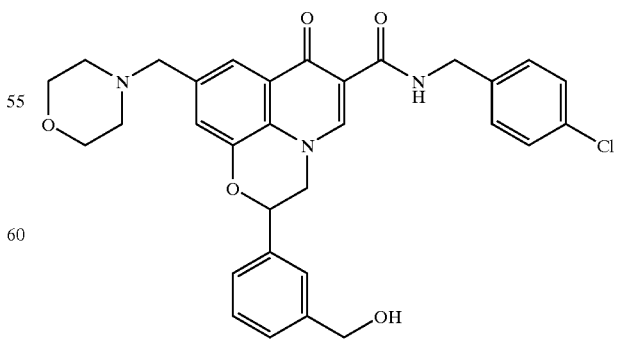

A solution of 122 mg of N-10 of Example 61 in 1 mL of ethanol and 0.5 mL of conc. HCl is stirred for 36 h at room temperature, then added to stirred aqueous NaHCO$_3$. The resulting solid is filtered, washed well with water, dried under vacuum, and then absorbed onto silica gel. Flash chromatography on silica gel using 3–5% methanol in dichloromethane provides 108 mg of the title compound as a white solid. Recrystallization from acetonitrile-methanol provides material with mp 229–233° C.

$^1$H NMR (CDCl$_3$+CD$_3$OD) δ2.49, 3.62, 3.72, 4.30, 4.49, 4.62, 4.72, 5.32, 7.30, 7.43, 7.54, 7.95, 8.63, 10.58 ppm. TLC R$_f$ 0.25 (5% methanol in dichloromethane). IR (diffuse reflectance) 1653, 1606, 1570, 1549, 1542, 1499, 1409, 1325, 1292, 1277, 1219, 1114, 1077, 807, 800 cm$^{-1}$; OAMS supporting ions at: ESI+ 560.3; HRMS (FAB) calcd for C$_{31}$H$_{30}$ClN$_3$O$_5$+H$_1$ 560.1952, found 560.1945; Anal. Calcd for C$_{31}$H$_{30}$ClN$_3$O$_5$: C, 66.48; H, 5.40; N, 7.50; Cl, 6.33; found (av): C, 64.94 H, 5.33; N, 7.29.

Preparation 56: 3-{[tert-Butyl(dimethyl)silyl]oxy}benzaldehyde (N-3 of Chart N, where substitution is meta, n=0, and P=tert-butyldimethylsilyl)

A solution of 3.66 g of 3-hydroxybenzaldehyde, 3.1 g of imidazole, and 4.39 g of tert-butyldimethylsilyl chloride in 10 ml of DMF is stirred at room temperature for 18 h, then partitioned between ether and water. The organic phase is washed with water, dried (MgSO$_4$), and concentrated under reduced pressure. Flash chromatography of the residue on silica gel using 5% ether-hexane provides 5.14 g of the title compound as a pale yellow liquid.

$^1$H NMR (CDCl$_3$) δ0.22, 1.00, 7.11, 7.33, 7.40, 7.48, 9.96 ppm. TLC R$_f$ 0.28 (5% ether-hexane). OAMS supporting ions at: ESI+ 237.1.

Preparation 57: 2-Amino-1-(3-{[tert-butyl(dimethyl)silyl]oxy}phenyl)ethanol (N-5 of Chart N, where substitution is meta, n=0, and P=tert-butyldimethylsilyl)

The procedure described in Preparation 51 is followed starting with 5.14 g of the product of Preparation 56 to provide 6.96 g of crude amino alcohol as an amber oil.

$^1$H NMR (CDCl$_3$) δ0.19, 0.98, 2.1, 2.79, 2.97, 4.59, 6.74, 6.85, 6.93, 7.19 ppm. OAMS supporting ions at: ESI+ 268.3.

Preparation 58: Ethyl 3-{[2-(3-{[tert-butyl(dimethyl)silyl]oxy}phenyl)-2-hydroxyethyl]amino}-2-(2,3-difluoro-5-iodobenzoyl)prop-2-enoate (N-6 of Chart N, where substitution is meta, n=0, and P=tert-butyldimethylsilyl)

The procedure described in Preparation 52 is followed starting with 5.14 g of the product of Preparation 57. Flash chromatography on silica using 30% ethyl acetate in hexane affords 4.11 g of the title compound as a yellow foam.

$^1$H NMR (CDCl$_3$) is complex due to E/Z isomers: δ0.20, 0.99, 1.04, 2.6, 3.6, 4.0, 4.8, 6.8, 6.9, 7.2, 7.4, 8.1, 9.68, 11.03 ppm. TLC R$_f$ 0.28 (30% ethyl acetate-hexane). OAMS supporting ions at: ESI+ 632.2.

Preparation 59: Ethyl 2-(3-{[tert-butyl(dimethyl)silyl]oxy}phenyl)-9-iodo-7-oxo-2,3-dihydro-7H-[1,4]oxazino[2,3,4-ij]quinoline-6-carboxylate (N-7 of Chart N, where substitution is meta, n=0, and P=tert-butyldimethylsilyl)

A mixture of 3.44 g of the product of Preparation 58 and 3.9 g of cesium carbonate in 10 ml of DMF is stirred and heated at 100° C. under argon for 18 h, then cooled. Acetic acid (1 ml) is added, followed by 75 ml of water, and dilute HCl is added to bring the pH to about 2. The resulting solid is filtered, washed well with water, and dried in vacuo to provide 2.53 g of insoluble yellow-tan solid. To a mixture of this solid and 723 mg of imidazole in 6 ml of DMF is added 1.20 g of tert-butyldimethylsilyl chloride. The solution is stirred overnight, then partitioned between ethyl acetate and water. The organic phase is washed with water and brine, dried (MgSO$_4$), and concentrated under reduced pressure. Flash chromatography on silica using 20–30% ethyl acetate in dichloromethane provides 2.15 g of the title compound as a tan solid. Recrystallization from acetonitrile provides an analytical sample; mp 227.0–228.5° C.

$^1$H NMR (CDCl$_3$) δ0.23, 1.00, 1.36, 4.25, 4.30, 5.34, 6.91, 6.99, 7.11, 7.34, 7.56, 8.19, 8.21 ppm. TLC R$_f$ 0.36 (20% ethyl acetate in dichloromethane). IR (diffuse reflectance) 1679, 1630, 1609, 1586, 1549, 1493, 1369, 1319, 1291, 1251, 878, 865, 840, 803, 786 cm$^{-1}$; OAMS supporting ions at: ESI+ 592.3; HRMS (FAB) calcd for C$_{26}$H$_{30}$INO$_5$SI+H$_1$ 592.1018, found 592.1013; Anal. Calcd for C$_{26}$H$_{30}$INO$_5$Si: C, 52.79; H, 5.11; N, 2.37; found: C, 52.57; H, 5.15; N, 2.34.

Preparation 60: Ethyl 2-(3-{[tert-butyl(dimethyl)silyl]oxy}phenyl)-9-formyl-7-oxo-2,3-dihydro-7H-[1,4]oxazino[2,3,4-ij]quinoline-6-carboxylate (N-8 of Chart N, where substitution is meta, n=0, and P=tert-butyldimethylsilyl)

A mixture of 592 mg of the product of Preparation 59 and 81 mg of tetrakis (triphenylphosphine) palladium (0) in 5 ml of dry THF is purged with CO, via a needle reaching to the bottom of the flask, and heated to 50° C. To the stirred mixture is added, via syringe pump, 0.35 ml of tributyltin hydride in 10 ml of dry THF. Bubbling of CO through the mixture is continued throughout the addition, which takes about 5 h. The mixture is then cooled and concentrated under reduced pressure. Flash chromatography of the residue on silica gel using 1–2% methanol in dichloromethane affords 625 mg of tan solid. This is triturated with ether-hexane, filtered, washed well with hexane, and dried in vacuo to provide 443 mg of the aldehyde as a tan solid. Recrystallization from acetonitrile affords white needles, mp 246–248° C.

$^1$H NMR (CDCl$_3$) δ0.22, 0.99, 1.41, 4.3, 4.39, 5.31, 6.9, 7.07, 7.35, 7.80, 8.36, 8.52, 10.05 ppm. TLC R$_f$ 0.31 (2% methanol in dichloromethane). Summary Analytical data for: 0071676; nbk#35116-SRT-37A: IR (diffuse reflectance) 1727, 1679, 1646, 1603, 1556, 1501, 1373, 1288, 1258, 899, 877, 861, 840, 804, 787 cm$^{-1}$; OAMS supporting ions at: ESI+ 494.3; HRMS (FAB) calcd for C$_{27}$H$_{31}$NO$_6$SI+H$_1$ 494.1999, found 494.2005; Anal. Calcd for C$_{27}$H$_{31}$NO$_6$Si: C, 65.69; H, 6.33; N, 2.84; found: C, 65.73; H, 6.41; N, 2.93

Preparation 61: Ethyl 2-(3-{[tert-butyl(dimethyl)silyl]oxy}phenyl)-9-(4-morpholinylmethyl)-7-oxo-2,3-dihydro-7H-[1,4]oxazino[2,3,4-ij]quinoline-6-carboxylate (N-9 of Chart N, where substitution is meta, n=0, and P=tert-butyldimethylsilyl)

To a mixture of 217 mg of the product of Preparation 60, 0.12 ml of morpholine, and 50 μL of acetic acid in 4 ml of THF is added 140 mg of sodium triacetoxyborohydride. After 18 h, additional borohydride (120 mg) is added, and the mixture is stirred for 2 h and then partitioned between dichloromethane and aqueous NaHCO$_3$. The organic phase is dried (Na$_2$SO$_4$) and concentrated under reduced pressure. Flash chromatography of the residue on silica using 3% methanol in dichloromethane provides 200 mg of the product as a white solid. Recrystallization from acetonitrile gives white crystals, mp 161–164° C.

$^1$H NMR (CDCl$_3$) δ0.23, 1.00, 1.39, 2.46, 3.57, 3.70, 4.22, 4.30, 4.35, 5.27, 6.91, 6.98, 7.10, 7.34, 7.38, 7.96, 8.29 ppm. TLC R$_f$ 0.33 (5% methanol in dichloromethane). IR (diffuse reflectance) 2955, 2931, 1725, 1692, 1607, 1555, 1503, 1287, 1261, 1253, 1222, 1115, 878, 863, 840 cm$^{-1}$; OAMS supporting ions at: ESI+ 565.4; HRMS (FAB) calcd for C$_{31}$H$_{40}$N$_2$O$_6$SI+H$_1$ 565.2734, found 565.2740; Anal. Calcd for C$_{31}$H$_{40}$N$_2$O$_6$Si: C, 65.93; H, 7.14; N, 4.96; found (av): C, 65.35; H, 7.16; N, 4.88.

Preparation 62: 2-(3-{[tert-Butyl(dimethyl)silyl]oxy}phenyl)-N-(4-chlorobenzyl)-9-(4-morpholinylmethyl)-7-oxo-2,3-dihydro-7H-[1,4]oxazino[2,3,4-ij]quinoline-6-carboxamide (N-10 of Chart N, where substitution is meta, n=0, and P=tert-butyldimethylsilyl)

A mixture of 341 mg of the product of Preparation 61 and 0.70 g of p-chlorobenzylamine is stirred neat at 150° C. for 18 h, then concentrated in vacuo. Flash chromatography of the residue on silica using 2–6% methanol in dichloromethane provides 233 mg of the title compound as a tan solid, as well as 130 mg of desilylated material. Recrystallization of the main product from acetonitrile gives yellow prisms, mp 174–180° C.

$^1$H NMR (CDCl$_3$) δ0.22, 1.00, 2.48, 3.61, 3.71, 4.27, 4.37, 4.63, 5.25, 6.92, 6.96, 7.06, 7.30, 7.34, 7.47, 7.98, 8.66, 10.45 ppm. TLC R$_f$ 0.29 (3% methanol in dichloromethane). IR (diffuse reflectance) 1655, 1607, 1569, 1551, 1499, 1411, 1281, 1262, 1114, 882, 863, 840, 809, 798, 782 cm$^{-1}$; OAMS supporting ions at: ESI+ 660.5; HRMS (FAB) calcd for C$_{36}$H$_{42}$CLN$_3$O$_5$SI+H$_1$ 660.2660, found 660.2632; Anal. Calcd for C$_{36}$H$_{42}$ClN$_3$O$_5$Si: C, 65.49; H, 6.41; N, 6.36; Cl, 5.37; found: C, 65.42 H, 6.36; N, 6.36.

Example 63

N-(4-Chlorobenzyl)-2-(3-hydroxyphenyl)-9-(4-morpholinylmethyl)-7-oxo-2,3-dihydro-7H-[1,4]oxazino[2,3,4-ij]quinoline-6-carboxamide (N-11 of Chart N, where substitution is meta, n=0, and P=tert-butyldimethylsilyl)

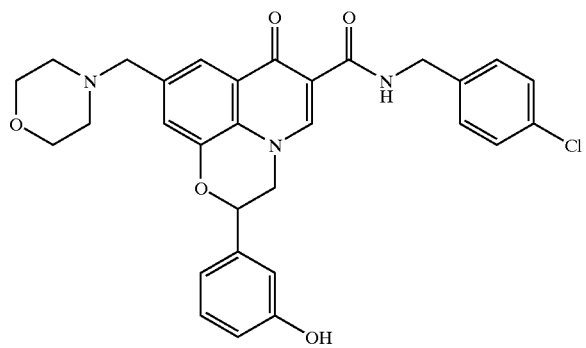

A solution of 167 mg of the product of Preparation 62 in 4 ml of ethanol and 2 ml of conc. HCl is stirred for 18 h at room temperature, then added to a stirred solution of 2 g NaHCO$_3$ in 50 ml of water. The resulting solid is filtered, washed well with water, dried under vacuum, and then absorbed onto silica gel. Flash chromatography on silica using 3–5% methanol in dichloromethane provides 126 mg of the title compound as a white solid. Recrystallization from acetonitrile gives glistening prisms, mp 213° C. (d).

$^1$H NMR (CDCl$_3$+CD$_3$OD) δ2.49, 3.62, 3.72, 4.29, 4.48, 4.63, 5.25, 6.89, 6.97, 7.30, 7.44, 7.94, 8.62, 10.61 ppm. TLC R$_f$ 0.35 (5% methanol in dichloromethane). Summary Analytical data for: 0071891; nbk#35116-SRT-53A: IR (diffuse reflectance) 3059, 2864, 2843, 1655, 1608, 1586, 1569, 1550, 1531, 1499, 1408, 1335, 1286, 1278, 1120 cm$^{-1}$; OAMS supporting ions at: ESI+ 546.3; HRMS (FAB) calcd for C$_{30}$H$_{28}$CLN$_3$O$_5$+H$_1$ 546.1796, found 546.1781; Anal. Calcd for C$_{30}$H$_{28}$ClN$_3$O$_5$: C, 65.99; H, 5.17; N, 7.70; Cl, 6.49; found: C, 65.57; H, 5.27; N, 8.57.

Example 64

N-(4-Chlorobenzyl)-2-[2-(methoxymethoxy)phenyl]-9-(morpholin-4-ylmethyl)-7-oxo-2,3-dihydro-7H-[1,4]oxazino[2,3,4-ij]quinoline-6-carboxamide (I-6 ofs Chart I, T=2-methoxymethoxyphenyl)

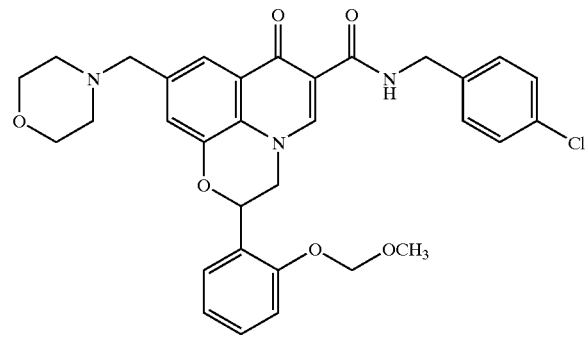

Following the procedures in Preparations 49 and 51–55 and Example 61 without making major changes except using 2-hydroxybenzaldehyde as the starting aldehyde, the title compound is obtained as a white solid. Recrystallization from acetonitrile gives 324 mg of white solid.

$^1$H NMR (CDCl$_3$) δ2.47, 3.49, 3,61, 3.71, 4.15, 4.50, 4.63, 4.64, 5.25, 5.29, 5.65, 7.15, 7.3, 7.39, 7.47, 7.61, 7.98, 8.68, 10.49 ppm. TLC Rf 0.34 (3% methanol in dichloromethane). OAMS supporting ions at: ESI+ 590.3.

Example 65

N-(4-Chlorobenzyl)-2-(4-hydroxyphenyl)-9-(morpholin-4-ylmethyl)-7-oxo-2,3-dihydro-7H-[1,4]oxazino[2,3,4-ij]quinoline-6-carboxamide (I-6 of Chart I, T=4-hydroxyphenyl)

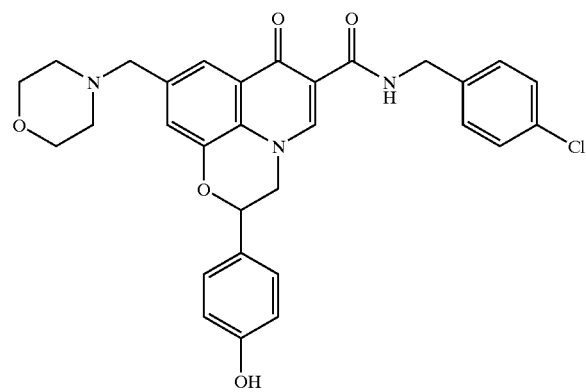

Following the procedures in Preparations 56, 51–52, and 59–62 and Example 63 without making major changes except using 4-hydroxybenzaldehyde as the starting aldehyde, the title compound is obtained as a beige solid. Recrystallization from acetonitrile gives pale yellow crystals, mp>260° C.:

$^1$H NMR (CDCl$_3$+CD$_3$OD) δ2.49, 3.63, 3.72, 4.33, 4.47, 4.64, 5.24, 6.93, 7.31, 7.34, 7.44, 7.95, 8.65, 10.62 ppm. TLC Rf 0.35 (5% methanol in dichloromethane). IR (diffuse reflectance) 3035, 1654, 1608, 1554, 1518, 1500, 1410, 1298, 1284, 1270, 1253, 1230, 1115, 809, 797 cm$^{-1}$ OAMS supporting ions at: ESI+ 546.3 HRMS (FAB) calcd for C$_{30}$H$_{28}$ClN$_3$O$_5$+H$_1$ 546.1796, found 546.1793 Anal. Calcd for C$_{30}$H$_{28}$ClN$_3$O$_5$: C, 65.99; H, 5.17; N, 7.70; Cl, 6.49; found (av): C, 65.37; H, 5.19; N, 7.60.

Example 66

N-(4-Chlorobenzyl)-2-{2-[(methoxymethoxy)methyl]phenyl}-9-(morpholin-4-ylmethyl)-7-oxo-2,3-dihydro-7H-[1,4]oxazino[2,3,4-ij]quinoline-6-carboxamide (I-6 of Chart I, T=2-methoxymethoxymethylphenyl)

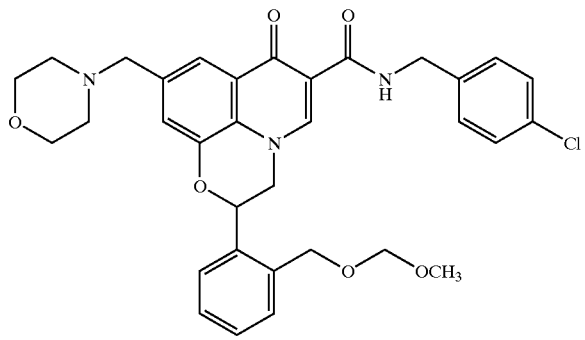

Following the procedures in Preparations 49–55 and Example 61 without making major changes except using 1,2-benzenedimethanol as the starting alcohol, the title compound is obtained as a white solid. Recrystallization from acetonitrile-methanol affords white crystals, mp 202.5–204.5° C.

$^1$H NMR (CDCl$_3$) δ2.48, 3.32, 3.62, 3.71, 4.23, 4.52, 4.6–4.7, 4.77, 5.57, 7.30, 7.4, 7.5, 7.66, 7.99, 8.64, 10.47 ppm. TLC Rf 0.30 (3% methanol in dichloromethane). IR (diffuse reflectance) 1652, 1607, 1569, 1552, 1500, 1410, 1352, 1283, 1228, 1150, 1116, 1092, 1034, 810, 748 cm$^{-1}$ OAMS supporting ions at: ESI+ 604.3 HRMS (FAB) calcd for C$_{33}$H$_{34}$ClN$_3$O$_6$+H$_1$ 604.2214, found 604.2215 Anal. Calcd for C$_{33}$H$_{34}$ClN$_3$O$_6$: C, 65.61; H, 5.67; N, 6.96; Cl, 5.87; found: C, 65.40; H, 5.69; N, 6.95.

Example 67

N-(4-Chlorobenzyl)-2-{4-[(methoxymethoxy)methyl]phenyl}-9-(morpholin-4-ylmethyl)-7-oxo-2,3-dihydro-7H-[1,4]oxazino[2,3,4-ij]quinoline-6-carboxamide (I-6 of Chart I, T=4-methoxymethoxymethylphenyl)

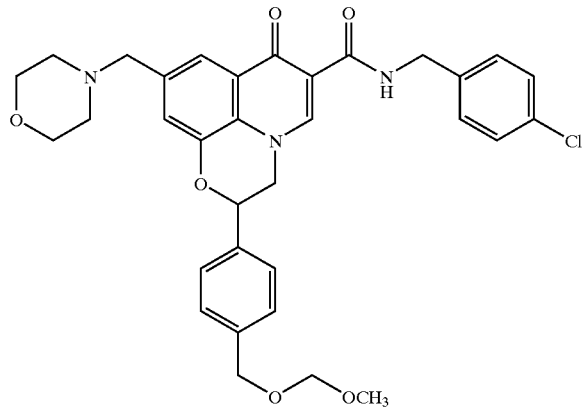

Following the procedures in Preparations 49–55 and Example 61 without making major changes except using 1,4-benzenedimethanol as the starting alcohol, the title compound is obtained as a tan solid. Recrystallization from acetonitrile-methanol affords tan crystals, mp 236–239° C.

$^1$H NMR (CDCl$_3$) δ2.47, 3.44, 3.60, 3.70, 4.29, 4.37, 4.63, 4.65, 4.74, 5.31, 7.3, 7.45, 7.49, 7.98, 8.67, 10.44 ppm. TLC Rf 0.27 (3% methanol in dichloromethane). IR (diffuse reflectance) 2931, 2852, 1653, 1607, 1569, 1551, 1536, 1500, 1411, 1328, 1280, 1149, 1113, 1044, 809 cm$^{-1}$ OAMS supporting ions at: ESI+ 604.3 HRMS (FAB) calcd for C$_{33}$H$_{34}$ClN$_3$O$_6$+H$^1$ 604.2214, found 604.2219 Anal. Calcd for C$_{33}$H$_{34}$ClN$_3$O$_6$: C, 65.61; H, 5.67; N, 6.96; Cl, 5.87; found: C, 65.49; H, 5.73; N, 6.90.

Example 68

N-(4-Chlorobenzyl)-2-(2-hydroxyphenyl)-9-(morpholin-4-ylmethyl)-7-oxo-2,3-dihydro-7H-[1,4]oxazino[2,3,4-ij]quinoline-6-carboxamide (I-6 of Chart I, T=2-hydroxyphenyl)

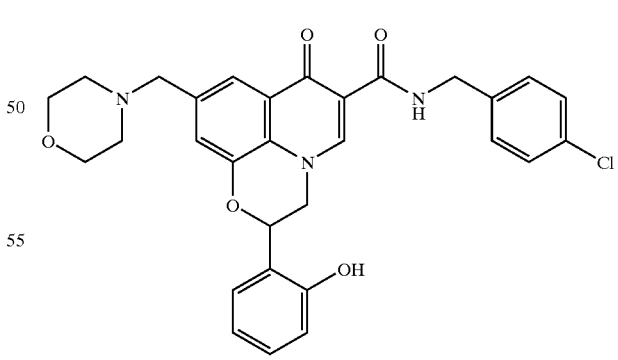

Following the procedure in Example 62 using the compound of Example 64 as the starting material, the title compound is obtained as a white solid. Trituration with hot acetonitrile affords an analytical sample; mp ~239° C.

$^1$H NMR (CDCl$_3$) δ2.48, 3.61, 3.71, 4.09, 4.62, 4.68, 5.63, 6.88, 6.97, 7.17, 7.3, 7.49, 7.52, 7.97, 8.57, 9.5, 10.86 ppm. TLC Rf 0.31 (5% methanol in dichloromethane). IR (diffuse reflectance) 3162, 1645, 1603, 1568, 1550, 1499, 1457, 1411, 1353, 1331, 1300, 1282, 1272, 1221, 809 cm$^{-1}$ OAMS supporting ions at: ESI+ 545.9 HRMS (FAB) calcd for $C_{30}H_{28}ClN_3O_5+H_1$ 546.1796, found 546.1796 Anal. Calcd for $C_{30}H_{28}ClN_3O_5$: C, 65.99; H, 5.17; N, 7.70; Cl, 6.49; found: C, 65.89; H, 5.23; N, 7.59.

Example 69

N-(4-Chlorobenzyl)-2-[2-(hydroxymethyl)phenyl]-9-(morpholin-4-ylmethyl)-7-oxo-2,3-dihydro-7H-[1,4]oxazino[2,3,4-ij]quinoline-6-carboxamide (I-6 of Chart I, T=2-hydroxymethylphenyl)

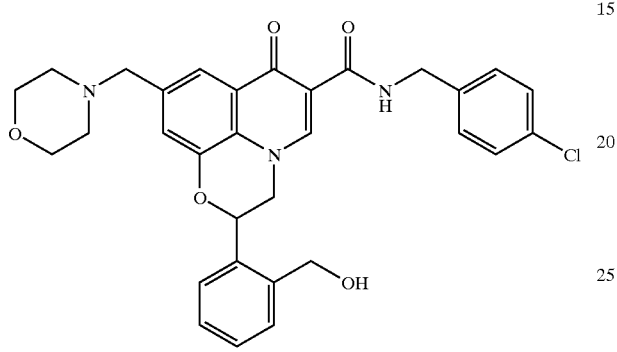

Following the procedure in Example 62 using the compound of Example 66 as the starting material, the title compound is obtained as a white solid. Recrystallization from acetonitrile gives white crystals, mp 218–223° C. (d).

$^1$H NMR (CDCl$_3$+CD$_3$OD) δ2.50, 3.65, 3.73, 4.24, 4.63, 4.67, 4.72, 4.83, 5.69, 7.3, 7.4–7.5, 7.65, 7.96, 8.59, 10.62 ppm. TLC Rf 0.32 (5% methanol in dichloromethane). IR (diffuse reflectance) 3406, 2863, 1670, 1609, 1569, 1551, 1500, 1410, 1349, 1330, 1285, 1105, 808, 798, 752 cm$^{-1}$ OAMS supporting ions at: ESI+ 560.3 HRMS (FAB) calcd for $C_{31}H_{30}ClN_3O_5+H_1$ 560.1952, found 560.1947 Anal. Calcd for $C_{31}H_{30}ClN_3O_5$: C, 66.48; H, 5.40; N, 7.50; Cl, 6.33; found: C, 66.11; H, 5.42; N, 7.47.

We claim:

1. A compound of formula I

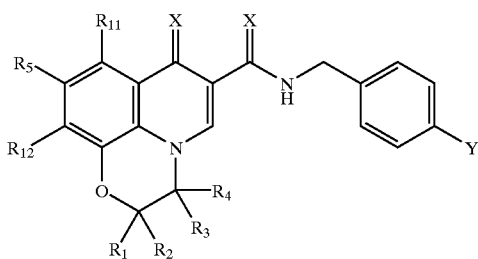

I or a pharmaceutically acceptable salt, racemate, solvate, tautomer, optical isomer or prodrug derivative thereof wherein:

each X is independently O or S;
Y is Cl, F, Br, CN or NO$_2$;
$R_1$, $R_2$, $R_3$ and $R_4$ are independently
  a) hydrogen,
  b) N$_3$,
  c) CN,
  d) fluoro,
  e) trifluoromethyl,
  f) aryl,
  g) het,
  h) C$_{1-8}$ alkyl, optionally substituted with R$_6$ or OR$_7$, or
  i) R$_1$ and R$_2$ or R$_3$ and R$_4$ together with the carbon to which they are attached form C$_{3-8}$cycloalkyl or het;
R$_5$ is C$_{1-8}$alkyl, which may be partially unsaturated and optionally substituted with one to three N$_3$, halo, CN, R$_6$ or R$_7$;
R$_6$ is
  a) aryl,
  b) het,
  c) SO$_i$R$_8$,
  d) OR$_8$,
  e) C(=O)OR$_8$,
  f) C(=O)R$_8$, or
  g) NR$_8$R$_9$;
R$_7$ is
  a) P(=O)(OR$_{10}$)$_2$,
  b) CO(CH$_2$)$_j$CON(CH$_3$)(CH$_2$)$_k$SO$_3^-$M$^+$,
  c) an amino acid,
  d) C(=O)C$_{1-6}$alkyl, optionally substituted by NR$^{10}$R$^{10}$, or
  e) CO(CH$_2$)$_n$CO$_2$H;
R$_8$ and R$_9$ are independently
  a) hydrogen,
  b) C$_{3-8}$cycloalkyl,
  c) aryl,
  d) het, or
  e) C$_{1-8}$alkyl which is further optionally substituted with one or more aryl, het, halo, CN, CO$_2$R$_{10}$, SO$_i$R$_{10}$, OR$_{10}$, NR$_{10}$R$_{10}$, CF$_3$, or C$_{3-8}$cycloalkyl;
R$_{10}$ is
  a) H or
  b) C$_{1-8}$alkyl, optionally substituted with OH or OC$_{1-4}$alkyl;
R$_{11}$ and R$_{12}$ are independently
  a) hydrogen
  b) halo,
  c) NO$_2$,
  d) CN,
  e) R$_6$,
  f) SO$_i$NR$_8$R$_9$, or
  g) C$_{1-8}$alkyl, which may be partially unsaturated and optionally substituted with one to three N$_3$, halo, CN, R$_6$ or OR$_7$;
aryl is
  a phenyl radical, optionally fused with a saturated or unsaturated carbocyclic or heterocyclic ring; at each occurrence, aryl may be substituted with one or more halo, CN, CO$_2$R$_{10}$, SO$_i$R$_{10}$, OR$_{10}$, NR$_{10}$R$_{10}$, CF$_3$, C$_{3-8}$cycloalkyl, or C$_{1-4}$alkyl wherein C$_{1-4}$alkyl is optionally substituted with OR$_{10}$;
het is
  a four- (4), five- (5), six- (6), or seven- (7) membered saturated or unsaturated heterocyclic ring having 1, 2, or 3 heteroatoms selected from the group consisting of O, S, and NW, wherein W is hydrogen, C$_{1-4}$alkyl, C(=O)OC$_{1-4}$alkyl or absent, wherein het is optionally fused with a benzene ring, a carbcyclic or a heterocyclic ring; at each occurrence, het may be substituted with one or more halo, CN, CO$_2$R$_{10}$, SO$_i$R$_{10}$, OR$_{10}$, NR$_{10}$R$_{10}$, C$_{1-4}$alkyl, CF$_3$, C$_{3-8}$cycloalkyl, or oxo;
at each occurrence, a cycloalkyl may be substituted with C$_{1-4}$alkyl, OR$^{10}$, oxo, or a spiro fused het;
i is 0, 1 or 2;
j is 1, 2, 3, 4, 5, or 6;
k is 1, 2, 3, 4, 5, or 6;
n is 1, 2, 3, 4, 5, or 6;
M is sodium, potassium, or lithium; and with the following provisos:

a) at least one of $R_1$, $R_2$, $R_3$ and $R_4$ is other than hydrogen;

b) where $R_1$, $R_2$, $R_3$ and $R_4$ are independently $C_{1-8}$ alkyl, at least one of the alkyl groups is substituted with $R_6$ or $OR_7$.

2. A compound of formula I according to claim 1 which is formula I-A

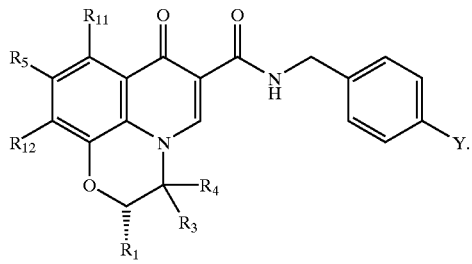

3. A compound of formula I according to claim 1 which is formula I-B

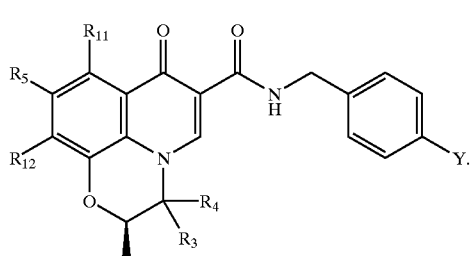

4. A compound of formula I according to claim 1 which is formula I-C

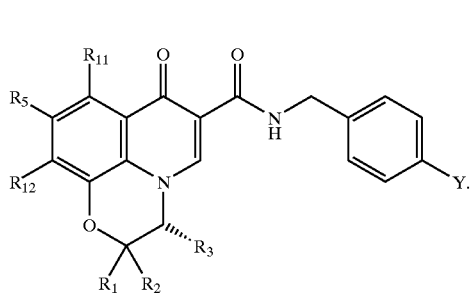

5. A compound of formula I according to claim 1 which is formula I-D

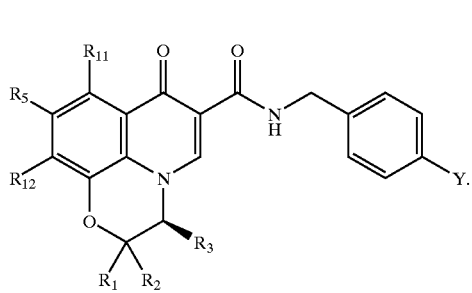

6. A compound of formula I according to claim 1 which is formula I-E

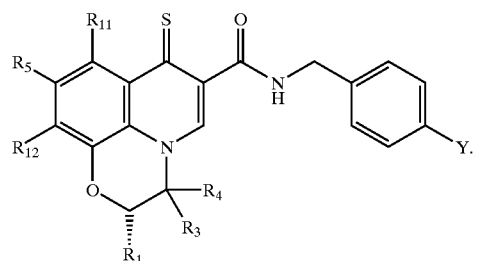

7. A compound of formula I according to claim 1 which is formula I-F

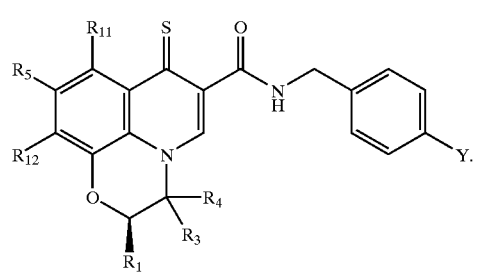

8. A compound of formula I according to claim 1 which is formula I-G

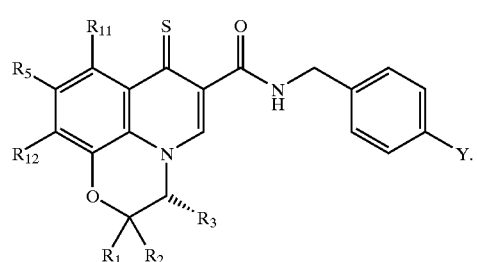

9. A compound of formula I according to claim 1 which is formula I-H

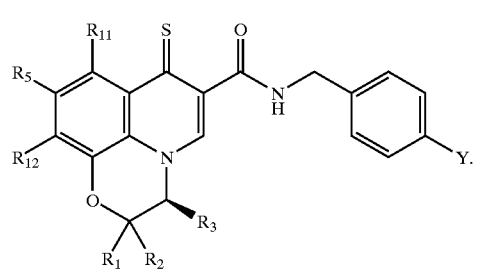

10. A compound of formula I according to claim 1 which is formula I-I

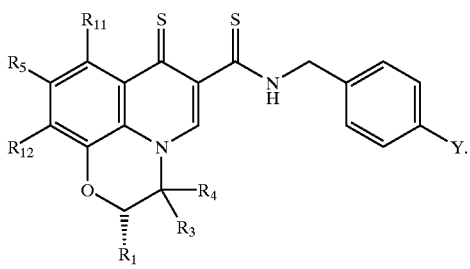

11. A compound of formula I according to claim 1 which is formula I-J

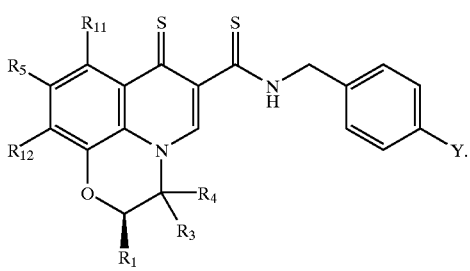

12. A compound of formula I according to claim 1 which is formula I-K

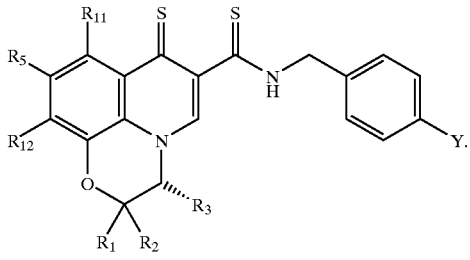

13. A compound of formula I according to claim 1 which is formula I-L

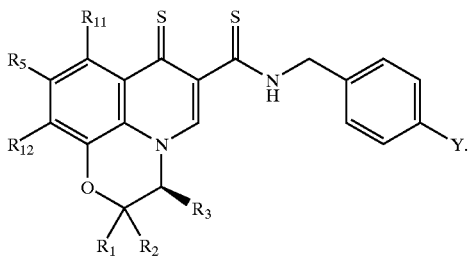

14. A compound of formula I according to claim 1 which is formula I-M

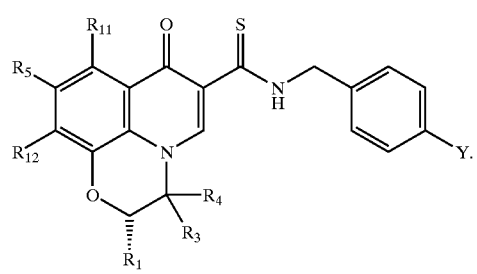

15. A compound of formula I according to claim 1 which is formula I-N

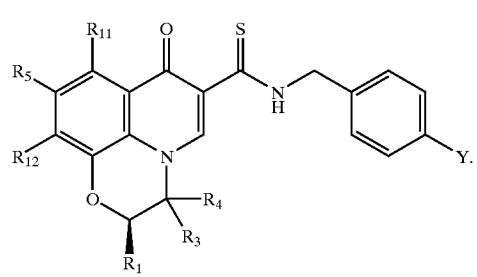

16. A compound of formula I according to claim 1 which is formula I-O

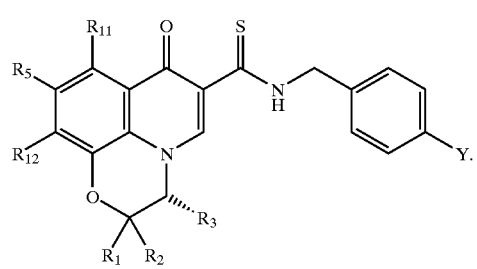

17. A compound of formula I according to claim 1 which is formula I-P

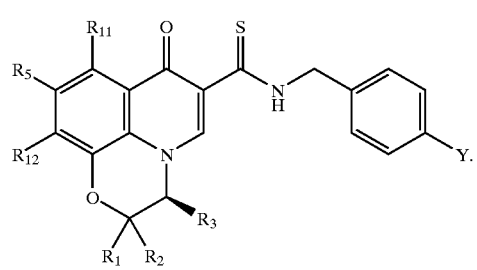

18. A compound of claims 1 to 17 wherein $R_{11}$ is H, halo, or $C_{1-4}$alkyl optionally substituted with one to three halo; and
$R_{12}$ is
 a) H,
 b) $SO_rR_8$,
 c) $OR_8$,
 d) $C(=O)OR_8$, e) C(=O)R$_8$, f) NR$_8$R$_9$, g) SO$_i$R$_8$R$_9$, or h) C$_{1-8}$alkyl, which may be partially unsaturated and optionally substituted with one to three N$_3$, halo, CN, or R$_6$.

19. A compound of claim 18 wherein R$_{11}$ and R$_{12}$ are hydrogen.

20. A compound of claim 19 wherein R$_5$ is C$_{1-8}$alkyl substituted with OR$_8$ or het.

21. A compound of claim 19 wherein R$_5$ is C$_{1-6}$alkyl substituted with OH.

22. A compound of claim 19 wherein R$_5$ is C$_{1-4}$alkyl substituted with het.

23. A compound of claim 22 wherein het is morpholinyl or thiomorpholinyl.

24. A compound claim 19 wherein R$_5$ is 4-morpholinylmethyl.

25. A compound of claim 19 wherein R$_5$ is C$_{1-8}$alkyl which is partially unsaturated and optionally substituted with OR$_8$.

26. A compound of claim 19 wherein R$_5$ is propynyl.

27. A compound of claim 26 wherein propynyl is substituted with OH.

28. A compound of claims 20 to 27 wherein Y is Cl.

29. A compound of claims 28 wherein R$_3$ and R$_4$ are independently hydrogen.

30. A compound of claim 29 wherein R$_1$ and R$_2$ are independently a) hydrogen, b) fluoro, c) C$_{1-8}$ alkyl substituted with R$_6$ or OR$_7$;

d) aryl, e) het, or f) R$_1$ and R$_2$ together with the carbon to which they are attached form a six-(6) membered cycloalkyl or a het;

wherein R$_6$ is a) het, b) SO$_i$R$_8$, c) OR$_8$ or d) NR$_8$R$_9$;

wherein R$_7$ is a) P(=O)(OR$_{10}$)$_2$, b) CO(CH$_2$)$_n$CON(CH$_3$)(CH$_2$)$_n$SO$_3^-$M$^+$, or c) C(=O)C$_{1-6}$alkyl, wherein R$_8$ and R$_9$ are independently a) hydrogen, b) aryl, c) het, or d) C$_{1-8}$alkyl which is further optionally substituted with one or more aryl, het, halo, CO$_2$R$_{10}$, SO$_i$R$_{10}$, or OR$_{10}$;

wherein R$_{10}$ is a) H or c) C$_{1-4}$alkyl, optionally substituted with OH.

31. A compound of claim 30 wherein R$_1$ and R$_2$ are independantly H, C$_{1-4}$alkylsubstituted with OR$_8$ wherein R$_8$ is H, or C$_{1-4}$alkyl substituted with OR$_{10}$.

32. A compound of claim 30 wherein R$_1$ is H; R$_2$ is aryl wherein aryl is optionally substituted with one or two halo, CN, OR$_{10}$, or C$_{1-4}$alkylsubstituted with OR$_{10}$.

33. A compound of claim 30 wherein R$_1$ is H; R$_2$ is aryl wherein aryl is fused with a heterocyclic ring.

34. A compound of claim 33 wherein the R$_2$ is 1,3-benzodioxolyl or 1,4-benxodioxinyl.

35. A compound of claim 30 wherein R$_1$ is H; R$_2$ is het.

36. A compound of claim 35 wherein het is a five- (5) or six- (6) membered saturated or unsaturated heterocyclic ring having 1, 2, or 3 heteroatoms selected from the group consisting of O, S, and NW, wherein W is hydrogen, C$_{1-4}$alkyl, C(=O)OC$_{1-4}$alkyl or absent, wherein het may be substituted with one or more halo, C$_{1-4}$alkyl, CF$_3$, or oxo.

37. A compound of claim 36 wherein het is pyridinyl.

38. A compound of claim 36 wherein het is a five-(5) membered heterocyclic ring.

39. A compound of claim 30 wherein R$_1$ and R$_2$ together with the carbon to which they are attached form a het.

40. A compound of claim 39 wherein het is a five- (5) or six- (6) membered heterocyclic ring having 1, 2, or 3 heteroatoms selected from the group consisting of O, S, and NW, wherein W is hydrogen, C$_{1-4}$alkyl, or C(=O)OC$_{1-4}$alkyl, wherein het may be substituted with one or more halo, OR$_{10}$, C$_{1-4}$alkyl, CF$_3$, or oxo.

41. A compound of claim 40 wherein het is a (6) membered heterocyclic ring.

42. A compound of claim 41 wherein het is pyran, piperdine, or thiopyran.

43. A compound of claim 30 wherein R$_1$ and R$_2$ together with the carbon to which they are attached form a six-(6) membered cycloalkyl.

44. A compound of claim 43 wherein cycloalkyl is optionally substituted with oxo, or OR$_{10}$.

45. A compound of claim 30 wherein

R$_2$ is hydrogen;

R$_1$ is C$_{1-8}$ alkyl substituted with R$_6$ or OR$_7$;

where R$_6$ is a) het, b) SR$_8$, c) OR$_8$ or d) NR$_8$R$_9$;

wherein R$_7$ is a) (P=O)(OCH$_3$)$_2$, b) CO(CH$_2$)$_n$CON(CH$_3$)(CH$_2$)$_n$SO$_3^-$M$^+$, or c) C(=O)CH$_3$, wherein R$_8$ and R$_9$ are independently a) hydrogen, b) het, or c) C$_{1-8}$alkyl, which is optionally substituted with one or two het, CO$_2$R$_{10}$, SO$_i$R$_{10}$, or OR$_{10}$; and wherein R$_{10}$ is a) H or b) C$_{1-4}$alkyl, optionally substituted with OH, or OC$_{1-4}$alkyl.

46. A compound of claim 45 wherein R$_1$ is C$_{1-8}$ alkyl substituted with het.

47. A compound of claim 46 wherein het is piperidinyl, morpholinyl, thiomorpholinyl, piperazinyl, N—C$_{1-4}$alky substituted piperazinyl, pyrrolidinyl, pyridyl, imidazolyl, or N—C$_{1-4}$alky substituted imidazol.

48. A compound of claim 47 wherein het is pyridinyl.

49. A compound of claim 45 wherein R$_1$ is C$_{1-8}$ alkyl substituted with OH or OC$_{1-4}$alkyl.

50. A compound of claim 49 wherein R$_1$ is C$_{1-4}$ alkyl substituted with OH.

51. A compound of claim 45 wherein R$_1$ is C$_{1-8}$ alkyl substituted with SR$_8$.

52. A compound of claim 51 wherein R$_8$ is het.

53. A compound of claim 51 wherein R$_8$ is C$_{1-4}$alkyl optionally substituted with one or two OR$_{10}$.

54. A compound of claim 45 wherein $R_1$ is $C_{1-4}$alkyl substituted with $NR_8R_9$.

55. A compound of claim 54 wherein $R_8$ is H, and $R_9$ is het.

56. A compound of claim 55 wherein het is a six-(6) membered heterocyclic ring having 1, 2, or 3 heteroatoms selected from the group consisting of O, S, and NW, wherein W is hydrogen, $C_{1-4}$alkyl, or absent.

57. A compound of claim 56 wherein het is pyridinyl.

58. A compound of claim 54 wherein $R_8$ is H, and $R_9$ is $C_{1-8}$alkyl optionally substituted with het.

59. A compound of claim 58 wherein het is a six-(6) membered heterocyclic ring having 1, 2, or 3 heteroatoms selected from the group consisting of O, S, and NW, wherein W is hydrogen, $C_{1-4}$alkyl, or absent.

60. A compound of claim 59 wherein het is pyridinyl.

61. A compound of claim 54 wherein $R_8$ is H, and $R_9$ is $C_{1-8}$alkyl optionally substituted with one or two $OR_{10}$.

62. A compound of claim 45 wherein $R_1$ is hydroxymethyl, morpholinylmethyl, (pyridinylmethyl) aminomethyl, (dimethylamino)methyl, (hydroxyethyl) sulfanylmethyl, (1-methyl-1H-imidazol-2-yl) sulfanylmethyl, —$CH_2OCO(CH_2)_6CON(CH_3)(CH_2)_2SO_3^-$ $M^+$, —$CH_2OC(=O)CH_3$, $CH_2OP(=O)(OMe)_2$, (4-methyl-1-piperazinyl)methyl, 1-pyrrolidinylmethyl, (2,3-dihydroxypropyl)aminomethyl, (2-hydroxyethyl) aminomethyl, 1-piperidinylmethyl, bis(2-hydroxyethyl) aminomethyl, 1H-imidazol-1-ylmethyl, (methylsulfanyl) methyl, (tert-butylsulfanyl)methyl, methylsulfanyl acetate, (2,3-dihydroxypropyl)sulfanylmethyl, phenyl or fluoro.

63. A compound of claim 62 wherein $R_1$ is hydroxymethyl, morpholinylmethyl, (2-pyridinylmethyl) aminomethyl, (3-pyridinylmethyl)aminomethyl, (dimethylamino)methyl, (2-hydroxyethyl)sulfanylmethyl, (1-methyl-1H-imidazol-2-yl)sulfanylmethyl, $OP(=O)(OCH_3)_2$, —$CH_2OCO(CH_2)_6CON(CH_3)(CH_2)_2SO_3^-M^+$, or —$CH_2OC(=O)CH_3$.

64. A compound of claim 12 wherein $R_1$ and $R_2$ are independently hydrogen, $R_3$ and $R_4$ are independently
   a) hydrogen,
   b) fluoro, or
   c) $C_{1-8}$alkyl substituted with $R_6$ or $OR_7$;
where $R_6$ is
   a) het,
   b) $SO_iR_8$,
   c) $OR_8$ or
   d) $NR_8R_9$;
wherein $R_7$ is
   a) $P=O)(OH)_2$,
   b) $(P=O)(C_{1-4}alkoxy)_2$,
   c) $CO(CH_2)_nCON(CH_3)(CH_2)_nSO_3^-M^+$, or
   d) $C(=O)C_{1-6}$alkyl,
wherein $R_8$ and $R_9$ are independently
   a) hydrogen,
   b) aryl,
   c) het, or
   d) $C_{1-8}$alkyl which is further optionally substituted with one or more aryl, het, halo, $CO_2R_{10}$, $SO_iR_{10}$, or $OR_{10}$;
wherein $R_{10}$ is
   a) H or
   d) $C_{1-4}$alkyl, optionally substituted with OH.

65. A compound of claim 20 wherein $R_3$ and $R_4$ are independently fluoro or hydroxymethyl.

66. A compound of claim 20 wherein $R_3$ is hydrogen and $R_4$ is phenyl, morpholinylmethyl, or hydroxymethyl.

67. A compound of claim 22 wherein $R_4$ is morpholinylmethyl.

68. A compound of claim 1 which is
a) N-(4-Chlorobenzyl)-2-(hydroxymethyl)-9-(morpholin-4-ylmethyl)-7-oxo-2,3-dihydro-7H-[1,4]oxazino[2,3,4-ij]quinoline-6-carboxamide,
b) N-(4-Chlorobenzyl)-2-(R or S)-(hydroxymethyl)-9-(morpholin-4-ylmethyl)-7-oxo-2,3-dihydro-7H-[1,4]oxazino[2,3,4-ij]quinoline-6-carboxamide,
c) N-(4-Chlorobenzyl)-9-(morpholin-4-ylmethyl)-7-oxo-2-pyridin-3-yl-2,3-dihydro-7H-[1,4]oxazino[2,3,4-ij]quinoline-6-carboxamide,
d) N-(4-Chlorobenzyl)-9-(morpholin-4-ylmethyl)-7-oxo-2-pyridin-4-yl-2,3-dihydro-7H-[1,4]oxazino[2,3,4-ij]quinoline-6-carboxamide,
e) N-(4-Chlorobenzyl)-9-(morpholin-4-ylmethyl)-7-oxo-2-pyridin-2-yl-2,3-dihydro-7H-[1,4]oxazino[2,3,4-ij]quinoline-6-carboxamide,
f) N-(4-Chlorobenzyl)-9-(morpholin-4-ylmethyl)-7-oxo-2-(R or S)-pyridin-3-yl-2,3-dihydro-7H-[1,4]oxazino[2,3,4-ij]quinoline-6-carboxamide,
g) N-(4-Chlorobenzyl)-2,9-bis(morpholin-4-ylmethyl)-7-oxo-2,3-dihydro-7H-[1,4]oxazino[2,3,4-ij]quinoline-6-carboxamide,
h) 2-[(tert-Butylsulfanyl)methyl]-N-(4-chlorobenzyl)-9-(morpholin-4-ylmethyl)-7-oxo-2,3-dihydro-7H-[1,4]oxazino[2,3,4-ij]quinoline-6-carboxamide,
i) N-(4-Chlorobenzyl)-2-{[(2-hydroxyethyl)sulfanyl]methyl}-9-(morpholin-4-ylmethyl)-7-oxo-2,3-dihydro-7H-[1,4]oxazino[2,3,4-ij]quinoline-6-carboxamide,
j) N-(4-Chlorobenzyl)-2-{[(1-methyl-1H-imidazol-2-yl)sulfanyl]methyl}-9-(morpholin-4-ylmethyl)-7-oxo-2,3-dihydro-7H-[1,4]oxazino[2,3,4-ij]quinoline-6-carboxamide,
k) N-(4-Chlorobenzyl)-9-(morpholin-4-ylmethyl)-7-oxo-2-{[(3-pyridinylmethyl)amino]methyl}-2,3-dihydro-7H-[1,4]oxazino[2,3,4-ij]quinoline-6-carboxamide,
l) [6-{[(4-Chlorobenzyl)amino]carbonyl}-9-(morpholin-4-ylmethyl)-7-oxo-2,3-dihydro-7H-[1,4]oxazino[2,3,4-ij]quinolin-2-yl]methyl acetate,
m) N-(4-Chlorobenzyl)-9-(morpholin-4-ylmethyl)-7-oxo-2-(R or S)-{[(3-pyridinylmethyl)amino]methyl}-2,3-dihydro-7H-[1,4]oxazino[2,3,4-ij]quinoline-6-carboxamide,
n) N-(4-Chlorobenzyl)-2-(3-hydroxyphenyl)-9-(morpholin-4-ylmethyl)-7-oxo-2,3-dihydro-7H-[1,4]oxazino[2,3,4-ij]quinoline-6-carboxamide,
o) N-(4-Chlorobenzyl)-9-(morpholin-4-ylmethyl)-7-oxo-2-(R or S)-pyridin-2-yl-2,3-dihydro-7H-[1,4]oxazino[2,3,4-ij]quinoline-6-carboxamide,
p) N-(4-Chlorobenzyl)-2-[3-(hydroxymethyl)phenyl]-9-(morpholin-4-ylmethyl)-7-oxo-2,3-dihydro-7H-[1,4]oxazino[2,3,4-ij]quinoline-6-carboxamide,
q) N-(4-Chlorobenzyl)-2-[2-(hydroxymethyl)phenyl]-9-(morpholin-4-ylmethyl)-7-oxo-2,3-dihydro-7H-[1,4]oxazino[2,3,4-ij]quinoline-6-carboxamide,
r) N-(4-Chlorobenzyl)-2-(1-methyl-1H-imidazol-2-yl)-9-(morpholin-4-ylmethyl)-7-oxo-2,3-dihydro-7H-[1,4]oxazino[2,3,4-ij]quinoline-6-carboxamide,
s) N-(4-Chlorobenzyl)-2-(2-furyl)-9-(morpholin-4-ylmethyl)-7-oxo-2,3-dihydro-7H-[1,4]oxazino[2,3,4-ij]quinoline-6-carboxamide,
t) N-(4-Chlorobenzyl)-2-(3-cyanophenyl)-9-(morpholin-4-ylmethyl)-7-oxo-2,3-dihydro-7H-[1,4]oxazino[2,3,4-ij]quinoline-6-carboxamide, u) N-(4-Chlorobenzyl)-2-(3-furyl)-9-(morpholin-4-ylmethyl)-7-oxo-2,3-dihydro-7H-[1,4]oxazino[2,3,4-ij]quinoline-6-carboxamide, v) N-(4-Chlorobenzyl)-9-(morpholin-4-ylmethyl)-7-oxo-2-thien-2-yl-2,3-dihydro-7H-[1,4]oxazino[2,3,4-ij]quinoline-6-carboxamide, w) N-(4-Chlorobenzyl)-2-(3,5-difluorophenyl)-9-(morpholin-4-ylmethyl)-7-oxo-2,3-dihydro-7H-[1,4]oxazino[2,3,4-ij]quinoline-6-carboxamide, x) 2-(13-Benzodioxol-5-yl)-N-(4-chlorobenzyl)-9-(morpholin-4-ylmethyl)-7-oxo-2,3-dihydro-7H-[1,4]oxazino[2,3,4-ij]quinoline-6-carboxamide, y) N-(4-Chlorobenzyl)-2-(2,3-dihydro-1,4-benzodioxin-6-yl)-9-(morpholin-4-ylmethyl)-7-oxo-2,3-dihydro-7H-[1,4]oxazino[2,3,4-ij]quinoline-6-carboxamide, z) 2-(1,3-Benzodioxol-4-yl)-N-(4-chlorobenzyl)-9-(morpholin-4-ylmethyl)-7-oxo-2,3-dihydro-7H-[1,4]oxazino[2,3,4-ij]quinoline-6-carboxamide, aa) 2-[3,5-bis(Methoxymethoxy)phenyl]-N-(4-chlorobenzyl)-9-(morpholin-4-ylmethyl)-7-oxo-2,3-dihydro-7H-[1,4]oxazino[2,3,4-ij]quinoline-6-carboxamide, bb) N-(4-Chlorobenzyl)-9-(morpholin-4-ylmethyl)-7-oxo-2-thien-3-yl-2,3-dihydro-7H-[1,4]oxazino[2,3,4-ij]quinoline-6-carboxamide, cc) N-(4-Chlorobenzyl)-2,2-bis[(methoxymethoxy)methyl]-9-(morpholin-4-ylmethyl)-7-oxo-2,3-dihydro-7H-[1,4]oxazino[2,3,4-ij]quinoline-6-carboxamide, dd) N-[(4-Chlorophenyl)methyl]-9'-(4-morpholinylmethyl)-4',7'-dioxospiro[cyclohexane-1,2'(3'H)-[7H]pyrido[1,2,3-de][1,4]benzoxazine]-6'-carboxamide, ee) N-[(4-Chlorophenyl)methyl]-4-hydroxy-9'-(4-morpholinylmethyl)-7'-oxospiro[cyclohexane-1,2'(3'H)-[7H]pyrido[1,2,3-de][1,4]benzoxazine]-6'-carboxamide, ff) N-(4-Chlorobenzyl)-3,9-bis(morpholin-4-ylmethyl)-7-oxo-2,3-dihydro-7H-[1,4]oxazino[2,3,4-ij]quinoline-6-carboxamide, gg) N-(4-Chlorobenzyl)-9-(morpholin-4-ylmethyl)-7-oxo-2-phenyl-2,3-dihydro-7H-[1,4]oxazino[2,3,4-ij]quinoline-6-carboxamide, hh) N-(4-Chlorobenzyl)-2,2-difluoro-9-(morpholin-4-ylmethyl)-7-oxo-2,3-dihydro-7H-[1,4]oxazino[2,3,4-ij]quinoline-6-carboxamide, ii) N-(4-Chlorobenzyl)-2-[(methylsulfanyl)methyl]-9-(morpholin-4-yl methyl)-7-oxo-2,3-dihydro-7H-[1,4]oxazino[2,3,4-ij]quinoline-6-carboxamide, jj) N-(4-Chlorobenzyl)-2-[(dimethylamino)methyl]-9-(morpholin-4-ylmethyl)-7-oxo-2,3-dihydro-7H-[1,4]oxazino[2,3,4-ij]quinoline-6-carboxamide, kk) N-(4-Chlorobenzyl)-2-[(4-methyl-1-piperazinyl)methyl]-9-(morpholin 4-ylmethyl)-7-oxo-2,3-dihydro-7H-[1,4]oxazino[2,3,4-ij]quinoline-6-carboxamide, ll) Methyl({[6-{[(4-chlorobenzyl)amino]carbonyl}-9-(morpholin-4-ylmethyl)-7-oxo-2,3-dihydro-7H-[1,4]oxazino[2,3,4-ij]quinolin-2-yl]methyl}thio)acetate, mm) N-(4-Chlorobenzyl)-9-(morpholin-4-ylmethyl)-7-oxo-2-(1-pyrrolidinylmethyl)-2,3-dihydro-7H-[1,4]oxazino[2,3,4-ij]quinoline-6-carboxamide, nn) N-(4-Chlorobenzyl)-2-{[(2,3-dihydroxypropyl)sulfanyl]methyl}-9-(morpholin-4-ylmethyl)-7-oxo-2,3-dihydro-7H-[1,4]oxazino[2,3,4-ij]quinoline-6-carboxamide, oo) N-(4-Chlorobenzyl)-2-{[(2,3-dihydroxypropyl)amino]methyl}-9-(morpholin-4-ylmethyl)-7-oxo-2,3-dihydro-7H-[1,4]oxazino[2,3,4-ij]quinoline-6-carboxamide, pp) N-(4-Chlorobenzyl)-2-{[(2-hydroxyethyl)amino]methyl}-9-(morpholin-4-ylmethyl)-7-oxo-2,3-dihydro-7H-[1,4]oxazino[2,3,4-ij]quinoline-6-carboxamide, qq) N-(4-Chlorobenzyl)-9-(morpholin-4-ylmethyl)-7-oxo-2-(1-piperidinylmethyl)-2,3-dihydro-7H-[1,4]oxazino[2,3,4-ij]quinoline-6-carboxamide, rr) 2-{[bis(2-Hydroxyethyl)amino]methyl}-N-(4-chlorobenzyl)-9-(morpholin-4-ylmethyl)-7-oxo-2,3-dihydro-7H-[1,4]oxazino[2,3,4-ij]quinoline-6-carboxamide, ss) N-(4-Chlorobenzyl)-9-(morpholin-4-ylmethyl)-7-oxo-2-{[(2-pyridinylmethyl)amino]methyl}-2,3-dihydro-7H-[1,4]oxazino[2,3,4-ij]quinoline-6-carboxamide, tt) 2-[(8-{[6-{[(4-Chlorobenzyl)amino]carbonyl}-9-(morpholin-4-ylmethyl)-7-oxo-2,3-dihydro-7H-[1,4]oxazino[2,3,4-ij]quinolin-2-yl]methoxy}-8-oxooctanoyl)(methyl)amino]ethanesulfonic acid sodium salt, uu) [6-{[(4-Chlorobenzyl)amino]carbonyl}-9-(morpholin-4-ylmethyl)-7-oxo-2,3-dihydro-7H-[1,4]oxazino[2,3,4-ij]quinolin-2-yl]methyl dimethyl phosphate, vv) N-(4-Chlorobenzyl)-9-(morpholin-4-ylmethyl)-7-oxo-2-{[(4-pyridinylmethyl)amino]methyl}-2,3-dihydro-7H-[1,4]oxazino[2,3,4-ij]quinoline-6-carboxamide, ww) N-(4-Chlorobenzyl)-2-(1H-imidazol-1-ylmethyl)-9-(morpholin-4-ylmethyl)-7-oxo-2,3-dihydro-7H-[1,4]oxazino[2,3,4-ij]quinoline-6-carboxamide, xx) N-(4-Chlorobenzyl)-2-{[(4-chlorobenzyl)amino]methyl}-9-(morpholin-4-ylmethyl)-7-oxo-2,3-dihydro-7H-[1,4]oxazino[2,3,4-ij]quinoline-6-carboxamide, yy) N-(4-Chlorobenzyl)-3-(hydroxymethyl)-9-(morpholin-4-ylmethyl)-7-oxo-2,3-dihydro-7H-[1,4]oxazino[2,3,4-ij]quinoline-6-carboxamide, zz) N-(4-Chlorobenzyl)-2-(4-hydroxyphenyl)-9-(morpholin-4-ylmethyl)-7-oxo-2,3-dihydro-7H-[1,4]oxazino[2,3,4-ij]quinoline-6-carboxamide, aaa) N-(4-Chlorobenzyl)-2-{3-[(methoxymethoxy)methyl]phenyl}-9-(morpholin-4-ylmethyl)-7-oxo-2,3-dihydro-7H-[1,4]oxazino[2,3,4-ij]quinoline-6-carboxamide, bbb) N-(4-Chlorobenzyl)-2-{2-[(methoxymethoxy)methyl]phenyl}-9-(morpholin-4-ylmethyl)-7-oxo-2,3-dihydro-7H-[1,4]oxazino[2,3,4-ij]quinoline-6-carboxamide, ccc) N-(4-Chlorobenzyl)-2-(2-hydroxyphenyl)-9-(morpholin-4-ylmethyl)-7-oxo-2,3-dihydro-7H-[1,4]oxazino[2,3,4-ij]quinoline-6-carboxamide, ddd) N-[(4-Chlorophenyl)methyl]-2,3,5,6-tetrahydro-9'-(4-morpholinylmethyl)-7'-oxospiro[4H-pyran-4,2'(3'H)-[7H]pyrido[1,2,3-de][1,4]benzoxazine]-6'-carboxamide, eee) 1,1-Dimethylethyl 6-[[[(4-chlorophenyl)methyl]amino]carbonyl]-9'-(4-morpholinylmethyl)-7'-oxospiro[piperidine-4,2'(3'H)-[7H]pyrido[1,2,3-de][1,4]benzoxazine]-1-carboxylate, fff) N-[(4-Chlorophenyl)methyl]-9'-(4-morpholinylmethyl)-7'-oxospiro[piperidine-4,2'(3'H)-[7H]pyrido[1,2,3-de][1,4]benzoxazine]-6'-carboxamide, ggg) N-(4-Chlorobenzyl)-2,2-bis(hydroxymethyl)-9-(morpholin-4-ylmethyl)-7-oxo-2,3-dihydro-7H-[1,4]oxazino[2,3,4-ij]quinoline-6-carboxamide, hhh) N-[(4-Chlorophenyl)methyl]-2',3',5',6'-tetrahydro-9-(4-morpholinylmethyl)-7-oxospiro[7H-pyrido[1,2,3-de]-1,4-benzoxazine-2(3H), 4'-[4H]thiopyran]-6-carboxamide, iii) N-(4-Chlorobenzyl)-9-(morpholin-4-ylmethyl)-7-oxo-3-phenyl-2,3-dihydro-7H-[1,4]oxazino[2,3,4-ij]quinoline-6-carboxamide, jjj) N-(4-Chlorobenzyl)-3,3-bis(hydroxymethyl)-9-(3-hydroxy-1-propynyl)-7-oxo-2,3-dihydro-7H-[1,4]oxazino[2,3,4-ij]quinoline-6-carboxamide, kkk) N-(4-Chlorobenzyl)-3,3-bis(hydroxymethyl)-9-(3-hydroxypropyl)-7-oxo-2,3-dihydro-7H-[1,4]oxazino[2,3,4-ij]quinoline-6-carboxamide, lll) N-(4-Chlorobenzyl)-2-[2-(methoxymethoxy)phenyl]-9-(morpholin-4-ylmethyl)-7-oxo-2,3-dihydro-7H-[1,4]oxazino[2,3,4-ij]quinoline-6-carboxamide, mmm) N-(4-Chlorobenzyl)-2-{4-[(methoxymethoxy)methyl]phenyl}-9-(morpholin-4-ylmethyl)-7-oxo-2,3-dihydro-7H-[1,4]oxazino[2,3,4-ij]quinoline-6-carboxamide, nnn) 2-[2,3-bis(Methoxymethoxy)phenyl]-N-(4-chlorobenzyl)-9-(morpholin-4-ylmethyl)-7-oxo-2,3-dihydro-7H-[1,4]oxazino[2,3,4-ij]quinoline-6-carboxamide, ooo) N-[(4-Chlorophenyl)methyl]-1-methyl-9'-(4-morpholinylmethyl)-7'-oxospiro[piperidine-4,2'(3'H)-[7H]pyrido[1,2,3-de][1,4]benzoxazine]-6'-carboxamide, ppp) N-[(4-Chlorophenyl)methyl]-9"-(4-morpholinylmethyl)dispiro[1,3-dioxolane-2,1'-cyclohexane-4',2"(3"H)-[7H]pyrido[1,2,3-de][1,4]benzoxazine]-6"-carboxamide, or a pharmaceutically acceptable salt.

69. A compound of claim 1 which is a) N-(4-Chlorobenzyl)-2-(hydroxymethyl)-9-(morpholin-4-ylmethyl)-7-thioxo-2,3-dihydro-7H-[1,4]oxazino[2,3,4-ij]quinoline-6-carboxamide, b) N-(4-Chlorobenzyl)-2-(R or S)-(hydroxymethyl)-9-(morpholin-4-ylmethyl)-7-thioxo-2,3-dihydro-7H-[1,4]oxazino[2,3,4-ij]quinoline-6-carboxamide, c) N-(4-Chlorobenzyl)-9-(morpholin-4-ylmethyl)-7-thioxo-2-pyridin-3-yl-2,3-dihydro-7H-[1,4]oxazino[2,3,4-ij]quinoline-6-carboxamide, d) N-(4-Chlorobenzyl)-9-(morpholin-4-ylmethyl)-7-thioxo-2-pyridin-4-yl-2,3-dihydro-7H-[1,4]oxazino[2,3,4-ij]quinoline-6-carboxamide, e) N-(4-Chlorobenzyl)-9-(morpholin-4-ylmethyl)-7-thioxo-2-pyridin-2-yl-2,3-dihydro-7H-[1,4]oxazino[2,3,4-ij]quinoline-6-carboxamide, f) N-(4-Chlorobenzyl)-9-(morpholin-4-ylmethyl)-7-thioxo-2-(R or S)-pyridin-3-yl-2,3-dihydro-7H-[1,4]oxazino[2,3,4-ij]quinoline-6-carboxamide, g) N-(4-Chlorobenzyl)-2,9-bis(morpholin-4-ylmethyl)-7-thioxo-2,3-dihydro-7H-[1,4]oxazino[2,3,4-ij]quinoline-6-carboxamide, h) 2-[(tert-Butylsulfanyl)methyl]-N-(4-chlorobenzyl)-9-(morpholin-4-ylmethyl)-7-thioxo-2,3-dihydro-7H-[1,4]oxazino[2,3,4-ij]quinoline-6-carboxamide, i) N-(4-Chlorobenzyl)-2-{[(2-hydroxyethyl)sulfanyl]methyl}-9-(morpholin-4-ylmethyl)-7-thioxo-2,3-dihydro-7H-[1,4]oxazino[2,3,4-ij]quinoline-6-carboxamide, j) N-(4-Chlorobenzyl)-2-{[(1-methyl-1H-imidazol-2-yl)sulfanyl]methyl}-9-(morpholin-4-ylmethyl)-7-thioxo-2,3-dihydro-7H-[1,4]oxazino[2,3,4-ij]quinoline-6-carboxamide, k) N-(4-Chlorobenzyl)-9-(morpholin-4-ylmethyl)-7-thioxo-2-{[(3-pyridinylmethyl)amino]methyl}-2,3-dihydro-7H-[1,4]oxazino[2,3,4-ij]quinoline-6-carboxamide, l) [6-{[(4-Chlorobenzyl)amino]carbonyl}-9-(morpholin-4-ylmethyl)-7-thioxo-2,3-dihydro-7H-[1,4]oxazino[2,3,4-ij]quinolin-2-yl]methyl acetate, m) N-(4-Chlorobenzyl)-9-(morpholin-4-ylmethyl)-7-thioxo-2-(R or S)-{[(3-pyridinylmethyl)amino]methyl}-2,3-dihydro-7H-[1,4]oxazino[2,3,4-ij]quinoline-6-carboxamide, n) N-(4-Chlorobenzyl)-2-(3-hydroxyphenyl)-9-(morpholin-4-ylmethyl)-7-thioxo-2,3-dihydro-7H-[1,4]oxazino[2,3,4-ij]quinoline-6-carboxamide, o) N-(4-Chlorobenzyl)-9-(morpholin-4-ylmethyl)-7-thioxo-2-(R or S)-pyridin-2-yl-2,3-dihydro-7H-[1,4]oxazino[2,3,4-ij]quinoline-6-carboxamide, p) N-(4-Chlorobenzyl)-2-[3-(hydroxymethyl)phenyl]-9-(morpholin-4-ylmethyl)-7-thioxo-2,3-dihydro-7H-[1,4]oxazino[2,3,4-ij]quinoline-6-carboxamide, q) N-(4-Chlorobenzyl)-2-[2-(hydroxymethyl)phenyl]-9-(morpholin-4-ylmethyl)-7-thioxo-2,3-dihydro-7H-[1,4]oxazino[2,3,4-ij]quinoline-6-carboxamide, r) N-(4-Chlorobenzyl)-2-(1-methyl-1H-imidazol-2-yl)-9-(morpholin-4-ylmethyl)-7-thioxo-2,3-dihydro-7H-[1,4]oxazino[2,3,4-ij]quinoline-6-carboxamide, s) N-(4-Chlorobenzyl)-2-(2-furyl)-9-(morpholin-4-ylmethyl)-7-thioxo-2,3-dihydro-7H-[1,4]oxazino[2,3,4-ij]quinoline-6-carboxamide, t) N-(4-Chlorobenzyl)-2-(3-cyanophenyl)-9-(morpholin-4-ylmethyl)-7-thioxo-2,3-dihydro-7H-[1,4]oxazino[2,3,4-ij]quinoline-6-carboxamide, u) N-(4-Chlorobenzyl)-2-(3-furyl)-9-(morpholin-4-ylmethyl)-7-thioxo-2,3-dihydro-7H-[1,4]oxazino[2,3,4-ij]quinoline-6-carboxamide, v) N-(4-Chlorobenzyl)-9-(morpholin-4-ylmethyl)-7-thioxo-2-thien-2-yl-2,3-dihydro-7H-[1,4]oxazino[2,3,4-ij]quinoline-6-carboxamide, w) N-(4-Chlorobenzyl)-2-(3,5-difluorophenyl)-9-(morpholin-4-ylmethyl)-7-thioxo-2,3-dihydro-7H-[1,4]oxazino[2,3,4-ij]quinoline-6-carboxamide, x) 2-(1,3-Benzodioxol-5-yl)-N-(4-chlorobenzyl)-9-(morpholin-4-ylmethyl)-7-thioxo-2,3-dihydro-7H-[1,4]oxazino[2,3,4-ij]quinoline-6-carboxamide, y) N-(4-Chlorobenzyl)-2-(2,3-dihydro-1,4-benzodioxin-6-yl)-9-(morpholin-4-ylmethyl)-7-thioxo-2,3-dihydro-7H-[1,4]oxazino[2,3,4-ij]quinoline-6-carboxamide, z) 2-(1,3-Benzodioxol-4-yl)-N-(4-chlorobenzyl)-9-(morpholin-4-ylmethyl)-7-thioxo-2,3-dihydro-7H-[1,4]oxazino[2,3,4-ij]quinoline-6-carboxamide, aa) 2-[3,5-bis(Methoxymethoxy)phenyl]-N-(4-chlorobenzyl)-9-(morpholin-4-ylmethyl)-7-thioxo-2,3-dihydro-7H-[1,4]oxazino[2,3,4-ij]quinoline-6-carboxamide, bb) N-(4-Chlorobenzyl)-9-(morpholin-4-ylmethyl)-7-thioxo-2-thien-3-yl-2,3-dihydro-7H-[1,4]oxazino[2,3,4-ij]quinoline-6-carboxamide, cc) N-(4-Chlorobenzyl)-2,2-bis[(methoxymethoxy)methyl]-9-(morpholin-4-ylmethyl)-7-thioxo-2,3-dihydro-7H-[1,4]oxazino[2,3,4-ij]quinoline-6-carboxamide, dd) N-[(4-Chlorophenyl)methyl]-9'-(4-morpholinylmethyl)-4-oxo-7'-thioxospiro[cyclohexane-1,2'(3'H)-[7H]pyrido[1,2,3-de][1,4]benzoxazine]-6'-carboxamide, ee) N-[(4-Chlorophenyl)methyl]-4-hydroxy-9'-(4-morpholinylmethyl)-7'-thioxospiro[cyclohexane-1,2'(3'H)-[7H]pyrido[1,2,3-de][1,4]benzoxazine]-6'-carboxamide, ff) N-(4-Chlorobenzyl)-3,9-bis(morpholin-4-ylmethyl)-7-thioxo-2,3-dihydro-7H-[1,4]oxazino[2,3,4-ij]quinoline-6-carboxamide, gg) N-(4-Chlorobenzyl)-9-(morpholin-4-ylmethyl)-7-thioxo-2-phenyl-2,3-dihydro-7H-[1,4]oxazino[2,3,4-ij]quinoline-6-carboxamide, hh) N-(4-Chlorobenzyl)-2,2-difluoro-9-(morpholin-4-ylmethyl)-7-thioxo-2,3-dihydro-7H-[1,4]oxazino[2,3,4-ij]quinoline-6-carboxamide, ii) N-(4-Chlorobenzyl)-2-[(methylsulfanyl)methyl]-9-(morpholin-4-ylmethyl)-7-thioxo-2,3-dihydro-7H-[1,4]oxazino[2,3,4-ij]quinoline-6-carboxamide, jj) N-(4-Chlorobenzyl)-2-[(dimethylamino)methyl]-9-(morpholin-4-ylmethyl)-7-thioxo-2,3-dihydro-7H-[1,4]oxazino[2,3,4-ij]quinoline-6-carboxamide, kk) N-(4-Chlorobenzyl)-2-[(4-methyl-1-piperazinyl)methyl]-9-(morpholin-4-ylmethyl)-7-thioxo-2,3-dihydro-7H-[1,4]oxazino[2,3,4-ij]quinoline-6-carboxamide, ll) Methyl({[6-{[(4-chlorobenzyl)amino]carbonyl}-9-(morpholin-4-ylmethyl)-7-thioxo-2,3-dihydro-7H-[1,4]oxazino[2,3,4-ij]quinolin-2-yl]methyl}thio)acetate, mm) N-(4-Chlorobenzyl)-9-(morpholin-4-ylmethyl)-7-thioxo-2-(1-pyrrolidinylmethyl)-2,3-dihydro-7H-[1,4]oxazino[2,3,4-ij]quinoline-6-carboxamide, nn) N-(4-Chlorobenzyl)-2-{[(2,3-dihydroxypropyl)sulfanyl]methyl}-9-(morpholin-4-ylmethyl)-7-thioxo-2,3-dihydro-7H-[1,4]oxazino[2,3,4-ij]quinoline-6-carboxamide, oo) N-(4-Chlorobenzyl)-2-{[(2,3-dihydroxypropyl)amino]methyl}-9-(morpholin-4-ylmethyl)-7-thioxo-2,3-dihydro-7H-[1,4]oxazino[2,3,4-ij]quinoline-6-carboxamide, pp) N-(4-Chlorobenzyl)-2-{[(2-hydroxyethyl)amino]methyl}-9-(morpholin-4-ylmethyl)-7-thioxo-2,3-dihydro-7H-[1,4]oxazino[2,3,4-ij]quinoline-6-carboxamide, qq) N-(4-Chlorobenzyl)-9-(morpholin-4-ylmethyl)-7-thioxo-2-(1-piperidinylmethyl)-2,3-dihydro-7H-[1,4]oxazino[2,3,4-ij]quinoline-6-carboxamide, rr) 2-{[bis(2-Hydroxyethyl)amino]methyl}-N-(4-chlorobenzyl)-9-(morpholin-4-ylmethyl)-7-thioxo-2,3-dihydro-7H-[1,4]oxazino[2,3,4-ij]quinoline-6-carboxamide, ss) N-(4-Chlorobenzyl)-9-(morpholin-4-ylmethyl)-7-thioxo-2-{[(2-pyridinylmethyl)amino]methyl}-2,3-dihydro-7H-[1,4]oxazino[2,3,4-ij]quinoline-6-carboxamide, tt) 2-[(8-{[6-{[(4-Chlorobenzyl)amino]carbonyl}-9-(morpholin-4-ylmethyl)-7-thioxo-2,3-dihydro-7H-[1,4]oxazino[2,3,4-ij]quinolin-2-yl]methoxy}-8-oxooctanoyl)(methyl)amino]ethanesulfonic acid sodium salt, uu) [6-{[(4-Chlorobenzyl)amino]carbonyl}-9-(morpholin-4-ylmethyl)-7-thioxo-2,3-dihydro-7H-[1,4]oxazino[2,3,4-ij]quinolin-2-yl]methyl dimethyl phosphate, vv) N-(4-Chlorobenzyl)-9-(morpholin-4-ylmethyl)-7-thioxo-2-{[(4-pyridinylmethyl)amino]methyl}-3-2,3-dihydro-7H-[1,4]oxazino[2,3,4-ij]quinoline-6-carboxamide, ww) N-(4-Chlorobenzyl)-2-(1H-imidazol-1-ylmethyl)-9-(morpholin-4-ylmethyl)-7-thioxo-2,3-dihydro-7H-[1,4]oxazino[2,3,4-ij]quinoline-6-carboxamide, xx) N-(4-Chlorobenzyl)-2-{[(4-chlorobenzyl)amino]methyl}-9-(morpholin-4-ylmethyl)-7-thioxo-2,3-dihydro-7H-[1,4]oxazino[2,3,4-ij]quinoline-6-carboxamide, yy) N-(4-Chlorobenzyl)-3-(hydroxymethyl)-9-(morpholin-4-ylmethyl)-7-thioxo-2,3-dihydro-7H-[1,4]oxazino[2,3,4-ij]quinoline-6-carboxamide, zz) N-(4-Chlorobenzyl)-2-(4-hydroxyphenyl)-9-(morpholin-4-ylmethyl)-7-thioxo-2,3-dihydro-7H-[1,4]oxazino[2,3,4-ij]quinoline-6-carboxamide, aaa) N-(4-Chlorobenzyl)-2-{3-[(methoxymethoxy)methyl]phenyl}-9-(morpholin-4-ylmethyl)-7-thioxo-2,3-dihydro-7H-[1,4]oxazino[2,3,4-ij]quinoline-6-carboxamide, bbb) N-(4-Chlorobenzyl)-2-{2-[(methoxymethoxy)methyl]phenyl}-9-(morpholin-4-ylmethyl)-7-thioxo-2,3-dihydro-7H-[1,4]oxazino[2,3,4-ij]quinoline-6-carboxamide, ccc) N-(4-Chlorobenzyl)-2-(2-hydroxyphenyl)-9-(morpholin-4-ylmethyl)-7-thioxo-2,3-dihydro-7H-[1,4]oxazino[2,3,4-ij]quinoline-6-carboxamide, ddd) N-[(4-Chlorophenyl)methyl]-2,3,5,6-tetrahydro-9'-(4-morpholinylmethyl)-7'-thioxospiro[4H-pyran-4,2'(3'H)-[7H]pyrido[1,2,3-de][1,4]benzoxazine]-6'-carboxamide, eee) 1,1-Dimethylethyl 6-[[[(4-chlorophenyl)methyl]amino]carbonyl]-9'-(4-morpholinylmethyl)-7'-thioxospiro[piperidine-4,2'(3'H)-[7H]pyrido[1,2,3-de][1,4]benzoxazine]-1-carboxylate, fff) N-[(4-Chlorophenyl)methyl]-9'-(4-morpholinylmethyl)-7'-thioxospiro[piperidine-4,2'(3'H)-[7H]pyrido[1,2,3-de][1,4]benzoxazine]-6'-carboxamide, ggg) N-(4-Chlorobenzyl)-2,2-bis(hydroxymethyl)-9-(morpholin-4-ylmethyl)-7-thioxo-2,3-dihydro-7H-[1,4]oxazino[2,3,4-ij]quinoline-6-carboxamide, hhh) N-[(4-Chlorophenyl)methyl]-2',3',5',6'-tetrahydro-9-(4-morpholinylmethyl)-7-thioxospiro[7H-pyrido[1,2,3-de]-1,4-benzoxazine-2(3H),4'-[4H]thiopyran]-6-carboxamide, iii) N-(4-Chlorobenzyl)-9-(morpholin-4-ylmethyl)-7-thioxo-3-phenyl-2,3-dihydro-7H-[1,4]oxazino[2,3,4-ij]quinoline-6-carboxamide, jjj) N-(4-Chlorobenzyl)-3,3-bis(hydroxymethyl)-9-(3-hydroxy-1-propynyl)-7-thioxo-2,3-dihydro-7H-[1,4]oxazino[2,3,4-ij]quinoline-6-carboxamide, kkk) N-(4-Chlorobenzyl)-3,3-bis(hydroxymethyl)-9-(3-hydroxypropyl)-7-thioxo-2,3-dihydro-7H-[1,4]oxazino[2,3,4-ij]quinoline-6-carboxamide, lll) N-(4-Chlorobenzyl)-2-[2-(methoxymethoxy)phenyl]-9-(morpholin-4-ylmethyl)-7-thioxo-2,3-dihydro-7H-[1,4]oxazino[2,3,4-ij]quinoline-6-carboxamide, mmm) N-(4-Chlorobenzyl)-2-{4-[(methoxymethoxy)methyl]phenyl}-9-(morpholin-4-ylmethyl)-7-thioxo-2,3-dihydro-7H-[1,4]oxazino[2,3,4-ij]quinoline-6-carboxamide, nnn) 2-[2,3-bis(Methoxymethoxy)phenyl]-N-(4-chlorobenzyl)-9-(morpholin-4-ylmethyl)-7-thioxo-2,3-dihydro-7H-[1,4]oxazino[2,3,4-ij]quinoline-6-carboxamide, ooo) N-[(4-Chlorophenyl)methyl]-1-methyl-9'-(4-morpholinylmethyl)-7'-thioxospiro[piperidine-4,2'(3'H)-[7H]pyrido[1,2,3-de][1,4]benzoxazine]-6'-carboxamide, or a pharmaceutically acceptable salt.

70. A compound of claim 1 which is a) N-(4-Chlorobenzyl)-2-(hydroxymethyl)-9-(morpholin-4-ylmethyl)-7-oxo-2,3-dihydro-7H-[1,4]oxazino[2,3,4-ij]quinoline-6-carboxamide, b) N-(4-Chlorobenzyl)-2-(R or S)-(hydroxymethyl)-9-(morpholin-4-ylmethyl)-7-oxo-2,3-dihydro-7H-[1,4]oxazino[2,3,4-ij]quinoline-6-carboxamide, c) N-(4-Chlorobenzyl)-9-(morpholin-4-ylmethyl)-7-oxo-2-pyridin-3-yl-2,3-dihydro-7H-[1,4]oxazino[2,3,4-ij]quinoline-6-carboxamide, d) N-(4-Chlorobenzyl)-9-(morpholin-4-ylmethyl)-7-oxo-2-pyridin-4-yl-2,3-dihydro-7H-[1,4]oxazino[2,3,4-ij]quinoline-6-carboxamide, e) N-(4-Chlorobenzyl)-9-(morpholin-4-ylmethyl)-7-oxo-2-pyridin-2-yl-2,3-dihydro-7H-[1,4]oxazino[2,3,4-ij]quinoline-6-carboxamide, f) N-(4-Chlorobenzyl)-9-(morpholin-4-ylmethyl)-7-oxo-2-(R or S)-pyridin-3-yl-2,3-dihydro-7H-[1,4]oxazino[2,3,4-ij]quinoline-6-carboxamide, g) N-(4-Chlorobenzyl)-2,9-bis(morpholin-4-ylmethyl)-7-oxo-2,3-dihydro-7H-[1,4]oxazino[2,3,4-ij]quinoline-6-carboxamide, h) 2-[(tert-Butylsulfanyl)methyl]-N-(4-chlorobenzyl)-9-(morpholin-4-ylmethyl)-7-oxo-2,3-dihydro-7H-[1,4]oxazino[2,3,4-ij]quinoline-6-carboxamide, i) N-(4-Chlorobenzyl)-2-{[(2-hydroxyethyl)sulfanyl]methyl}-9-(morpholin-4-ylmethyl)-7-oxo-2,3-dihydro-7H-[1,4]oxazino[2,3,4-ij]quinoline-6-carboxamide, j) N-(4-Chlorobenzyl)-2-{[(1-methyl-1H-imidazol-2-yl)sulfanyl]methyl}-9-(morpholin-4-ylmethyl)-7-oxo-2,3-dihydro-7H-[1,4]oxazino[2,3,4-ij]quinoline-6-carboxamide, k) N-(4-Chlorobenzyl)-9-(morpholin-4-ylmethyl)-7-oxo-2-{[(3-pyridinylmethyl)amino]methyl}-2,3-dihydro-7H-[1,4]oxazino[2,3,4-ij]quinoline-6-carboxamide, l) [6-{[(4-Chlorobenzyl)amino]carbonyl}-9-(morpholin-4-ylmethyl)-7-oxo-2,3-dihydro-7H-[1,4]oxazino[2,3,4-ij]quinolin-2-yl]methyl acetate, m) N-(4-Chlorobenzyl)-9-(morpholin-4-ylmethyl)-7-oxo-2-(R or S)-{[(3-pyridinylmethyl)amino]methyl}-2,3-dihydro-7H-[1,4]oxazino[2,3,4-ij]quinoline-6-carboxamide, n) N-(4-Chlorobenzyl)-2-(3-hydroxyphenyl)-9-(morpholin-4-ylmethyl)-7-oxo-2,3-dihydro-7H-[1,4]oxazino[2,3,4-ij]quinoline-6-carboxamide, o) N-(4-Chlorobenzyl)-9-(morpholin-4-ylmethyl)-7-oxo-2-(R or S)-pyridin-2-yl-2,3-dihydro-7H-[1,4]oxazino[2,3,4-ij]quinoline-6-carboxamide, p) N-(4-Chlorobenzyl)-2-[3-(hydroxymethyl)phenyl]-9-(morpholin-4-ylmethyl)-7-oxo-2,3-dihydro-7H-[1,4]oxazino[2,3,4-ij]quinoline-6-carboxamide, q) N-(4-Chlorobenzyl)-2-[2-(hydroxymethyl)phenyl]-9-(morpholin-4-ylmethyl)-7-oxo-2,3-dihydro-7H-[1,4]oxazino[2,3,4-ij]quinoline-6-carboxamide, r) N-(4-Chlorobenzyl)-2-(1-methyl-1H-imidazol-2-yl)-9-(morpholin-4-ylmethyl)-7-oxo-2,3-dihydro-7H-[1,4]oxazino[2,3,4-ij]quinoline-6-carboxamide, s) N-(4-Chlorobenzyl)-2-(2-furyl)-9-(morpholin-4-ylmethyl)-7-H-[1,4]oxazino[2,3,4-ij]quinoline-6-carboxamide, t) N-(4-Chlorobenzyl)-2-(3-cyanophenyl)-9-(morpholin-4-ylmethyl)-7-oxo-2,3-dihydro-7H-[1,4]oxazino[2,3,4-ij]quinoline-6-carboxamide, u) N-(4-Chlorobenzyl)-2-(3-furyl)-9-(morpholin-4-ylmethyl)-7-oxo-2,3-dihydro-7H-[1,4]oxazino[2,3,4-ij]quinoline-6-carboxamide, v) N-(4-Chlorobenzyl)-9-(morpholin-4-ylmethyl)-7-oxo-2,3-dihydro-7H-[1,4]oxazino[2,3,4-ij]quinoline-6-carboxamide, w) N-(4-Chlorobenzyl)-2-(3,5-difluorophenyl)-9-(morpholin-4-ylmethyl)-7-oxo-2,3-dihydro-7H-[1,4]oxazino[2,3,4-ij]quinoline-6-carboxamide, x) 2-(1,3-Benzodioxol-5-yl)-N-(4-chlorobenzyl)-9-(morpholin-4-ylmethyl)-7-oxo-2,3-dihydro-7H-[1,4]oxazino[2,3,4-ij]quinoline-6-carboxamide, y) N-(4-Chlorobenzyl)-2-(2,3-dihydro-1,4-benzodioxin-6-yl)-9-(morpholin-4-ylmethyl)-7-oxo-2,3-dihydro-7H-[1,4]oxazino[2,3,4-ij]quinoline-6-carboxamide, z) 2-(1,3-Benzodioxol-4-yl)-N-(4-chlorobenzyl)-9-(morpholin-4-ylmethyl)-7-oxo-2,3-dihydro-7H-[1,4]oxazino[2,3,4-ij]quinoline-6-carboxamide, aa) 2-[3,5-bis(Methoxymethoxy)phenyl]-N-(4-chlorobenzyl)-9-(morpholin-4-ylmethyl)-7-oxo-2,3-dihydro-7H-[1,4]oxazino[2,3,4-ij]quinoline-6-carboxamide, bb) N-(4-Chlorobenzyl)-9-(morpholin-4-ylmethyl)-7-oxo-2-thien-3-yl-2,3-dihydro-7H-[1,4]oxazino[2,3,4-ij]quinoline-6-carboxamide, cc) N-(4-Chlorobenzyl)-2,2-bis[(methoxymethoxy)methyl]-9-(morpholin-4-ylmethyl)-7-oxo-2,3-dihydro-7H-[1,4]oxazino[2,3,4-ij]quinoline-6-carboxamide, dd) N-[(4-Chlorophenyl)methyl]-9'-(4-morpholinylmethyl)-4,7'-dioxospiro[cyclohexane-1,2'(3'H)-[7H]pyrido[1,2,3-de][1,4]benzoxazine]-6'-carboxamide, ee) N-[(4-Chlorophenyl)methyl]-4-hydroxy-9'-(4-morpholinylmethyl)-7'-oxospiro[cyclohexane-1,2'(3'H)-[7H]pyrido[1,2,3-de][1,4]benzoxazine]-6'-carboxamide, ff) N-(4-Chlorobenzyl)-3,9-bis(morpholin-4-ylmethyl)-7-oxo-2,3-dihydro-7H-[1,4]oxazino[2,3,4-ij]quinoline-6-carboxamide, gg) N-(4-Chlorobenzyl)-9-(morpholin-4-ylmethyl)-7-oxo-2-phenyl-2,3-dihydro-7H-[1,4]oxazino[2,3,4-ij]quinoline-6-carboxamide, hh) N-(4-Chlorobenzyl)-2,2-difluoro-9-(morpholin-4-ylmethyl)-7-oxo-2,3-dihydro-7H-[1,4]oxazino[2,3,4-ij]quinoline-6-carboxamide, ii) N-(4-Chlorobenzyl)-2-[(methylsulfanyl)methyl]-9-(morpholin-4-ylmethyl)-7-oxo-2,3-dihydro-7H-[1,4]oxazino[2,3,4-ij]quinoline-6-carboxamide, jj) N-(4-Chlorobenzyl)-2-[(dimethylamino)methyl]-9-(morpholin-4-ylmethyl)-7-oxo-2,3-dihydro-7H-[1,4]oxazino[2,3,4-ij]quinoline-6-carboxamide, kk) N-(4-Chlorobenzyl)-2-[(4-methyl-1-piperazinyl)methyl]-9-(morpholin-4-ylmethyl)-7-oxo-2,3-dihydro-7H-[1,4]oxazino[2,3,4-ij]quinoline-6-carboxamide, ll) Methyl({[6-{[(4-chlorobenzyl)amino]carbonyl}-9-(morpholin-4-ylmethyl)-7-oxo-2,3-dihydro-7H-[1,4]oxazino[2,3,4-ij]quinolin-2-yl]methyl}thio)acetate, mm) N-(4-Chlorobenzyl)-9-(morpholin-4-ylmethyl)-7-oxo-2-(1-pyrrolidinylmethyl)-2,3-dihydro-7H-[1,4]oxazino[2,3,4-ij]quinoline-6-carboxamide, nn) N-(4-Chlorobenzyl)-2-{[(2,3-dihydroxypropyl)sulfanyl]methyl}-9-(morpholin-4-ylmethyl)-7-oxo-2,3-dihydro-7H-[1,4]oxazino[2,3,4-ij]quinoline-6-carboxamide, oo) N-(4-Chlorobenzyl)-2-{[(2,3-dihydroxypropyl) amino]methyl}-9-(morpholin-4-ylmethyl)-7-oxo-2,3-dihydro-7H-[1,4]oxazino[2,3,4-ij]quinoline-6-carboxamide, pp) N-(4-Chlorobenzyl)-2-{[(2-hydroxyethyl)amino] methyl}-9-(morpholin-4-ylmethyl)-7-oxo-2,3-dihydro-7H-[1,4]oxazino[2,3,4-ij]quinoline-6-carboxamide, qq) N-(4-Chlorobenzyl)-9-(morpholin-4-ylmethyl)-7-oxo-2-(1-piperidinylmethyl)-2,3-dihydro-7H-[1,4]oxazino[2,3,4-ij]quinoline-6-carboxamide, rr) 2-{[bis(2-Hydroxyethyl)amino]methyl}-N-(4-chlorobenzyl)-9-(morpholin-4-ylmethyl)-7-oxo-2,3-dihydro-7H-[1,4]oxazino[2,3,4-ij]quinoline-6-carboxamide, ss) N-(4-Chlorobenzyl)-9-(morpholin-4-ylmethyl)-7-oxo-2-{[(2-pyridinylmethyl)amino]methyl}-2,3-dihydro-7H-[1,4]oxazino[2,3,4-ij]quinoline-6-carboxamide, tt) 2-[(8-{[6-{[(4-Chlorobenzyl)amino]carbonyl}-9-(morpholin-4-ylmethyl)-7-oxo-2,3-dihydro-7H-[1,4] oxazino[2,3,4-ij]quinolin-2-yl]methoxy}-8-oxooctanoyl)(methyl)amino]ethanesulfonic acid sodium salt, uu) [6-{[(4-Chlorobenzyl)amino]carbonyl}-9-(morpholin-4-ylmethyl)-7-oxo-2,3-dihydro-7H-[1,4] oxazino[2,3,4-ij]quinolin-2-yl]methyl dimethyl phosphate, vv) N-(4-Chlorobenzyl)-9-(morpholin-4-ylmethyl)-7-oxo-2-{[(4-pyridinylmethyl)amino]methyl}-2,3-dihydro-7H-[1,4]oxazino[2,3,4-ij]quinoline-6-carboxamide, ww) N-(4-Chlorobenzyl)-2-(1H-imidazol-1-ylmethyl)-9-(morpholin-4-ylmethyl)-7-oxo-2,3-dihydro-7H-[1,4]oxazino[2,3,4-ij]quinoline-6-carboxamide, xx) N-(4-Chlorobenzyl)-2-{[(4-chlorobenzyl)amino] methyl}-9-(morpholin-4-ylmethyl)-7-oxo-2,3-dihydro-7H-[1,4]oxazino[2,3,4-ij]quinoline-6-carboxamide, yy) N-(4-Chlorobenzyl)-3-(hydroxymethyl)-9-(morpholin-4-ylmethyl)-7-oxo-2,3-dihydro-7H-[1,4] oxazino[2,3,4-ij]quinoline-6-carboxamide, zz) N-(4-Chlorobenzyl)-2-(4-hydroxyphenyl)-9-(morpholin-4-ylmethyl)-7-oxo-2,3-dihydro-7H-[1,4] oxazino[2,3,4-ij]quinoline-6-carboxamide, aaa) N-(4-Chlorobenzyl)-2-{3-[(methoxymethoxy) methyl]phenyl}-9-(morpholin-4-ylmethyl)-7-oxo-2,3-dihydro-7H-[1,4]oxazino[2,3,4-ij]quinoline-6-carboxamide, bbb) N-(4-Chlorobenzyl)-2-{2-[(methoxymethoxy) methyl]phenyl}-9-(morpholin-4-ylmethyl)-7-oxo-2,3-dihydro-7H-[1,4]oxazino[2,3,4-ij]quinoline-6-carboxamide, ccc) N-(4-Chlorobenzyl)-2-(2-hydroxyphenyl)-9-(morpholin-4-ylmethyl)-7-oxo-2,3-dihydro-7H-[1,4] oxazino[2,3,4-ij]quinoline-6-carboxamide, ddd) N-[(4-Chlorophenyl)methyl]-2,3,5,6-tetrahydro-9'-(4-morpholinylmethyl)-7'-oxospiro[4H-pyran-4,2' (3'H)-[7H]pyrido[1,2,3-de][1,4]benzoxazine]-6'-carboxamide, eee) 1,1-Dimethylethyl6-[[[(4-chlorophenyl)methyl] amino]carbonyl]-9'-(4-morpholinylmethyl)-7'-oxospiro[piperidine-4,2'(3'H)-[7H]pyrido[1,2,3-de][1,4]benzoxazine]-1-carboxylate, fff) N-[(4-Chlorophenyl)methyl]-9'-(4-morpholinylmethyl)-7'-oxospiro[piperidine-4,2'(3'H)-[7H]pyrido[1,2,3-de][1,4]benzoxazine]-6'-carboxamide, ggg) N-(4-Chlorobenzyl)-2,2-bis(hydroxymethyl)-9-(morpholin-4-ylmethyl)-7-oxo-2,3-dihydro-7H-[1,4] oxazino[2,3,4-ij]quinoline-6-carboxamide, hhh) N-[(4-Chlorophenyl)methyl]-2',3',5',6'-tetrahydro-9-(4-morpholinylmethyl)-7-oxospiro[7H-pyrido[1,2,3-de]-1,4-benzoxazine-2(3H),4'-[4H]thiopyran]-6-carboxamide, or a pharmaceutically acceptable salt.

71. A compound of claim 1 which is a) N-(4-Chlorobenzyl)-2-(hydroxymethyl)-9-(morpholin-4-ylmethyl)-7-thioxo-2,3-dihydro-7H-[1,4]oxazino[2,3,4-ij]quinoline-6-carboxamide, b) N-(4-Chlorobenzyl)-2-(R or S)-(hydroxymethyl)-9-(morpholin-4-ylmethyl)-7-thioxo-2,3-dihydro-7H-[1,4]oxazino[2,3,4-ij]quinoline-6-carboxamide, c) N-(4-Chlorobenzyl)-9-(morpholin-4-ylmethyl)-7-thioxo-2-pyridin-3-yl-2,3-dihydro-7H-[1,4]oxazino[2,3,4-ij]quinoline-6-carboxamide, d) N-(4-Chlorobenzyl)-9-(morpholin-4-ylmethyl)-7-thioxo-2-pyridin-4-yl-2,3-dihydro-7H-[1,4]oxazino[2,3,4-ij]quinoline-6-carboxamide, e) N-(4-Chlorobenzyl)-9-(morpholin-4-ylmethyl)-7-thioxo-2-pyridin-2-yl-2,3-dihydro-7H-[1,4]oxazino[2,3,4-ij]quinoline-6-carboxamide, f) N-(4-Chlorobenzyl)-9-(morpholin-4-ylmethyl)-7-thioxo-2-(R or S)-pyridin-3-yl-2,3-dihydro-7H-[1,4] oxazino[2,3,4-ij]quinoline-6-carboxamide, g) N-(4-Chlorobenzyl)-2,9-bis(morpholin-4-ylmethyl)-7-thioxo-2,3-dihydro-7H-[1,4]oxazino[2,3,4-ij] quinoline-6-carboxamide, h) 2-[(tert-Butylsulfanyl)methyl]-N-(4-chlorobenzyl)-9-(morpholin-4-ylmethyl)-7-thioxo-2,3-dihydro-7H-[1,4]oxazino[2,3,4-ij]quinoline-6-carboxamide, i) N-(4-Chlorobenzyl)-2-{[(2-hydroxyethyl)sulfanyl] methyl}-9-(morpholin-4-ylmethyl)-7-thioxo-2,3-dihydro-7H-[1,4]oxazino[2,3,4-ij]quinoline-6-carboxamide, j) N-(4-Chlorobenzyl)-2-{[(1-methyl-1H-imidazol-2-yl) sulfanyl]methyl}-9-(morpholin-4-ylmethyl)-7-thioxo-2,3-dihydro-7H-[1,4]oxazino[2,3,4-ij]quinoline-6-carboxamide, k) N-(4-Chlorobenzyl)-9-(morpholin-4-ylmethyl)-7-thioxo-2-{[(3-pyridinylmethyl)amino]methyl}-2,3-dihydro-7H-[1,4]oxazino[2,3,4-ij]quinoline-6-carboxamide, l) [6-{[(4-Chlorobenzyl)amino]carbonyl}-9-(morpholin-4-ylmethyl)-7-thioxo-2,3-dihydro-7H-[1,4]oxazino[2,3,4-ij]quinolin-2-yl]methyl acetate, m) N-(4-Chlorobenzyl)-9-(morpholin-4-ylmethyl)-7-thioxo-2-(R or S)-{[(3-pyridinylmethyl)amino] methyl}-2,3-dihydro-7H-[1,4]oxazino[2,3,4-ij] quinoline-6-carboxamide, n) N-(4-Chlorobenzyl)-2-(3-hydroxyphenyl)-9-(morpholin-4-ylmethyl)-7-thioxo-2,3-dihydro-7H-[1,4]oxazino[2,3,4-ij]quinoline-6-carboxamide, o) N-(4-Chlorobenzyl)-9-(morpholin-4-ylmethyl)-7-thioxo-2-(R or S)-pyridin-2-yl-2,3-dihydro-7H-[1,4] oxazino[2,3,4-ij]quinoline-6-carboxamide, p) N-(4-Chlorobenzyl)-2-[3-(hydroxymethyl)phenyl]-9-(morpholin-4-ylmethyl)-7-thioxo-2,3-dihydro-7H-[1,4]oxazino[2,3,4-ij]quinoline-6-carboxamide, q) N-(4-Chlorobenzyl)-2-[2-(hydroxymethyl)phenyl]-9-(morpholin-4-ylmethyl)-7-thioxo-2,3-dihydro-7H-[1,4]oxazino[2,3,4-ij]quinoline-6-carboxamide, r) N-(4-Chlorobenzyl)-2-(1-methyl-1H-imidazol-2-yl)-9-(morpholin-4-ylmethyl)-7-thioxo-2,3-dihydro-7H-[1,4]oxazino[2,3,4-ij]quinoline-6-carboxamide, s) N-(4-Chlorobenzyl)-2-(2-furyl)-9-(morpholin-4-ylmethyl)-7-thioxo-2,3-dihydro-7H-[1,4]oxazino[2,3,4-ij]quinoline-6-carboxamide, t) N-(4-Chlorobenzyl)-2-(3-cyanophenyl)-9-(morpholin-4-ylmethyl)-7-thioxo-2,3-dihydro-7H-[1,4]oxazino[2,3,4-ij]quinoline-6-carboxamide, u) N-(4-Chlorobenzyl)-2-(3-furyl)-9-(morpholin-4-ylmethyl)-7-thioxo-2,3-dihydro-7H-[1,4]oxazino[2,3,4-ij]quinoline-6-carboxamide, v) N-(4-Chlorobenzyl)-9-(morpholin-4-ylmethyl)-7-thioxo-2-thien-2-yl-2,3-dihydro-7H-[1,4]oxazino[2,3,4-ij]quinoline-6-carboxamide, w) N-(4-Chlorobenzyl)-2-(3,5-difluorophenyl)-9-(morpholin-4-ylmethyl)-7-thioxo-2,3-dihydro-7H-[1,4]oxazino[2,3,4-ij]quinoline-6-carboxamide, x) 2-(1,3-Benzodioxol-5-yl)-N-(4-chlorobenzyl)-9-(morpholin-4-ylmethyl)-7-thioxo-2,3-dihydro-7H-[1,4]oxazino[2,3,4-ij]quinoline-6-carboxamide, y) N-(4-Chlorobenzyl)-2-(2,3-dihydro-1,4-benzodioxin-6-yl)-9-(morpholin-4-ylmethyl)-7-thioxo-2,3-dihydro-7H-[1,4]oxazino[2,3,4-ij]quinoline-6-carboxamide, z) 2-(1,3-Benzodioxol-4-yl)-N-(4-chlorobenzyl)-9-(morpholin-4-ylmethyl)-7-thioxo-2,3-dihydro-7H-[1,4]oxazino[2,3,4-ij]quinoline-6-carboxamide, aa) 2-[3,5-bis(Methoxymethoxy)phenyl]-N-(4-chlorobenzyl)-9-(morpholin-4-ylmethyl)-7-thioxo-2,3-dihydro-7H-[1,4]oxazino[2,3,4-ij]quinoline-6-carboxamide, bb) N-(4-Chlorobenzyl)-9-(morpholin-4-ylmethyl)-7-thioxo-2-thien-3-yl-2,3-dihydro-7H-[1,4]oxazino[2,3,4-ij]quinoline-6-carboxamide, cc) N-(4-Chlorobenzyl)-2,2-bis[(methoxymethoxy)methyl]-9-(morpholin-4-ylmethyl)-7-thioxo-2,3-dihydro-7H-[1,4]oxazino[2,3,4-ij]quinoline-6-carboxamide, dd) N-[(4-Chlorophenyl)methyl]-9'-(4-morpholinylmethyl)-4-oxo-7'-thioxospiro[cyclohexane-1,2'(3'H)-[7H]pyrido[1,2,3-de][1,4]benzoxazine]-6'-carboxamide, ee) N-[(4-Chlorophenyl)methyl]-4-hydroxy-9'-(4-morpholinylmethyl)-7'-thioxospiro[cyclohexane-1,2'(3'H)-[7H]pyrido[1,2,3-de][1,4]benzoxazine]-6'-carboxamide, ff) N-(4-Chlorobenzyl)-3,9-bis(morpholin-4-ylmethyl)-7-thioxo-2,3-dihydro-7H-[1,4]oxazino[2,3,4-ij]quinoline-6-carboxamide, gg) N-(4-Chlorobenzyl)-9-(morpholin-4-ylmethyl)-7-thioxo-2-phenyl-2,3-dihydro-7H-[1,4]oxazino[2,3,4-ij]quinoline-6-carboxamide, hh) N-(4-Chlorobenzyl)-2,2-difluoro-9-(morpholin-4-ylmethyl)-7-thioxo-2,3-dihydro-7H-[1,4]oxazino[2,3,4-ij]quinoline-6-carboxamide, ii) N-(4-Chlorobenzyl)-2-[(methylsulfanyl)methyl]-9-(morpholin-4-ylmethyl)-7-thioxo-2,3-dihydro-7H-[1,4]oxazino[2,3,4-ij]quinoline-6-carboxamide, jj) N-(4-Chlorobenzyl)-2-[(dimethylamino)methyl]-9-(morpholin-4-ylmethyl)-7-thioxo-2,3-dihydro-7H-[1,4]oxazino[2,3,4-ij]quinoline-6-carboxamide, kk) N-(4-Chlorobenzyl)-2-[(4-methyl-1-piperazinyl)methyl]-9-(morpholin-4-ylmethyl)-7-thioxo-2,3-dihydro-7H-[1,4]oxazino[2,3,4-ij]quinoline-6-carboxamide, ll) Methyl({[6-{[(4-chlorobenzyl)amino]carbonyl}-9-(morpholin-4-ylmethyl)-7-thioxo-2,3-dihydro-7H-[1,4]oxazino[2,3,4-ij]quinolin-2-yl]methyl}thio)acetate, mm) N-(4-Chlorobenzyl)-9-(morpholin-4-ylmethyl)-7-thioxo-2-(1-pyrrolidinylmethyl)-2,3-dihydro-7H-[1,4]oxazino[2,3,4-ij]quinoline-6-carboxamide, nn) N-(4-Chlorobenzyl)-2-{[(2,3-dihydroxypropyl)sulfanyl]methyl}-9-(morpholin-4-ylmethyl)-7-thioxo-2,3-dihydro-7H-[1,4]oxazino[2,3,4-ij]quinoline-6-carboxamide, oo) N-(4-Chlorobenzyl)-2-{[(2,3-dihydroxypropyl)amino]methyl}-9-(morpholin-4-ylmethyl)-7-thioxo-2,3-dihydro-7H-[1,4]oxazino[2,3,4-ij]quinoline-6-carboxamide, pp) N-(4-Chlorobenzyl)-2-{[(2-hydroxyethyl)amino]methyl}-9-(morpholin-4-ylmethyl)-7-thioxo-2,3-dihydro-7H-[1,4]oxazino[2,3,4-ij]quinoline-6-carboxamide, qq) N-(4-Chlorobenzyl)-9-(morpholin-4-ylmethyl)-7-thioxo-2-(1-piperidinylmethyl)-2,3-dihydro-7H-[1,4]oxazino[2,3,4-ij]quinoline-6-carboxamide, rr) 2-{[bis(2-Hydroxyethyl)amino]methyl}-N-(4-chlorobenzyl)-9-(morpholin-4-ylmethyl)-7-thioxo-2,3-dihydro-7H-[1,4]oxazino[2,3,4-ij]quinoline-6-carboxamide, ss) N-(4-Chlorobenzyl)-9-(morpholin-4-ylmethyl)-7-thioxo-2-{[(2-pyridinylmethyl)amino]methyl}-2,3-dihydro-7H-[1,4]oxazino[2,3,4-ij]quinoline-6-carboxamide, tt) 2-[(8-{[6-{[(4-Chlorobenzyl)amino]carbonyl}-9-(morpholin-4-ylmethyl)-7-thioxo-2,3-dihydro-7H-[1,4]oxazino[2,3,4-ij]quinolin-2-yl]methoxy}-8-oxooctanoyl)(methyl)amino]ethanesulfonic acid sodium salt, uu) [6-{[(4-Chlorobenzyl)amino]carbonyl}-9-(morpholin-4-ylmethyl)-7-thioxo-2,3-dihydro-7H-[1,4]oxazino[2,3,4-ij]quinolin-2-yl]methyl dimethyl phosphate, vv) N-(4-Chlorobenzyl)-9-(morpholin-4-ylmethyl)-7-thioxo-2-{[(4-pyridinylmethyl)amino]methyl}-2,3-dihydro-7H-[1,4]oxazino[2,3,4-ij]quinoline-6-carboxamide, ww) N-(4-Chlorobenzyl)-2-(1H-imidazol-1-ylmethyl)-9-(morpholin-4-ylmethyl)-7-thioxo-2,3-dihydro-7H-[1,4]oxazino[2,3,4-ij]quinoline-6-carboxamide, xx) N-(4-Chlorobenzyl)-2-{[(4-chlorobenzyl)amino]methyl}-9-(morpholin-4-ylmethyl)-7-thioxo-2,3-dihydro-7H-[1,4]oxazino[2,3,4-ij]quinoline-6-carboxamide, yy) N-(4-Chlorobenzyl)-3-(hydroxymethyl)-9-(morpholin-4-ylmethyl)-7-thioxo-2,3-dihydro-7H-[1,4]oxazino[2,3,4-ij]quinoline-6-carboxamide, zz) N-(4-Chlorobenzyl)-2-(4-hydroxyphenyl)-9-(morpholin-4-ylmethyl)-7-thioxo-2,3-dihydro-7H-[1,4]oxazino[2,3,4-ij]quinoline-6-carboxamide, aaa) N-(4-Chlorobenzyl)-2-{3-[(methoxymethoxy)methyl]phenyl}-9-(morpholin-4-ylmethyl)-7-thioxo-2,3-dihydro-7H-[1,4]oxazino[2,3,4-ij]quinoline-6-carboxamide, bbb) N-(4-Chlorobenzyl)-2-{2-[(methoxymethoxy)methyl]phenyl}-9-(morpholin-4-ylmethyl)-7-thioxo-2,3-dihydro-7H-[1,4]oxazino[2,3,4-ij]quinoline-6-carboxamide, ccc) N-(4-Chlorobenzyl)-2-(2-hydroxyphenyl)-9-(morpholin-4-ylmethyl)-7-thioxo-2,3-dihydro-7H-[1,4]oxazino[2,3,4-ij]quinoline-6-carboxamide, ddd) N-[(4-Chlorophenyl)methyl]-2,3,5,6-tetrahydro-9'-(4-morpholinylmethyl)-7'-thioxospiro[4H-pyran-4,2'(3'H)-[7H]pyrido[1,2,3-de][1,4]benzoxazine]-6'-carboxamide, eee) 1,1-Dimethylethyl 6-[[[(4-chlorophenyl) methylamino]carbonyl]-9'-(4-morpholinylmethyl)-7'-thioxospiro[piperidine-4,2'(3'H)-[7H]pyrido 1,2,3-de] [1,4]benzoxazine]-1-carboxylate, fff) N-[(4-Chlorophenyl)methyl]-9'-(4-morpholinylmethyl)-7'-thioxospiro[piperidine-4,2' (3'H)-[7H]pyrido[1,2,3-de][1,4]benzoxazine]-6'-carboxamide, ggg) N-(4-Chlorobenzyl)-2,2-bis[(hydroxymethoxy) methyl]-9-(morpholin-4-ylmethyl)-7-thioxo-2,3-dihydro-7H-[1,4]oxazino[2,3,4-ij]quinoline-6-carboxamide, hhh) N-[(4-Chlorophenyl)methyl]-2',3',5',6'-tetrahydro-9-(4-morpholinylmethyl)-7-thioxospiro[7H-pyrido[1,2,3-de]-1,4-benzoxazine-2(3H),4'-[4H]thiopyran]-6-carboxamide, or a pharmaceutically acceptable salt.

72. A compound of claim 1 which is a) N-(4-Chlorobenzyl)-2-(hydroxymethyl)-9-(morpholin-4-ylmethyl)-7-oxo-2,3-dihydro-7H-[1,4]oxazino[2,3,4-ij]quinoline-6-carboxamide, b) N-(4-Chlorobenzyl)-2-(R or S)-(hydroxymethyl)-9-(morpholin-4-ylmethyl)-7-oxo-2,3-dihydro-7H-[1,4] oxazino[2,3,4-ij]quinoline-6-carboxamide, c) N-(4-Chlorobenzyl)-9-(morpholin-4-ylmethyl)-7-oxo-2-pyridin-3-yl-2,3-dihydro-7H-[1,4]oxazino[2,3,4-ij] quinoline-6-carboxamide, d) N-(4-Chlorobenzyl)-9-(morpholin-4-ylmethyl)-7-oxo-2-pyridin-4-yl-2,3-dihydro-7H-[1,4]oxazino[2,3,4-ij] quinoline-6-carboxamide, e) N-(4-Chlorobenzyl)-9-(morpholin-4-ylmethyl)-7-oxo-2-pyridin-2-yl-2,3-dihydro-7H-[1,4]oxazino[2,3,4-ij] quinoline,-6-carboxamide, f) N-(4-Chlorobenzyl)-9-(morpholin-4-ylmethyl)-7-oxo-2-(R or S)-pyridin-3-yl-2,3-dihydro-7H-[1,4]oxazino [2,3,4-ij]quinoline-6-carboxamide, g) N-(4-Chlorobenzyl)-2,9-bis(morpholin-4-ylmethyl)-7-oxo-2,3-dihydro-7H-[1,4]oxazino[2,3,4-ij]quinoline-6-carboxamide, h) 2-[(tert-Butylsulfanyl)methyl]-N-(4-chlorobenzyl)-9-(morpholin-4-ylmethyl)-7-oxo-2,3-dihydro-7H-[1,4] oxazino[2,3,4-ij]quinoline-6-carboxamide, i) N-(4-Chlorobenzyl)-2-{[(2-hydroxyethyl)sulfanyl] methyl}-9-(morpholin-4-ylmethyl)-7-oxo-2,3-dihydro-7H-[1,4]oxazino[2,3,4-ij]quinoline-6-carboxamide, j) N-(4-Chlorobenzyl)-2-{[(1-methyl-1H-imidazol-2-yl) sulfanyl]methyl}-9-(morpholin-4-ylmethyl)-7-oxo-2, 3-dihydro-7H-[1,4]oxazino[2,3,4-ij]quinoline-6-carboxamide, k) N-(4-Chlorobenzyl)-9-(morpholin-4-ylmethyl)-7-oxo-2-{[(3-pyridinylmethyl)amino]methyl}-2,3-dihydro-7H-[1,4]oxazino[2,3,4-ij]quinoline-6-carboxamide, l) [6-{[(4-Chlorobenzyl)amino]carbonyl}-9-(morpholin-4-ylmethyl)-7-oxo-2,3-dihydro-7H-[1,4]oxazino[2,3,4-ij]quinolin-2-yl]methyl acetate, m) N-(4-Chlorobenzyl)-9-(morpholin-4-ylmethyl)-7-oxo-2-(R or S)-{[(3-pyridinylmethyl)amino]methyl}-2,3-dihydro-7H-[1,4]oxazino[2,3,4-ij]quinoline-6-carboxamide, n) N-(4-Chlorobenzyl)-2-(3-hydroxyphenyl)-9-(morpholin-4-ylmethyl)-7-oxo-2,3-dihydro-7H-[1,4] oxazino[2,3,4-ij]quinoline-6-carboxamide, o) N-(4-Chlorobenzyl)-9-(morpholin-4-ylmethyl)-7-oxo-2-(R or S)-pyridin-2-yl-2,3-dihydro-7H-[1,4]oxazino [2,3,4-ij]quinoline-6-carboxamide, p) N-(4-Chlorobenzyl)-2-[3-(hydroxymethyl)phenyl]-9-(morpholin-4-ylmethyl)-7-oxo-2,3-dihydro-7H-[1,4] oxazino[2,3,4-ij]quinoline-6-carboxamide, q) N-(4-Chlorobenzyl)-2-[2-(hydroxymethyl)phenyl]-9-(morpholin-4-ylmethyl)-7-oxo-2,3-dihydro-7H-[1,4] oxazino[2,3,4-ij]quinoline-6-carboxamide, r) N-(4-Chlorobenzyl)-2-(1-methyl-1H-imidazol-2-yl)-9-(morpholin-4-ylmethyl)-7-oxo-2,3-dihydro-7H-[1,4] oxazino[2,3,4-ij]quinoline-6-carboxamide, s) N-(4-Chlorobenzyl)-2-(2-furyl)-9-(morpholin-4-ylmethyl)-7-oxo-2,3-dihydro-7H-[1,4]oxazino[2,3,4-ij]quinoline-6-carboxamide, t) N-(4-Chlorobenzyl)-2-(3-cyanophenyl)-9-(morpholin-4-ylmethyl)-7-oxo-2,3-dihydro-7H-[1,4]oxazino[2,3,4-ij]quinoline-6-carboxamide, u) N-(4-Chlorobenzyl)-2-(3-furyl)-9-(morpholin-4-ylmethyl)-7-oxo-2,3-dihydro-7H-[1,4]oxazino[2,3,4-ij]quinoline-6-carboxamide, v) N-(4-Chlorobenzyl)-9-(morpholin-4-ylmethyl)-7-oxo-2-thien-2-yl-2,3-dihydro-7H-[1,4]oxazino[2,3,4-ij] quinoline-6-carboxamide, w) N-(4-Chlorobenzyl)-2-(3,5-difluorophenyl)-9-(morpholin-4-ylmethyl)-7-oxo-2,3-dihydro-7H-[1,4] oxazino[2,3,4-ij]quinoline-6-carboxamide, x) 2-(1,3-Benzodioxol-5-yl)-N-(4-chlorobenzyl)-9-(morpholin-4-ylmethyl)-7-oxo-2,3-dihydro-7H-[1,4] oxazino[2,3,4-ij]quinoline-6-carboxamide, y) N-(4-Chlorobenzyl)-2-(2,3-dihydro-1,4-benzodioxin-6-yl)-9-(morpholin-4-ylmethyl)-7-oxo-2,3-dihydro-7H-[1,4]oxazino[2,3,4-ij]quinoline-6-carboxamide, z) 2-(1,3-Benzodioxol-4-yl)-N-(4-chlorobenzyl)-9-(morpholin-4-ylmethyl)-7-oxo-2,3-dihydro-7H-[1,4] oxazino[2,3,4-ij]quinoline-6-carboxamide, aa) 2-[3,5-bis(Methoxymethoxy)phenyl]-N-(4-chlorobenzyl)-9-(morpholin-4-ylmethyl)-7-oxo-2,3-dihydro-7H-[1,4]oxazino[2,3,4-ij]quinoline-6-carboxamide, bb) N-(4-Chlorobenzyl)-9-(morpholin-4-ylmethyl)-7-oxo-2-thien-3-yl-2,3-dihydro-7H-[1,4]oxazino[2,3,4-ij]quinoline-6-carboxamide, cc) N-(4-Chlorobenzyl)-2,2-bis[(methoxymethoxy) methyl]-9-(morpholin-4-ylmethyl)-7-oxo-2,3-dihydro-7H-[1,4]oxazino[2,3,4-ij]quinoline-6-carboxamide, dd) N-[(4-Chlorophenyl)methyl]-9'-(4-morpholinylmethyl)-4,7'-dioxospiro[cyclohexane-1,2' (3'H)-[7H]pyrido[1,2,3-de][1,4]benzoxazine]-6'-carboxamide, ee) N-[(4-Chlorophenyl)methyl]4-hydroxy-9'-(4-morpholinylmethyl)-7'-oxospiro[cyclohexane-1,2' (3'H)-[7H]pyrido[1,2,3-de][1,4]benzoxazine]-6'-carboxamide, or a pharmaceutically acceptable salt.

73. A compound of claim 1 which is a) N-(4-Chlorobenzyl)-2-(hydroxymethyl)-9-(morpholin-4-ylmethyl)-7-thioxo-2,3-dihydro-7H-[1,4]oxazino[2, 3,4-ij]quinoline-6-carboxamide, b) N-(4-Chlorobenzyl)-2-(R or S)-(hydroxymethyl)-9-(morpholin-4-ylmethyl)-7-thioxo-2,3-dihydro-7H-[1, 4]oxazino[2,3,4-ij]quinoline-6-carboxamide, c) N-(4-Chlorobenzyl)-9-(morpholin-4-ylmethyl)-7-thioxo-2-pyridin-3-yl-2,3-dihydro-7H-[1,4]oxazino[2, 3,4-ij]quinoline-6-carboxamide, d) N-(4-Chlorobenzyl)-9-(morpholin-4-ylmethyl)-7-thioxo-2-pyridin4-yl-2,3-dihydro-7H-[1,4]oxazino[2, 3,4-ij]quinoline-6-carboxamide, e) N-(4-Chlorobenzyl)-9-(morpholin-4-ylmethyl)-7-thioxo-2-pyridin-2-yl-2,3-dihydro-7H-[1,4]oxazino[2,3,4-ij]quinoline-6-carboxamide, f) N-(4-Chlorobenzyl)-9-(morpholin-4-ylmethyl)-7-thioxo-2-(R or S)-pyridin-3-yl-2,3-dihydro-7H-[1,4]oxazino[2,3,4-ij]quinoline-6-carboxamide, g) N-(4-Chlorobenzyl)-2,9-bis(morpholin-4-ylmethyl)-7-thioxo-2,3-dihydro-7H-[1,4]oxazino[2,3,4-ij]quinoline-6-carboxamide, h) 2-[(tert-Butylsulfanyl)methyl]-N-(4-chlorobenzyl)-9-(morpholin-4-ylmethyl)-7-thioxo-2,3-dihydro-7H-[1,4]oxazino[2,3,4-ij]quinoline-6-carboxamide, i) N-(4-Chlorobenzyl)-2-{[(2-hydroxyethyl)sulfanyl]methyl}-9-(morpholin-4-ylmethyl)-7-thioxo-2,3-dihydro-7H-[1,4]oxazino[2,3,4-ij]quinoline-6-carboxamide, j) N-(4-Chlorobenzyl)-2-{[(1-methyl-1 H-imidazol-2-yl)sulfanyl]methyl}-9-(morpholin-4-ylmethyl)-7-thioxo-2,3-dihydro-7H-[1,4]oxazino[2,3,4-ij]quinoline-6-carboxamide, k) N-(4-Chlorobenzyl)-9-(morpholin-4-ylmethyl)-7-thioxo-2-{[(3-pyridinylmethyl)amino]methyl}-2,3-dihydro-7H-[1,4]oxazino[2,3,4-ij]quinoline-6-carboxamide, l) [6-{[(4-Chlorobenzyl)amino]carbonyl}-9-(morpholin-4-ylmethyl)-7-thioxo-2,3-dihydro-7H-[1,4]oxazino[2,3,4-ij]quinolin-2-yl]methyl acetate, m) N-(4-Chlorobenzyl)-9-(morpholin-4-ylmethyl)-7-thioxo-2-(R or S)-{[(3-pyridinylmethyl)amino]methyl}-2,3-dihydro-7H-[1,4]oxazino[2,3,4-ij]quinoline-6-carboxamide, n) N-(4-Chlorobenzyl)-2-(3-hydroxyphenyl)-9-(morpholin-4-ylmethyl)-7-thioxo-2,3-dihydro-7H-[1,4]oxazino[2,3,4-ij]quinoline-6-carboxamide, o) N-(4-Chlorobenzyl)-9-(morpholin-4-ylmethyl)-7-thioxo-2-(R or S)-pyridin-2-yl-2,3-dihydro-7H-[1,4]oxazino[2,3,4-ij]quinoline-6-carboxamide, p) N-(4-Chlorobenzyl)-2-[3-(hydroxymethyl)phenyl]-9-(morpholin-4-ylmethyl)-7-thioxo-2,3-dihydro-7H-[1,4]oxazino[2,3,4-ij]quinoline-6-carboxamide, q) N-(4-Chlorobenzyl)-2-[2-(hydroxymethyl)phenyl]-9-(morpholin-4-ylmethyl)-7-thioxo-2,3-dihydro-7H-[1,4]oxazino[2,3,4-ij]quinoline-6-carboxamide, r) N-(4-Chlorobenzyl)-2-(1-methyl-1H-imidazol-2-yl)-9-(morpholin-4-ylmethyl)-7-thioxo-2,3-dihydro-7H-[1,4]oxazino[2,3,4-ij]quinoline-6-carboxamide, s) N-(4-Chlorobenzyl)-2-(2-furyl)-9-(morpholin-4-ylmethyl)-7-thioxo-2,3-dihydro-7H-[1,4]oxazino[2,3,4-ij]quinoline-6-carboxamide, t) N-(4-Chlorobenzyl)-2-(3-cyanophenyl)-9-(morpholin-4-ylmethyl)-7-thioxo-2,3-dihydro-7H-[1,4]oxazino[2,3,4-ij]quinoline-6-carboxamide, u) N-(4-Chlorobenzyl)-2-(3-furyl)-9-(morpholin-4-ylmethyl)-7-thioxo-2,3-dihydro-7H-[1,4]oxazino[2,3,4-ij]quinoline-6-carboxamide, v) N-(4-Chlorobenzyl)-9-(morpholin-4-ylmethyl)-7-thioxo-2-thien-2-yl-2,3-dihydro-7H-[1,4]oxazino[2,3,4-ij]quinoline-6-carboxamide, w) N-(4-Chlorobenzyl)-2-(3,5-difluorophenyl)-9-(morpholin-4-ylmethyl)-7-thioxo-2,3-dihydro-7H-[1,4]oxazino[2,3,4-ij]quinoline-6-carboxamide, x) 2-(1,3-Benzodioxol-S-yl)-N-(4-chlorobenzyl)-9-(morpholin-4-ylmethyl)-7-thioxo-2,3-dihydro-7H-[1,4]oxazino[2,3,4-ij]quinoline-6-carboxamide, y) N-(4-Chlorobenzyl)-2-(2,3-dihydro-1,4-benzodioxin-6-yl)-9-(morpholin-4-ylmethyl)-7-thioxo-2,3-dihydro-7H-[1,4]oxazino[2,3,4-ij]quinoline-6-carboxamide, z) 2-(1,3-Benzodioxol-4-yl)-N-(4-chlorobenzyl)-9-(morpholin-4-ylmethyl)-7-thioxo-2,3-dihydro-7H-[1,4]oxazino[2,3,4-ij]quinoline-6-carboxamide, aa) 2-[3,5-bis(Methoxymethoxy)phenyl]-N-(4-chlorobenzyl)-9-(morpholin-4-ylmethyl)-7-thioxo-2,3-dihydro-7H-[1,4]oxazino[2,3,4-ij]quinoline-6-carboxamide, bb) N-(4-Chlorobenzyl)-9-(morpholin-4-ylmethyl)-7-thioxo-2-thien-3-yl-2,3-dihydro-7H-[1,4]oxazino[2,3,4-ij]quinoline-6-carboxamide, cc) N-(4-Chlorobenzyl)-2,2-bis[(methoxymethoxy)methyl]-9-(morpholin-4-ylmethyl)-7-thioxo-2,3-dihydro-7H-[1,4]oxazino[2,3,4-ij]quinoline-6-carboxamide, dd) N-[(4-Chlorophenyl)methyl]-9'-(4-morpholinylmethyl)-4-oxo-7'-thioxospiro[cyclohexane-1,2'(3'H)-[7H]pyrido[1,2,3-de][1,4]benzoxazine]-6'-carboxamide, ee) N-[(4-Chlorophenyl)methyl]-4-hydroxy-9'-(4-morpholinylmethyl)-7'-thioxospiro[cyclohexane-1,2'(3'H)-[7H]pyrido 1,2,3-de][1,4]benzoxazine]-6'-carboxamide, or a pharmaceutically acceptable salt.

74. A compound of claim 1 which is a) N-(4-Chlorobenzyl)-2-(hydroxymethyl)-9-(morpholin-4-ylmethyl)-7-oxo-2,3-dihydro-7H-[1,4]oxazino[2,3,4-ij]quinoline-6-carboxamide, b) N-(4-Chlorobenzyl)-2-(R or S)-(hydroxymethyl)-9-(morpholin-4-ylmethyl)-7-oxo-2,3-dihydro-7H-[1,4]oxazino[2,3,4-ij]quinoline-6-carboxamide, c) N-(4-Chlorobenzyl)-9-(morpholin-4-ylmethyl)-7-oxo-2-pyridin-3-yl-2,3-dihydro-7H-[1,4]oxazino[2,3,4-ij]quinoline-6-carboxamide, d) N-(4-Chlorobenzyl)-9-(morpholin-4-ylmethyl)-7-oxo-2-pyridin-4-yl-2,3-dihydro-7H-[1,4]oxazino[2,3,4-ij]quinoline-6-carboxamide, e) N-(4-Chlorobenzyl)-9-(morpholin-4-ylmethyl)-7-oxo-2-pyridin-2-yl-2,3-dihydro-7H-[1,4]oxazino[2,3,4-ij]quinoline-6-carboxamide, f) N-(4-Chlorobenzyl)-9-(morpholin-4-ylmethyl)-7-oxo-2-(R or S)-pyridin-3-yl-2,3-dihydro-7H-[1,4]oxazino[2,3,4-ij]quinoline-6-carboxamide, g) N-(4-Chlorobenzyl)-9-(morpholin-4-ylmethyl)-7-oxo-2-(R or S)-pyridin-2-yl-2,3-dihydro-7H-[1,4]oxazino[2,3,4-ij]quinoline-6-carboxamide, h) N-(4-Chlorobenzyl)-2-(1-methyl-1H-imidazol-2-yl)-9-(morpholin-4-ylmethyl)-7-oxo-2,3-dihydro-7H-[1,4]oxazino[2,3,4-ij]quinoline-6-carboxamide, or a pharmaceutically acceptable salt.

75. A compound of claim 1 which is a) N-(4-Chlorobenzyl)-2-(hydroxymethyl)-9-(morpholin-4-ylmethyl)-7-thioxo-2,3-dihydro-7H-[1,4]oxazino[2,3,4-ij]quinoline-6-carboxamide, b) N-(4-Chlorobenzyl)-2-(R or S)-(hydroxymethyl)-9-(morpholin-4-ylmethyl)-7-thioxo-2,3-dihydro-7H-[1,4]oxazino[2,3,4-ij]quinoline-6-carboxamide, c) N-(4-Chlorobenzyl)-9-(morpholin-4-ylmethyl)-7-thioxo-2-pyridin-3-yl-2,3-dihydro-7H-[1,4]oxazino[2,3,4-ij]quinoline-6-carboxamide, d) N-(4-Chlorobenzyl)-9-(morpholin-4-ylmethyl)-7-thioxo-2-pyridin-4-yl-2,3-dihydro-7H-[1,4]oxazino[2,3,4-ij]quinoline-6-carboxamide, e) N-(4-Chlorobenzyl)-9-(morpholin-4-ylmethyl)-7-thioxo-2-pyridin-2-yl-2,3-dihydro-7H-[1,4]oxazino[2,3,4-ij]quinoline-6-carboxamide, f) N-(4-Chlorobenzyl)-9-(morpholin-4-ylmethyl)-7-thioxo-2-(R or S)-pyridin-3-yl-2,3-dihydro-7H-[1,4]oxazino[2,3,4-ij]quinoline-6-carboxamide, g) N-(4-Chlorobenzyl)-9-(morpholin-4-ylmethyl)-7-thioxo-2-(R or S)-pyridin-2-yl-2,3-dihydro-7H-[1,4]oxazino[2,3,4-ij]quinoline-6-carboxamide, h) N-(4-Chlorobenzyl)-2-(1-methyl-1H-imidazol-2-yl)-9-(morpholin-4-ylmethyl)-7-thioxo-2,3-dihydro-7H-[1,4]oxazino[2,3,4-ij]quinoline-6-carboxamide, or a pharmaceutically acceptable salt.

76. A compound of claim 1 which is a) N-(4-Chlorobenzyl)-2-(hydroxymethyl)-9-(morpholin-4-ylmethyl)-7-thioxo-2,3-dihydro-7H-[1,4]oxazino[2,3,4-ij]quinoline-6-carboxthioamide, b) N-(4-Chlorobenzyl)-2-(R or S)-(hydroxymethyl)-9-(morpholin-4-ylmethyl)-7-thioxo-2,3-dihydro-7H-[1,4]oxazino[2,3,4-ij]quinoline-6-carboxthioamide, c) N-(4-Chlorobenzyl)-9-(morpholin-4-ylmethyl)-7-thioxo-2-pyridin-3-yl-2,3-dihydro-7H-[1,4]oxazino[2,3,4-ij]quinoline-6-carboxthioamide, d) N-(4-Chlorobenzyl)-9-(morpholin-4-ylmethyl)-7-thioxo-2-pyridin-4-yl-2,3-dihydro-7H-[1,4]oxazino[2,3,4-ij]quinoline-6-carboxthioamide, e) N-(4-Chlorobenzyl)-9-(morpholin-4-ylmethyl)-7-thioxo-2-pyridin-2-yl-2,3-dihydro-7H-[1,4]oxazino[2,3,4-ij]quinoline-6-carboxthioamide, f) N-(4-Chlorobenzyl)-9-(morpholin-4-ylmethyl)-7-thioxo-2-(R or S)-pyridin-3-yl-2,3-dihydro-7H-[1,4]oxazino[2,3,4-ij]quinoline-6-carboxthioamide, e) N-(4-Chlorobenzyl)-9-(morpholin-4-ylmethyl)-7-thioxo-2-(R or S)-pyridin-3-yl-2,3-dihydro-7H-[1,4]oxazino[2,3,4-ij]quinoline-6-carboxthioamide, f) N-(4-Chlorobenzyl)-2-(1-methyl-1H-imidazol-2-yl)-9-(morpholin-4-ylmethyl)-7-thioxo-2,3-dihydro-7H-[1,4]oxazino[2,3,4-ij]quinoline-6-carboxthioamide, or a pharmaceutically acceptable salt.

77. A compound of claim 1 which is a) N-(4-Chlorobenzyl)-2-(hydroxymethyl)-9-(morpholin-4-ylmethyl)-7-oxo-2,3-dihydro-7H-[1,4]oxazino[2,3,4-ij]quinoline-6-carboxthioamide, b) N-(4-Chlorobenzyl)-2-(R or S)-(hydroxymethyl)-9-(morpholin-4-ylmethyl)-7-oxo-2,3-dihydro-7H-[1,4]oxazino[2,3,4-ij]quinoline-6-carboxthioamide, c) N-(4-Chlorobenzyl)-9-(morpholin-4-ylmethyl)-7-oxo-2-pyridin-3-yl-2,3-dihydro-7H-[1,4]oxazino[2,3,4-ij]quinoline-6-carboxthioamide, d) N-(4-Chlorobenzyl)-9-(morpholin-4-ylmethyl)-7-oxo-2-pyridin-4-yl-2,3-dihydro-7H-[1,4]oxazino[2,3,4-ij]quinoline-6-carboxthioamide, e) N-(4-Chlorobenzyl)-9-(morpholin-4-ylmethyl)-7-oxo-2-pyridin-2-yl-2,3-dihydro-7H-[1,4]oxazino[2,3,4-ij]quinoline-6-carboxthioamide, f) N-(4-Chlorobenzyl)-9-(morpholin-4-ylmethyl)-7-oxo-2-(R or S)-pyridin-3-yl-2,3-dihydro-7H-[1,4]oxazino[2,3,4-ij]quinoline-6-carboxthioamide, g) N-(4-Chlorobenzyl)-9-(morpholin-4-ylmethyl)-7-oxo-2-(R or S)-pyridin-2-yl-2,3-dihydro-7H-[1,4]oxazino[2,3,4-ij]quinoline-6-carboxthioamide, h) N-(4-Chlorobenzyl)-2-(1-methyl-1H-imidazol-2-yl)-9-(morpholin-4-ylmethyl)-7-oxo-2,3-dihydro-7H-[1,4]oxazino[2,3,4-ij]quinoline-6-carboxthioamide, or a pharmaceutically acceptable salt.

78. A compound of claim 1 which is N-(4-chlorobenzyl)-9-(morpholin-4-ylmethyl)-7-oxo-2-(S)-pyridin-2-yl-2,3-dihydro-7H-[1,4]oxazino[2,3,4-ij]quinoline-6-carboxamide, or a pharmaceutically acceptable salt.

79. A compound of claim 1 which is N-(4-chlorobenzyl)-9-(morpholin-4-ylmethyl)-7-oxo-2-(R)-pyridin-2-yl-2,3-dihydro-7H-[1,4]oxazino[2,3,4-ij]quinoline-6-carboxamide, or a pharmaceutically acceptable salt.

80. A compound of claim 1 which is N-(4-chlorobenzyl)-9-(morpholin-4-ylmethyl)-7-oxo-2-(R)-pyridin-3-yl-2,3-dihydro-7H-[1,4]oxazino[2,3,4-ij]quinoline-6-carboxamide, or a pharmaceutically acceptable salt.

81. A compound of claim 1 which is N-(4-chlorobenzyl)-9-(morpholin-4-ylmethyl)-7-oxo-2-(S)-pyridin-3-yl-2,3-dihydro-7H-[1,4]oxazino[2,3,4-ij]quinoline-6-carboxamide, or a pharmaceutically acceptable salt.

82. A compound of claim 1 which is N-(4-Chlorobenzyl)-2-(1-methyl-1H-imidazol-2-yl)-9-(morpholin-4-ylmethyl)-7-oxo-2,3-dihydro-7H-[1,4]oxazino[2,3,4-ij]quinoline-6-carboxamide, or a pharmaceutically acceptable salt.

83. A pharmaceutical composition comprising a compound of claim 1 and a pharmaceutically acceptable carrier.

84. A method for inhibiting a viral DNA polymerase, comprising contacting the polymerase with an effective inhibitory amount of a compound of claim 1.

85. A method of treating infections from herpesviruses which comprises administering to a mammal in need thereof an effective amount of a compound of claim 1.

86. The method of claim 85 wherein said herpesviruses is herpes simplex virus types 1, herpes simplex virus types 2, varicella zoster virus, cytomegalovirus, Epstein-Barr virus, human herpes viruses 6, human herpes viruses 7 or human herpes viruses 8.

87. The method of claim 85 wherein said herpesviruses is herpes simplex virus types 1, herpes simplex virus types 2, varicella zoster virus, cytomegalovirus, Epstein-Barr virus, human herpes viruses 7 or human herpes viruses 8.

88. The method of claim 85 wherein said herpesviruses is human cytomegalovirus.

89. The method of claim 85 wherein the effective amount of a compound of claim 1 is administered orally, parenterally, topically, rectally, nasally, dublingually, or transdermally.

90. The method of claim 85 wherein the effective amount of a compound of claim 1 is in an amount of from about 0.1 to about 300 mg/kg of body weight.

91. The method of claim 85 wherein the effective amount of a compound of claim 1 is in an amount of from about 1 to about 30 mg/kg of body weight.

92. The method of claim 85 wherein the mammal is human.

93. The method of claim 85 wherein the mammal is a food animal or a companion animal.

94. A compound of claim 46 wherein het is morpholinyl.

* * * * *